US011793887B2

(12) United States Patent
Braverman et al.

(10) Patent No.: US 11,793,887 B2
(45) Date of Patent: Oct. 24, 2023

(54) GENE THERAPY FOR TREATING PEROXISOMAL DISORDERS

(71) Applicants: The Trustees of the University of Pennsylvania, Philadelphia, PA (US); University of Southern California, Los Angles, CA (US); The Research Institute of the McGill University Health Centre, Montreal (CA)

(72) Inventors: Nancy Braverman, Montreal (CA); Catherine Argyriou, Montreal (CA); Joseph Hacia, Pasadena, CA (US); Jean Bennett, Philadelphia, PA (US); Junwei Sun, Philadelphia, PA (US); Ji Yun Song, Lower Gwynedd, PA (US); Devin McDougald, Philadelphia, PA (US)

(73) Assignees: The Trustees of the University of Pennsylvania, Philadelphia, PA (US); University of Southern California, Los Angeles, CA (US); The Research Institute of McGill University Health Centre, Montreal (CA)

( * ) Notice: Subject to any disclaimer, the term of this patent is extended or adjusted under 35 U.S.C. 154(b) by 182 days.

(21) Appl. No.: 16/615,941

(22) PCT Filed: May 31, 2018

(86) PCT No.: PCT/CA2018/050642
§ 371 (c)(1),
(2) Date: Nov. 22, 2019

(87) PCT Pub. No.: WO2018/218359
PCT Pub. Date: Dec. 6, 2018

(65) Prior Publication Data
US 2020/0093937 A1    Mar. 26, 2020

Related U.S. Application Data

(60) Provisional application No. 62/513,156, filed on May 31, 2017.

(51) Int. Cl.
*A61K 48/00*   (2006.01)
*C12N 15/79*   (2006.01)
*C07H 21/04*   (2006.01)
*A61K 35/761*  (2015.01)
*C12N 9/14*    (2006.01)
*C12N 15/86*   (2006.01)
*C12N 15/864*  (2006.01)

(52) U.S. Cl.
CPC .......... *A61K 48/005* (2013.01); *A61K 35/761* (2013.01); *C12N 9/14* (2013.01); *C12N 15/86* (2013.01); *C07H 21/04* (2013.01); *C12N 15/8645* (2013.01); *C12N 2750/14143* (2013.01); *C12N 2800/22* (2013.01)

(58) Field of Classification Search
CPC .. A61K 48/005; C12N 15/86; C12N 15/8645; C12N 2750/14143; C12N 2800/22; C07H 21/04
See application file for complete search history.

(56) References Cited

U.S. PATENT DOCUMENTS

| 5,139,941 | A  | 8/1992  | Muzyczka et al.   |
|-----------|----|---------|--------------------|
| 5,478,745 | A  | 12/1995 | Samulski et al.   |
| 5,741,683 | A  | 4/1998  | Zhou et al.       |
| 6,057,152 | A  | 5/2000  | Samulski et al.   |
| 6,204,059 | B1 | 3/2001  | Samulski et al.   |
| 6,268,213 | B1 | 7/2001  | Samulski et al.   |
| 6,491,907 | B1 | 12/2002 | Rabinowitz et al. |
| 6,596,535 | B1 | 7/2003  | Carter et al.     |
| 6,660,514 | B1 | 12/2003 | Zolotukhin et al. |
| 6,951,753 | B2 | 10/2005 | Shenk et al.      |
| 7,094,604 | B2 | 8/2006  | Snyder et al.     |
| 7,125,717 | B2 | 10/2006 | Carter et al.     |
| 7,172,893 | B2 | 2/2007  | Rabinowitz et al. |
| 7,201,898 | B2 | 4/2007  | Monahan et al.    |
| 7,229,823 | B2 | 6/2007  | Samulski et al.   |
| 7,282,199 | B2 | 10/2007 | Gao et al.        |
| 7,439,065 | B2 | 10/2008 | Ferrari et al.    |
| 7,456,683 | B2 | 11/2008 | Takano et al.     |

(Continued)

FOREIGN PATENT DOCUMENTS

| EP | 1310571       | 5/2003 |
|----|---------------|--------|
| WO | WO-2003/042397 | 5/2003 |

(Continued)

OTHER PUBLICATIONS

Reuber et al., 1997, GenBank Accession No. AF026086.*
Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Durymanov et al., 2018, Frontiers in Pharmacology, vol. 9, Article 971, p. 1-15.*
Moore et al., 2018, Expert Opinion on Biological Therapy, vol. 18, No. 1, p. 37-49.*
Argyriou, C. et al., A longitudinal study of retinopathy in the PEX1-Gly844Asp mouse model for mild Zellweger Spectrum Disorder, Experimental Eye Research, vol. 186:107713, Sep. 2019.

(Continued)

*Primary Examiner* — Shin Lin Chen
(74) *Attorney, Agent, or Firm* — Howson & Howson LLP; Colleen M. Schaller

(57) ABSTRACT

Methods and compositions are provided for treatment of peroxisomal biogenesis disorders (PBDs). More particularly, recombinant adeno-associated viruses (rAAV) provided in the form of compositions are used to deliver a nucleic acid encoding human PEX1 to host cells. The rAAVs comprise a AAV capsid, and packaged therein a vector genome comprising an AAV 5' inverted terminal repeat (ITR) sequence; a promoter; a coding sequence encoding a human PEX1; and an AAV 3' ITR.

21 Claims, 42 Drawing Sheets

Specification includes a Sequence Listing.

(56) References Cited

U.S. PATENT DOCUMENTS

| | | | |
|---|---|---|---|
| 7,588,772 | B2 | 9/2009 | Kay et al. |
| 7,629,322 | B2 | 12/2009 | Kleinschmidt et al. |
| 7,790,449 | B2 | 9/2010 | Gao et al. |
| 7,906,111 | B2 | 3/2011 | Wilson et al. |
| 8,147,823 | B2 | 4/2012 | Acland et al. |
| 8,326,547 | B2 | 12/2012 | Liu et al. |
| 2006/0136184 | A1 | 6/2006 | Gustafsson et al. |
| 2007/0036760 | A1 | 2/2007 | Wilson et al. |
| 2009/0197338 | A1 | 8/2009 | Vandenberghe et al. |
| 2009/0227030 | A1 | 9/2009 | Gao et al. |
| 2014/0032186 | A1 | 1/2014 | Gustafsson et al. |

FOREIGN PATENT DOCUMENTS

| | | |
|---|---|---|
| WO | WO-2005/033321 | 4/2005 |
| WO | WO-2006/110689 | 10/2006 |
| WO | WO-2010/053572 | 5/2010 |
| WO | WO-2011/126808 | 10/2011 |
| WO | WO-2012/158757 | 11/2012 |
| WO | WO-2012/170930 | 12/2012 |
| WO | WO-2013/049493 | 4/2013 |
| WO | WO-2013/182683 | 12/2013 |
| WO | WO-2014/011210 | 1/2014 |
| WO | WO-2014/124282 | 8/2014 |
| WO | WO-2015/012924 | 1/2015 |
| WO | WO-2015/176066 | 11/2015 |

OTHER PUBLICATIONS

Beltran, W. A., et al, rAAV2/5 gene-targeting to rods:dose-dependent efficiency and complications associated with different promoters, Gene Therapy, vol. 17:1162-74, Sep. 2010.

Bennett J. Taking Stock of Retinal Gene Therapy: Looking Back and Moving Forward, Molecular Therapy, vol. 25(5): 1076-1094, May 2017.

Braverman, N.E., et al., Peroxisome biogenesis disorders in the Zellweger spectrum: An overview of current diagnosis, clinical manifestations, and treatment guidelines, Molecular Genetics and Metabolism, vol. 117(3):313-321, Mar. 2016.

Buning H. et al., Recent developments in adeno-associated virus vector technology, The Journal of Gene Medicine, vol. 10(7):717-733, Jul. 2008.

Cai X. et al., A 350 bp region of the proximal promoter of Rds drives cell-type specific gene expression, Expert Eye Research, vol. 91(2): 186-94, Aug. 2010.

Cearley C. N. et al., Expanded repertoire of AAV vector serotypes mediate unique patterns of transduction in mouse brain, Molecular Therapy, vol. 16(10): 1710-1718, Oct. 2008.

Daber R., Lewis M., A novel molecular switch. Journal Molecular Biology, vol. 391(4):661-70, Aug. 2009.

Dalkara D. et al., In Vivo-Directed Evolution of a New Adeno-Associated Virus for Therapeutic Outer Retinal Gene Delivery from the Vitreous, Science Translational Medicine, vol. 5(189):189ra76, Jun. 2013.

Damdindorj L. et al., A Comparative Analysis of Constitutive Promoters Located in Adeno-Associated Viral Vectors, PLoS ONE, vol. 9(8): e106472, Aug. 2014.

David A. L. et al., Recombinant adeno-associated virus-mediated in utero gene transfer gives therapeutic transgene expression in the sheep, Human Gene Therapy, vol. 22(4):419-26, Apr. 2011.

Diehl K. H. et al., A good practice guide to the administration of substances and removal of blood, including routes and volumes, Journal Applied Toxicology, vol. 21(1):15-23, Jan. 2001.

Fagarasanu A. et al., Maintaining peroxisome populations: a story of division and inheritance, Annual Review of Cell and Developmental Biology, vol. 23: 321-344, Jun. 2007.

Fidler, Ben, Bluebird Bio's Gene Therapy Shows Promise for ALD Treatment., online publication Apr. 20, 2016.

Fisher K. J., et al., Transduction with recombinant adeno-associated virus for gene therapy is limited by leading-strand synthesis, Journal of Virology, vol. 70(1):520-532, Jan. 1993.

Grieger J.C. & R. J. Samulski, Adeno-associated virus as a gene therapy vector: Vector development, production and clinical applications, Advanced Biochemical Engineering Biotechnology, vol. 99:119-145, Oct. 2005.

Grieger J.C. et al., Production and characterization of adeno-associated viral vectors, Nature Protocols, vol. 1(3):1412-1428, Nov. 2006.

Hacia, J. G. et al., Retinal Gene Therapy for Peroxisome Biogenesis Disorders, Molecular Therapy, vol. 23, Supplement 1, S119, Mar. 2015.

Hiebler, S., et al., The Pex1-G844D mouse: a model for mild human Zellweger spectrum disorder, Molecular Genetics and Metabolism, vol. 111(4):522-532, Apr. 2014.

Holehonnur R. et al., Adeno-associated viral serotypes produce differing titers and differentially transduce neurons within the rat basal and lateral amygdala, BMC Neuroscience, vol. 15:28, Feb. 2014.

Kachi et al., Equine Infectious Anemia Viral Vector-Mediated Codelivery of Endostatin and Angiostatin Driven by Retinal Pigmented Epithelium-SpecificVMD2 Promoter Inhibits Choroidal Neovascularization, Human Gene Therapy, vol. 20(1):31-9, Jan. 2009.

Kay, C. N. et al., Targeting Photoreceptors via Intravitreal Delivery Using Novel, Capsid-Mutated AAV Vectors, PLoS One, vol. 8(4):e62097, Apr. 2013.

Lambard et al., Expression of Rod-Derived Cone Viability Factor: Dual Role of CRX in Regulating Promoter Activity and Cell-Type Specificity, PLoS One, vol. 5(10):e13025, Oct. 2010.

Lock M. et al., Absolute Determination of Single-Stranded and Self-Complementary Adeno-Associated Viral Vector Genome Titers by Droplet Digital PCR, Human Gene Therapy Methods, vol. 25(2):115-25, Apr. 2014.

Majewski, J. et al., A new ocular phenotype associated with an unexpected but known systemic disorder and mutation: novel use of genomic diagnostics and exome sequencing, Journal of Medical Genetics, vol. 48(9):593-596, Sep. 2011.

McCarty, D. M. et al., Self-complementary recombinant adeno-associated virus (scAAV) vectors promote efficient transduction independently of DNA synthesis, Gene Therapy, vol. 8(16):1248-1254, Aug. 2001.

McLaughlin, S.K. et al., Adeno-associated virus general transduction vectors: analysis of proviral structures, Journal of Virology, vol. 62(6):1963-1973, Jun. 1988.

Morrissey et al., PRE-1, a cis element sufficient to enhance cone- and rod-specific expression in differentiating zebrafish photoreceptors, BMC Developmental Biology, vol. 11:3, Jan. 2011.

Mowat, F. M. et al., Tyrosine capsid-mutant AAV vectors for gene delivery to the canine retina from a subretinal or intravitreal approach, Gene Therapy, vol. 21(1):96-105, Nov. 2014.

Mussolino C. et al., AAV-mediated photoreceptor transduction of the pig cone-enriched retina, Gene Therapy, vol. 18(7):637-45, Mar. 2011.

Nathans J. & D. S. Hogness, Isolation and nucleotide sequence of the gene encoding human rhodopsin, PNAS, vol. 81:4851-5, Aug. 1984.

Nicoud M. et al., Development of photoreceptor-specific promoters and their utility to investigate EIAV lentiviral vector mediated gene transfer to photoreceptors, Journal of Gene Medicine, vol. 9(12):1015-23, Dec. 2007.

Ogueta S. B. et al., The human cGMP-PDE beta-subunit promoter region directs expression of the gene to mouse photoreceptors, Invest Ophthalmology & Visual Science, vol. 41(13):4059-63, Dec. 2000.

Petrosyan H. A. et al., Transduction efficiency of neurons and glial cells by AAV-1, -5, -9, -rh10 and -hu11 serotypes in rat spinal cord following contusion injury, Gene Therapy, vol. 21(12):991-1000, Dec. 2014.

Reuber, B. E., et al., GenBank AAB87880.1, 1997.

Reuber, B. E et al., Mutations in PEX1 are the most common cause of peroxisome biogenesis disorders, Nature Genetics, vol. 17(4):445-448, Dec. 1997.

(56) References Cited

OTHER PUBLICATIONS

Royo, N. C. et al., Specific AAV serotypes stably transduce primary hippocampal and cortical cultures with high efficiency and low toxicity, Brain Research, vol. 1190:15-22, Jan. 2008.

Shu X. et al., Functional Characterization of the Human RPGR Proximal Promoter, Invest Ophthalmology & Visual Science, vol. 53(7):3951-3958, Jun. 2012.

Sochor M. A. et al., An Autogenously Regulated Expression System for Gene Therapeutic Ocular Applications, Scientific Reports, vol. 5:17105, Nov. 2015.

Steinberg S. J. et al., Peroxisome Biogenesis Disorders, Zellweger Syndrome Spectrum. In: Pagon RA, et al., editors. GeneReviews. Seattle (WA), (original submission 2003, updated 2017).

Su, X., et al., In vitro and in vivo mRNA delivery using lipid-enveloped pH-responsive polymer nanoparticles. Molecular Pharmaceutics, vol. 8(3):774-787, Mar. 2011.

Sun X. et al., Gene Therapy with a Promoter Targeting Both Rods and Cones Rescues Retinal Degeneration Caused by AIPL1 Mutations, Gene Therapy, vol. 17(1):117-131, Aug. 2010.

Thompson, J. D. et al., A comprehensive comparison of multiple sequence alignment programs, Nucleic Acids Research, vol. 27(13):2682-2690, Jul. 1999.

Vandenberghe L, H. et al., Dosage Thresholds for AAV2 and AAV8 Photoreceptor Gene Therapy in Monkey, Science Translational Medicine, vol. 3(88):88ra54, Jun. 2011.

Zhang H. et al., Adenovirus-adeno-associated virus hybrid for large-scale recombinant adeno-associated virus production, Human Gene Therapy, vol. 20(9):922-929, Sep. 2009.

International Search Report and Written Opinion on International Patent Application No. PCT/CA2018/050642, dated Aug. 24, 2018.

\* cited by examiner

Plasmid: pAAV.CMV.hPEX1 (SEQ ID NO : 13)
AAV Expression Cassette: 1253-6235
5' ITR: 1253-1382
CMV Enhancer: 1433-1736
CMV Promoter: 1737-1940
Kozak: 1958-1966
PEX1: 1967-5818
bGH Poly(A): 5849-6056
3' ITR: 6106-6235

AAV8.hPEX1-HA

AAV8.eGFP

FIG. 14A  FIG. 14B  FIG. 14C
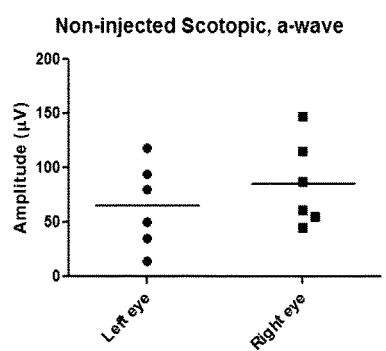
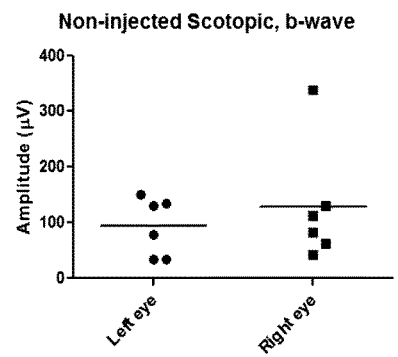
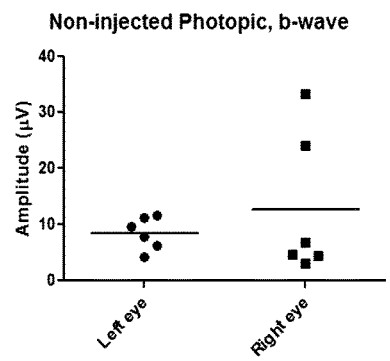
FIG. 15
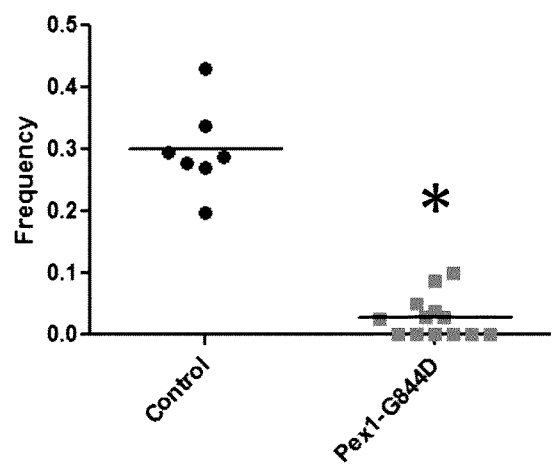

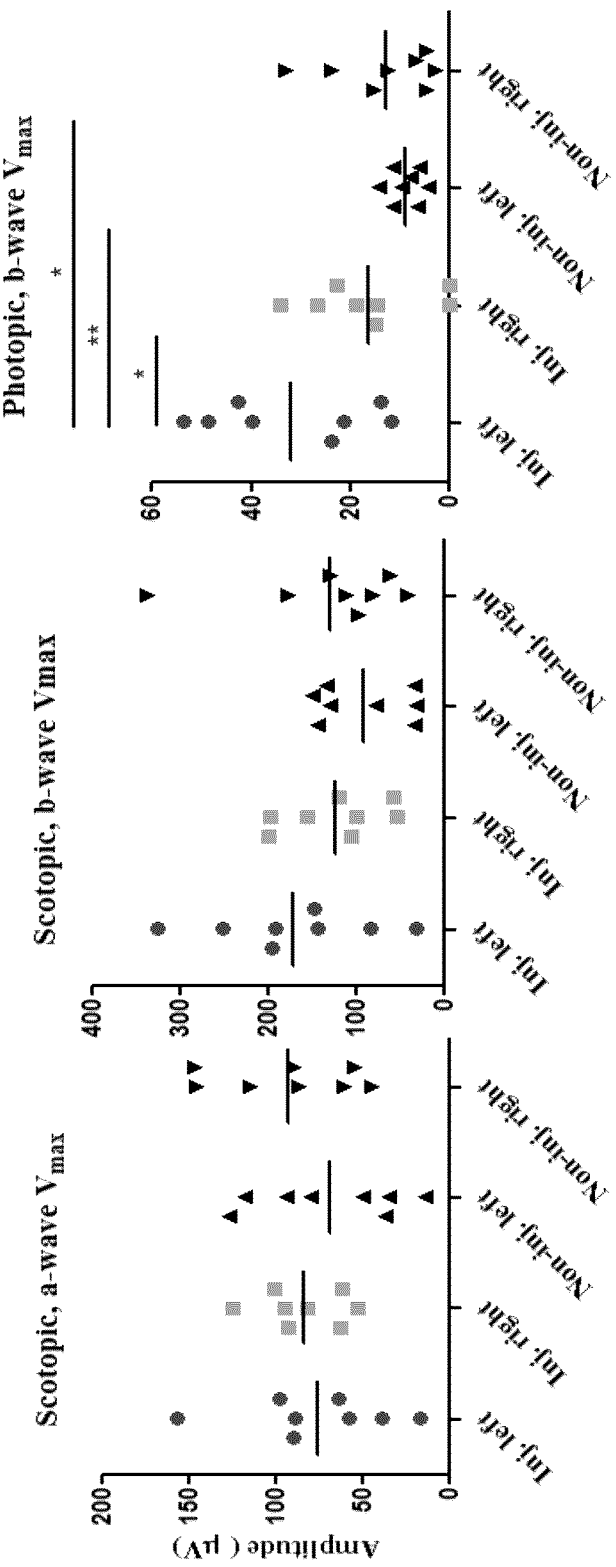

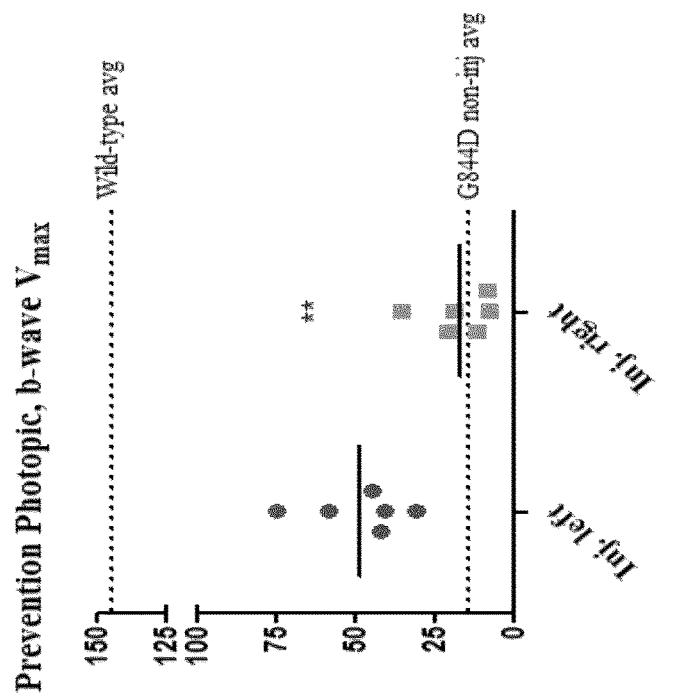
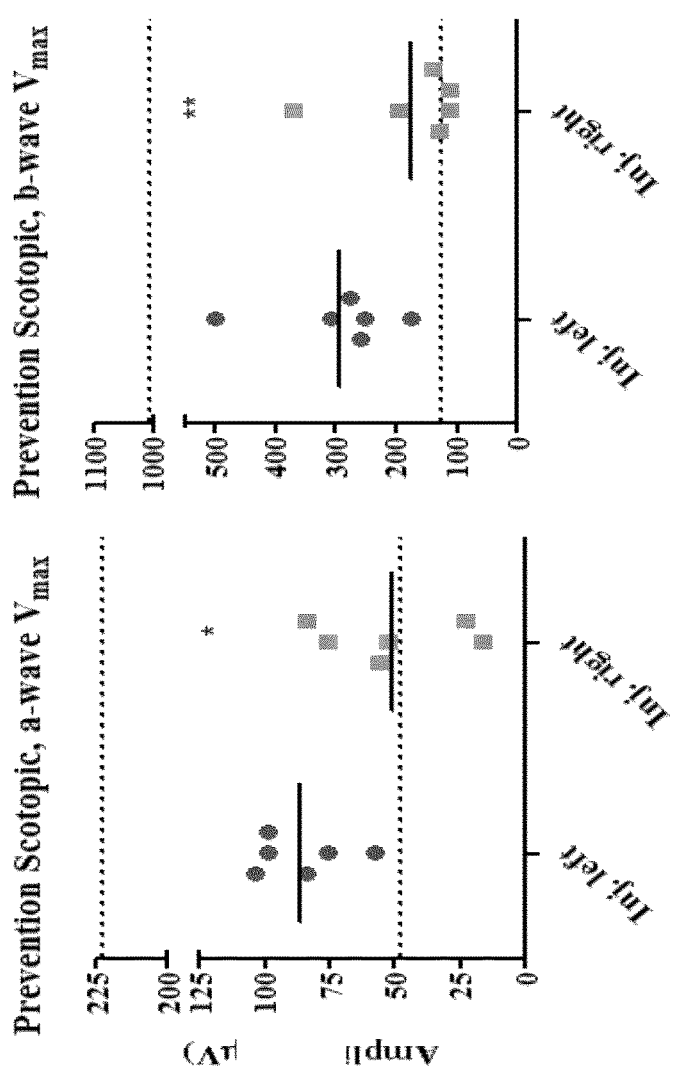
FIG. 19A  FIG. 19B  FIG. 19C

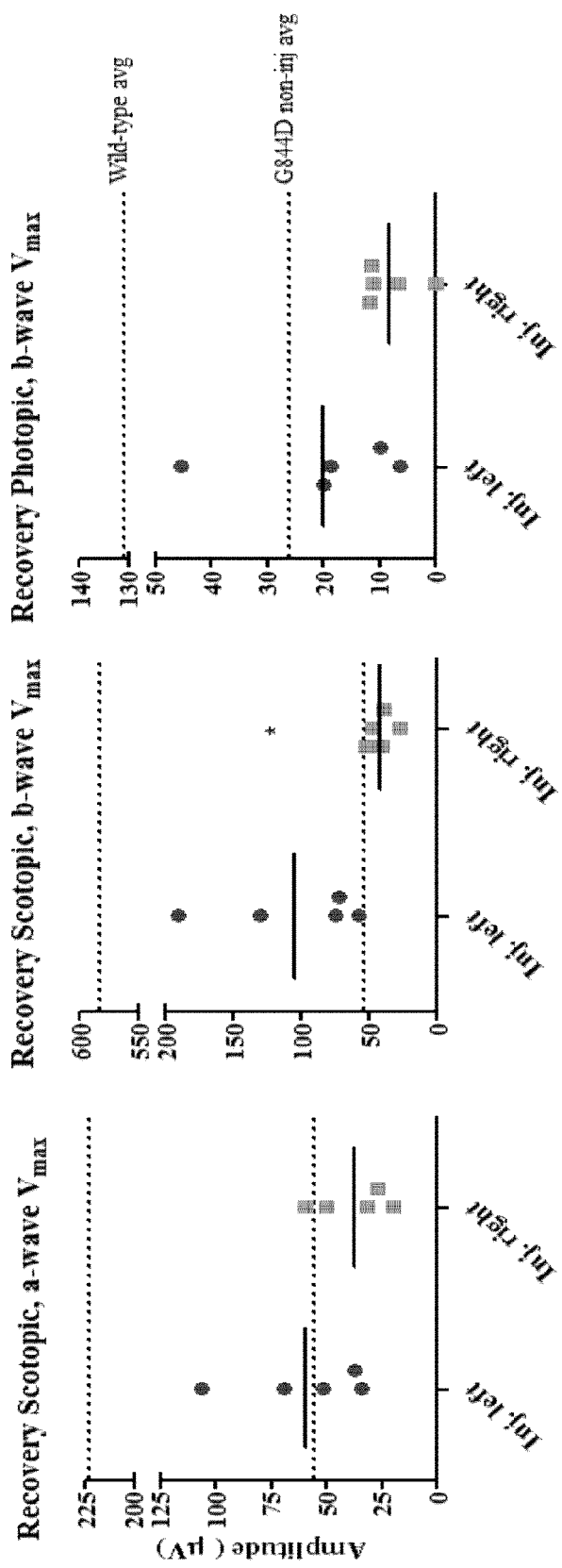

FIG. 24A

CLUSTAL O(1.2.4) multiple sequence alignment

```
Codon_optimized_hPEX1              atgtgggaagcgacagactgcgccggagctgcgggagctggaggagcagccgtcaccgtgcg    60
CDS_of_transcript_variant_2        atgtggggcagcgagatcgcctgcaggtgctgtggggaagccggcgagtgactgtgtgcc    60
CDS_of_transcript_variant_1        atgtgggcagcgagatcgcctgcaggtgctgtggggagccggcgagtgactgtgtgcc    60
CDS_of_transcript_variant_3        ------------------------------------------------------------     0
CDS_of_transcript_variant_X2       ------------------------------------------------------------     0

Codon_optimized_hPEX1              ttcactaacgcgcgggactgctttctccatctgccgcggaggctggtcgcccagctgcac   120
CDS_of_transcript_variant_2        tcaccaacgctcgcgactgcttcttcctccacctgccgccggcgtctcgtggccagctgcat  120
CDS_of_transcript_variant_1        tcaccaacgctcgcgactgcttcttcctccacctgccgccggcgtctcgtggccagctgcat  120
CDS_of_transcript_variant_3        ------------------------------------------------------------     0
CDS_of_transcript_variant_X2       ------------------------------------------------------------     0

Codon_optimized_hPEX1              ctcctgcagaaccaggccatcgagttggtgtggtcccaccaacggcctttttgagctgg   180
CDS_of_transcript_variant_2        ctgctgcagaatcaagctatagaagctgaagtgtctggagtctggaccagcctgcattcttgagctgg   180
CDS_of_transcript_variant_1        ctgctgcagaatcaagctatagaagctgaagtgtctggagtctggaccagcctgcattcttgagctgg   180
CDS_of_transcript_variant_3        ------------------------------------------------------------     0
CDS_of_transcript_variant_X2       ------------------------------------------------------------     0

Codon_optimized_hPEX1              gtcgagggaaggcactttcggaccagggagaaaatgtggcggagatcaaccgccaagtc   240
CDS_of_transcript_variant_2        gtggaaggcaggcaggcattttagtgatcaagtgatgaaaatgtggctgaaattaacagacaagtt   240
CDS_of_transcript_variant_1        gtggaaggcaggcaggcattttagtgatcaagtgatgaaaatgtggctgaaattaacagacaagtt   240
CDS_of_transcript_variant_3        ------------------------------------------------------------     0
CDS_of_transcript_variant_X2       ------------------------------------------------------------     0
```

FIG. 24B

```
codon_optimized_hPEX1       ggccagaagctgggactggtccaacggcggacaggtgttcctcaagccgtgcagccacgtg   300
CDS_of_transcript_variant_2 ggtcaaaaaactggactctcaaatggggacaggtattctcaagccatgttcccatgtg     300
CDS_of_transcript_variant_1 ggtcaaaaaactggactctcaaatggggacaggtattctcaagccatgttcccatgtg     300
CDS_of_transcript_variant_3 ggtcaaaaaactggactctcaaatggggacaggtattctcaagccatgttcccatgtg     300
CDS_of_transcript_variant_X2 ---------------------------------------------------------        0 codon_optimized_hPEX1       gtgtcctgccaacaggtggaagtggagccgctccgccgacgactggagagatcctcgaa    360
CDS_of_transcript_variant_2 gtatcttgtcaacaagttgagtggaacaagttgaacccctctcagcagatgatgggagatactggag  360
CDS_of_transcript_variant_1 gtatcttgtcaacaagttgagtggaacaagttgaacccctctcagcagatgatgggagatactggag  360
CDS_of_transcript_variant_3 gtatcttgtcaacaagttgagtggaacaagttgaacccctctcagcagatgatgggagatactggag  360
CDS_of_transcript_variant_X2 ---------------------------------------------------------        0 codon_optimized_hPEX1       ttgcatgccgtgagcctcgaacagcatctgtttgaccagacctatatcttcatccagattgtggcctc   420
CDS_of_transcript_variant_2 ctgcatgctgttccccttgaacaacatcttctagatcaaattcaaattcaaattccaaaa  420
CDS_of_transcript_variant_1 ctgcatgctgttccccttgaacaacatcttctagatcaaattcaaattcaaattccaaaa  420
CDS_of_transcript_variant_3 ctgcatgctgttccccttgaacaacatcttctagatcaaattcaaattcaaattccaaaa  420
CDS_of_transcript_variant_X2 ---------------------------------------------------------        0 codon_optimized_hPEX1       gccatattcccgtgtgggtcgatcagcagacctatatcttcatccagattgtggcctc    480
CDS_of_transcript_variant_2 gccattttcctgtgtttgggttgatcaacaaacgtacatatttatccaaattgttgcacta  480
CDS_of_transcript_variant_1 gccattttcctgtgtttgggttgatcaacaaacgtacatatttatccaaattgttgcacta  480
CDS_of_transcript_variant_3 gccattttcctgtgtttgggttgatcaacaaacgtacatatttatccaaattgttgcacta  480
CDS_of_transcript_variant_X2 ---------------------------------------------------------        0 codon_optimized_hPEX1       atcccggccgctcatacggacggctggaaactgacaccaagctgctgattcaacctaag   540
CDS_of_transcript_variant_2 ataccagctgcctcttatggaaggctggaaactgacaccaaaactccttattcagccaaag  540
CDS_of_transcript_variant_1 ataccagctgcctcttatggaaggctggaaactgacaccaaaactccttattcagccaaag  540
CDS_of_transcript_variant_3 ataccagctgcctcttatggaaggctggaaactgacaccaaaactccttattcagccaaag  540
CDS_of_transcript_variant_X2 ---------------------------------------------------------        0
```

FIG. 24C

```
codon_optimized_hPEX1           accggagggccaagaaaacacttccaaggccgacgctgagtacaagaagctccac      600
CDS_of_transcript_variant_2     acacgccgagccaagaaagagaaccagaatacattttcaaaagctgatgctgaat      600
CDS_of_transcript_variant_1     acacgccgagccaagaaagagaaccagaatacattttcaaaagctgatgctgaat      600
CDS_of_transcript_variant_3     ---------------------------------------------------           0
CDS_of_transcript_variant_X2    ---------------------------------------------------           0 codon_optimized_hPEX1           tcctacggacggaccagaagggatgatgaaggagctgcaaaccaagcagctccagagc    660
CDS_of_transcript_variant_2     agttatgaagagaccagagagaaggaatgatgaaagaatgatgaaagaactcaaacc    660
CDS_of_transcript_variant_1     agttatgaagagaccagagagaaggaatgatgaaagaatgatgaaagaactcaaacc    660
CDS_of_transcript_variant_3     ---------------------------atgatgaaagaactcaaacc               36
CDS_of_transcript_variant_X2    ---------------------------------------------------           0 codon_optimized_hPEX1           acacccgtgggatcaccgagtcactcactcactcactgtgggaatctcctaatctaat    720
CDS_of_transcript_variant_2     aatactgtgggaatctcactcactcactgtgggaatctaatctaatgaaaacgagtca   720
CDS_of_transcript_variant_1     aatactgtgggaatctcactcactcactgtgggaatctaatctaatgaaaacgagtca   720
CDS_of_transcript_variant_3     aagcaacttcaagttcagtca                                         96
CDS_of_transcript_variant_X2    ---------------------------------------------------           0 codon_optimized_hPEX1           tccgtggccagcctgtggactatgatcgttccatttctcgttccaatctgagaagaag    780
CDS_of_transcript_variant_2     tcagtagcaagtttatggactgactgactggaagaagcattttttccttcaatctgag   780
CDS_of_transcript_variant_1     tcagtagcaagtttatggactgactgactggaagaagcattttttccttcaatctgag   780
CDS_of_transcript_variant_3     tcagtagcaagtttaactggaagaagcattttttccttcaatctgagaagaaa       156
CDS_of_transcript_variant_X2    ---------------------------------------------------           0 codon_optimized_hPEX1           caggaaactagctggggctgactgactgactgaagcatgcagtcaaagtg            840
CDS_of_transcript_variant_2     caagagacatcttggggtttaactgaactgaactgaactgatgcattcaatcagt      840
CDS_of_transcript_variant_1     caagagacatcttggggtttaactgaactgaactgaactgatgcattcaatcagt      840
CDS_of_transcript_variant_3     caagagacatcttggggtttaactgaactgaactgaactgatgcattcaatcagt      216
CDS_of_transcript_variant_X2    ---------------------------------------------------           0
```

FIG. 24D

```
codon_optimized_hPEX1        gtgcctctggataacatcttttcgtgtgcaagtccaaacgccctcaatctacaacgcg  900
CDS_of_transcript_variant_2  gttcctctagacaatatattttcagagtatgcaagtccaaatctacaactctatataacgcg  900
CDS_of_transcript_variant_1  gttcctctagacaatatattttcagagtatgcaaatctcaaatctctagtatatataacgcg  900
CDS_of_transcript_variant_3  gttcctctagacaatatattttcagagtatgcaaatctcaaatctctagtatatataacgcg  276
CDS_of_transcript_variant_X2 ------------------------------------------------------------    0 codon_optimized_hPEX1        tccgctacctccgtgtttcataagcactgtgccatccacgtgttcccatgggatccaggaa  960
CDS_of_transcript_variant_2  tcagcaacctctgtgttttttcataaacactgtgccattcatgtattccatgggaccaggaa  960
CDS_of_transcript_variant_1  tcagcaacctctgtgttttttcataaacactgtgccattcatgtattccatgggaccaggaa  960
CDS_of_transcript_variant_3  tcagcaacctctgtgttttttcataaacactgtgccattcatgtattccatgggaccaggaa  336
CDS_of_transcript_variant_X2 ------------------------------------------------------------    0 codon_optimized_hPEX1        tacttcgatgtcgaacttccttcaccgtgacttacggaagcttgtcaagctcctcagc    1020
CDS_of_transcript_variant_2  tattttgatgtagtgagagcccagctttactgtgactatatgacattgaaagctagtactttct 1020
CDS_of_transcript_variant_1  tattttgatgtagtgagagcccagctttactgtgactatatgacattgaaagctagtactttct 1020
CDS_of_transcript_variant_3  tattttgatgtagtgagagcccagctttactgtgactatatgacattgaaagctagtactttct 396
CDS_of_transcript_variant_X2 ------------------------------------------------------------    0 codon_optimized_hPEX1        cccaaagcagcaacagcagccaatcgaaaactaagcagaacgtgcttttcccggaggaagagcaa 1080
CDS_of_transcript_variant_2  ccaaagcaacagcagccaaatgtaaaacaaacaaaaatgtgttatcacctgaaaagaagcag  1080
CDS_of_transcript_variant_1  ccaaagcaacagcagccaaatgtaaaacaaacaaaaatgtgttatcacctgaaaagaagcag  1080
CDS_of_transcript_variant_3  ccaaagcaacagcagccaaatgtaaaacaaacaaaaatgtgttatcacctgaaaagaagcag   456
CDS_of_transcript_variant_X2 ------------------------------------------------------------    0 codon_optimized_hPEX1        atgtcagaccactcgaccagagaaatcagatcggatcataacgaagaggacgagaag    1140
CDS_of_transcript_variant_2  atgtcagagccactagatcaaaaaaaaattagtcagatcagatcataatgaagaagagaag  1140
CDS_of_transcript_variant_1  atgtcagagccactagatcaaaaaaaaattagtcagatcagatcataatgaagaagagaag  1140
CDS_of_transcript_variant_3  atgtcagagccactagatcaaaaaaaaattagtcagatcagatcataatgaagaagagaag   516
CDS_of_transcript_variant_X2 ------------------------------------------------------------    0
```

FIG. 24E

```
codon_optimized_hPEX1         gcctgcgtcctcaggtggtctgaacggcctgaagagctggagaagctgaacaacgcgattaagtac    1200
CDS_of_transcript_variant_2   gcctgtgtgctacaagtagtctggaagacttgaatgacttgaagaattgaacaatgccatcaaatat   1200
CDS_of_transcript_variant_1   gcctgtgtgctacaagtagtctggaagacttgaatgacttgaagaattgaacaatgccatcaaatat   1200
CDS_of_transcript_variant_3   gcctgtgtgctacaagtagtctggaagacttgaatgacttgaagaattgaacaatgccatcaaatat    576
CDS_of_transcript_variant_X2                                                                             0 codon_optimized_hPEX1         accaagaacgtcgaggtcctccacctgggaaagtgtggattccggatgatctgaggaaa           1260
CDS_of_transcript_variant_2   accaaaaaatgtagaagttctccatctcttgggaaagtctggattccagatgacctgaggaag      1260
CDS_of_transcript_variant_1   accaaaaaatgtagaagttctccatctcttgggaaagtctggattccagatgacctgaggaag      1260
CDS_of_transcript_variant_3   accaaaaaatgtagaagttctccatctcttgggaaagtctggattccagatgacctgaggaag       636
CDS_of_transcript_variant_X2                                                                             0 codon_optimized_hPEX1         cgcctcaacatcgaaatgcacgctgtgtgcggattaccccgtcgaggtcacccccaaag          1320
CDS_of_transcript_variant_2   agactaaaatctctaaagatgcatgcctagtccgtcaggatcagtggaattccagttaccccctaaa  1320
CDS_of_transcript_variant_1   agactaaaatctctaaagatgcatgcctagtccgtcaggatcagtggaattccagttaccccctaaa  1320
CDS_of_transcript_variant_3   agactaaaatctctaaagatgcatgcctagtccgtcaggatcagtggaattccagttaccccctaaa   696
CDS_of_transcript_variant_X2                                                                             0 codon_optimized_hPEX1         atcccctcgctccttgaagctgcagccgcgagaaaaacttgcccaaggacatttctgaagag       1380
CDS_of_transcript_variant_2   attccaagatctctaaagttacaaccctagagagagaaattacctaaagacataagtgaagaa      1380
CDS_of_transcript_variant_1   attccaagatctctaaagttacaaccctagagagagaaattacctaaagacataagtgaagaa      1380
CDS_of_transcript_variant_3   attccaagatctctaaagttacaaccctagagagagaaattacctaaagacataagtgaagaa       756
CDS_of_transcript_variant_X2                                                                             0 codon_optimized_hPEX1         gatatcaagactgtgttctactcctggctgcaacagagcactaccaccatgctccctctg         1440
CDS_of_transcript_variant_2   gacataaaaactgtattttattcatggctacagcagtctctaccaccatgctcctttg           1440
CDS_of_transcript_variant_1   gacataaaaactgtattttattcatggctacagcagtctctaccaccatgctcctttg           1440
CDS_of_transcript_variant_3   gacataaaaactgtattttattcatggctacagcagtctctaccaccatgctcctttg            816
CDS_of_transcript_variant_X2                                                                             0
```

FIG. 24F

```
codon_optimized_hPEX1        gtcatttcggaggaagaattcatcaaactgaaaccaaggacggactgaaagaattctcc      1500
CDs_of_transcript_variant_3  gtaatatcagagaggaagaagaatttattaagctgaaactgaaagatggactgaagaatttct  1500
CDs_of_transcript_variant_1  gtaatatcagagaggaagaagaatttattaagctgaaactgaaagatggactgaagaatttct  1500
CDs_of_transcript_variant_3  gtaatatcagagaggaagaagaatttattaagctgaaactgaaagatggactgaagaatttct  876
CDs_of_transcript_variant_X2 ---------------------------------------------------------------  0 codon_optimized_hPEX1        ctgtccatcgtgcactcctgggaaaagagagaagaacaagatatcttcctgtctgtcccc    1560
CDs_of_transcript_variant_2  ctgagtatagttcattcttcttgggaaaagaaagaaaaataaaatattttctgttgagtccc   1560
CDs_of_transcript_variant_1  ctgagtatagttcattcttcttgggaaaagaaagaaaaataaaatattttctgttgagtccc   1560
CDs_of_transcript_variant_3  ctgagtagttcattcttcttgggaaaagaaagaaaaataaaatattttctgttgagtccc    936
CDs_of_transcript_variant_X2 ---------------------------------------------------------------  0 codon_optimized_hPEX1        aatctgctgcaaagagaccacgatccaggtgctgctgaccccatgtgaaggaggaaaac    1620
CDs_of_transcript_variant_2  aatttgctgcagaagactacaataacaagtcctctagatcctagatcctatgtaaaagaaac   1620
CDs_of_transcript_variant_1  aatttgctgcagaagactacaataacaagtcctctagatcctagatcctatgtaaaagaaac   1620
CDs_of_transcript_variant_3  aatttgctgcagaagactacaataacaagtcctctagatcctagatcctatgtaaaagaaac   996
CDs_of_transcript_variant_X2 ---------------------------------------------------------------  0 codon_optimized_hPEX1        tcagaagagatgactcatcctgcgtccgttcctaagctgagtcactgggaggcgtgaaac   1680
CDs_of_transcript_variant_2  agtgaggaaattgacttgacttattcttcttcttttaaaagctgagctcttcggagagtgaat  1680
CDs_of_transcript_variant_1  agtgaggaaattgacttgacttattcttcttcttttaaaagctgagctcttcggagagtgaat  1680
CDs_of_transcript_variant_3  agtgaggaaattgacttgacttattcttcttcttttaaaagctgagctcttcggagagtgaat  1056
CDs_of_transcript_variant_X2 ---------------------------------------------------------------  0 codon_optimized_hPEX1        tcccttggcgtgtcctcgtggagcacatcactcactgctggccggcctctgagc        1740
CDs_of_transcript_variant_2  tccttaggcgtatcctcctcctggagcacatcactcacagcctcctgggacgcccttgtct    1740
CDs_of_transcript_variant_1  tccttaggcgtatcctcctcctggagcacatcactcacagcctcctgggacgcccttgtct    1740
CDs_of_transcript_variant_3  tccttaggcgtatcctcctcctggagcacatcactcacagcctcctgggacgcccttgtct    1116
CDs_of_transcript_variant_X2 ---------------------------------------------------------------  0
```

FIG. 24G

```
codon_optimized_hPEX1      agacagcttatgagcttggtcgccggactcagaaacggtgccctcctgctcaccggcggc 1800
CDS_of_transcript_variant_2 cggcagctgatgtgtctcttgttgttgcaggactgttagaatggagctctcttttactcacaggagga 1800
CDS_of_transcript_variant_1 cggcagctgatgtgtctcttgttgttgcaggacttaggactgttaggaatggagctcttttactcacaggagga 1800
CDS_of_transcript_variant_3 cggcagctgatgtgtctcttgttgttgcaggacttaggacttaggaatggagctcttttactcacaggagga 1176
CDS_of_transcript_variant_X2 -----atgtctctttgttgcaggacttaggaatggagctctttttactcacaggagga 51
                                     *   **   *  ***   ***** codon_optimized_hPEX1      aagggatcggaaagtccacctcgtaaggccattgcaaagaggcattgataagctg 1860
CDS_of_transcript_variant_2 aagggaagtgaaaatcaacttagccaaagcaaatctgtaaagaagcattgtgacaaactg 1860
CDS_of_transcript_variant_1 aagggaagtgaaaatcaacttagccaaagcaaatctgtaaagaagcattgtgacaaactg 1860
CDS_of_transcript_variant_3 aagggaagtgaaaatcaacttagccaaagcaaatctgtaaagaagcattgtgacaaactg 1236
CDS_of_transcript_variant_X2 aagggaagtgaaaatcaacttagccaaagcaaatctgtaaagaagcattgtgacaaactg 111
                             ******   *   ** *  ****  *  **  **  * **** codon_optimized_hPEX1      gactgccatgtgagcgggtgactgtaaggccctcgcggaaagcgattgaaaatatt 1920
CDS_of_transcript_variant_2 gatgcccatgtggagagagagttgactgactgtaaagcttaaagcttacga------------ 1899
CDS_of_transcript_variant_1 gatgcccatgtggagagagagttgactgactgtaaagcttaaagcttacgaaaaacata 1920
CDS_of_transcript_variant_3 gatgcccatgtggagagagagttgactgactgtaaagcttaaagcttacgaaaaacata 1296
CDS_of_transcript_variant_X2 gatgcccatgtggagagagagttgactgactgtaaagcttaaagcttacgaaaaacata 171
                              *   *     * * ***  * ** codon_optimized_hPEX1      caaaagactctcgaagtcgcctttccgaagccgtctcggatcgagccctcggtcgtcctg 1980
CDS_of_transcript_variant_2 ------caaaaaacccctagaggtggcttgcttttctcagaggcagtgtggatcagcagtctgttgtcctg 1899
CDS_of_transcript_variant_1 caaaaaacccctagaggtggcttgcttttctcagaggcagtgtggatcagcagtctgttgtcctg 1980
CDS_of_transcript_variant_3 caaaaaacccctagaggtggcttgcttttctcagaggcagtgtggatcagcatctgttgtcctg 1356
CDS_of_transcript_variant_X2 caaaaaacccctagaggtggcttgcttttctcagaggcagtgtggatcagcatctgttgtcctg 231
                                           *           * **  *      *   *** codon_optimized_hPEX1      ctcgacgatctggaccttgacctcatcgtgggctgcgccgtgccggagcatgaacactcccct 2040
CDS_of_transcript_variant_2 ctggatgaccttgacctgacctcattgctgactgctggactggtccccggaacatgagcacagtcct 1899
CDS_of_transcript_variant_1 ctggatgaccttgacctgacctcattgctgactgctggactggtccccggaacatgagcacagtcct 2040
CDS_of_transcript_variant_3 ctggatgaccttgacctgacctcattgctgactgctggactgctccccggaacatgagcacagtcct 1416
CDS_of_transcript_variant_X2 ctggatgaccttgacctgacctcattgctgactgctggactgctccccggaacatgagcacagtcct 291
```

FIG. 24H

```
Codon_optimized_hPEX1           gacgcggtccagtcgcaacggcgctcgccacggccctgaacgatatgattaaggaattcatc    2100
CDS_of_transcript_variant_2     ------------------------------gctttgaatgatatgatgataaagagtttatc    1929
CDS_of_transcript_variant_1     gatgcggtgcagagccagccggcttgctcatgctttgaatgatatgatgataaagagtttatc    2100
CDS_of_transcript_variant_3     gatgcggtgcagagccagccggcttgctcatgctttgaatgatatgatgataaagagtttatc    2160
CDS_of_transcript_variant_X2    gatgcggtgcagagccagccggcttgctcatgctttgaatgatatgatgataaagagtttatc    1476
                                         **  **** ***********  **  ** *** ***

Codon_optimized_hPEX1           tcaatgggatcactggtggccctgatcgcgacttcccaagccagccagtccctgcaccct    2160
CDS_of_transcript_variant_2     tccatgggaagtttggttgcactgattgccacaagtcagtctcagcaatctctacatcct    1989
CDS_of_transcript_variant_1     tccatgggaagtttggttgcactgattgccacaagtcagtctcagcaatctctacatcct    2160
CDS_of_transcript_variant_3     tccatgggaagtttggttgcactgattgccacaagtcagtctcagcaatctctacatcct    1536
CDS_of_transcript_variant_X2    tccatgggaagtttggttgcactgattgccacaagtcagtctcagcaatctctacatcct    411
                                ** **  **  ******  ** *****  **  ** *** **

Codon_optimized_hPEX1           ctgctggtgtcggcccaggggcgtgcacattttcagtgtgtgcaacacatccagccgccc    2220
CDS_of_transcript_variant_2     ttacttgttctgctcaaggagttcacatatttcagtgcgtccaacacattcagcctcct    2049
CDS_of_transcript_variant_1     ttacttgttctgctcaaggagttcacatatttcagtgcgtccaacacattcagcctcct    2220
CDS_of_transcript_variant_3     ttacttgttctgctcaaggagttcacatatttcagtgcgtccaacacattcagcctcct    1596
CDS_of_transcript_variant_X2    ttacttgttctgctcaaggagttcacatatttcagtgcgtccaacacattcagcctcct    472
                                *  ** ** ** ******    ** ***** *******  **  ****** ***  **

Codon_optimized_hPEX1           aaccaggagcagcggtgtgcgaaatcctgtgcaacgtgattaaggaacaagtggactgcgat    2280
CDS_of_transcript_variant_2     aatcaggaacaaagatgtgaaaattctgtgtaatgtaatctgtgaatctgtgtaatgtaatt    2109
CDS_of_transcript_variant_1     aatcaggaacaaagatgtgaaaattctgtgtaatgtaatctgtgaatctgtgtaatgtaatt    2280
CDS_of_transcript_variant_3     aatcaggaacaaagatgtgaaaattctgtgtaatgtaatctgtgaatctgtgtaatgtaatt    1656
CDS_of_transcript_variant_X2    aatcaggaacaaagatgtgaaaattctgtgtaatgtaatctgtgaatctgtgtaatgtaatt    531
                                ** *****  **  * ** ******* **  **  *** ** ** ****  *

Codon_optimized_hPEX1           atcaacaagttaccgacttcaccgatctcaacatgtggctaaggagaactggggcttcgtg    2340
CDS_of_transcript_variant_2     ataaacaagttcaccgatcttgacctgcagcatgtagctaaagaaactggcggtttgtg    2169
CDS_of_transcript_variant_1     ataaacaagttcaccgatcttgacctgcagcatgtagctaaagaaactggcggtttgtg    2340
CDS_of_transcript_variant_3     ataaacaagttcaccgatcttgacctgcagcatgtagctaaagaaactggcggtttgtg    1716
CDS_of_transcript_variant_X2    ataaacaagttcaccgatcttgacctgcagcatgtagctaaagaaactggcggtttgtg    591
                                ** ******* ******  **  ** *****   ***  **   ***** **
```

FIG. 24I

```
codon_optimized_hPEX1           gctcgggacttcacagtgttgtggaccggtggcaattcactccagactgtcccgccagagc   2400
CDS_of_transcript_variant_2     gctagagatttttacagtacttgtgtgatcggatcgagccagccatacatctcgactctcgtcgtcagagt   2229
CDS_of_transcript_variant_1     gctagagatttttacagtacttgtgtgatcggatcgagccagccatacatctcgactctcgtcgtcagagt   2400
CDS_of_transcript_variant_3     gctagagatttttacagtacttgtgtgatcggatcgagccagccatacatctcgactctcgtcgtcagagt   1776
CDS_of_transcript_variant_X2    gctagagatttttacagtacttgtgtgatcggatcgagccagccatacatctcgactctcgtcgtcagagt   651
                                ***    ****   *   *  *   **     **** codon_optimized_hPEX1           atttccacccgcgaaaaactggtcctgaccacctcgacttccagaaggcctcagaggc   2460
CDS_of_transcript_variant_2     atatccaccagagagaaaaaattagttttaacaacattggacttccaaaaggctctccgcgga   2289
CDS_of_transcript_variant_1     atatccaccagagagaaaaaattagttttaacaacattggacttccaaaaggctctccgcgga   2460
CDS_of_transcript_variant_3     atatccaccagagagaaaaaattagttttaacaacattggacttccaaaaggctctccgcgga   1836
CDS_of_transcript_variant_X2    atatccaccagagagaaaaaattagttttaacaacattggacttccaaaaggctctccgcgga   711
                                 *       *  *     ** *    *  *** codon_optimized_hPEX1           ttccttcctgcgagcctcagatccgtcaacctcacaagccgcggaccttggctggac   2520
CDS_of_transcript_variant_2     tttcttcctgcgtcgtctttgcgaagtgtcaacctgcataaacctagagaccctagttggttgggac   2349
CDS_of_transcript_variant_1     tttcttcctgcgtcgtctttgcgaagtgtcaacctgcataaacctagagaccctagttggttgggac   2520
CDS_of_transcript_variant_3     tttcttcctgcgtcgtctttgcgaagtgtcaacctgcataaacctagagaccctagttggttgggac   1896
CDS_of_transcript_variant_X2    tttcttcctgcgtcgtctttgcgaagtgtcaacctgcataaacctagagaccctagttggttgggac   771
                                 **      * *  ****  *  *  * * * *** * codon_optimized_hPEX1           aagatcggtgggctccacgaggtgcggcaggttgaagttaggcagcaccattcagctgcctgca   2580
CDS_of_transcript_variant_2     aagattgttggttgggttacatgaagcatgcagcagtactgaatactactactgtactactgcc   2409
CDS_of_transcript_variant_1     aagattgttggttgggttacatgaagcatgcagcagtactgaatactactactgtactactgcc   2580
CDS_of_transcript_variant_3     aagattgttggttgggttacatgaagcatgcagcagtactgaatactactactgtactactgcc   1956
CDS_of_transcript_variant_X2    aagattgttggttgggttacatgaagcatgcagcagtactgaatactactactgtactactgcc   831
                                **** *   * *  *  *  *    *  * * *** codon_optimized_hPEX1           aagtacccgagctgttcgccaacttgccgattcgccagcgcacgggaatcctgctctac   2640
CDS_of_transcript_variant_2     aagtatccagaattattttgcaaactttgcaatacgacaaagaacaggaacaggaatactgttgtat   2469
CDS_of_transcript_variant_1     aagtatccagaattattttgcaaactttgcaatacgacaaagaacaggaacaggaatactgttgtat   2640
CDS_of_transcript_variant_3     aagtatccagaattattttgcaaactttgcaatacgacaaagaacaggaacaggaatactgttgtat   2016
CDS_of_transcript_variant_X2    aagtatccagaattattttgcaaactttgcaatacgacaaagaacaggaacaggaatactgttgtat   891
                                ***** ** *     **  ** **   ***   **   *  **   **  ***** *
```

FIG. 24J

```
codon_optimized_hPEX1          ggtccccgggcaccggaaagaccctgctggccggtgtgatcgcccggggaatcgaggatg    2700
CDS_of_transcript_variant_2    ggtccgcgcctggaacaggaacaggaaaaaaccttactagctgggtaattgcacgagagtagaatg  2529
CDS_of_transcript_variant_1    ggtccgcgcctggaacaggaacaggaaaaaaccttactagctgggtaattgcacgagagagtagaatg  2700
CDS_of_transcript_variant_3    ggtccgcgcctggaacaggaacaggaaaaaaccttactagctgggtaattgcacgagagagtagaatg  2076
CDS_of_transcript_variant_X2   ggtccgcgcctggaacaggaacaggaaaaaaccttactagctgggtaattgcacgagagagtagaatg  951
                                 *  **** **        *** *  * codon_optimized_hPEX1          aacttcatctccgtgaaggaccccgaactcctgtccaagtacatcggtgcctccgaacag    2760
CDS_of_transcript_variant_2    aattttataagtgtcaaggggccagagttactcagcagcaaatacacattggagcaagtgaacaa   2589
CDS_of_transcript_variant_1    aattttataagtgtcaaggggccagagttactcagcagcaaatacacattggagcaagtgaacaa   2760
CDS_of_transcript_variant_3    aattttataagtgtcaaggggccagagttactcagcagcaaatacacattggagcaagtgaacaa   2136
CDS_of_transcript_variant_X2   aattttataagtgtcaaggggccagagttactcagcagcaaatacacattggagcaagtgaacaa   1011
                                  *               *      **     *** codon_optimized_hPEX1          gccgtgcgcgatatattcattaggcccaggccgcgaagccctgcattctgttcttcgac    2820
CDS_of_transcript_variant_2    gctgttcgggatatatttttattagagagcgcaggcagctgcaaagccctgcattcttcttttgat  2649
CDS_of_transcript_variant_1    gctgttcgggatatatttttattagagagcgcaggcagctgcaaagccctgcattcttcttttgat  2820
CDS_of_transcript_variant_3    gctgttcgggatatatttttattagagagcgcaggcagctgcaaagccctgcattcttcttttgat  2196
CDS_of_transcript_variant_X2   gctgttcgggatatatttttattagagagcgcaggcagctgcaaagccctgcattcttcttttgat  1071
                                 *  *** *  *****     *  **** *    ** codon_optimized_hPEX1          gagtttgaatcgatcgcgcccggaggggccacgacaacacggagtgaccgaccgggtg    2880
CDS_of_transcript_variant_2    gaatttgaatccattgctgactgctccctccggcgcgggtggggtcatgtatgataatgatacagaccgagtag  2709
CDS_of_transcript_variant_1    gaatttgaatccattgctgactgctccctccggcgcgggtggggtcatgtatgataatgatacagaccgagtag  2880
CDS_of_transcript_variant_3    gaatttgaatccattgctgactgctccctccggcgcgggtggggtcatgtatgataatgatacagaccgagtag  2256
CDS_of_transcript_variant_X2   gaatttgaatccattgctgactgctccctccggcgcgggtggggtcatgtatgataatgatacagaccgagtag  1131
                                 ***      * **  *   *  ** *       *** * ** codon_optimized_hPEX1          gtgaaccagctgctcacccaactggatggcgttcaggaggtcctcaggagtgtacgtgctg    2940
CDS_of_transcript_variant_2    gttaaccagttgctgactcagttgctgactcagttggatggatggaaggcttacaggggtgtttatgtattg  2769
CDS_of_transcript_variant_1    gttaaccagttgctgactcagttgctgactcagttggatggatggaaggcttacaggggtgtttatgtattg  2940
CDS_of_transcript_variant_3    gttaaccagttgctgactcagttgctgactcagttggatggatggaaggcttacaggggtgtttatgtattg  2316
CDS_of_transcript_variant_X2   gttaaccagttgctgactcagttgctgactcagttggatggatggaaggcttacaggggtgtttatgtattg  1191
                                ** *****   **  **** **       *****  **  **    *  **  **
```

FIG. 24K

```
Codon_optimized_hPEX1         gcggctacctccagaccggaccgatcgatccggccctgctgcgcccggagactggac       3000
CDS_of_transcript_variant_2   gctgctactagtcgcctgactgacttgattgacctgccctgcttaggcctgactagat    2829
CDS_of_transcript_variant_1   gctgctactagtcgcctgactgacttgattgacctgccctgcttaggcctgactagat    3000
CDS_of_transcript_variant_3   gctgctactagtcgcctgactgacttgattgacctgccctgcttaggcctgactagat    2376
CDS_of_transcript_variant_X2  gctgctactagtcgcctgactgacttgattgacctgccctgcttaggcctgactagat    1251
                              ** ******   ***  *** ***** **  ***** ****  ****

Codon_optimized_hPEX1         aagtgcgtgtattgcctccccctgaccaggtgtcaaggttggaaatcctcaagtgctc      3060
CDS_of_transcript_variant_2   aaatgtgtatactgtcctcctcctgatcaggtgtcacgtgtcttgaaattttaaatgtcctc  2889
CDS_of_transcript_variant_1   aaatgtgtatactgtcctcctcctgatcaggtgtcacgtgtcttgaaattttaaatgtcctc  3060
CDS_of_transcript_variant_3   aaatgtgtatactgtcctcctcctgatcaggtgtcacgtgtcttgaaattttaaatgtcctc  2436
CDS_of_transcript_variant_X2  aaatgtgtatactgtcctcctcctgatcaggtgtcacgtgtcttgaaattttaaatgtcctc  1911
                              ** ** *** ** *  **  ***** **   *  * ** ***

Codon_optimized_hPEX1         tcggactcccctgccacctggcactctccagcatgtggcctccgtgactgac          3120
CDS_of_transcript_variant_2   agtgactctctcctctggcagatgatgatgttgacctttgacctcagcatgcatcagtaactgac  2949
CDS_of_transcript_variant_1   agtgactctctcctctggcagatgatgatgttgacctttgacctcagcatgcatcagtaactgac  3120
CDS_of_transcript_variant_3   agtgactctctcctctggcagatgatgatgttgacctttgacctcagcatgcatcagtaactgac  2496
CDS_of_transcript_variant_X2  agtgactctctcctctggcagatgatgatgttgacctttgacctcagcatgcatcagtaactgac  1371
                              ** ** **  *****  *** ****** ******  ****

Codon_optimized_hPEX1         agcttcacaggagccgatctgaaggcccctgcttactttacaacgcccagttggaggcgctgcac  3180
CDS_of_transcript_variant_2   tcctttactggagctgatctgatctgaaagcttttactttactttacaagttcccaattggaggccttacat  3009
CDS_of_transcript_variant_1   tcctttactggagctgatctgatctgaaagcttttactttactttacaagttcccaattggaggccttacat  3180
CDS_of_transcript_variant_3   tcctttactggagctgatctgatctgaaagcttttactttactttacaagttcccaattggaggccttacat  2556
CDS_of_transcript_variant_X2  tcctttactggagctgatctgatctgaaagcttttactttactttacaagttcccaattggaggccttacat  1431
                              ***  ******* ** **  *****  *  *** *******

Codon_optimized_hPEX1         ggtatgctgctctccggtcctgcaggatggctcctcctcttccgatagcgacctgtcg       3240
CDS_of_transcript_variant_2   ggaatgctgtctctcgagtggactccaggatggaagttccagttccagtctgatagtgacctaagt  3069
CDS_of_transcript_variant_1   ggaatgctgtctctcgagtggactccaggatggaagttccagttccagtctgatagtgacctaagt  3240
CDS_of_transcript_variant_3   ggaatgctgtctctcgagtggactccaggatggaagttccagttccagtctgatagtgacctaagt  2616
CDS_of_transcript_variant_X2  ggaatgctgtctctcgagtggactccaggatggaagttccagttccagtctgatagtgacctaagt  1491
                              ** ***** ***** ** ***   ***   *** *****
```

```
Codon_optimized_hPEX1         agccaggaaggtgtgccaggaattgaccaagagcagcggaccaactgcgcgcggacatt    3600
CDS_of_transcript_variant_2   tcacaagagagggtttgccaagaacttacacaagaacaaagagatcaactgaggcagatatc 3429
CDS_of_transcript_variant_1   tcacaagagagggtttgccaagaacttacacaagaacaaagagatcaactgaggcagatatc 3600
CDS_of_transcript_variant_3   tcacaagagagggtttgccaagaacttacacaagaacaaagagatcaactgaggcagatatc 2976
CDS_of_transcript_variant_X2  tcacaagagagggtttgccaagaacttacacaagaacaaagagatcaactgaggcagatatc 1851
                                ** ** **** *** ** ***** ** ****** ** **

Codon_optimized_hPEX1         tcgatcatcaaaggcagatacccgctcccaatccggggagagaaagcatgaaccagccc    3660
CDS_of_transcript_variant_2   agtattatcaaagcagatacccggagccaaagtgagaggacgaatccatgaaccaacca   3489
CDS_of_transcript_variant_1   agtattatcaaagcagatacccggagccaaagtgagaggacgaatccatgaaccaacca   3660
CDS_of_transcript_variant_3   agtattatcaaagcagatacccggagccaaagtgagaggacgaatccatgaaccaacca   3036
CDS_of_transcript_variant_X2  agtattatcaaagcagatacccggagccaaagtgagaggacgaatccatgaaccaacca   1911
                                  ** **** ** ********* ** *********** ******** **

Codon_optimized_hPEX1         gggcctatcaagactagactggcaatctcccaaagccacctgatgaccgcactgggacac   3720
CDS_of_transcript_variant_2   ggaccaatcaaaaccaagactggctattagtcagtcactcacattcacttaatgactgtcac 3549
CDS_of_transcript_variant_1   ggaccaatcaaaaccaagactggctattagtcagtcactcacattcacttaatgactgtcac 3720
CDS_of_transcript_variant_3   ggaccaatcaaaaccaagactggctattagtcagtcactcacattcacttaatgactgtcac 3096
CDS_of_transcript_variant_X2  ggaccaatcaaaaccaagactggctattagtcagtcactcacattcacttaatgactgtcac 1971
                                ** *** ******** **

Codon_optimized_hPEX1         accggccctcgatctcggaggacgactggaagaactcgctgagctgtacgaatccttc    3780
CDS_of_transcript_variant_2   acaagaccatccattagtgaagatgaagaattttgctgagctatatgaaagcttt       3609
CDS_of_transcript_variant_1   acaagaccatccattagtgaagatgaagaattttgctgagctatatgaaagcttt       3780
CDS_of_transcript_variant_3   acaagaccatccattagtgaagatgaagaattttgctgagctatatgaaagcttt       3156
CDS_of_transcript_variant_X2  acaagaccatccattagtgaagatgaagaattttgctgagctatatgaaagcttt       2031
                                 *  * ****** ** ** **** *** *** ** ** *** *** **

Codon_optimized_hPEX1         cagaatccgagcggagaaagagacagagcggaactatgttccggcccgacagaagtg     3840
CDS_of_transcript_variant_2   caaaatccaaagagaggaaaaaatcaaagtgaacaatcaaagtttcgacctgacctgacagaaagta  3669
CDS_of_transcript_variant_1   caaaatccaaagagaggaaaaaatcaaagtgaacaatcaaagtttcgacctgacctgacagaaagta  3840
CDS_of_transcript_variant_3   caaaatccaaagagaggaaaaaatcaaagtgaacaatcaaagtttcgacctgacctgacagaaagta  3216
CDS_of_transcript_variant_X2  caaaatccaaagagaggaaaaaatcaaagtgaacaatcaaagtttcgacctgacctgacagaaagta  2091
                                ** ***     **     ** **   *   ** ***** ** **
```

FIG. 24N

| | | |
|---|---|---|
| Codon_optimized_hPEX1 | accctggcctga | 3852 |
| CDS_of_transcript_variant_2 | actttagcataa | 3681 |
| CDS_of_transcript_variant_1 | actttagcataa | 3852 |
| CDS_of_transcript_variant_3 | actttagcataa | 3228 |
| CDS_of_transcript_variant_X2 | actttagcataa | 2103 |
| | ** * *** * * | |

Plasmid Name: pAAV.CAG.copt.hPEX1 (SEQ ID NO: 9)
Promoter Type: ubiquitous
Total size: 13990 bp
AAV cassette size: 6138 bp

AAV Expression Cassette: 1253-7390
5' ITR: 1253-1382
CMV Enhancer: 1493-1796
CBA Promoter: 1798-2075
Chimeric Intron: 2076-3104
Kozak: 3113-3121
PEX1: 3122-6973
bGH Poly(A): 7004-7211
3' ITR: 7261-7390

Plasmid Name: pAAV.EF1ac.copt.hPEX1 (SEQ ID NO: 10)
Promoter Type: ubiquitous
Total size: 12560 bp
AAV cassette size: 4708 bp AAV Expression Cassette: 1253-5960
5' ITR: 1253-1382
EF1a Core Promoter: 1463-1674
Kozak: 1683-1691
PEX1: 1692-5543
bGH Poly(A): 5574-5781
3' ITR: 5831-5960

Plasmid Name: pAAV.GRK1.copt.hPEX1 (SEQ ID NO: 11)
Promoter Type: photoreceptor-specific
Total size: 12796 bp
AAV cassette size: 4944 bp AAV Expression Cassette: 1253-6196
5' ITR: 1253-1382
GRK1 Promoter: 1427-1790
SV40 Intron: 1791-1887
Kozak: 1940-1948
PEX1: 1949-5800
bGH Poly(A): 5822-5933
3' ITR: 6067-6196

Plasmid Name: pAAV.MECP2.copt.hPEX1 (SEQ ID NO: 12)
Promoter Type: neuron-specific
Total size: 12551 bp
AAV cassette size: 4699 bp AAV Expression Cassette: 1253-5951
5' ITR: 1253-1382
MECP2 Promoter: 1437-1665
Kozak: 1674-1682
PEX1: 1683-5534
bGH Poly(A): 5565-5772
3' ITR: 5822-5951

SEQUENCE LISTING

<160> NUMBER OF SEQ ID NOS: 13

<210> SEQ ID NO 1
<211> LENGTH: 3852
<212> TYPE: DNA
<213> ORGANISM: Artificial Sequence
<220> FEATURE:
<223> OTHER INFORMATION: Codon optimized human PEX1

<400> SEQUENCE: 1

```
atgtggggaa gcgacagact ggccggagct ggaggggag gagcagccgt caccgtggcg      60
ttcactaacg cgcgggactg ctttctccat ctgccgcgga ggctggtcgc ccagctgcac    120
ctcctgcaga accaggccat cgaggtggtg tggtcccacc aaccgccctt tttgagctgg    180
gtcgagggaa ggcacttttc ggaccaggga gaaaatgtgg cggagatcaa ccgccaggtc    240
ggccagaagc tgggactgtc caacggcgga caggtgttcc tcaagccgtg cagccacgtg    300
gtgtcctgcc aacaggtgga agtggagccg ctctccgccg acgactggga gatcctcgaa    360
ttgcatgccg tgagcctcga acagcatctg ttggaccaga ttcgcattgt gttcccgaag    420
gccatattcc ccgtgtgggt cgatcagcag acctatatct tcatccagat tgtggccctc    480
atcccggccg cctcatacgg acggctgaaa actgacacca agctgctgat tcaacctaag    540
acccggaggg ccaaagaaaa cacccttctcc aaggccgacg ctgagtacaa gaagctccac    600
tcctacggac gggaccagaa ggggatgatg aaggagctgc aaaccaagca gctccagagc    660
aacaccgtgg ggatcaccga gtccaatgaa acgagtcgg aaatcccagt cgattcatct    720
tccgtggcca gcctgtggac tatgatcggt tccattttct cgttccaatc tgagaagaag    780
caggaaacta gctgggggct gactgagatc aacgccttca agaacatgca gtccaaagtg    840
```

```
gtgcctctgg ataacatctt tcgcgtgtgc aagtcccaac cgccctcaat ctacaacgcg    900
tccgctacct ccgtgtttca taagcactgt gccatccacg tgttcccatg ggatcaggaa    960
tacttcgatg tcgaaccttc cttcaccgtg acttacggga agcttgtcaa gctcctcagc   1020
cccaagcagc agcaatcgaa aactaagcag aacgtgcttt ccccggagaa ggagaagcaa   1080
atgtcagaac cactcgacca gaagaaaatc agatcggatc ataacgaaga ggacgagaag   1140
gcctgcgtcc ttcaggtggt ctggaacggc ctggaggagc tgaacaacgc gattaagtac   1200
accaagaacg tcgaggtcct tcacctggga aaggtgtgga ttccggatga tctgaggaaa   1260
cgcctcaaca tcgaaatgca cgctgtggtg cggattaccc cggtcgaggt caccccaaag   1320
atccctcgct ccttgaagct gcagccgcga gaaaacttgc caaggacatt tctgaagag    1380
gatatcaaga ctgtgttcta ctcctggctg caacagagca ctaccaccat gctccctctg   1440
gtcatttcgg aggaagaatt catcaaactg gaaaccaagg acggactgaa agaattctcc   1500
ctgtccatcg tgcactcctg ggaaaaggag aaggacaaga atatcttcct gctgtccccc   1560
aatctgctgc aaaagaccac gatccaggtg ctgctcgacc ccatggtgaa ggaggaaaac   1620
tcagaagaga tcgacttcat cctgccgttc cttaagctga gttcactggg aggcgtgaac   1680
tcccttggcg tgtcctcgct ggagcacatc actcactcac tgctgggccg gcctctgagc   1740
agacagctta tgagcttggt cgccggactc agaaacggtg ccctcctgct caccggcggc   1800
aagggatcgg aaagtccac cctcgctaag gccatttgca agaggcatt cgataagctg    1860
gacgcccatg tggagcgggt ggactgtaag gccctccgcg gaaagcgatt ggaaaatatt   1920
caaaagactc tcgaagtcgc cttttccgaa gccgtctgga tgcagccctc ggtcgtcctg   1980
ctcgacgatc tggacctcat cgctgggctg ccggccgtgc cggagcatga acactcccct   2040
gacgcggtcc agtcgcaacg gctcgcccac gccctgaacg atatgattaa ggaattcatc   2100
tcaatgggat cactggtggc cctgatcgcg acttcccaga gccagcagtc cctgcaccct   2160
ctgctggtgt cggcccaggg cgtgcacatt tttcagtgtg tgcaacacat ccagccgccc   2220
aaccaggagc agcggtgcga atcctgtgc aacgtgatta agaacaagct ggactgcgat   2280
atcaacaagt ttaccgacct tgatctccaa catgtggcta aggagactgg gggcttcgtg   2340
gctcgggact tcacagtgtt ggtggaccgg gcaattcact ccagactgtc ccgccagagc   2400
atttccaccc gcgaaaaact ggtcctgacc accctcgact tccagaaggc cctcagaggc   2460
ttccttcctg cgagcctcag atccgtcaac cttcacaagc gcgggacct tggctgggac    2520
aagatcggtg ggctccacga ggtgcggcag atcctcatgg acaccattca gctgcctgca   2580
aagtaccccg agctgttcgc caacttgccg attcgccagc gcacgggaat cctgctctac   2640
ggcccccgg gcaccggaaa gaccctgctg gccggtgtga tcgcccggga atcgaggatg   2700
aacttcatct ccgtgaaggg acccgaactc ctgtccaagt acatcggtgc ctccgaacag   2760
gccgtgcgcg atatattcat tagggcccag gccgcgaagc cctgcattct gttcttcgac   2820
gagtttgaat cgatcgcgcc ccggagggc cacgacaaca cgggagtgac cgaccgggtg    2880
gtgaaccagc tgctcaccca actggatggc gtggaaggcc ttcagggagt gtacgtgctg   2940
gcggctacct ccagaccgga cctgatcgat ccggccctgc tgcgccccgg agactggac    3000
aagtgcgtgt attgccctcc ccctgaccag gtgtcaaggt tggaaatcct caacgtgctc   3060
tcggactccc tgccactggc agatgatgtg gacctccagc atgtggcctc cgtgactgac   3120
agcttcacag gagccgatct gaaggccctg ctttacaacg cccagttgga ggcgctgcac   3180
```

| | |
|---|---|
| ggtatgctgc tgtcctccgg tctgcaggat ggctcctcct cttccgatag cgacctgtcg | 3240 |
| ctgagcagca tggtgttcct gaaccattcc agcggctccg atgacagcgc gggcgacgga | 3300 |
| gaatgtggac tggatcaatc cctggtgtcc ctggagatga gcgagattct gccagacgag | 3360 |
| tccaagttca acatgtacag gctgtacttc ggcagcagct acgagtccga gctgggaaat | 3420 |
| ggtacctcgt ccgacctgtc aagccagtgc ctgtccgcgc cttcctccat gacccaggac | 3480 |
| ctccctggag tgccagggaa ggatcagctg ttcagccagc ctcccgtgct gcgcactgcg | 3540 |
| agccaggaag ggtgccagga attgacccaa gagcagcggg accaactgcg cgcggacatt | 3600 |
| tcgatcatca aaggcagata ccgctcccaa tccggggagg acgaaagcat gaaccagccc | 3660 |
| gggcctatca agactagact ggcaatctcc caaagccacc tgatgaccgc actgggacac | 3720 |
| acccggccct cgatctcgga ggacgactgg aagaacttcg ctgagctgta cgaatccttc | 3780 |
| cagaatccga agcggagaaa gaaccagagc ggaactatgt tccggcccgg acagaaggtg | 3840 |
| accctggcct ga | 3852 |

<210> SEQ ID NO 2
<211> LENGTH: 4390
<212> TYPE: DNA
<213> ORGANISM: Homo sapiens

<400> SEQUENCE: 2

| | |
|---|---|
| cgatcgatct cctccggctc cgacgtcctc ggcctgccgg gtcccgggtc ctttgcggcg | 60 |
| ctagggtggg cgaacccaga gcgacgctcc gggacgatgt ggggcagcga tcgcctggcg | 120 |
| ggtgctgggg gaggcggggc ggcagtgact gtggccttca ccaacgctcg cgactgcttc | 180 |
| ctccacctgc cgcggcgtct cgtggcccag ctgcatctgc tgcagaatca agctatagaa | 240 |
| gtggtctgga gtcaccagcc tgcattcttg agctgggtgg aaggcaggca ttttagtgat | 300 |
| caaggtgaaa atgtggctga aattaacaga caagttggtc aaaaacttgg actctcaaat | 360 |
| gggggacagg tatttctcaa gccatgttcc catgtggtat cttgtcaaca gttgaggtg | 420 |
| gaaccctct cagcagatga ttgggagata ctggagctgc atgctgtttc ccttgaacaa | 480 |
| catcttctag atcaaattcg aatagttttt ccaaaagcca tttttcctgt ttgggttgat | 540 |
| caacaaacgt acatatttat ccaaattgtt gcactaatac cagctgcctc ttatggaagg | 600 |
| ctggaaactg acaccaaact cccttattcag ccaaagacac gccgagccaa agagaataca | 660 |
| ttttcaaaag ctgatgctga atataaaaaa cttcatagtt atggaagaga ccagaaagga | 720 |
| atgatgaaaa aacttcaaac caagcaactt cagtcaaata ctgtgggaat cactgaatct | 780 |
| aatgaaaacg agtcagagat tccagttgac tcatcatcag tagcaagttt atggactatg | 840 |
| ataggaagca ttttttcctt tcaatctgag aagaaacaag agacatcttg gggtttaact | 900 |
| gaaatcaatg cattcaaaaa tatgcagtca aaggttgttc ctctagacaa tattttcaga | 960 |
| gtatgcaaat ctcaacctcc tagtatatat aacgcgtcag caacctctgt ttttcataaa | 1020 |
| cactgtgcca ttcatgtatt tccatgggac caggaatatt ttgatgtaga gcccagcttt | 1080 |
| actgtgacat atggaaagct agttaagcta cttttctccaa agcaacagca agtaaaaca | 1140 |
| aaacaaaatg tgttatcacc tgaaaaagag aagcagatgt cagagccact agatcaaaaa | 1200 |
| aaaattaggt cagatcataa tgaagaagat gagaaggcct gtgtgctaca gtagtctgg | 1260 |
| aatggacttg aagaattgaa caatgccatc aaatatacca aaaatgtaga agttctccat | 1320 |
| cttgggaaag tctggattcc agatgacctg aggaagagac taaatataga aatgcatgcc | 1380 |
| gtagtcagga taactccagt ggaagttacc cctaaaattc caagatctct aaagttacaa | 1440 |

```
cctagagaga atttacctaa agacataagt gaagaagaca taaaaactgt attttattca    1500
tggctacagc agtctactac caccatgctt cctttggtaa tatcagagga agaatttatt    1560
aagctggaaa ctaaagatgg actgaaggaa ttttctctga gtatagttca ttcttgggaa    1620
aaagaaaaag ataaaaatat ttttctgttg agtcccaatt tgctgcagaa gactacaata    1680
caagtccttc tagatcctat ggtaaaagaa gaaaacagtg aggaaattga ctttattctt    1740
ccttttttaa agctgagctc tttgggagga gtgaattcct taggcgtatc ctccttggag    1800
cacatcactc acagcctcct gggacgccct tgtctcggc agctgatgtc tcttgttgca     1860
ggacttagga atggagctct tttactcaca ggaggaaagg gaagtggaaa atcaacttta    1920
gccaaagcaa tctgtaaaga agcatttgac aaactggatg cccatgtgga gagagttgac    1980
tgtaaagctt tacgaggaaa aaggcttgaa aacatacaaa aaaccctaga ggtggctttc    2040
tcagaggcag tgtggatgca gccatctgtt gtcctgctgg atgaccttga cctcattgct    2100
ggactgcctg ctgtcccgga acatgagcac agtcctgatg cggtgcagag ccagcggctt    2160
gctcatgctt tgaatgatat gataaaagag tttatctcca tgggaagttt ggttgcactg    2220
attgccacaa gtcagtctca gcaatctcta catcctttac ttgtttctgc tcaaggagtt    2280
cacatatttc agtgcgtcca acacattcag cctcctaatc aggaacaaag atgtgaaatt    2340
ctgtgtaatg taataaaaaa taaattggac tgtgatataa acaagttcac cgatcttgac    2400
ctgcagcatg tagctaaaga aactggcggg tttgtggcta gagattttac agtacttgtg    2460
gatcgagcca tacattctcg actctctcgt cagagtatat ccaccagaga aaaattagtt    2520
ttaacaacat tggacttcca aaaggctctc cgcggatttc ttcctgcgtc tttgcgaagt    2580
gtcaacctgc ataaacctag agacctgggt tgggacaaga ttggtgggtt acatgaagtt    2640
aggcagatac tcatggatac tatccagtta cctgccaagt atccagaatt atttgcaaac    2700
ttgcccatac gacaaagaac aggaatactg ttgtatggtc cgcctggaac aggaaaaacc    2760
ttactagctg gggtaattgc acgagagagt agaatgaatt ttataagtgt caaggggcca    2820
gagttactca gcaaatacat tggagcaagt gaacaagctg ttcgggatat ttttattaga    2880
gcacaggctg caaagccctg cattcttttc tttgatgaat tgaatccat tgctcctcgg     2940 cggggtcatg ataatacagg agttacagac cgagtagtta accagttgct gactcagttg    3000
gatggagtag aaggcttaca gggtgtttat gtattggctg ctactagtcg ccctgacttg    3060
attgaccctg ccctgcttag gcctggtcga ctagataaat gtgtatactg tcctcctcct    3120
gatcaggtgt cacgtcttga aatttttaaat gtcctcagtg actctctacc tctggcagat    3180
gatgttgacc ttcagcatgt agcatcagta actgactcct ttactggagc tgatctgaaa    3240
gctttacttt acaatgccca attggaggcc ttacatggaa tgctgctctc gagtggactc    3300
caggatggaa gttccagctc tgatagtgac ctaagtctgt cttcaatggt ctttcttaac    3360
catagcagtg gctctgacga ttcagctgga gatggagaat gtggcttaga tcagtccctt    3420
gtttctttag agatgtccga gatccttcca gatgaatcaa aattcaatat gtaccggctc    3480
tactttggaa gctcttatga atcagaactt ggaaatggaa cctcttctga tttgagctca    3540
caatgtctct ctgcaccaag ctccatgact caggatttgc ctggagttcc tgggaaagac    3600
cagttgtttt cacagcctcc agtgttaagg acagcttcac aagagggttg ccaagaactt    3660
acacaagaac aaagagatca actgagggca gatatcagta ttatcaaagg cagataccgg    3720
agccaaagtg gagaggacga atccatgaac caaccaggac caatcaaaac cagactggct    3780
```

| | |
|---|---:|
| attagtcagt cacatttaat gactgcactt ggtcacacaa gaccatccat tagtgaagat | 3840 |
| gactggaaga attttgctga gctatatgaa agctttcaaa atccaaagag gagaaaaaat | 3900 |
| caaagtggaa caatgtttcg acctggacag aaagtaactt tagcataaaa tatacttctt | 3960 |
| tttgatttgg ttctgttaag ttttttgatg gcttttccat atgttgtaac aggaaaaaaa | 4020 |
| tggtgtctat gaatttcttc ttaatttaac aaatttggtt aatttataaa atcacagatt | 4080 |
| ggtaaatgct ataattatgt aatgatcagg attgagatta atactgtagt ataaattggg | 4140 |
| acattataac agattccata ttttatttcc taaaatctaa attcagtctt taatgaaata | 4200 |
| atattagcca aatggtggaa ctaatttatt tcttttgagg aaaagataat aaagaatgta | 4260 |
| attaaattta aatttcttgg aattcccagt tgtatattca tcacctttgt agcatttgac | 4320 |
| aaatttatg cttagcagct tcttcactgt tttgaaataa aatatcctat tacctactga | 4380 |
| taaaaaaaa | 4390 |

<210> SEQ ID NO 3
<211> LENGTH: 4221
<212> TYPE: DNA
<213> ORGANISM: Homo sapiens

<400> SEQUENCE: 3

| | |
|---|---:|
| cgatcgatct cctccggctc cgacgtcctc ggcctgccgg gtcccgggtc ctttgcggcg | 60 |
| ctagggtggg cgaacccaga gcgacgctcc gggacgatgt ggggcagcga tcgcctggcg | 120 |
| ggtgctgggg gaggcggggc ggcagtgact gtggccttca ccaacgctcg cgactgcttc | 180 |
| ctccacctgc cgcggcgtct cgtggcccag ctgcatctgc tgcagaatca agctatagaa | 240 |
| gtggtctgga gtcaccagcc tgcattcttg agctgggtgg aaggcaggca ttttagtgat | 300 |
| caaggtgaaa atgtggctga aattaacaga caagttggtc aaaaacttgg actctcaaat | 360 |
| gggggacagg tatttctcaa gccatgttcc catgtggtat cttgtcaaca agttgaggtg | 420 |
| gaaccctct cagcagatga ttgggagata ctggagctgc atgctgtttc ccttgaacaa | 480 |
| catcttctag atcaaattcg aatagttttt ccaaaagcca ttttcctgt ttgggttgat | 540 |
| caacaaacgt acatatttat ccaaattgtt gcactaatac cagctgcctc ttatggaagg | 600 |
| ctggaaactg acaccaaact ccttattcag ccaaagacac gccgagccaa agagaataca | 660 |
| ttttcaaaag ctgatgctga atataaaaaa cttcatagtt atggaagaga ccagaaagga | 720 |
| atgatgaaag aacttcaaac caagcaactt cagtcaaata ctgtgggaat cactgaatct | 780 |
| aatgaaaacg agtcagagat tccagttgac tcatcatcag tagcaagttt atggactatg | 840 |
| ataggaagca ttttttcctt tcaatctgag aagaaacaag agacatcttg ggtttaact | 900 |
| gaaatcaatg cattcaaaaa tatgcagtca aaggttgttc ctctagacaa tattttcaga | 960 |
| gtatgcaaat ctcaacctcc tagtatatat aacgcgtcag caacctctgt ttttcataaa | 1020 |
| cactgtgcca ttcatgtatt tccatgggac caggaatatt ttgatgtaga gcccagcttt | 1080 |
| actgtgacat atggaaagct agttaagcta ctttctccaa agcaacagca aagtaaaaca | 1140 |
| aaacaaaatg tgttatcacc tgaaaaagag aagcagatgt cagagccact agatcaaaaa | 1200 |
| aaaattaggt cagatcataa tgaagaagat gagaaggcct gtgtgctaca agtagtctgg | 1260 |
| aatggacttg aagaattgaa caatgccatc aaatatacca aaaatgtaga agttctccat | 1320 |
| cttgggaaag tctggattcc agatgaccty aggaagagac taaatataga aatgcatgcc | 1380 |
| gtagtcagga taactccagt ggaagttacc cctaaaattc caagatctct aaagttacaa | 1440 |
| cctagagaga atttacctaa agacataagt gaagaagaca taaaaactgt attttattca | 1500 |

```
tggctacagc agtctactac caccatgctt cctttggtaa tatcagagga agaatttatt    1560
aagctggaaa ctaaagatgg actgaaggaa ttttctctga gtatagttca ttcttgggaa    1620
aaagaaaaag ataaaaatat ttttctgttg agtcccaatt tgctgcagaa gactacaata    1680
caagtccttc tagatcctat ggtaaaagaa gaaaacagtg aggaaattga ctttattctt    1740 cctttttaa agctgagctc tttgggagga gtgaattcct taggcgtatc ctccttggag    1800
cacatcactc acagcctcct gggacgccct ttgtctcggc agctgatgtc tcttgttgca    1860
ggacttagga atggagctct tttactcaca ggaggaaagg gaagtggaaa atcaacttta    1920
gccaaagcaa tctgtaaaga agcatttgac aaactggatg cccatgtgga gagagttgac    1980
tgtaaagctt tacgagcttt gaatgatatg ataaaagagt ttatctccat gggaagtttg    2040
gttgcactga ttgccacaag tcagtctcag caatctctac atcctttact tgtttctgct    2100
caaggagttc acatatttca gtgcgtccaa cacattcagc ctcctaatca ggaacaaaga    2160
tgtgaaattc tgtgtaatgt aataaaaaat aaattggact gtgatataaa caagttcacc    2220
gatcttgacc tgcagcatgt agctaaagaa actggcgggt tgtggctag agattttaca    2280 gtacttgtgg atcgagccat acattctcga ctctctcgtc agagtatatc caccagagaa    2340
aaattagttt taacaacatt ggacttccaa aaggctctcc gcggatttct tcctgcgtct    2400
ttgcgaagtc tcaacctgca taaacctaga gacctgggtt gggacaagat tggtgggtta    2460
catgaagtta ggcagatact catggatact atccagttac ctgccaagta tccagaatta    2520
tttgcaaact tgcccatacg acaaagaaca ggaatactgt tgtatggtcc gcctggaaca    2580
ggaaaaacct tactagctgg ggtaattgca cgagagagta gaatgaatt tataagtgtc    2640 aaggggccag agttactcag caaatacatt ggagcaagtg aacaagctgt tcgggatatt    2700
tttattagag cacaggctgc aaagccctgc attctttct ttgatgaatt tgaatccatt    2760
gctcctcggc ggggtcatga taatacagga gttacagacc gagtagttaa ccagttgctg    2820
actcagttgg atggagtaga aggcttacag ggtgtttatg tattggctgc tactagtcgc    2880
cctgacttga ttgaccctgc cctgcttagg cctggtcgac tagataaatg tgtatactgt    2940
cctcctcctg atcaggtgtc acgtcttgaa attttaaatg tcctcagtga ctctctacct    3000
ctggcagatg atgttgacct tcagcatgta gcatcagtaa ctgactcctt tactggagct    3060
gatctgaaag ctttacttta caatgcccaa ttggaggcct acatggaat gctgctctcg    3120 agtggactcc aggatggaag ttccagctct gatagtgacc taagtctgtc ttcaatggtc    3180
tttcttaacc atagcagtgg ctctgacgat tcagctggag atggagaatg tggcttagat    3240
cagtcccttg tttctttaga gatgtccgag atccttccag atgaatcaaa attcaatatg    3300
taccggctct actttggaag ctcttatgaa tcagaacttg gaaatggaac ctcttctgat    3360
ttgagctcac aatgtctctc tgcaccaagc tccatgactc aggatttgcc tggagttcct    3420
gggaaagacc agttgttttc acagcctcca gtgttaagga cagcttcaca agagggttgc    3480
caagaactta cacaagaaca aagagatcaa ctgagggcag atatcagtat tatcaaaggc    3540
agataccgga gccaaagtgg agaggacgaa tccatgaacc aaccaggacc aatcaaaacc    3600
agactggcta ttagtcagtc acatttaatg actgcacttg gtcacacaag accatccatt    3660
agtgaagatg actggaagaa ttttgctgag ctatatgaaa gctttcaaaa tccaagagg    3720 agaaaaaatc aaagtggaac aatgtttcga cctggacaga aagtaacttt agcataaaat    3780
atacttcttt ttgatttggt tctgttaagt tttttgatgg ctttttccata tgttgtaaca    3840
```

| | |
|---|---|
| ggaaaaaaat ggtgtctatg aatttcttct taatttaaca aatttggtta atttataaaa | 3900 |
| tcacagattg gtaaatgcta taattatgta atgatcagga ttgagattaa tactgtagta | 3960 |
| taaattggga cattataaca gattccatat tttatttcct aaaatctaaa ttcagtcttt | 4020 |
| aatgaaataa tattagccaa atggtggaac taatttattt cttttgagga aaagataata | 4080 |
| aagaatgtaa ttaaatttaa atttcttgga attcccagtt gtatattcat cacctttgta | 4140 |
| gcatttgaca aattttatgc ttagcagctt cttcactgtt ttgaaataaa atatcctatt | 4200 |
| acctactgat aaaaaaaaaa a | 4221 |

<210> SEQ ID NO 4
<211> LENGTH: 4427
<212> TYPE: DNA
<213> ORGANISM: Homo sapiens

<400> SEQUENCE: 4

| | |
|---|---|
| cgatcgatct cctccggctc cgacgtcctc ggcctgccgg gtcccgggtc ctttgcggcg | 60 |
| ctagggtggg cgaacccaga gcgacgctcc gggacgatgt ggggcagcga tcgcctggcg | 120 |
| ggtgctgggg gaggcgggc ggcagtgact gtggccttca ccaacgctcg cgactgcttc | 180 |
| ctccacctgc cgcggcgtct cgtggcccag ctgcatctgc tgcagaatca agctatagaa | 240 |
| gtggtctgga gtcaccagcc tgcattcttg agctgggtgg aaggcaggca ttttagtgat | 300 |
| caaggtgaaa atgtggctga aattaacaga caagttggtc aaaaacttgg actctcaaat | 360 |
| gggggacagg tatttctcaa gccatgttcc catgtggtat cttgtcaaca agttgaggtg | 420 |
| gaaccctct cagcagatga ttgggagata ctggtaaaga aaccaaata gaactatct | 480 |
| catttaagga gctgcatgct gtttcccttg aacaacatct tctagatcaa attcgaatag | 540 |
| tttttccaaa agccattttt cctgtttggg ttgatcaaca aacgtacata tttatccaaa | 600 |
| ttgttgcact aataccagct gcctcttatg aaggctgga aactgacacc aaactcctta | 660 |
| ttcagccaaa gacacgccga gccaaagaga atacattttc aaaagctgat gctgaatata | 720 |
| aaaaacttca tagttatgga agagaccaga aggaatgat gaaagaactt caaaccaagc | 780 |
| aacttcagtc aaatactgtg ggaatcactg aatctaatga aaacgagtca gagattccag | 840 |
| ttgactcatc atcagtagca agtttatgga ctatgatagg aagcattttt tccttttcaat | 900 |
| ctgagaagaa acaagagaca tcttggggtt taactgaaat caatgcattc aaaaatatgc | 960 |
| agtcaaaggt tgttcctcta gacaatattt tcagagtatg caaatctcaa cctcctagta | 1020 |
| tatataacgc gtcagcaacc tctgtttttc ataaacactg tgccattcat gtatttccat | 1080 |
| gggaccagga atattttgat gtagagccca gctttactgt gacatatgga aagctagtta | 1140 |
| agctactttc tccaaagcaa cagcaaagta aacaaaaca aatgtgtta tcacctgaaa | 1200 |
| aagagaagca gatgtcagag ccactagatc aaaaaaaaat taggtcagat cataatgaag | 1260 |
| aagatgagaa ggcctgtgtg ctacaagtag tctggaatgg acttgaagaa ttgaacaatg | 1320 |
| ccatcaaata taccaaaaat gtagaagttc tccatcttgg aaagtctgg attccagatg | 1380 |
| acctgaggaa gagactaaat atagaaatgc atgccgtagt caggataact ccagtggaag | 1440 |
| ttacccctaa aattccaaga tctctaaagt tacaacctag agagaattta cctaaagaca | 1500 |
| taagtgaaga agacataaaa actgtatttt attcatggct acagcagtct actaccacca | 1560 |
| tgcttccttt ggtaatatca gaggaagaat ttattaagct ggaaactaaa gatggactga | 1620 |
| aggaattttc tctgagtata gttcattctt gggaaaaaga aaaagataaa aatatttttc | 1680 |
| tgttgagtcc caatttgctg cagaagacta caatacaagt ccttctagat cctatggtaa | 1740 |

```
aagaagaaaa cagtgaggaa attgacttta ttcttccttt tttaaagctg agctctttgg    1800
gaggagtgaa ttccttaggc gtatcctcct tggagcacat cactcacagc ctcctgggac    1860
gccctttgtc tcggcagctg atgtctcttg ttgcaggact taggaatgga gctcttttac    1920
tcacaggagg aaagggaagt ggaaaatcaa ctttagccaa agcaatctgt aaagaagcat    1980
ttgacaaact ggatgcccat gtggagagag ttgactgtaa agctttacga ggaaaaaggc    2040
ttgaaaacat acaaaaaacc ctagaggtgg ctttctcaga ggcagtgtgg atgcagccat    2100
ctgttgtcct gctggatgac cttgacctca ttgctggact gcctgctgtc ccggaacatg    2160
agcacagtcc tgatgcggtg cagagccagc ggcttgctca tgctttgaat gatatgataa    2220
aagagtttat ctccatggga agtttggttg cactgattgc cacaagtcag tctcagcaat    2280
ctctacatcc tttacttgtt tctgctcaag gagttcacat atttcagtgc gtccaacaca    2340
ttcagcctcc taatcaggaa caaagatgtg aaattctgtg taatgtaata aaaaataaat    2400
tggactgtga tataaacaag ttcaccgatc ttgacctgca gcatgtagct aaagaaactg    2460
gcgggtttgt ggctagagat tttacagtac ttgtggatcg agccatacat tctcgactct    2520
ctcgtcagag tatatccacc agagaaaaat tagttttaac aacattggac ttccaaaagg    2580
ctctccgcgg atttcttcct gcgtctttgc gaagtgtcaa cctgcataaa cctagagacc    2640
tgggttggga caagattggt gggttacatg aagttaggca gatactcatg gatactatcc    2700
agttacctgc caagtatcca gaattatttg caaacttgcc catacgacaa agaacaggaa    2760
tactgttgta tggtccgcct ggaacaggaa aaaccttact agctgggta attgcacgag    2820 agagtagaat gaattttata agtgtcaagg ggccagagtt actcagcaaa tacattggag    2880
caagtgaaca agctgttcgg gatatttta ttagagcaca ggctgcaaag ccctgcattc    2940

тттттcтттga tgaatttgaa tccattgctc ctcggcgggg tcatgataat acaggagtta    3000
cagaccgagt agttaaccag ttgctgactc agttggatgg agtagaaggc ttacagggtg    3060

ttatgtatt ggctgctact agtcgccctg acttgattga ccctgccctg cttaggcctg    3120
gtcgactaga taaatgtgta tactgtcctc ctcctgatca ggtgtcacgt cttgaaattt    3180

taaatgtcct cagtgactct ctacctctgg cagatgatgt tgaccttcag catgtagcat    3240
cagtaactga ctcctttact ggagctgatc tgaaagcttt actttacaat gcccaattgg    3300
aggccttaca tggaatgctg ctctcgagtg gactccagga tggaagttcc agctctgata    3360
gtgacctaag tctgtcttca atggtctttc ttaaccatag cagtggctct gacgattcag    3420
ctggagatgg agaatgtggc ttagatcagt cccttgtttc tttagagatg tccgagatcc    3480

ttccagatga atcaaaattc aatatgtacc ggctctactt tggaagctct tatgaatcag    3540
aacttggaaa tggaacctct tctgatttga gctcacaatg tctctctgca ccaagctcca    3600 tgactcagga ттттgccтgga gttcctggga agaccagtt gтттттcacag cctccagtgt    3660 taaggacagc ttcacaagag ggttgccaag aacttacaca agaacaaaga gatcaactga    3720
gggcagatat cagtattatc aaaggcagat accggagcca aagtggagag gacgaatcca    3780
tgaaccaacc aggaccaatc aaaaccagac tggctattag tcagtcacat ttaatgactg    3840
cacttggtca cacaagacca tccattagtg aagatgactg gaagaattt gctgagctat    3900

atgaaagctt tcaaaatcca aagaggagaa aaaatcaaag tggaacaatg tttcgacctg    3960
gacagaaagt aacттттagca taaaatatac ттcттттттga tttggttctg ttaagtttt    4020

tgatggctt tccatatgtt gtaacaggaa aaaaatggtg tctatgaatt tcttcttaat    4080
```

| | |
|---|---|
| ttaacaaatt tggttaattt ataaaatcac agattggtaa atgctataat tatgtaatga | 4140 |
| tcaggattga gattaatact gtagtataaa ttgggacatt ataacagatt ccatatttta | 4200 |
| tttcctaaaa tctaaattca gtctttaatg aaataatatt agccaaatgg tggaactaat | 4260 |
| ttatttcttt tgaggaaaag ataataaaga atgtaattaa atttaaattt cttggaattc | 4320 |
| ccagttgtat attcatcacc tttgtagcat ttgacaaatt ttatgcttag cagcttcttc | 4380 |
| actgttttga aataaaatat cctattacct actgataaaa aaaaaaa | 4427 |

<210> SEQ ID NO 5
<211> LENGTH: 3192
<212> TYPE: DNA
<213> ORGANISM: Homo sapiens

<400> SEQUENCE: 5

| | |
|---|---|
| cagcaacctc tgtttttcat aaacactgtg ccattcatgt atttccatgg gaccaggaat | 60 |
| attttgatgt agagcccagc tttactgtga catatggaaa gctagttaag ctactttctc | 120 |
| caaagcaaca gcaaagtaaa acaaacaaa atgtgttatc acctgaaaaa gagaagcaga | 180 |
| tgtcagagcc actagatcaa aaaaaatta ggtcagatca taatgaagaa gatgagaagg | 240 |
| cctgtgtgct acaagtagtc tggaatggac ttgaagaatt gaacaatgcc atcaaatata | 300 |
| ccaaaaatgt agaagttctc catcttggga agtctggat tccagatgac ctgaggaaga | 360 |
| gactaaatat agaaatgcat gccgtagtca ggataactcc agtggaagtt acccctaaaa | 420 |
| ttccaagatc tctaaagtta caacctagag agaatttacc taaagacata agtgaagaag | 480 |
| acataaaaac tgtattttat tcatggctac agcagtctac taccaccatg cttcctttgg | 540 |
| taatatcaga ggaagaattt attaagctgg aaactaaaga tggactgaag gaattttctc | 600 |
| tgagtatagt tcattcttgg gaaaagaaa agataaaaa tatttttctg ttgagtccca | 660 |
| atttgctgca gaagactaca atacaaagga gtgaattcct taggcgtatc ctccttggag | 720 |
| cacatcactc acagcctcct gggacgccct ttgtctcggc agctgatgtc tcttgttgca | 780 |
| ggacttagga atggagctct tttactcaca ggaggaaagg gaagtggaaa atcaacttta | 840 |
| gccaaagcaa tctgtaaaga agcatttgac aaactggatg cccatgtgga gagagttgac | 900 |
| tgtaaagctt tacgaggaaa aaggcttgaa aacatacaaa aaaccctaga ggtggctttc | 960 |
| tcagaggcag tgtggatgca gccatctgtt gtcctgctgg atgaccttga cctcattgct | 1020 |
| ggactgcctg ctgtcccgga acatgagcac agtcctgatg cggtgcagag ccagcggctt | 1080 |
| gctcatgctt tgaatgatat gataaaagag tttatctcca tgggaagttt ggttgcactg | 1140 |
| attgccacaa gtcagtctca gcaatctcta catccttac ttgtttctgc tcaaggagtt | 1200 |
| cacatatttc agtgcgtcca acacattcag cctcctaatc aggaacaaag atgtgaaatt | 1260 |
| ctgtgtaatg taataaaaaa taaattggac tgtgatataa acaagttcac cgatcttgac | 1320 |
| ctgcagcatg tagctaaaga aactggcggg tttgtggcta gagattttac agtacttgtg | 1380 |
| gatcgagcca tacattctcg actctctcgt cagagtatat ccaccagaga aaaattagtt | 1440 |
| ttaacaacat tggacttcca aaaggctctc cgcggatttc ttcctgcgtc tttgcgaagt | 1500 |
| gtcaacctgc ataaacctag agacctgggt tgggacaaga ttggtgggtt acatgaagtt | 1560 |
| aggcagatac tcatggatac tatccagtta cctgccaagt atccagaatt atttgcaaac | 1620 |
| tgcccatac gacaaagaac aggaatactg ttgtatggtc cgcctggaac aggaaaaacc | 1680 |
| ttactagctg gggtaattgc acgagagagt agaatgaatt ttataagtgt caggggccaa | 1740 |
| gagttactca gcaaatacat tggagcaagt gaacaagctg ttcgggatat ttttattaga | 1800 |

```
gcacaggctg caaagccctg cattcttttc tttgatgaat ttgaatccat tgctcctcgg    1860
cggggtcatg ataatacagg agttacagac cgagtagtta accagttgct gactcagttg    1920
gatggagtag aaggcttaca gggtgtttat gtattggctg ctactagtcg ccctgacttg    1980
attgaccctg ccctgcttag gcctggtcga ctagataaat gtgtatactg tcctcctcct    2040
gatcaggtgt cacgtcttga aattttaaat gtcctcagtg actctctacc tctggcagat    2100
gatgttgacc ttcagcatgt agcatcagta actgactcct ttactggagc tgatctgaaa    2160
gctttacttt acaatgccca attggaggcc ttacatggaa tgctgctctc gagtggactc    2220
caggatggaa gttccagctc tgatagtgac ctaagtctgt cttcaatggt ctttcttaac    2280
catagcagtg gctctgacga ttcagctgga gatggagaat gtggcttaga tcagtccctt    2340
gtttctttag agatgtccga gatccttcca gatgaatcaa aattcaatat gtaccggctc    2400
tactttggaa gctcttatga atcagaactt ggaaatggaa cctcttctga tttgagctca    2460
caatgtctct ctgcaccaag ctccatgact caggatttgc ctggagttcc tgggaaagac    2520
cagttgtttt cacagcctcc agtgttaagg acagcttcac aagagggttg ccaagaactt    2580
acacaagaac aaagagatca actgagggca gatatcagta ttatcaaagg cagataccgg    2640
agccaaagtg gagaggacga atccatgaac caaccaggac caatcaaaac cagactggct    2700
attagtcagt cacatttaat gactgcactt ggtcacacaa gaccatccat tagtgaagat    2760
gactggaaga attttgctga gctatatgaa agctttcaaa atccaaagag gagaaaaaat    2820
caaagtggaa caatgtttcg acctggacag aaagtaactt tagcataaaa tatacttctt    2880
tttgatttgg ttctgttaag tttttttgatg gcttttccat atgttgtaac aggaaaaaaa    2940
tggtgtctat gaatttcttc ttaatttaac aaatttggtt aatttataaa atcacagatt    3000
ggtaaatgct ataattatgt aatgatcagg attgagatta atactgtagt ataaattggg    3060
acattataac agattccata ttttatttcc taaaatctaa attcagtctt taatgaaata    3120
atattagcca aatggtggaa ctaatttatt tcttttgagg aaaagataat aaagaatgta    3180
attaaattta aa                                                        3192
```

<210> SEQ ID NO 6
<211> LENGTH: 4983
<212> TYPE: DNA
<213> ORGANISM: Artificial Sequence
<220> FEATURE:
<223> OTHER INFORMATION: CMV.hPEX1
<220> FEATURE:
<221> NAME/KEY: repeat_region
<222> LOCATION: (1)..(130)
<223> OTHER INFORMATION: 5' ITR
<220> FEATURE:
<221> NAME/KEY: misc_feature
<222> LOCATION: (113)..(130)
<223> OTHER INFORMATION: ITR D Segment
<220> FEATURE:
<221> NAME/KEY: enhancer
<222> LOCATION: (181)..(484)
<223> OTHER INFORMATION: human cytomegalovirus (CMV) immediate early
    enhancer
<220> FEATURE:
<221> NAME/KEY: promoter
<222> LOCATION: (485)..(688)
<223> OTHER INFORMATION: human cytomegalovirus (CMV) immediate early
    promoter
<220> FEATURE:
<221> NAME/KEY: misc_feature
<222> LOCATION: (706)..(714)
<223> OTHER INFORMATION: Kozak
<220> FEATURE:

```
<221> NAME/KEY: CDS
<222> LOCATION: (715)..(4566)
<223> OTHER INFORMATION: codon-optimized human PEX1
<220> FEATURE:
<221> NAME/KEY: polyA_signal
<222> LOCATION: (4597)..(4804)
<223> OTHER INFORMATION: bovine growth hormone polyadenylation signal
      (bGH poly(A) signal)
<220> FEATURE:
<221> NAME/KEY: repeat_region
<222> LOCATION: (4854)..(4983)
<223> OTHER INFORMATION: 3' ITR
<220> FEATURE:
<221> NAME/KEY: repeat_region
<222> LOCATION: (4854)..(4871)
<223> OTHER INFORMATION: ITR D Segment

<400> SEQUENCE: 6
```

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gcaagctagc | 180 |
| cgttacataa cttacggtaa atggcccgcc tggctgaccg cccaacgacc cccgcccatt | 240 |
| gacgtcaata atgacgtatg ttcccatagt aacgccaata gggactttcc attgacgtca | 300 |
| atgggtggag tatttacggt aaactgccca cttggcagta catcaagtgt atcatatgcc | 360 |
| aagtacgccc cctattgacg tcaatgacgg taaatggccc gcctggcatt atgcccagta | 420 |
| catgacctta tgggactttc ctacttggca gtacatctac gtattagtca tcgctattac | 480 |
| catggtgatg cggttttggc agtacatcaa tgggcgtgga tagcggtttg actcacgggg | 540 |
| atttccaagt ctccacccca ttgacgtcaa tgggagtttg ttttggcacc aaaatcaacg | 600 |
| ggactttcca aaatgtcgta caactccgcc ccattgacg caaatgggcg gtaggcgtgt | 660 |
| acggtgggag gtctatataa gcagagcttg tacactagcg ccgcgccgc cacc atg | 717 |
|                                                                                                              Met | |
|                                                                                                               1 | |
| tgg gga agc gac aga ctg gcc gga gct gga ggg gga gca gcc gtc<br>Trp Gly Ser Asp Arg Leu Ala Gly Ala Gly Gly Gly Ala Ala Val<br>         5                  10               15 | 765 |
| acc gtg gcg ttc act aac gcg cgg gac tgc ttt ctc cat ctg ccg cgg<br>Thr Val Ala Phe Thr Asn Ala Arg Asp Cys Phe Leu His Leu Pro Arg<br>       20                 25               30 | 813 |
| agg ctg gtc gcc cag ctg cac ctc ctg cag aac cag gcc atc gag gtg<br>Arg Leu Val Ala Gln Leu His Leu Leu Gln Asn Gln Ala Ile Glu Val<br> 35                 40               45 | 861 |
| gtg tgg tcc cac caa ccg gcc ttt ttg agc tgg gtc gag gga agg cac<br>Val Trp Ser His Gln Pro Ala Phe Leu Ser Trp Val Glu Gly Arg His<br>50               55               60               65 | 909 |
| ttt tcg gac cag gga gaa aat gtg gcg gag atc aac cgc cag gtc ggc<br>Phe Ser Asp Gln Gly Glu Asn Val Ala Glu Ile Asn Arg Gln Val Gly<br>                 70               75               80 | 957 |
| cag aag ctg gga ctg tcc aac ggc gga cag gtg ttc ctc aag ccg tgc<br>Gln Lys Leu Gly Leu Ser Asn Gly Gly Gln Val Phe Leu Lys Pro Cys<br>       85                 90               95 | 1005 |
| agc cac gtg gtg tcc tgc caa cag gtg gaa gtg gag ccg ctc tcc gcc<br>Ser His Val Val Ser Cys Gln Gln Val Glu Val Glu Pro Leu Ser Ala<br>              100             105             110 | 1053 |
| gac gac tgg gag atc ctc gaa ttg cat gcc gtg agc ctc gaa cag cat<br>Asp Asp Trp Glu Ile Leu Glu Leu His Ala Val Ser Leu Glu Gln His<br>115              120             125 | 1101 |
| ctg ttg gac cag att cgc att gtg ttc ccg aag gcc ata ttc ccc gtg<br>Leu Leu Asp Gln Ile Arg Ile Val Phe Pro Lys Ala Ile Phe Pro Val | 1149 |

-continued

| | |
|---|---|
| tgg gtc gat cag cag acc tat atc ttc atc cag att gtg gcc ctc atc<br>Trp Val Asp Gln Gln Thr Tyr Ile Phe Ile Gln Ile Val Ala Leu Ile<br>                150                      155                    160 | 1197 |
| ccg gcc gcc tca tac gga cgg ctg gaa act gac acc aag ctg ctg att<br>Pro Ala Ala Ser Tyr Gly Arg Leu Glu Thr Asp Thr Lys Leu Leu Ile<br>         165                    170                    175 | 1245 |
| caa cct aag acc cgg agg gcc aaa gaa aac acc ttc tcc aag gcc gac<br>Gln Pro Lys Thr Arg Arg Ala Lys Glu Asn Thr Phe Ser Lys Ala Asp<br>180                      185                    190 | 1293 |
| gct gag tac aag aag ctc cac tcc tac gga cgg gac cag aag ggg atg<br>Ala Glu Tyr Lys Lys Leu His Ser Tyr Gly Arg Asp Gln Lys Gly Met<br>       195                    200                    205 | 1341 |
| atg aag gag ctg caa acc aag cag ctc cag agc aac acc gtg ggg atc<br>Met Lys Glu Leu Gln Thr Lys Gln Leu Gln Ser Asn Thr Val Gly Ile<br>210                      215                    220                    225 | 1389 |
| acc gag tcc aat gaa aac gag tcg gaa atc cca gtc gat tca tct tcc<br>Thr Glu Ser Asn Glu Asn Glu Ser Glu Ile Pro Val Asp Ser Ser Ser<br>                      230                    235                    240 | 1437 |
| gtg gcc agc ctg tgg act atg atc ggt tcc att ttc tcg ttc caa tct<br>Val Ala Ser Leu Trp Thr Met Ile Gly Ser Ile Phe Ser Phe Gln Ser<br>             245                    250                    255 | 1485 |
| gag aag aag cag gaa act agc tgg ggg ctg act gag atc aac gcc ttc<br>Glu Lys Lys Gln Glu Thr Ser Trp Gly Leu Thr Glu Ile Asn Ala Phe<br>260                      265                    270 | 1533 |
| aag aac atg cag tcc aaa gtg gtg cct ctg gat aac atc ttt cgc gtg<br>Lys Asn Met Gln Ser Lys Val Val Pro Leu Asp Asn Ile Phe Arg Val<br>       275                    280                    285 | 1581 |
| tgc aag tcc caa ccg ccc tca atc tac aac gcg tcc gct acc tcc gtg<br>Cys Lys Ser Gln Pro Pro Ser Ile Tyr Asn Ala Ser Ala Thr Ser Val<br>290                      295                    300                    305 | 1629 |
| ttt cat aag cac tgt gcc atc cac gtg ttc cca tgg gat cag gaa tac<br>Phe His Lys His Cys Ala Ile His Val Phe Pro Trp Asp Gln Glu Tyr<br>                      310                    315                    320 | 1677 |
| ttc gat gtc gaa cct tcc ttc acc gtg act tac ggg aag ctt gtc aag<br>Phe Asp Val Glu Pro Ser Phe Thr Val Thr Tyr Gly Lys Leu Val Lys<br>             325                    330                    335 | 1725 |
| ctc ctc agc ccc aag cag cag caa tcg aaa act aag cag aac gtg ctt<br>Leu Leu Ser Pro Lys Gln Gln Gln Ser Lys Thr Lys Gln Asn Val Leu<br>             340                    345                    350 | 1773 |
| tcc ccg gag aag gag aag caa atg tca gaa cca ctc gac cag aag aaa<br>Ser Pro Glu Lys Glu Lys Gln Met Ser Glu Pro Leu Asp Gln Lys Lys<br>355                      360                    365 | 1821 |
| atc aga tcg gat cat aac gaa gag gac gag aag gcc tgc gtc ctt cag<br>Ile Arg Ser Asp His Asn Glu Glu Asp Glu Lys Ala Cys Val Leu Gln<br>370                      375                    380                    385 | 1869 |
| gtg gtc tgg aac ggc ctg gag gag ctg aac aac gcg att aag tac acc<br>Val Val Trp Asn Gly Leu Glu Glu Leu Asn Asn Ala Ile Lys Tyr Thr<br>                      390                    395                    400 | 1917 |
| aag aac gtc gag gtc ctt cac ctg gga aag gtg tgg att ccg gat gat<br>Lys Asn Val Glu Val Leu His Leu Gly Lys Val Trp Ile Pro Asp Asp<br>             405                    410                    415 | 1965 |
| ctg agg aaa cgc ctc aac atc gaa atg cac gct gtg gtg cgg att acc<br>Leu Arg Lys Arg Leu Asn Ile Glu Met His Ala Val Val Arg Ile Thr<br>420                      425                    430 | 2013 |
| ccg gtc gag gtc acc cca aag atc cct cgc tcc ttg aag ctg cag ccg<br>Pro Val Glu Val Thr Pro Lys Ile Pro Arg Ser Leu Lys Leu Gln Pro<br>       435                    440                    445 | 2061 |
| cga gaa aac ttg ccc aag gac att tct gaa gag gat atc aag act gtg | 2109 |

```
                Arg Glu Asn Leu Pro Lys Asp Ile Ser Glu Glu Asp Ile Lys Thr Val
                450             455                 460                 465 ttc tac tcc tgg ctg caa cag agc act acc acc atg ctc cct ctg gtc              2157
Phe Tyr Ser Trp Leu Gln Gln Ser Thr Thr Thr Met Leu Pro Leu Val
                470                 475                 480 att tcg gag gaa gaa ttc atc aaa ctg gaa acc aag gac gga ctg aaa              2205
Ile Ser Glu Glu Glu Phe Ile Lys Leu Glu Thr Lys Asp Gly Leu Lys
                485                 490                 495 gaa ttc tcc ctg tcc atc gtg cac tcc tgg gaa aag gag aag gac aag              2253
Glu Phe Ser Leu Ser Ile Val His Ser Trp Glu Lys Glu Lys Asp Lys
                500                 505                 510 aat atc ttc ctg ctg tcc ccc aat ctg ctg caa aag acc acg atc cag              2301
Asn Ile Phe Leu Leu Ser Pro Asn Leu Leu Gln Lys Thr Thr Ile Gln
                515                 520                 525 gtg ctg ctc gac ccc atg gtg aag gag gaa aac tca gaa gag atc gac              2349
Val Leu Leu Asp Pro Met Val Lys Glu Glu Asn Ser Glu Glu Ile Asp
530                 535                 540                 545 ttc atc ctg ccg ttc ctt aag ctg agt tca ctg gga ggc gtg aac tcc              2397
Phe Ile Leu Pro Phe Leu Lys Leu Ser Ser Leu Gly Gly Val Asn Ser
                550                 555                 560 ctt ggc gtg tcc tcg ctg gag cac atc act cac tca ctg ctg ggc cgg              2445
Leu Gly Val Ser Ser Leu Glu His Ile Thr His Ser Leu Leu Gly Arg
                565                 570                 575 cct ctg agc aga cag ctt atg agc ttg gtc gcc gga ctc aga aac ggt              2493
Pro Leu Ser Arg Gln Leu Met Ser Leu Val Ala Gly Leu Arg Asn Gly
                580                 585                 590 gcc ctc ctg ctc acc ggc ggc aag gga tcg gga aag tcc acc ctc gct              2541
Ala Leu Leu Leu Thr Gly Gly Lys Gly Ser Gly Lys Ser Thr Leu Ala
595                 600                 605 aag gcc att tgc aaa gag gca ttc gat aag ctg gac gcc cat gtg gag              2589
Lys Ala Ile Cys Lys Glu Ala Phe Asp Lys Leu Asp Ala His Val Glu
610                 615                 620                 625 cgg gtg gac tgt aag gcc ctc cgc gga aag cga ttg gaa aat att caa              2637
Arg Val Asp Cys Lys Ala Leu Arg Gly Lys Arg Leu Glu Asn Ile Gln
                630                 635                 640 aag act ctc gaa gtc gcc ttt tcc gaa gcc gtc tgg atg cag ccc tcg              2685
Lys Thr Leu Glu Val Ala Phe Ser Glu Ala Val Trp Met Gln Pro Ser
                645                 650                 655 gtc gtc ctg ctc gac gat ctg gac ctc atc gct ggg ctg ccg gcc gtg              2733
Val Val Leu Leu Asp Asp Leu Asp Leu Ile Ala Gly Leu Pro Ala Val
                660                 665                 670 ccg gag cat gaa cac tcc cct gac gcg gtc cag tcg caa cgg ctc gcc              2781
Pro Glu His Glu His Ser Pro Asp Ala Val Gln Ser Gln Arg Leu Ala
675                 680                 685 cac gcc ctg aac gat atg att aag gaa ttc atc tca atg gga tca ctg              2829
His Ala Leu Asn Asp Met Ile Lys Glu Phe Ile Ser Met Gly Ser Leu
690                 695                 700                 705 gtg gcc ctg atc gcg act tcc cag agc cag cag tcc ctg cac cct ctg              2877
Val Ala Leu Ile Ala Thr Ser Gln Ser Gln Gln Ser Leu His Pro Leu
                710                 715                 720 ctg gtg tcg gcc cag ggc gtg cac att ttt cag tgt gtg caa cac atc              2925
Leu Val Ser Ala Gln Gly Val His Ile Phe Gln Cys Val Gln His Ile
                725                 730                 735 cag ccg ccc aac cag gag cag cgg tgc gaa atc ctg tgc aac gtg att              2973
Gln Pro Pro Asn Gln Glu Gln Arg Cys Glu Ile Leu Cys Asn Val Ile
                740                 745                 750 aag aac aag ctg gac tgc gat atc aac aag ttt acc gac ctt gat ctc              3021
Lys Asn Lys Leu Asp Cys Asp Ile Asn Lys Phe Thr Asp Leu Asp Leu
                755                 760                 765
```

```
                                              -continued
caa cat gtg gct aag gag act ggg ggc ttc gtg gct cgg gac ttc aca    3069
Gln His Val Ala Lys Glu Thr Gly Gly Phe Val Ala Arg Asp Phe Thr
770             775                 780                 785 gtg ttg gtg gac cgg gca att cac tcc aga ctg tcc cgc cag agc att    3117
Val Leu Val Asp Arg Ala Ile His Ser Arg Leu Ser Arg Gln Ser Ile
            790                 795                 800 tcc acc cgc gaa aaa ctg gtc ctg acc acc ctc gac ttc cag aag gcc    3165
Ser Thr Arg Glu Lys Leu Val Leu Thr Thr Leu Asp Phe Gln Lys Ala
        805                 810                 815 ctc aga ggc ttc ctt cct gcg agc ctc aga tcc gtc aac ctt cac aag    3213
Leu Arg Gly Phe Leu Pro Ala Ser Leu Arg Ser Val Asn Leu His Lys
    820                 825                 830 ccg cgg gac ctt ggc tgg gac aag atc ggt ggg ctc cac gag gtg cgg    3261
Pro Arg Asp Leu Gly Trp Asp Lys Ile Gly Gly Leu His Glu Val Arg
835                 840                 845 cag atc ctc atg gac acc att cag ctg cct gca aag tac ccc gag ctg    3309
Gln Ile Leu Met Asp Thr Ile Gln Leu Pro Ala Lys Tyr Pro Glu Leu
850             855                 860                 865 ttc gcc aac ttg ccg att cgc cag cgc acg gga atc ctg ctc tac ggc    3357
Phe Ala Asn Leu Pro Ile Arg Gln Arg Thr Gly Ile Leu Leu Tyr Gly
            870                 875                 880 ccc ccg ggc acc gga aag acc ctg ctg gcc ggt gtg atc gcc cgg gaa    3405
Pro Pro Gly Thr Gly Lys Thr Leu Leu Ala Gly Val Ile Ala Arg Glu
        885                 890                 895 tcg agg atg aac ttc atc tcc gtg aag gga ccc gaa ctc ctg tcc aag    3453
Ser Arg Met Asn Phe Ile Ser Val Lys Gly Pro Glu Leu Leu Ser Lys
    900                 905                 910 tac atc ggt gcc tcc gaa cag gcc gtg cgc gat ata ttc att agg gcc    3501
Tyr Ile Gly Ala Ser Glu Gln Ala Val Arg Asp Ile Phe Ile Arg Ala
915                 920                 925 cag gcc gcg aag ccc tgc att ctg ttc ttc gac gag ttt gaa tcg atc    3549
Gln Ala Ala Lys Pro Cys Ile Leu Phe Phe Asp Glu Phe Glu Ser Ile
930             935                 940                 945 gcg ccc cgg agg ggc cac gac aac acg gga gtg acc gac cgg gtg gtg    3597
Ala Pro Arg Arg Gly His Asp Asn Thr Gly Val Thr Asp Arg Val Val
            950                 955                 960 aac cag ctg ctc acc caa ctg gat ggc gtg gaa ggc ctt cag gga gtg    3645
Asn Gln Leu Leu Thr Gln Leu Asp Gly Val Glu Gly Leu Gln Gly Val
        965                 970                 975 tac gtg ctg gcg gct acc tcc aga ccg gac ctg atc gat ccg gcc ctg    3693
Tyr Val Leu Ala Ala Thr Ser Arg Pro Asp Leu Ile Asp Pro Ala Leu
    980                 985                 990 ctg cgc ccc ggg aga ctg gac aag tgc gtg tat tgc cct ccc cct gac    3741
Leu Arg Pro Gly Arg Leu Asp Lys Cys Val Tyr Cys Pro Pro Pro Asp
995                 1000                1005 cag gtg tca agg ttg gaa atc ctc aac gtg ctc tcg gac tcc ctg        3786
Gln Val Ser Arg Leu Glu Ile Leu Asn Val Leu Ser Asp Ser Leu
1010                1015                1020 cca ctg gca gat gat gtg gac ctc cag cat gtg gcc tcc gtg act        3831
Pro Leu Ala Asp Asp Val Asp Leu Gln His Val Ala Ser Val Thr
1025                1030                1035 gac agc ttc aca gga gcc gat ctg aag gcc ctg ctt tac aac gcc        3876
Asp Ser Phe Thr Gly Ala Asp Leu Lys Ala Leu Leu Tyr Asn Ala
1040                1045                1050 cag ttg gag gcg ctg cac ggt atg ctg ctg tcc tcc ggt ctg cag        3921
Gln Leu Glu Ala Leu His Gly Met Leu Leu Ser Ser Gly Leu Gln
1055                1060                1065 gat ggc tcc tcc tct tcc gat agc gac ctg tcg ctg agc agc atg        3966
Asp Gly Ser Ser Ser Ser Asp Ser Asp Leu Ser Leu Ser Ser Met
1070                1075                1080
```

| | | | | | | | | | | |
|---|---|---|---|---|---|---|---|---|---|---|
| gtg | ttc | ctg | aac | cat | tcc | agc | ggc | tcc | gat | gac | agc | gcg | ggc | gac | 4011 |
| Val | Phe | Leu | Asn | His | Ser | Ser | Gly | Ser | Asp | Asp | Ser | Ala | Gly | Asp | |
| 1085 | | | | | 1090 | | | | | 1095 | | | | | |

```
gtg ttc ctg aac cat tcc agc ggc tcc gat gac agc gcg ggc gac      4011
Val Phe Leu Asn His Ser Ser Gly Ser Asp Asp Ser Ala Gly Asp
1085                 1090                1095 gga gaa tgt gga ctg gat caa tcc ctg gtg tcc ctg gag atg agc      4056
Gly Glu Cys Gly Leu Asp Gln Ser Leu Val Ser Leu Glu Met Ser
1100                 1105                1110 gag att ctg cca gac gag tcc aag ttc aac atg tac agg ctg tac      4101
Glu Ile Leu Pro Asp Glu Ser Lys Phe Asn Met Tyr Arg Leu Tyr
1115                 1120                1125 ttc ggc agc agc tac gag tcc gag ctg gga aat ggt acc tcg tcc      4146
Phe Gly Ser Ser Tyr Glu Ser Glu Leu Gly Asn Gly Thr Ser Ser
1130                 1135                1140 gac ctg tca agc cag tgc ctg tcc gcg cct tcc tcc atg acc cag      4191
Asp Leu Ser Ser Gln Cys Leu Ser Ala Pro Ser Ser Met Thr Gln
1145                 1150                1155 gac ctc cct gga gtg cca ggg aag gat cag ctg ttc agc cag cct      4236
Asp Leu Pro Gly Val Pro Gly Lys Asp Gln Leu Phe Ser Gln Pro
1160                 1165                1170 ccc gtg ctg cgc act gcg agc cag gaa ggg tgc cag gaa ttg acc      4281
Pro Val Leu Arg Thr Ala Ser Gln Glu Gly Cys Gln Glu Leu Thr
1175                 1180                1185 caa gag cag cgg gac caa ctg cgc gcg gac att tcg atc atc aaa      4326
Gln Glu Gln Arg Asp Gln Leu Arg Ala Asp Ile Ser Ile Ile Lys
1190                 1195                1200 ggc aga tac cgc tcc caa tcc ggg gag gac gaa agc atg aac cag      4371
Gly Arg Tyr Arg Ser Gln Ser Gly Glu Asp Glu Ser Met Asn Gln
1205                 1210                1215 ccc ggg cct atc aag act aga ctg gca atc tcc caa agc cac ctg      4416
Pro Gly Pro Ile Lys Thr Arg Leu Ala Ile Ser Gln Ser His Leu
1220                 1225                1230 atg acc gca ctg gga cac acc cgg ccc tcg atc tcg gag gac gac      4461
Met Thr Ala Leu Gly His Thr Arg Pro Ser Ile Ser Glu Asp Asp
1235                 1240                1245 tgg aag aac ttc gct gag ctg tac gaa tcc ttc cag aat ccg aag      4506
Trp Lys Asn Phe Ala Glu Leu Tyr Glu Ser Phe Gln Asn Pro Lys
1250                 1255                1260 cgg aga aag aac cag agc gga act atg ttc cgg ccc gga cag aag      4551
Arg Arg Lys Asn Gln Ser Gly Thr Met Phe Arg Pro Gly Gln Lys
1265                 1270                1275 gtg acc ctg gcc tga agtactgcgg atcctgcaga tctgcctcga ctgtgccttc  4606
Val Thr Leu Ala
1280 tagttgccag ccatctgttg tttgcccctc cccgtgcct tccttgaccc tggaaggtgc   4666 cactcccact gtcctttcct aataaaatga ggaaattgca tcgcattgtc tgagtaggtg  4726 tcattctatt ctgggggggtg gggtggggca ggacagcaag ggggaggatt gggaagacaa  4786 tagcaggcat gctggggact cgagttctac gtagataagt agcatggcgg gttaatcatt  4846 aactacaagg aaccctagt gatggagttg gccactccct ctctgcgcgc tcgctcgctc   4906 actgaggccg ggcgaccaaa ggtcgcccga cgcccgggct tgcccgggc ggcctcagtg    4966 agcgagcgag cgcgcag                                                 4983

<210> SEQ ID NO 7
<211> LENGTH: 1283
<212> TYPE: PRT
<213> ORGANISM: Artificial Sequence
<220> FEATURE:
<223> OTHER INFORMATION: Synthetic Construct
```

<400> SEQUENCE: 7

```
Met Trp Gly Ser Asp Arg Leu Ala Gly Ala Gly Gly Gly Ala Ala
1               5                   10                  15

Val Thr Val Ala Phe Thr Asn Ala Arg Asp Cys Phe Leu His Leu Pro
            20                  25                  30

Arg Arg Leu Val Ala Gln Leu His Leu Leu Gln Asn Gln Ala Ile Glu
            35                  40                  45

Val Val Trp Ser His Gln Pro Ala Phe Leu Ser Trp Val Glu Gly Arg
    50                  55                  60

His Phe Ser Asp Gln Gly Glu Asn Val Ala Glu Ile Asn Arg Gln Val
65                  70                  75                  80

Gly Gln Lys Leu Gly Leu Ser Asn Gly Gly Gln Val Phe Leu Lys Pro
                85                  90                  95

Cys Ser His Val Val Ser Cys Gln Gln Val Glu Val Glu Pro Leu Ser
            100                 105                 110

Ala Asp Asp Trp Glu Ile Leu Glu Leu His Ala Val Ser Leu Glu Gln
            115                 120                 125

His Leu Leu Asp Gln Ile Arg Ile Val Phe Pro Lys Ala Ile Phe Pro
            130                 135                 140

Val Trp Val Asp Gln Gln Thr Tyr Ile Phe Ile Gln Ile Val Ala Leu
145                 150                 155                 160

Ile Pro Ala Ala Ser Tyr Gly Arg Leu Glu Thr Asp Thr Lys Leu Leu
                165                 170                 175

Ile Gln Pro Lys Thr Arg Arg Ala Lys Glu Asn Thr Phe Ser Lys Ala
            180                 185                 190

Asp Ala Glu Tyr Lys Lys Leu His Ser Tyr Gly Arg Asp Gln Lys Gly
            195                 200                 205

Met Met Lys Glu Leu Gln Thr Lys Gln Leu Gln Ser Asn Thr Val Gly
            210                 215                 220

Ile Thr Glu Ser Asn Glu Asn Glu Ser Glu Ile Pro Val Asp Ser Ser
225                 230                 235                 240

Ser Val Ala Ser Leu Trp Thr Met Ile Gly Ser Ile Phe Ser Phe Gln
                245                 250                 255

Ser Glu Lys Lys Gln Glu Thr Ser Trp Gly Leu Thr Glu Ile Asn Ala
            260                 265                 270

Phe Lys Asn Met Gln Ser Lys Val Val Pro Leu Asp Asn Ile Phe Arg
            275                 280                 285

Val Cys Lys Ser Gln Pro Pro Ser Ile Tyr Asn Ala Ser Ala Thr Ser
            290                 295                 300

Val Phe His Lys His Cys Ala Ile His Val Phe Pro Trp Asp Gln Glu
305                 310                 315                 320

Tyr Phe Asp Val Glu Pro Ser Phe Thr Val Thr Tyr Gly Lys Leu Val
                325                 330                 335

Lys Leu Leu Ser Pro Lys Gln Gln Ser Lys Thr Lys Gln Asn Val
            340                 345                 350

Leu Ser Pro Glu Lys Glu Lys Gln Met Ser Glu Pro Leu Asp Gln Lys
            355                 360                 365

Lys Ile Arg Ser Asp His Asn Glu Glu Asp Glu Lys Ala Cys Val Leu
            370                 375                 380

Gln Val Val Trp Asn Gly Leu Glu Glu Leu Asn Asn Ala Ile Lys Tyr
385                 390                 395                 400

Thr Lys Asn Val Glu Val Leu His Leu Gly Lys Val Trp Ile Pro Asp
                405                 410                 415
```

-continued

```
Asp Leu Arg Lys Arg Leu Asn Ile Glu Met His Ala Val Val Arg Ile
            420                 425                 430

Thr Pro Val Glu Val Thr Pro Lys Ile Pro Arg Ser Leu Lys Leu Gln
            435                 440                 445

Pro Arg Glu Asn Leu Pro Lys Asp Ile Ser Glu Asp Ile Lys Thr
450                 455                 460

Val Phe Tyr Ser Trp Leu Gln Gln Ser Thr Thr Thr Met Leu Pro Leu
465                 470                 475                 480

Val Ile Ser Glu Glu Glu Phe Ile Lys Leu Glu Thr Lys Asp Gly Leu
                485                 490                 495

Lys Glu Phe Ser Leu Ser Ile Val His Ser Trp Glu Lys Glu Lys Asp
            500                 505                 510

Lys Asn Ile Phe Leu Leu Ser Pro Asn Leu Leu Gln Lys Thr Thr Ile
            515                 520                 525

Gln Val Leu Leu Asp Pro Met Val Lys Glu Glu Asn Ser Glu Glu Ile
            530                 535                 540

Asp Phe Ile Leu Pro Phe Leu Lys Leu Ser Ser Leu Gly Gly Val Asn
545                 550                 555                 560

Ser Leu Gly Val Ser Ser Leu Glu His Ile Thr His Ser Leu Leu Gly
                565                 570                 575

Arg Pro Leu Ser Arg Gln Leu Met Ser Leu Val Ala Gly Leu Arg Asn
            580                 585                 590

Gly Ala Leu Leu Leu Thr Gly Gly Lys Gly Ser Gly Lys Ser Thr Leu
                595                 600                 605

Ala Lys Ala Ile Cys Lys Glu Ala Phe Asp Lys Leu Asp Ala His Val
            610                 615                 620

Glu Arg Val Asp Cys Lys Ala Leu Arg Gly Lys Arg Leu Glu Asn Ile
625                 630                 635                 640

Gln Lys Thr Leu Glu Val Ala Phe Ser Glu Ala Val Trp Met Gln Pro
                645                 650                 655

Ser Val Val Leu Leu Asp Asp Leu Asp Leu Ile Ala Gly Leu Pro Ala
            660                 665                 670

Val Pro Glu His Glu His Ser Pro Asp Ala Val Gln Ser Gln Arg Leu
            675                 680                 685

Ala His Ala Leu Asn Asp Met Ile Lys Glu Phe Ile Ser Met Gly Ser
690                 695                 700

Leu Val Ala Leu Ile Ala Thr Ser Gln Ser Gln Gln Ser Leu His Pro
705                 710                 715                 720

Leu Leu Val Ser Ala Gln Gly Val His Ile Phe Gln Cys Val Gln His
                725                 730                 735

Ile Gln Pro Pro Asn Gln Glu Gln Arg Cys Glu Ile Leu Cys Asn Val
            740                 745                 750

Ile Lys Asn Lys Leu Asp Cys Asp Ile Asn Lys Phe Thr Asp Leu Asp
            755                 760                 765

Leu Gln His Val Ala Lys Glu Thr Gly Gly Phe Val Ala Arg Asp Phe
            770                 775                 780

Thr Val Leu Val Asp Arg Ala Ile His Ser Arg Leu Ser Arg Gln Ser
785                 790                 795                 800

Ile Ser Thr Arg Glu Lys Leu Val Leu Thr Thr Leu Asp Phe Gln Lys
                805                 810                 815

Ala Leu Arg Gly Phe Leu Pro Ala Ser Leu Arg Ser Val Asn Leu His
            820                 825                 830
```

```
Lys Pro Arg Asp Leu Gly Trp Asp Lys Ile Gly Gly Leu His Glu Val
        835                 840                 845

Arg Gln Ile Leu Met Asp Thr Ile Gln Leu Pro Ala Lys Tyr Pro Glu
    850                 855                 860

Leu Phe Ala Asn Leu Pro Ile Arg Gln Arg Thr Gly Ile Leu Leu Tyr
865                 870                 875                 880

Gly Pro Pro Gly Thr Gly Lys Thr Leu Leu Ala Gly Val Ile Ala Arg
                885                 890                 895

Glu Ser Arg Met Asn Phe Ile Ser Val Lys Gly Pro Glu Leu Leu Ser
            900                 905                 910

Lys Tyr Ile Gly Ala Ser Glu Gln Ala Val Arg Asp Ile Phe Ile Arg
        915                 920                 925

Ala Gln Ala Ala Lys Pro Cys Ile Leu Phe Phe Asp Glu Phe Glu Ser
    930                 935                 940

Ile Ala Pro Arg Arg Gly His Asp Asn Thr Gly Val Thr Asp Arg Val
945                 950                 955                 960

Val Asn Gln Leu Leu Thr Gln Leu Asp Gly Val Glu Gly Leu Gln Gly
                965                 970                 975

Val Tyr Val Leu Ala Ala Thr Ser Arg Pro Asp Leu Ile Asp Pro Ala
            980                 985                 990

Leu Leu Arg Pro Gly Arg Leu Asp  Lys Cys Val Tyr Cys  Pro Pro Pro
            995                 1000                1005

Asp Gln  Val Ser Arg Leu Glu  Ile Leu Asn Val Leu  Ser Asp Ser
    1010                1015                1020

Leu Pro  Leu Ala Asp Asp Val  Asp Leu Gln His Val  Ala Ser Val
    1025                1030                1035

Thr Asp  Ser Phe Thr Gly Ala  Asp Leu Lys Ala Leu  Leu Tyr Asn
    1040                1045                1050

Ala Gln  Leu Glu Ala Leu His  Gly Met Leu Leu Ser  Ser Gly Leu
    1055                1060                1065

Gln Asp  Gly Ser Ser Ser Ser  Asp Ser Asp Leu Ser  Leu Ser Ser
    1070                1075                1080

Met Val  Phe Leu Asn His Ser  Ser Gly Ser Asp Asp  Ser Ala Gly
    1085                1090                1095

Asp Gly  Glu Cys Gly Leu Asp  Gln Ser Leu Val Ser  Leu Glu Met
    1100                1105                1110

Ser Glu  Ile Leu Pro Asp Glu  Ser Lys Phe Asn Met  Tyr Arg Leu
    1115                1120                1125

Tyr Phe  Gly Ser Ser Tyr Glu  Ser Glu Leu Gly Asn  Gly Thr Ser
    1130                1135                1140

Ser Asp  Leu Ser Ser Gln Cys  Leu Ser Ala Pro Ser  Ser Met Thr
    1145                1150                1155

Gln Asp  Leu Pro Gly Val Pro  Gly Lys Asp Gln Leu  Phe Ser Gln
    1160                1165                1170

Pro Pro  Val Leu Arg Thr Ala  Ser Gln Glu Gly Cys  Gln Glu Leu
    1175                1180                1185

Thr Gln  Glu Gln Arg Asp Gln  Leu Arg Ala Asp Ile  Ser Ile Ile
    1190                1195                1200

Lys Gly  Arg Tyr Arg Ser Gln  Ser Gly Glu Asp Glu  Ser Met Asn
    1205                1210                1215

Gln Pro  Gly Pro Ile Lys Thr  Arg Leu Ala Ile Ser  Gln Ser His
    1220                1225                1230

Leu Met  Thr Ala Leu Gly His  Thr Arg Pro Ser Ile  Ser Glu Asp
```

Asp Trp Lys Asn Phe Ala Glu Leu Tyr Glu Ser Phe Gln Asn Pro
    1250                1255                1260

Lys Arg Arg Lys Asn Gln Ser Gly Thr Met Phe Arg Pro Gly Gln
    1265                1270                1275

Lys Val Thr Leu Ala
    1280

<210> SEQ ID NO 8
<211> LENGTH: 4947
<212> TYPE: DNA
<213> ORGANISM: Artificial Sequence
<220> FEATURE:
<223> OTHER INFORMATION: hRK1.hPEX1
<220> FEATURE:
<221> NAME/KEY: repeat_region
<222> LOCATION: (1)..(130)
<223> OTHER INFORMATION: 5' ITR
<220> FEATURE:
<221> NAME/KEY: misc_feature
<222> LOCATION: (113)..(130)
<223> OTHER INFORMATION: ITR D Segment
<220> FEATURE:
<221> NAME/KEY: promoter
<222> LOCATION: (175)..(684)
<223> OTHER INFORMATION: hRK1 promoter
<220> FEATURE:
<221> NAME/KEY: misc_feature
<222> LOCATION: (691)..(699)
<223> OTHER INFORMATION: Kozak
<220> FEATURE:
<221> NAME/KEY: misc_feature
<222> LOCATION: (700)..(4551)
<223> OTHER INFORMATION: codon-optimized human PEX1
<220> FEATURE:
<221> NAME/KEY: polyA_signal
<222> LOCATION: (4573)..(4684)
<223> OTHER INFORMATION: bovine growth hormone (bGH) polyadenylation
      (poly(A)) signal
<220> FEATURE:
<221> NAME/KEY: repeat_region
<222> LOCATION: (4818)..(4947)
<223> OTHER INFORMATION: 3' ITR
<220> FEATURE:
<221> NAME/KEY: misc_feature
<222> LOCATION: (4818)..(4835)
<223> OTHER INFORMATION: ITR D segment

<400> SEQUENCE: 8
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gcaagctagc    180
aagatccaag ctcagatctc gatcgagttg ggccccagaa gcctggtggt tgtttgtcct    240
tctcagggga aaagtgaggc ggccccttgg aggaagggggc cgggcagaat gatctaatcg    300
gattccaagc agctcagggg attgtctttt tctagcacct tcttgccact cctaagcgtc    360
ctccgtgacc ccggctggga tttagcctgg tgctgtgtca gccccggtct cccagggggct    420 tcccagtggt ccccaggaac cctcgacagg gcccggtctc tctcgtccag caagggcagg    480
gacgggccac aggccaaggg ccctcgatcg aggaactgaa aaaccagaaa gttaactggt    540
aagtttagtc tttttgtctt ttatttcagg tcccggatcc ggtggtggtg caaatcaaag    600
aactgctcct cagtggatgt tgcctttact tctaggcctg tacgaagtg ttacttctgc    660 tctaaaagct gcggaattgt acccgcggcc gcgccacca tgtggggaag cgacagactg    720
gccggagctg gagggggagg agcagccgtc accgtggcgt tcactaacgc gcgggactgc    780

-continued

```
tttctccatc tgccgcggag gctggtcgcc cagctgcacc tcctgcagaa ccaggccatc      840
gaggtggtgt ggtcccacca accggccttt ttgagctggg tcgagggaag gcacttttcg      900
gaccagggag aaaatgtggc ggagatcaac cgccaggtcg ccagaagct gggactgtcc       960 aacggcggac aggtgttcct caagccgtgc agccacgtgg tgtcctgcca acaggtggaa     1020
gtggagccgc tctccgccga cgactgggag atcctcgaat tgcatgccgt gagcctcgaa     1080
cagcatctgt tggaccagat tcgcattgtg ttcccgaagg ccatattccc cgtgtgggtc     1140
gatcagcaga cctatatctt catccagatt gtggccctca tcccggccgc ctcatacgga     1200
cggctggaaa ctgacaccaa gctgctgatt caacctaaga cccggagggc aaagaaaaac     1260
accttctcca aggccgacgc tgagtacaag aagctccact cctacggacg ggaccagaag     1320
gggatgatga aggagctgca aaccaagcag ctccagagca caccgtgggg gatcaccgag     1380
tccaatgaaa acgagtcgga aatcccagtc gattcatctt ccgtggccag cctgtggact     1440
atgatcggtt ccattttctc gttccaatct gagaagaagc aggaaactag ctgggggctg     1500
actgagatca acgccttcaa gaacatgcag tccaaagtgg tgcctctgga taacatcttt     1560
cgcgtgtgca gtcccaacc gccctcaatc tacaacgcgt ccgctacctc cgtgtttcat     1620
aagcactgtg ccatccacgt gttcccatgg gatcaggaat acttcgatgt cgaaccttcc     1680
ttcaccgtga cttacgggaa gcttgtcaag ctcctcagcc ccaagcagca gcaatcgaaa     1740
actaagcaga acgtgctttc cccggagaag gagaagcaaa tgtcagaacc actcgaccag     1800
aagaaaatca gatcggatca taacgaagag gacgagaagg cctgcgtcct tcaggtggtc     1860
tggaacggcc tggaggagct gaacaacgcg attaagtaca ccaagaacgt cgaggtcctt     1920
cacctgggaa aggtgtggat tccggatgat ctgaggaaac gcctcaacat cgaaatgcac     1980
gctgtggtgc ggattacccc ggtcgaggtc accccaaaga tccctcgctc cttgaagctg     2040
cagccgcgag aaaacttgcc caaggacatt tctgaagagg atatcaagac tgtgttctac     2100
tcctggctgc aacagagcac taccaccatg ctccctctgg tcatttcgga ggaagaattc     2160
atcaaactgg aaaccaagga cggactgaaa gaattctccc tgtccatcgt gcactcctgg     2220
gaaaaggaga aggacaagaa tatcttcctg ctgtcccca atctgctgca aaagaccacg     2280
atccaggtgc tgctcgaccc catggtgaag gaggaaaact cagaagagat cgacttcatc     2340
ctgccgttcc ttaagctgag ttcactggga ggcgtgaact cccttggcgt gtcctcgctg     2400
gagcacatca ctcactcact gctgggccgg cctctgagca gacagcttat gagcttggtc     2460
gccggactca gaaacggtgc cctcctgctc accggcggca agggatcggg aaagtccacc     2520
ctcgctaagg ccatttgcaa agaggcattc gataagctgg acgcccatgt ggagcgggtg     2580
gactgtaagg ccctccgcgg aaagcgattg gaaaatattc aaaagactct cgaagtcgcc     2640
ttttccgaag ccgtctggat gcagccctcg gtcgtcctgc tcgacgatct ggacctcatc     2700
gctgggctgc cggccgtgcc ggagcatgaa cactcccctg acgcggtcca gtcgcaacgg     2760
ctcgcccacg ccctgaacga tatgattaag gaattcatct caatgggatc actggtggcc     2820
ctgatcgcga cttcccagag ccagcagtcc ctgcaccctc tgctggtgtc ggcccagggc     2880
gtgcacattt tcagtgtgt gcaacacatc cagccgccca accaggagca gcggtgcgaa     2940
atcctgtgca acgtgattaa gaacaagctg gactgcgata tcaacaagtt taccgacctt     3000
gatctccaac atgtggctaa ggagactggg ggcttcgtgg ctcgggactt cacagtgttg     3060
gtggaccggg caattcactc cagactgtcc cgccagagca tttccacccg cgaaaaactg     3120
```

```
gtcctgacca ccctcgactt ccagaaggcc ctcagaggct tccttcctgc gagcctcaga    3180
tccgtcaacc ttcacaagcc gcgggacctt ggctgggaca agatcggtgg gctccacgag    3240
gtgcggcaga tcctcatgga caccattcag ctgcctgcaa agtaccccga gctgttcgcc    3300
aacttgccga ttcgccagcg cacgggaatc ctgctctacg gccccccggg caccggaaag    3360
accctgctgg ccggtgtgat cgcccgggaa tcgaggatga acttcatctc cgtgaaggga    3420
cccgaactcc tgtccaagta catcggtgcc tccaacagg ccgtgcgcga tatattcatt    3480
agggcccagg ccgcgaagcc ctgcattctg ttcttcgacg agtttgaatc gatcgcgccc    3540
cggaggggcc acgacaacac gggagtgacc gaccgggtgg tgaaccagct gctcacccaa    3600
ctggatggcg tggaaggcct tcagggagtg tacgtgctgg cggctacctc cagaccggac    3660
ctgatcgatc cggccctgct gcgccccggg agactggaca agtgcgtgta ttgccctccc    3720
cctgaccagg tgtcaaggtt ggaaatcctc aacgtgctct cggactccct gccactggca    3780
gatgatgtgg acctccagca tgtggcctcc gtgactgaca gcttcacagg agccgatctg    3840
aaggccctgc tttacaacgc ccagttggag gcgctgcacg gtatgctgct gtcctccggt    3900
ctgcaggatg gctcctcctc ttccgatagc gacctgtcgc tgagcagcat ggtgttcctg    3960
aaccattcca gcggctccga tgacagcgcg ggcgacggag aatgtggact ggatcaatcc    4020
ctggtgtccc tggagatgag cgagattctg ccagacgagt ccaagttcaa catgtacagg    4080
ctgtacttcg gcagcagcta cgagtccgag ctggaaatg gtacctcgtc cgacctgtca    4140
agccagtgcc tgtccgcgcc ttcctccatg acccaggacc tccctggagt gccagggaag    4200
gatcagctgt tcagccagcc tcccgtgctg cgcactgcga gccaggaagg gtgccaggaa    4260
ttgacccaag agcagcggga ccaactgcgc gcggacattt cgatcatcaa aggcagatac    4320
cgctcccaat ccggggagga cgaaagcatg aaccagcccg ggcctatcaa gactagactg    4380
gcaatctccc aaagccacct gatgaccgca ctgggacaca cccggccctc gatctcggag    4440
gacgactgga gaacttcgc tgagctgtac gaatccttcc agaatccgaa gcggagaaag    4500
aaccagagcg gaactatgtt ccggcccgga cagaaggtga ccctggcctg atgtacaagt    4560
aataagcctc gactgtgcct tctagttgcc agccatctgt tgtttgcccc tcccccgtgc    4620
cttccttgac cctggaaggt gccactccca ctgtcctttc ctaataaaat gaggaaattg    4680
catcgcattg tctgagtagg tgtcattcta ttctgggggg tggggtgggg caggacagca    4740
agggggagga ttgggaagac aatagcaggt cgagttctac gtagataagt agcatggcgg    4800
gttaatcatt aactacaagg aaccctagt gatggagttg gccactccct ctctgcgcgc    4860
tcgctcgctc actgaggccg ggcgaccaaa ggtcgcccga cgcccgggct ttgcccgggc    4920
ggcctcagtg agcgagcgag cgcgcag                                        4947
```

<210> SEQ ID NO 9
<211> LENGTH: 13990
<212> TYPE: DNA
<213> ORGANISM: Artificial Sequence
<220> FEATURE:
<223> OTHER INFORMATION: pAAV.CAG.copt.hPEX1
<220> FEATURE:
<221> NAME/KEY: misc_feature
<222> LOCATION: (1253)..(7390)
<223> OTHER INFORMATION: AAV expression cassette
<220> FEATURE:
<221> NAME/KEY: misc_feature
<222> LOCATION: (1253)..(1382)
<223> OTHER INFORMATION: 5' ITR
<220> FEATURE:
<221> NAME/KEY: enhancer

```
<222> LOCATION: (1493)..(1796)
<223> OTHER INFORMATION: CMV enhancer
<220> FEATURE:
<221> NAME/KEY: promoter
<222> LOCATION: (1798)..(2075)
<223> OTHER INFORMATION: CBA promoter
<220> FEATURE:
<221> NAME/KEY: Intron
<222> LOCATION: (2076)..(3104)
<223> OTHER INFORMATION: Chimeric intron
<220> FEATURE:
<221> NAME/KEY: misc_feature
<222> LOCATION: (3113)..(3121)
<223> OTHER INFORMATION: Kozak
<220> FEATURE:
<221> NAME/KEY: misc_feature
<222> LOCATION: (3122)..(6973)
<223> OTHER INFORMATION: codon optimized hPEX1
<220> FEATURE:
<221> NAME/KEY: polyA_signal
<222> LOCATION: (7004)..(7211)
<223> OTHER INFORMATION: bGH poly(A)
<220> FEATURE:
<221> NAME/KEY: misc_feature
<222> LOCATION: (7261)..(7390)
<223> OTHER INFORMATION: 3' ITR

<400> SEQUENCE: 9
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga atcaccatg agtgacgact      240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
ataggggtca gtgttacaac caattaacca attctgaaca ttatcgcgag cccatttata     960
cctgaatatg gctcataaca ccccttgttt gcctggcggc agtagcgcgg tggtcccacc    1020 tgacccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttagggggtg tcgcccttat tcgactctat agtgaagttc    1200
ctattctcta gaaagtatag gaacttctga agtggggtcg acttaattaa ggctgcgcgc    1260
tcgctcgctc actgaggccg cccgggcaaa gcccgggcgt cgggcgacct ttggtcgccc    1320
ggcctcagtg agcgagcgag cgcgcagaga gggagtggcc aactccatca ctaggggttc    1380
cttgtagtta atgattaacc cgccatgcta cttatctacg tagcaagcta gctagttatt    1440
aatagtaatc aattacgggg tcattagttc atagcccata tatggagttc cgcgttacat    1500
```

```
aacttacggt aaatggcccg cctggctgac cgcccaacga cccccgccca ttgacgtcaa    1560
taatgacgta tgttcccata gtaacgccaa tagggacttt ccattgacgt caatgggtgg    1620
agtatttacg gtaaactgcc cacttggcag tacatcaagt gtatcatatg ccaagtacgc    1680
cccctattga cgtcaatgac ggtaaatggc ccgcctggca ttatgcccag tacatgacct    1740
tatgggactt tcctacttgg cagtacatct acgtattagt catcgctatt aacatggtcg    1800
aggtgagccc cacgttctgc ttcactctcc ccatctcccc ccctcccca ccccaatttt    1860
tgtatttatt tatttttaa ttattttgtg cagcgatggg ggcggggggg ggggggggc     1920
gcgcgccagg cggggcgggg cggggcgagg ggcggggcgg ggcgaggcgg agaggtgcgg    1980
cggcagccaa tcagagcggc gcgctccgaa agtttccttt tatggcgagg cggcggcggc    2040
ggcggcccta taaaaagcga agcgcgcggc gggcggggag tcgctgcgac gctgccttcg    2100
ccccgtgccc cgctccgccg ccgcctcgcg ccgcccgccc cggtctctgac tgaccgcgtt    2160
actcccacag gtgagcgggc gggacggccc ttctcctccg ggctgtaatt agcgcttggt    2220
ttaatgacgg cttgtttctt ttctgtggct gcgtgaaagc cttgagggc tccgggaggg     2280
cccttttgtgc gggggagcg gctcgggggg tgcgtgcgtg tgtgtgtgcg tggggagcgc    2340
cgcgtgcggc tccgcgctgc ccggcggctg tgagcgctgc gggcgcggcg cggggctttg    2400
tgcgctccgc agtgtgcgcg aggggagcgc ggccgggggc ggtgccccgc ggtgcggggg    2460
gggctgcgag gggaacaaag gctgcgtgcg gggtgtgtgc gtgggggggt gagcagggg     2520
tgtgggcgcg tcggtcgggc tgcaaccccc cctgcacccc cctccccgag ttgctgagca    2580
cggcccggct tcgggtgcgg ggctccgtac ggggcgtggc gcggggctcg ccgtgccggg    2640
cgggggtgg cggcaggtgg gggtgccggg cggggcgggg ccgcctcggg ccggggaggg    2700
ctcggggag gggcgcggcg gccccggag cgccggcggc tgtcgaggcg cggcgagccg      2760
cagccattgc cttttatggt aatcgtgcga gagggcgcag ggacttcctt tgtcccaaat    2820
ctgtgcggag ccgaaatctg ggaggcgccg ccgcacccc tctagcgggc gcggggcgaa     2880
gcggtgcggc gccggcagga aggaaatggg cggggagggc cttcgtgcgt cgccgcgccg    2940
ccgtccccctt ctccctctcc agcctcgggg ctgtccgcgg ggggacggct gccttcgggg   3000
gggacggggc agggcggggt tcggcttctg gcgtgtgacc ggcggctcta gacaattgta    3060
ctaaccttct tctctttcct ctcctgacag gttggtgtac actagcggcc gcgccgccac    3120
catgtgggga agcgacagac tggccggagc tggagggga ggagcagccg tcaccgtggc      3180
gttcactaac gcgcgggact gctttctcca tctgccgcgg aggctggtcg cccagctgca    3240
cctcctgcag aaccaggcca tcgaggtggt gtggtcccac caaccggcct ttttgagctg    3300
ggtcgaggga aggcacttttt cggaccaggg agaaaatgtg gcggagatca accgccaggt    3360
cggccagaag ctgggactgt ccaacggcgg acaggtgttc ctcaagccgt gcagccacgt    3420
ggtgtccctgc caacaggtgg aagtggagcc gctctccgcc gacgactggg agatcctcga    3480
attgcatgcc gtgagcctcg aacagcatct gttggaccag attcgcattg tgttcccgaa    3540
ggccatattc cccgtgtggg tcgatcagca gacctatatc ttcatccaga ttgtggccct    3600
catcccggcc gcctcatacg gacggctgga aactgacacc aagctgctga ttcaacctaa    3660
gacccggagg gccaaagaaa acaccttctc caaggccgac gctgagtaca agaagctcca    3720
ctcctacgga cgggaccaga aggggatgat gaaggagctg caaaccaagc agctccagag    3780
caacaccgtg gggatcaccg agtccaatga aaacgagtcg gaaatcccag tcgattcatc    3840
ttccgtggcc agcctgtgga ctatgatcgg ttccattttc tcgttccaat ctgagaagaa    3900
```

```
gcaggaaact agctgggggc tgactgagat caacgccttc aagaacatgc agtccaaagt   3960
ggtgcctctg gataacatct ttcgcgtgtg caagtcccaa ccgccctcaa tctacaacgc   4020
gtccgctacc tccgtgtttc ataagcactg tgccatccac gtgttcccat gggatcagga   4080
atacttcgat gtcgaacctt ccttcaccgt gacttacggg aagcttgtca agctcctcag   4140
ccccaagcag cagcaatcga aaactaagca gaacgtgctt tccccggaga aggagaagca   4200
aatgtcagaa ccactcgacc agaagaaaat cagatcggat cataacgaag aggacgagaa   4260
ggcctgcgtc cttcaggtgg tctggaacgg cctggaggag ctgaacaacg cgattaagta   4320
caccaagaac gtcgaggtcc ttcacctggg aaaggtgtgg attccggatg atctgaggaa   4380
acgcctcaac atcgaaatgc acgctgtggt gcggattacc ccggtcgagg tcaccccaaa   4440
gatccctcgc tccttgaagc tgcagccgcg agaaaacttg cccaaggaca tttctgaaga   4500
ggatatcaag actgtgttct actcctggct gcaacagagc actaccacca tgctccctct   4560
ggtcatttcg gaggaagaat tcatcaaact ggaaaccaag gacggactga agaattctc   4620
cctgtccatc gtgcactcct gggaaaagga gaaggacaag aatatcttcc tgctgtcccc   4680
caatctgctg caaaagacca cgatccaggt gctgctcgac cccatggtga aggaggaaaa   4740
ctcagaagag atcgacttca tcctgccgtt ccttaagctg agttcactgg gaggcgtgaa   4800
ctcccttggc gtgtcctcgc tggagcacat cactcactca ctgctgggcc ggcctctgag   4860
cagacagctt atgagcttgg tcgccggact cagaaacggt gccctcctgc tcaccggcgg   4920
caagggatcg ggaaagtcca ccctcgctaa ggccatttgc aaagaggcat tcgataagct   4980
ggacgcccat gtggagcggg tggactgtaa ggccctccgc ggaaagcgat ggaaaatat   5040
tcaaaagact ctcgaagtcg ccttttccga agccgtctgg atgcagccct cggtcgtcct   5100
gctcgacgat ctggacctca tcgctgggct gccggccgtg ccggagcatg aacactcccc   5160
tgacgcggtc cagtcgcaac ggctcgccca cgccctgaac gatatgatta aggaattcat   5220
ctcaatggga tcactggtgg ccctgatcgc gacttcccag agccagcagt ccctgcaccc   5280
tctgctggtg tcggcccagg gcgtgcacat ttttcagtgt gtgcaacaca tccagccgcc   5340
caaccaggag cagcggtgcg aaatcctgtg caacgtgatt aagaacaagc tggactgcga   5400
tatcaacaag tttaccgacc ttgatctcca acatgtggct aaggagactg ggggcttcgt   5460
ggctcgggac ttcacagtgt tggtggaccg ggcaattcac tccagactgt cccgccagag   5520
catttccacc cgcgaaaaac tggtcctgac caccctcgac ttccagaagg ccctcagagg   5580
cttccttcct gcgagcctca gatccgtcaa ccttcacaag ccgcgggacc ttggctggga   5640
caagatcggt gggctccacg aggtgcggca gatcctcatg gacaccattc agctgcctgc   5700
aaagtacccc gagctgttcg ccaacttgcc gattcgccag cgcacgggaa tcctgctcta   5760
cggcccccg ggcaccggaa agaccctgct ggccggtgtg atcgcccggg aatcgaggat   5820
gaacttcatc tccgtgaagg acccgaact cctgtccaag tacatcggtg cctccgaaca   5880
ggccgtgcgc gatatattca ttagggccca ggccgcgaag ccctgcattc tgttcttcga   5940
cgagtttgaa tcgatcgcgc cccggagggg ccacgacaac acgggagtga ccgaccgggt   6000
ggtgaaccag ctgctcaccc aactggatgg cgtggaaggc cttcagggag tgtacgtgct   6060
ggcggctacc tccagaccgg acctgatcga tccggccctg ctgcgccccg ggagactgga   6120
caagtgcgtg tattgccctc cccctgacca ggtgtcaagg ttggaaatcc tcaacgtgct   6180
ctcggactcc ctgccactgg cagatgatgt ggacctccag catgtggcct ccgtgactga   6240
```

```
cagcttcaca ggagccgatc tgaaggccct gctttacaac gcccagttgg aggcgctgca   6300
cggtatgctg ctgtcctccg gtctgcagga tggctcctcc tcttccgata gcgacctgtc   6360
gctgagcagc atggtgttcc tgaaccattc cagcggctcc gatgacagcg cgggcgacgg   6420
agaatgtgga ctggatcaat ccctggtgtc cctggagatg agcgagattc tgccagacga   6480
gtccaagttc aacatgtaca ggctgtactt cggcagcagc tacgagtccg agctgggaaa   6540
tggtacctcg tccgacctgt caagccagtg cctgtccgcg ccttcctcca tgacccagga   6600
cctccctgga gtgccaggga aggatcagct gttcagccag cctcccgtgc tgcgcactgc   6660
gagccaggaa gggtgccagg aattgaccca agagcagcgg gaccaactgc gcgcggacat   6720
ttcgatcatc aaaggcagat accgctccca atccggggag gacgaaagca tgaaccagcc   6780
cgggcctatc aagactagac tggcaatctc ccaaagccac ctgatgaccg cactgggaca   6840 caccggccc tcgatctcgg aggacgactg gaagaacttc gctgagctgt acgaatcctt   6900
ccagaatccg aagcggagaa agaaccgag cggaactatg ttccggcccg gacagaaggt   6960
gaccctggcc tgaagtactg cggatcctgc agatctgcct cgactgtgcc ttctagttgc   7020
cagccatctg ttgtttgccc ctccccgtg ccttccttga ccctggaagg tgccactccc   7080
actgtccttt cctaataaaa tgaggaaatt gcatcgcatt gtctgagtag gtgtcattct   7140
attctggggg gtggggtggg gcaggacagc aaggggagg attgggaaga caatagcagg   7200
catgctgggg actcgagttc tacgtagata agtagcatgg cgggttaatc attaactaca   7260
aggaacccct agtgatggag ttggccactc cctctctgcg cgctcgctcg ctcactgagg   7320
ccgggcgacc aaaggtcgcc cgacgcccgg gctttgcccg gcggcctca gtgagcgagc   7380 gagcgcgcag ccttaattaa cctaaggaaa atgaagtgaa gttcctatac tttctagaga   7440
ataggaactt ctatagtgag tcgaataagg gcgacacaaa atttattcta aatgcataat   7500
aaatactgat aacatcttat agtttgtatt atattttgta ttatcgttga catgtataat   7560
tttgatatca aaaactgatt ttcccttat tattttcgag atttatttc ttaattctct   7620 ttaacaaact agaaatattg tatatacaaa aaatcataaa taatagatga atagtttaat   7680
tataggtgtt catcaatcga aaagcaacg tatcttattt aaagtgcgtt gctttttct    7740 catttataag gttaaataat tctcatatat caagcaaagt gacaggcgcc cttaaatatt   7800
ctgacaaatg ctcttcccct aaactccccc cataaaaaa cccgccgaag cgggttttta   7860
cgttatttgc ggattaacga ttactcgtta tcagaaccgc ccagggggcc cgagcttaac   7920 cttttattt ggggggagagg gaagtcatga aaaaactaac ctttgaaatt cgatctccag   7980
cacatcagca aaacgctatt cacgcagtac agcaaatcct tccagaccca accaaaccaa   8040
tcgtagtaac cattcaggaa cgcaaccgca gcttagacca aaacaggaag ctatgggcct   8100
gcttaggtga cgtctctcgt caggttgaat ggcatggtcg ctggctggat gcagaaagct   8160
ggaagtgtgt gttaccgca gcattaaagc agcaggatgt tgttcctaac cttgccggga   8220
atggctttgt ggtaataggc cagtcaacca gcaggatgcg tgtaggcgaa tttgcggagc   8280
tattagagct tatacaggca ttcggtacag agcgtggcgt taagtggtca gacgaagcga   8340
gactggctct ggagtggaaa gcgagatggg gagacagggc tgcatgataa atgtcgttag   8400
tttctccggt ggcaggacgt cagcatattt gctctggcta atggagcaaa agcgacgggc   8460
aggtaaagac gtgcattacg ttttcatgga tacaggttgt gaacatccaa tgacatatcg   8520
gtttgtcagg gaagttgtga agttctggga tataccgctc accgtattgc aggttgatat   8580
caacccggag cttggacagc caaatggtta tacggtatgg gaaccaaagg atattcagac   8640
```

```
gcgaatgcct gttctgaagc catttatcga tatggtaaag aaatatggca ctccatacgt   8700
cggcggcgcg ttctgcactg acagattaaa actcgttccc ttcaccaaat actgtgatga   8760
ccatttcggg cgagggaatt acaccacgtg gattggcatc agagctgatg aaccgaagcg   8820
gctaaagcca aagcctggaa tcagatatct tgctgaactg tcagactttg agaaggaaga   8880
tatcctcgca tggtggaagc aacaaccatt cgatttgcaa ataccggaac atctcggtaa   8940
ctgcatattc tgcattaaaa aatcaacgca aaaaatcgga cttgcctgca agatgagga    9000
gggattgcag cgtgttttta atgaggtcat cacgggatcc catgtgcgtg acggacatcg   9060
ggaaacgcca aaggagatta tgtaccgagg aagaatgtcg ctggacggta tcgcgaaaat   9120
gtattcagaa aatgattatc aagccctgta tcaggacatg gtacgagcta aaagattcga   9180
taccggctct tgttctgagt catgcgaaat atttggaggg cagcttgatt tcgacttcgg   9240
gagggaagct gcatgatgcg atgttatcgg tgcggtgaat gcaagaaga taaccgcttc     9300
cgaccaaatc aaccttactg gaatcgatgg tgtctccggt gtgaaagaac accaacaggg   9360
gtgttaccac taccgcagga aaaggaggac gtgtggcgag acagcgacga agtatcaccg   9420
acataatctg cgaaaactgc aaataccttc aacgaaacg caccagaaat aaacccaagc     9480
caatcccaaa agaatctgac gtaaaaacct tcaactacac ggctcacctg tgggatatcc   9540
ggtggctaag acgtcgtgcg aggaaaacaa ggtgattgac caaatcgaa gttacgaaca     9600
agaaagcgtc gagcgagctt taacgtgcgc taactgcggt cagaagctgc atgtgctgga   9660
agttcacgtg tgtgagcact gctgcgcaga actgatgagc gatccgaata gctcgatgca   9720
cgaggaagaa gatgatggct aaaccagcgc gaagacgatg taaaaacgat gaatgccggg   9780
aatggtttca ccctgcattc gctaatcagt ggtggtgctc tccagagtgt ggaaccaaga   9840
tagcactcga acgacgaagt aaagaacgcg aaaaagcgga aaaagcagca gagaagaaac   9900
gacgacgaga ggagcagaaa cagaaagata aacttaagat tcgaaaactc gccttaaagc   9960
cccgcagtta ctggattaaa caagcccaac aagccgtaaa cgccttcatc agagaaagag   10020
accgcgactt accatgtatc tcgtgcggaa cgctcacgtc tgctcagtgg gatgccggac   10080
attaccggac aactgctgcg gcacctcaac tccgatttaa tgaacgcaat attcacaagc   10140
aatgcgtggt gtgcaaccag cacaaaagcg gaaatctcgt tccgtatcgc gtcgaactga   10200
ttagccgcat cgggcaggaa gcagtagacg aaatcgaatc aaaccataac cgccatcgct   10260
ggactatcga agagtgcaag gcgatcaagg cagagtacca acagaaactc aaagacctgc   10320
gaaatagcag aagtgaggcc gcatgacgtt ctcagtaaaa accattccag acatgctcgt   10380
tgaagcatac ggaaatcaga cagaagtagc acgcagactg aaatgtagtc gcggtacggt   10440
cagaaaatac gttgatgata agacgggaa aatgcacgcc atcgtcaacg acgttctcat    10500
ggttcatcgc ggatggagtg aaagagatgc gctattacga aaaattgat ggcagcaaat     10560
accgaaatat ttgggtagtt ggcgatctgc acggatgcta cacgaacctg atgaacaaac   10620
tggatacgat tggattcgac aacaaaaaag acctgcttat ctcggtgggc gatttggttg   10680
atcgtggtgc agagaacgtt gaatgcctgg aattaatcac attccctgg ttcagagctg     10740
tacgtggaaa ccatgagcaa atgatgattg atggcttatc agagcgtgga aacgttaatc   10800
actggctgct taatggcggt ggctggttct ttaatctcga ttacgacaaa gaaattctgg   10860
ctaaagctct tgcccataaa gcagatgaac ttccgttaat catcgaactg gtgagcaaag   10920
ataaaaaata tgttatctgc cacgccgatt atcccttga cgaatacgag tttggaaagc     10980
```

```
cagttgatca tcagcaggta atctggaacc gcgaacgaat cagcaactca caaaacggga    11040
tcgtgaaaga aatcaaaggc gcggacacgt tcatctttgg tcatacgcca gcagtgaaac    11100
cactcaagtt tgccaaccaa atgtatatcg ataccggcgc agtgttctgc ggaaacctaa    11160
cattgattca ggtacaggga gaaggcgcat gagactcgaa agcgtagcta aatttcattc    11220
gccaaaaagc ccgatgatga gcgactcacc acgggccacg gcttctgact ctctttccgg    11280
tactgatgtg atggctgcta tggggatggc gcaatcacaa gccggattcg gtatggctgc    11340
attctgcggt aagcacgaac tcagccagaa cgacaaacaa aaggctatca actatctgat    11400
gcaatttgca cacaaggtat cggggaaata ccgtggtgtg gcaaagcttg aaggaaatac    11460
taaggcaaag gtactgcaag tgctcgcaac attcgcttat gcggattatt gccgtagtgc    11520
cgcgacgccg ggggcaagat gcagagattg ccatggtaca ggccgtgcgg ttgatattgc    11580
caaaacagag ctgtggggga gagttgtcga gaaagagtgc ggaagatgca aaggcgtcgg    11640
ctattcaagg atgccagcaa gcgcagcata tcgcgctgtg acgatgctaa tcccaaacct    11700
tacccaaccc acctggtcac gcactgttaa gccgctgtat gacgctctgg tggtgcaatg    11760
ccacaaagaa gagtcaatcg cagacaacat tttgaatgcg gtcacacgtt agcagcatga    11820
ttgccacgga tggcaacata ttaacggcat gatattgact tattgaataa aattgggtaa    11880
atttgactca acgatgggtt aattcgctcg ttgtggtagt gagatgaaaa gaggcggcgc    11940
ttactaccga ttccgcctag ttggtcactt cgacgtatcg tctggaactc caaccatcgc    12000
aggcagagag gtctgcaaaa tgcaatcccg aaacagttcg caggtaatag ttagagcctg    12060
cataacggtt tcgggatttt ttatatctgc acaacaggta agagcattga gtcgataatc    12120
gtgaagagtc ggcgagcctg gttagccagt gctctttccg ttgtgctgaa ttaagcgaat    12180
accggaagca gaaccggatc accaaatgcg tacaggcgtc atcgccgccc agcaacagca    12240
caacccaaac tgagccgtag ccactgtctg tcctgaattc attagtaata gttacgctgc    12300
ggccttttac acatgacctt cgtgaaagcg ggtggcagga ggtcgcgcta acaacctcct    12360
gccgttttgc ccgtgcatat cggtcacgaa caaatctgat tactaaacac agtagcctgg    12420
atttgttcta tcagtaatcg accttattcc taattaaata gagcaaatcc ccttattggg    12480
ggtaagacat gaagatgcca gaaaaacatg acctgttggc cgccattctc gcggcaaagg    12540
aacaaggcat cggggcaatc cttgcgtttg caatggcgta ccttcgcggc agatataatg    12600
gcggtgcgtt tacaaaaaca gtaatcgacg caacgatgtg cgccattatc gcctggttca    12660
ttcgtgacct tctcgacttc gccggactaa gtagcaatct cgcttatata acgagcgtgt    12720
ttatcggcta catcggtact gactcgattg gttcgcttat caaacgcttc gctgctaaaa    12780
aagccggagt agaagatggt agaaatcaat aatcaacgta aggcgttcct cgatatgctg    12840
gcgtggtcgg agggaactga taacggacgt cagaaaacca gaaatcatgg ttatgacgtc    12900
attgtaggcg gagagctatt tactgattac tccgatcacc ctcgcaaact tgtcacgcta    12960
aacccaaaac tcaaatcaac aggcgcttaa gactggccgt cgttttacaa cacagaaaga    13020
gtttgtagaa acgcaaaaag gccatccgtc aggggccttc tgcttagttt gatgcctggc    13080
agttccctac tctcgccttc cgcttcctcg ctcactgact cgctgcgctc ggtcgttcgg    13140
ctgcggcgag cggtatcagc tcactcaaag gcggtaatac ggttatccac agaatcaggg    13200
gataacgcag gaaagaacat gtgagcaaaa ggccagcaaa aggccaggaa ccgtaaaaag    13260
gccgcgttgc tggcgttttt ccataggctc cgcccccctg acgagcatca caaaaatcga    13320
cgctcaagtc agaggtggcg aaacccgaca ggactataaa gataccaggc gtttccccct    13380
```

-continued

```
ggaagctccc tcgtgcgctc tcctgttccg accctgccgc ttaccggata cctgtccgcc   13440 tttctcccttt cgggaagcgt ggcgctttct catagctcac gctgtaggta tctcagttcg   13500
gtgtaggtcg ttcgctccaa gctgggctgt gtgcacgaac ccccgttca gcccgaccgc    13560 tgcgccttat ccgtaacta tcgtcttgag tccaacccgg taagacacga cttatcgcca    13620
ctggcagcag ccactggtaa caggattagc agagcgaggt atgtaggcgg tgctacagag   13680
ttcttgaagt ggtgggctaa ctacggctac actagaagaa cagtatttgg tatctgcgct   13740
ctgctgaagc cagttacctt cggaaaaaga gttggtagct cttgatccgg caaacaaacc   13800
accgctggta gcggtggttt ttttgtttgc aagcagcaga ttacgcgcag aaaaaaagga   13860
tctcaagaag atcctttgat cttttctacg gggtctgacg ctcagtggaa cgacgcgcgc   13920
gtaactcacg ttaagggatt ttggtcatga gcttgcgccg tcccgtcaag tcagcgtaat   13980
gctctgcttt                                                          13990
```

<210> SEQ ID NO 10
<211> LENGTH: 12560
<212> TYPE: DNA
<213> ORGANISM: Artificial Sequence
<220> FEATURE:
<223> OTHER INFORMATION: pAAV.EF1ac.copt.hPEX1
<220> FEATURE:
<221> NAME/KEY: misc_feature
<222> LOCATION: (1253)..(5960)
<223> OTHER INFORMATION: AAV expression cassette
<220> FEATURE:
<221> NAME/KEY: misc_feature
<222> LOCATION: (1253)..(1382)
<223> OTHER INFORMATION: 5' ITR
<220> FEATURE:
<221> NAME/KEY: promoter
<222> LOCATION: (1463)..(1674)
<223> OTHER INFORMATION: EF1a core promoter
<220> FEATURE:
<221> NAME/KEY: misc_feature
<222> LOCATION: (1683)..(1691)
<223> OTHER INFORMATION: Kozak
<220> FEATURE:
<221> NAME/KEY: misc_feature
<222> LOCATION: (1692)..(5543)
<223> OTHER INFORMATION: Codon optimized hPEX1
<220> FEATURE:
<221> NAME/KEY: polyA_signal
<222> LOCATION: (5574)..(5781)
<223> OTHER INFORMATION: bGH Poly(A)
<220> FEATURE:
<221> NAME/KEY: misc_feature
<222> LOCATION: (5831)..(5960)
<223> OTHER INFORMATION: 3' ITR

<400> SEQUENCE: 10

```
tagaaaaact catcgagcat caaatgaaac tgcaatttat tcatatcagg attatcaata     60
ccatattttt gaaaagccg tttctgtaat gaaggagaaa actcaccgag gcagttccat    120
aggatggcaa gatcctggta tcggtctgcg attccgactc gtccaacatc aatacaacct    180
attaatttcc cctcgtcaaa ataaggttta tcaagtgaga atcaccatg agtgacgact    240 gaatccggtg agaatggcaa aagtttatgc atttcttttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgttttttccg gggatcgcag tggtgagtaa ccatgcatca    540
```

```
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020 tgacccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttagggggtg tcgcccttat tcgactctat agtgaagttc   1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gcgagtggga   1440
attggctccg gtgcccgtca gtgggcagag cgcacatcgc ccacagtccc cgagaagttg   1500
gggggagggg tcggcaattg atccggtgcc tagagaaggt ggcgcggggt aaactgggaa   1560
agtgatgtcg tgtactggct ccgccttttt cccgagggtg ggggagaacc gtatataagt   1620
gcagtagtcg ccgtgaacgt tcttttcgc aacgggtttg ccgccagaac acaggcggcc   1680
gcgccgccac catgtgggga agcgacagac tggccggagc tggaggggga ggagcagccg   1740
tcaccgtggc gttcactaac gcgcgggact gctttctcca tctgccgcgg aggctggtcg   1800
cccagctgca cctcctgcag aaccaggcca tcgaggtggt gtggtcccac caaccggcct   1860
ttttgagctg ggtcgaggga aggcactttt cggaccaggg agaaaatgtg gcggagatca   1920
accgccaggt cggccagaag ctgggactgt ccaacggcgg acaggtgttc ctcaagccgt   1980
gcagccacgt ggtgtcctgc caacaggtgg aagtggagcc gctctccgcc gacgactggg   2040
agatcctcga attgcatgcc gtgagcctcg aacagcatct gttggaccag attcgcattg   2100
tgttcccgaa ggccatattc cccgtgtggg tcgatcagca gacctatatc ttcatcaga   2160 ttgtggccct catcccggcc gcctcatacg gacggctgga aactgacacc aagctgctga   2220
ttcaacctaa gacccggagg gccaaagaaa acaccttctc caaggccgac gctgagtaca   2280
agaagctcca ctcctacgga cgggaccaga aggggatgat gaaggagctg caaaccaagc   2340
agctccagag caacaccgtg gggatcaccg agtccaatga aaacgagtcg gaaatcccag   2400
tcgattcatc ttccgtggcc agcctgtgga ctatgatcgg ttccattttc tcgttccaat   2460
ctgagaagaa gcaggaaact agctgggggc tgactgagat caacgccttc aagaacatgc   2520
agtccaaagt ggtgcctctg gataacatct ttcgcgtgtg caagtcccaa ccgccctcaa   2580
tctacaacgc gtccgctacc tccgtgtttc ataagcactg tgccatccac gtgttcccat   2640
gggatcagga atacttcgat gtcgaaccct ccttcaccgt gacttacggg aagcttgtca   2700
agctcctcag ccccaagcag cagcaatcga aaactaagca gaacgtgctt tccccggaga   2760
aggagaagca aatgtcagaa ccactcgacc agaagaaaat cagatcggat cataacgaag   2820
aggacgagaa ggcctgcgtc cttcaggtgg tctggaacgg cctggaggag ctgaacaacg   2880
cgattaagta caccaagaac gtcgaggtcc ttcacctggg aaaggtgtgg attccggatg   2940
```

```
atctgaggaa acgcctcaac atcgaaatgc acgctgtggt gcggattacc ccggtcgagg    3000
tcaccccaaa gatccctcgc tccttgaagc tgcagccgcg agaaaacttg cccaaggaca    3060
tttctgaaga ggatatcaag actgtgttct actcctggct gcaacagagc actaccacca    3120
tgctccctct ggtcatttcg gaggaagaat tcatcaaact ggaaaccaag gacggactga    3180
aagaattctc cctgtccatc gtgcactcct gggaaaagga aaggacaag aatatcttcc     3240
tgctgtcccc caatctgctg caaaagacca cgatccaggt gctgctcgac ccatggtga     3300
aggaggaaaa ctcagaagag atcgacttca tcctgccgtt ccttaagctg agttcactgg    3360
gaggcgtgaa ctcccttggc gtgtcctcgc tggagcacat cactcactca ctgctgggcc    3420
ggcctctgag cagacagctt atgagcttgg tcgccggact cagaaacggt gccctcctgc    3480
tcaccggcgg caagggatcg ggaaagtcca ccctcgctaa ggccatttgc aaagaggcat    3540
tcgataagct ggacgcccat gtggagcggg tggactgtaa ggccctccgc ggaaagcgat    3600
tggaaaatat tcaaaagact ctcgaagtcg cctttccga agccgtctgg atgcagccct     3660
cggtcgtcct gctcgacgat ctggacctca tcgctgggct gccggccgtg ccggagcatg    3720
aacactcccc tgacgcggtc cagtcgcaac ggctcgccca cgccctgaac gatatgatta    3780
aggaattcat ctcaatggga tcactggtgg ccctgatcgc gacttcccag agccagcagt    3840
ccctgcaccc tctgctggtg tcggcccagg gcgtgcacat ttttcagtgt gtgcaacaca    3900
tccagccgcc caaccaggag cagcggtgcg aaatcctgtg caacgtgatt aagaacaagc    3960
tggactgcga tatcaacaag tttaccgacc ttgatctcca acatgtggct aaggagactg    4020
ggggcttcgt ggctcgggac ttcacagtgt tggtggaccg ggcaattcac tccagactgt    4080
cccgccagag catttccacc cgcgaaaaac tggtcctgac caccctcgac ttccagaagg    4140
ccctcagagg cttccttcct gcgagcctca gatccgtcaa ccttcacaag ccgcgggacc    4200
ttggctggga caagatcggt gggctccacg aggtgcggca gatcctcatg gacaccattc    4260
agctgcctgc aaagtacccc gagctgttcg ccaacttgcc gattcgccag cgcacgggaa    4320
tcctgctcta cggccccccg ggcaccggaa agaccctgct ggccggtgtg atcgcccggg    4380
aatcgaggat gaacttcatc tccgtgaagg acccgaact cctgtccaag tacatcggtg      4440
cctccgaaca ggccgtgcgc gatatattca ttagggccca ggccgcgaag ccctgcattc    4500
tgttcttcga cgagtttgaa tcgatcgcgc cccggagggg ccacgacaac acgggagtga    4560
ccgaccgggt ggtgaaccag ctgctcaccc aactggatgg cgtggaaggc cttcagggag    4620
tgtacgtgct ggcggctacc tccagaccgg acctgatcga tccggccctg ctgcgccccg    4680
ggagactgga caagtgcgtg tattgccctc cccctgacca ggtgtcaagg ttggaaatcc    4740
tcaacgtgct ctcggactcc ctgccactgg cagatgatgt ggacctccag catgtggcct    4800
ccgtgactga cagcttcaca ggagccgatc tgaaggccct gctttacaac gcccagttgg    4860
aggcgctgca cggtatgctg ctgtcctccg gtctgcagga tggctcctcc tcttccgata    4920
gcgacctgtc gctgagcagc atggtgttcc tgaaccattc cagcggctcc gatgacagcg    4980
cgggcgacgg agaatgtgga ctggatcaat ccctggtgtc cctggagatg agcgagattc    5040
tgccagacga gtccaagttc aacatgtaca ggctgtactt cggcagcagc tacgagtccg    5100
agctgggaaa tggtacctcg tccgacctgt caagccagtg cctgtccgcg ccttcctcca    5160
tgacccagga cctccctgga gtgccaggga aggatcagct gttcagccag cctcccgtgc    5220
tgcgcactgc gagccaggaa gggtgccagg aattgaccca agagcagcgg gaccaactgc    5280
```

| | |
|---|---|
| gcgcggacat ttcgatcatc aaaggcagat accgctccca atccgggag gacgaaagca | 5340 |
| tgaaccagcc cgggcctatc aagactagac tggcaatctc ccaaagccac ctgatgaccg | 5400 |
| cactgggaca cacccggccc tcgatctcgg aggacgactg gaagaacttc gctgagctgt | 5460 |
| acgaatcctt ccagaatccg aagcggagaa agaaccagag cggaactatg ttccggcccg | 5520 |
| gacagaaggt gaccctggcc tgaagtactg cggatcctgc agatctgcct cgactgtgcc | 5580 |
| ttctagttgc cagccatctg ttgtttgccc ctcccccgtg ccttccttga ccctggaagg | 5640 |
| tgccactccc actgtccttt cctaataaaa tgaggaaatt gcatcgcatt gtctgagtag | 5700 |
| gtgtcattct attctggggg gtggggtggg gcaggacagc aaggggagg attgggaaga | 5760 |
| caatagcagg catgctgggg actcgagttc tacgtagata agtagcatgg cgggttaatc | 5820 |
| attaactaca aggaacccct agtgatgag ttggccactc cctctctgcg cgctcgctcg | 5880 |
| ctcactgagg ccgggcgacc aaaggtcgcc cgacgcccgg gctttgcccg ggcggcctca | 5940 |
| gtgagcgagc gagcgcgcag ccttaattaa cctaaggaaa atgaagtgaa gttcctatac | 6000 |
| tttctagaga ataggaactt ctatagtgag tcgaataagg cgacacaaa atttattcta | 6060 |
| aatgcataat aaatactgat aacatcttat agtttgtatt atattttgta ttatcgttga | 6120 |
| catgtataat tttgatatca aaaactgatt ttcccttttat tattttcgag atttattttc | 6180 |
| ttaattctct ttaacaaact agaaatattg tatatacaaa aaatcataaa taatagatga | 6240 |
| atagtttaat tataggtgtt catcaatcga aaaagcaacg tatcttattt aaagtgcgtt | 6300 |
| gcttttttct catttataag gttaaataat tctcatatat caagcaaagt gacaggcgcc | 6360 |
| cttaaatatt ctgacaaatg ctctttccct aaactccccc cataaaaaaa cccgccgaag | 6420 |
| cgggttttta cgttatttgc ggattaacga ttactcgtta tcagaaccgc ccaggggcc | 6480 |
| cgagcttaac cttttttattt gggggagagg gaagtcatga aaaaactaac ctttgaaatt | 6540 |
| cgatctccag cacatcagca aaacgctatt cacgcagtac agcaaatcct tccagaccca | 6600 |
| accaaaccaa tcgtagtaac cattcaggaa cgcaaccgca gcttagacca aaacaggaag | 6660 |
| ctatgggcct gcttaggtga cgtctctcgt caggttgaat ggcatggtcg ctggctggat | 6720 |
| gcagaaagct ggaagtgtgt gtttaccgca gcattaaagc agcaggatgt tgttcctaac | 6780 |
| cttgccggga atggctttgt ggtaataggc cagtcaacca gcaggatgcg tgtaggcgaa | 6840 |
| tttgcggagc tattagagct tatacaggca ttcggtacag agcgtggcgt taagtggtca | 6900 |
| gacgaagcga gactggctct ggagtggaaa gcgagatggg gagacagggc tgcatgataa | 6960 |
| atgtcgttag tttctccggt ggcaggacgt cagcatattt gctctggcta atggagcaaa | 7020 |
| agcgacgggc aggtaaagac gtgcattacg ttttcatgga tacaggttgt gaacatccaa | 7080 |
| tgacatatcg gtttgtcagg gaagttgtga agttctggga ataccgctc accgtattgc | 7140 |
| aggttgatat caacccggag cttggacagc caaatggtta tacggtatgg gaaccaaagg | 7200 |
| atattcagac gcgaatgcct gttctgaagc catttatcga tatggtaaag aaatatggca | 7260 |
| ctccatacgt cggcggcgcg ttctgcactg acagattaaa actcgttccc ttcaccaaat | 7320 |
| actgtgatga ccatttcggg cgagggaatt acaccacgtg gattggcatc agagctgatg | 7380 |
| aaccgaagcg gctaaagcca aagcctggaa tcagatatct tgctgaactg tcagactttg | 7440 |
| agaaggaaga tatcctcgca tggtggaagc aacaaccatt cgatttgcaa ataccggaac | 7500 |
| atctcggtaa ctgcatattc tgcattaaaa aatcaacgca aaaatcgga cttgcctgca | 7560 |
| aagatgagga gggattgcag cgtgttttta atgaggtcat cacggatcc catgtgcgtg | 7620 |
| acggacatcg ggaaacgcca aaggagatta tgtaccgagg aagaatgtcg ctggacggta | 7680 |

```
tcgcgaaaat gtattcagaa aatgattatc aagccctgta tcaggacatg gtacgagcta    7740
aaagattcga taccggctct tgttctgagt catgcgaaat atttggaggg cagcttgatt    7800
tcgacttcgg gagggaagct gcatgatgcg atgttatcgg tgcggtgaat gcaaagaaga    7860
taaccgcttc cgaccaaatc aaccttactg gaatcgatgg tgtctccggt gtgaaagaac    7920
accaacaggg gtgttaccac taccgcagga aaaggaggac gtgtggcgag acagcgacga    7980
agtatcaccg acataatctg cgaaaactgc aaataccttc caacgaaacg caccagaaat    8040
aaacccaagc caatcccaaa agaatctgac gtaaaaacct caactacacg gctcacctg     8100
tgggatatcc ggtggctaag acgtcgtgcg aggaaaacaa ggtgattgac caaaatcgaa    8160
gttacgaaca agaaagcgtc gagcgagctt taacgtgcgc taactgcggt cagaagctgc    8220
atgtgctgga agttcacgtg tgtgagcact gctgcgcaga actgatgagc gatccgaata    8280
gctcgatgca cgaggaagaa gatgatggct aaaccagcgc gaagacgatg taaaaacgat    8340
gaatgccggg aatggtttca ccctgcattc gctaatcagt ggtggtgctc tccagagtgt    8400
ggaaccaaga tagcactcga acgacgaagt aaagaacgcg aaaaagcgga aaaagcagca    8460
gagaagaaac gacgacgaga ggagcagaaa cagaaagata aacttaagat tcgaaaactc    8520
gccttaaagc cccgcagtta ctggattaaa caagcccaac aagccgtaaa cgccttcatc    8580
agagaaagag accgcgactt accatgtatc tcgtgcggaa cgctcacgtc tgctcagtgg    8640
gatgccggac attaccggac aactgctgcg gcacctcaac tccgatttaa tgaacgcaat    8700
attcacaagc aatgcgtggt gtgcaaccag cacaaaagcg gaaatctcgt tccgtatcgc    8760
gtcgaactga ttagccgcat cgggcaggaa gcagtagacg aaatcgaatc aaaccataac    8820
cgccatcgct ggactatcga agagtgcaag gcgatcaagg cagagtacca acagaaactc    8880
aaagacctgc gaaatagcag aagtgaggcc gcatgacgtt ctcagtaaaa accattccag    8940
acatgctcgt tgaagcatac ggaaatcaga cagaagtagc acgcagactg aaatgtagtc    9000
gcggtacggt cagaaaatac gttgatgata agacgggaa aatgcacgcc atcgtcaacg    9060
acgttctcat ggttcatcgc ggatggagtg aaagagatgc gctattacga aaaaattgat    9120
ggcagcaaat accgaaatat ttgggtagtt ggcgatctgc acggatgcta cacgaacctg    9180
atgaacaaac tggatacgat tggattcgac aacaaaaaag acctgcttat ctcggtgggc    9240
gatttggttg atcgtggtgc agagaacgtt gaatgcctgg aattaatcac attccctgg    9300
ttcagagctg tacgtggaaa ccatgagcaa atgatgattg atggcttatc agagcgtgga    9360
aacgttaatc actggctgct taatggcggt ggctggttct ttaatctcga ttacgacaaa    9420
gaaattctgg ctaaagctct tgcccataaa gcagatgaac ttccgttaat catcgaactg    9480
gtgagcaaag ataaaaaata tgttatctgc cacgccgatt atcccttga cgaatacgag    9540
tttggaaagc cagttgatca tcagcaggta atctggaacc gcgaacgaat cagcaactca    9600
caaaacggga tcgtgaaaga aatcaaaggc gcggacacgt tcatctttgg tcatacgcca    9660
gcagtgaaac cactcaagtt tgccaaccaa atgtatatcg ataccggcgc agtgttctgc    9720
ggaaacctaa cattgattca ggtacaggga gaaggcgcat gagactcgaa agcgtagcta    9780
aatttcattc gccaaaaagc ccgatgatga gcgactcacc acgggccacg gcttctgact    9840
ctctttccgg tactgatgtg atggctgcta tggggatggc gcaatcacaa gccggattcg    9900
gtatggctgc attctgcggt aagcacgaac tcagccagaa cgacaaacaa aaggctatca    9960
actatctgat gcaatttgca cacaaggtat cggggaaata ccgtggtgtg gcaaagcttg   10020
```

```
aaggaaatac taaggcaaag gtactgcaag tgctcgcaac attcgcttat gcggattatt    10080
gccgtagtgc cgcgacgccg ggggcaagat gcagagattg ccatggtaca ggccgtgcgg    10140
ttgatattgc caaaacagag ctgtggggga gagttgtcga gaaagagtgc ggaagatgca    10200
aaggcgtcgg ctattcaagg atgccagcaa gcgcagcata tcgcgctgtg acgatgctaa    10260
tcccaaacct tacccaaccc acctggtcac gcactgttaa gccgctgtat gacgctctgg    10320
tggtgcaatg ccacaaagaa gagtcaatcg cagacaacat tttgaatgcg gtcacacgtt    10380
agcagcatga ttgccacgga tggcaacata ttaacggcat gatattgact tattgaataa    10440 aatttgggtaa atttgactca acgatgggtt aattcgctcg ttgtggtagt gagatgaaaa    10500
gaggcggcgc ttactaccga ttccgcctag ttggtcactt cgacgtatcg tctggaactc    10560
caaccatcgc aggcagagag gtctgcaaaa tgcaatcccg aaacagttcg caggtaatag    10620
ttagagcctg cataacggtt tcgggatttt ttatatctgc acaacaggta agagcattga    10680
gtcgataatc gtgaagagtc ggcgagcctg gttagccagt gctctttccg ttgtgctgaa    10740
ttaagcgaat accggaagca gaaccggatc accaaatgcg tacaggcgtc atcgccgccc    10800
agcaacagca caacccaaac tgagccgtag ccactgtctg tcctgaattc attagtaata    10860
gttacgctgc ggccttttac acatgacctt cgtgaaagcg ggtggcagga ggtcgcgcta    10920
acaacctcct gccgttttgc ccgtgcatat cggtcacgaa caaatctgat tactaaacac    10980
agtagcctgg atttgttcta tcagtaatcg accttattcc taattaaata gagcaaatcc    11040
ccttattggg ggtaagacat gaagatgcca gaaaaacatg acctgttggc cgccattctc    11100
gcggcaaagg aacaaggcat cggggcaatc cttgcgtttg caatggcgta ccttcgcggc    11160
agatataatg gcggtgcgtt tacaaaaaca gtaatcgacg caacgatgtg cgccattatc    11220
gcctggttca ttcgtgacct tctcgacttc gccggactaa gtagcaatct cgcttatata    11280
acgagcgtgt ttatcggcta catcggtact gactcgattg gttcgcttat caaacgcttc    11340
gctgctaaaa aagccggagt agaagatggt agaaatcaat aatcaacgta aggcgttcct    11400
cgatatgctg gcgtggtcgg agggaactga taacggacgt cagaaaacca gaaatcatgg    11460
ttatgacgtc attgtaggcg gagagctatt tactgattac tccgatcacc ctcgcaaact    11520
tgtcacgcta aacccaaaac tcaaatcaac aggcgcttaa gactggccgt cgttttacaa    11580
cacagaaaga gtttgtagaa acgcaaaaag gccatccgtc aggggccttc tgcttagttt    11640
gatgcctggc agttccctac tctcgccttc cgcttcctcg ctcactgact cgctgcgctc    11700
ggtcgttcgg ctgcggcgag cggtatcagc tcactcaaag gcggtaatac ggttatccac    11760
agaatcaggg gataacgcag gaaagaacat gtgagcaaaa ggccagcaaa aggccaggaa    11820
ccgtaaaaag gccgcgttgc tggcgttttt ccataggctc cgcccccctg acgagcatca    11880
caaaaatcga cgctcaagtc agaggtggcg aaacccgaca ggactataaa gataccaggc    11940
gtttccccct ggaagctccc tcgtgcgctc tcctgttccg accctgccgc ttaccggata    12000
cctgtccgcc tttctccctt cgggaagcgt ggcgctttct catagctcac gctgtaggta    12060
tctcagttcg gtgtaggtcg ttcgctccaa gctgggctgt gtgcacgaac cccccgttca    12120
gcccgaccgc tgcgccttat ccggtaacta tcgtcttgag tccaacccgg taagacacga    12180
cttatcgcca ctggcagcag ccactggtaa caggattagc agagcgaggt atgtaggcgg    12240
tgctacagag ttcttgaagt ggtgggctaa ctacggctac actagaagaa cagtatttgg    12300
tatctgcgct ctgctgaagc cagttacctt cggaaaaaga gttggtagct cttgatccgg    12360
caaacaaacc accgctggta gcggtggttt ttttgtttgc aagcagcaga ttacgcgcag    12420
```

```
aaaaaaagga tctcaagaag atcctttgat cttttctacg gggtctgacg ctcagtggaa    12480
cgacgcgcgc gtaactcacg ttaagggatt ttggtcatga gcttgcgccg tcccgtcaag    12540
tcagcgtaat gctctgcttt                                                12560
```

<210> SEQ ID NO 11
<211> LENGTH: 12796
<212> TYPE: DNA
<213> ORGANISM: Artificial Sequence
<220> FEATURE:
<223> OTHER INFORMATION: pAAV.GRK1.copt.hPEX1
<220> FEATURE:
<221> NAME/KEY: misc_feature
<222> LOCATION: (1253)..(6196)
<223> OTHER INFORMATION: AAV expression cassette
<220> FEATURE:
<221> NAME/KEY: misc_feature
<222> LOCATION: (1253)..(1382)
<223> OTHER INFORMATION: 5' ITR
<220> FEATURE:
<221> NAME/KEY: promoter
<222> LOCATION: (1427)..(1790)
<223> OTHER INFORMATION: GRK1 promoter
<220> FEATURE:
<221> NAME/KEY: Intron
<222> LOCATION: (1791)..(1887)
<223> OTHER INFORMATION: SV40 intron
<220> FEATURE:
<221> NAME/KEY: misc_feature
<222> LOCATION: (1940)..(1948)
<223> OTHER INFORMATION: Kozak
<220> FEATURE:
<221> NAME/KEY: misc_feature
<222> LOCATION: (1949)..(5800)
<223> OTHER INFORMATION: codon optimized hPEX1
<220> FEATURE:
<221> NAME/KEY: polyA_signal
<222> LOCATION: (5822)..(5933)
<223> OTHER INFORMATION: bGH Poly(A)
<220> FEATURE:
<221> NAME/KEY: misc_feature
<222> LOCATION: (6067)..(6196)
<223> OTHER INFORMATION: 3' ITR

<400> SEQUENCE: 11

```
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa ataaggttat caagtgagaa atcaccatga gtgacgact      240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgtttttccg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
```

```
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140
gggcctttcg cccgggctaa ttaggggtg tcgcccttat tcgactctat agtgaagttc    1200
ctattctcta gaaagtatag gaacttctga agtggggtcg acttaattaa ggctgcgcgc   1260
tcgctcgctc actgaggccg cccgggcaaa gcccgggcgt cgggcgacct ttggtcgccc   1320
ggcctcagtg agcgagcgag cgcgcagaga gggagtggcc aactccatca ctaggggttc   1380
cttgtagtta atgattaacc cgccatgcta cttatctacg tagcaagcta gcaagatcca   1440
agctcagatc tcgatcgagt tgggcccag aagcctggtg gttgtttgtc cttctcaggg    1500
gaaaagtgag gcggccccttg gaggaaggg gccgggcaga atgatctaat cggattccaa   1560
gcagctcagg ggattgtctt tttctagcac cttcttgcca ctcctaagcg tcctccgtga   1620
ccccggctgg gatttagcct ggtgctgtgt cagccccggt ctcccagggg cttcccagtg   1680
gtccccagga accctcgaca gggcccggtc tctctcgtcc agcaagggca gggacgggcc   1740
acaggccaag ggccctcgat cgaggaactg aaaaaccaga aagttaactg gtaagtttag   1800
tcttttttgtc ttttatttca ggtcccggat ccggtggtgg tgcaaatcaa agaactgctc  1860
ctcagtggat gttgccttta cttctaggcc tgtacgaag tgttacttct gctctaaaag    1920
ctgcggaatt gtacccgcgg ccgccaccat gtggggaagc gacagactgg ccggagctgg   1980
agggggagga gcagccgtca ccgtggcgtt cactaacgcg cgggactgct ttctccatct   2040
gccgcggagg ctggtcgccc agctgcacct cctgcagaac caggccatcg aggtggtgtg   2100
gtcccaccaa ccgcctttt tgagctgggt cgagggaagg cacttttcgg accagggaga    2160
aaatgtggcg gagatcaacc gccaggtcgg ccagaagctg ggactgtcca acggcggaca   2220
ggtgttcctc aagccgtgca gccacgtggt gtcctgccaa caggtggaag tggagccgct   2280
ctccgccgac gactgggaga tcctcgaatt gcatgccgtg agcctcgaac agcatctgtt   2340
ggaccagatt cgcattgtgt tcccgaaggc catattcccc gtgtgggtcg atcagcagac   2400
ctatatcttc atccagattg tggccctcat cccggccgcc tcatacggac ggctggaaac   2460
tgacaccaag ctgctgattc aacctaagac ccggagggcc aaagaaaaca ccttctccaa   2520
ggccgacgct gagtacaaga agctccactc ctacggacgg gaccagaagg ggatgatgaa   2580
ggagctgcaa accaagcagc tccagagcaa caccgtgggg atcaccgagt ccaatgaaaa   2640
cgagtcggaa atcccagtcg attcatcttc cgtggccagc ctgtggacta tgatcggttc   2700
cattttctcg ttccaatctg agaagaagca ggaaactagc tggggggctga ctgagatcaa   2760
cgccttcaag aacatgcagt ccaaagtggt gcctctggat aacatctttc gcgtgtgcaa   2820
gtcccaaccg ccctcaatct acaacgcgtc cgctacctcc gtgtttcata agcactgtgc   2880
catccacgtg ttcccatggg atcaggaata cttcgatgtc gaaccttcct tcaccgtgac   2940
ttacgggaag cttgtcaagc tcctcagccc caagcagcag caatcgaaaa ctaagcagaa   3000
cgtgctttcc ccggagaagg agaagcaaat gtcagaacca ctcgaccaga agaaaatcag   3060
atcggatcat aacgaagagg acgagaaggc ctgcgtcctt caggtggtct ggaacggcct   3120
ggaggagctg aacaacgcga ttaagtacac caagaacgtc gaggtccttc acctgggaaa   3180
ggtgtggatt ccggatgatc tgaggaaacg cctcaacatc gaaatgcacg ctgtggtgcg   3240
gattaccccg gtcgaggtca ccccaaagat ccctcgctcc ttgaagctgc agccgcgaga   3300
```

```
aaacttgccc aaggacattt ctgaagagga tatcaagact gtgttctact cctggctgca    3360
acagagcact accaccatgc tccctctggt catttcggag gaagaattca tcaaactgga    3420
aaccaaggac ggactgaaag aattctccct gtccatcgtg cactcctggg aaaaggagaa    3480
ggacaagaat atcttcctgc tgtccccaa tctgctgcaa aagaccacga tccaggtgct     3540
gctcgacccc atggtgaagg aggaaaactc agaagagatc gacttcatcc tgccgttcct   3600
taagctgagt tcactgggag gcgtgaactc ccttggcgtg tcctcgctgg agcacatcac   3660
tcactcactg ctgggccggc tctgagcag acagcttatg agcttggtcg ccggactcag    3720
aaacggtgcc ctcctgctca ccggcggcaa gggatcggga agtccaccc tcgctaaggc    3780
catttgcaaa gaggcattcg ataagctgga cgcccatgtg gagcgggtgg actgtaaggc   3840
cctccgcgga aagcgattgg aaaatattca aaagactctc gaagtcgcct tttccgaagc   3900
cgtctggatg cagccctcgg tcgtcctgct cgacgatctg gacctcatcg ctgggctgcc   3960
ggccgtgccg gagcatgaac actcccctga cgcggtccag tcgcaacggc tcgcccacgc   4020
cctgaacgat atgattaagg aattcatctc aatgggatca ctggtggccc tgatcgcgac   4080
ttcccagagc cagcagtccc tgcaccctct gctggtgtcg gcccagggcg tgcacatttt   4140
tcagtgtgtg caacacatcc agccgcccaa ccaggagcag cggtgcgaaa tcctgtgcaa   4200
cgtgattaag aacaagctgg actgcgatat caacaagttt accgaccttg atctccaaca   4260
tgtggctaag gagactgggg gcttcgtggc tcgggacttc acagtgttgg tggaccgggc   4320
aattcactcc agactgtccc gccagagcat ttccacccgc gaaaaactgg tcctgaccac   4380
cctcgacttc cagaaggccc tcagaggctt ccttcctgcg agcctcagat ccgtcaacct   4440
tcacaagccg cgggaccttg ctgggacaa gatcggtggg ctccacgagg tgcggcagat    4500
cctcatggac accattcagc tgcctgcaaa gtaccccgag ctgttcgcca acttgccgat   4560
tcgccagcgc acgggaatcc tgctctacgg cccccccgggc accggaaaga ccctgctggc  4620
cggtgtgatc gcccgggaat cgaggatgaa cttcatctcc gtgaagggac ccgaactcct   4680
gtccaagtac atcggtgcct ccgaacaggc cgtgcgcgat atattcatta gggcccaggc   4740
cgcgaagccc tgcattctgt tcttcgacga gtttgaatcg atcgcgcccc ggaggggcca   4800
cgacaacacg ggagtgaccg accgggtggt gaaccagctg ctcacccaac tggatggcgt   4860
ggaaggcctt cagggagtgt acgtgctggc ggctacctcc agaccggacc tgatcgatcc   4920
ggccctgctg cgccccggga gactggacaa gtgcgtgtat tgccctcccc ctgaccaggt   4980
gtcaaggttg gaaatcctca acgtgctctc ggactcctg ccactggcag atgatgtgga    5040
cctccagcat gtggcctccg tgactgacag cttcacagga gccgatctga aggccctgct   5100
ttacaacgcc cagttggagg cgctgcacgg tatgctgctg tcctccggtc tgcaggatgg   5160
ctcctcctct tccgatagcg acctgtcgct gagcagcatg gtgttcctga accattccag   5220
cggctccgat gacagcgcgg cgacggaga atgtggactg gatcaatccc tggtgtccct    5280
ggagatgagc gagattctgc cagacgagtc caagttcaac atgtacaggc tgtacttcgg   5340
cagcagctac gagtccgagc tgggaaatgg tacctcgtcc gacctgtcaa gccagtgcct   5400
gtccgcgcct tcctccatga cccaggacct ccctggagtg ccagggaagg atcagctgtt   5460
cagccagcct ccgtgctgc gcactgcgag ccaggaaggg tgccaggaat tgacccaaga    5520
gcagcgggac caactgcgcg cggacatttc gatcatcaaa ggcagatacc gctcccaatc   5580
cggggaggac gaaagcatga accagcccgg gcctatcaag actagactgg caatctccca   5640
```

```
aagccacctg atgaccgcac tgggacacac ccggccctcg atctcggagg acgactggaa    5700
gaacttcgct gagctgtacg aatccttcca gaatccgaag cggagaaaga accagagcgg    5760
aactatgttc cggcccggac agaaggtgac cctggcctga tgtacaagta ataagcctcg    5820
actgtgcctt ctagttgcca gccatctgtt gtttgcccct cccccgtgcc ttccttgacc    5880
ctggaaggtg ccactcccac tgtcctttcc taataaaatg aggaaattgc atcgcattgt    5940
ctgagtaggt gtcattctat tctggggggt ggggtggggc aggacagcaa ggggaggat    6000 tgggaagaca atagcaggtc gagttctacg tagataagta gcatggcggg ttaatcatta    6060
actacaagga acccctagtg atggagttgg ccactccctc tctgcgcgct cgctcgctca    6120
ctgaggccgg gcgaccaaag gtcgcccgac gcccgggctt gcccgggcg gcctcagtga    6180 gcgagcgagc gcgcagcctt aattaaccta aggaaaatga agtgaagttc ctatactttc    6240
tagagaatag gaacttctat agtgagtcga taagggcga cacaaaattt attctaaatg    6300
cataataaat actgataaca tcttatagtt tgtattatat tttgtattat cgttgacatg    6360
tataattttg atatcaaaaa ctgattttcc ctttattatt ttcgagattt attttcttaa    6420
ttctctttaa caaactagaa atattgtata tacaaaaaat cataataat agatgaatag    6480 tttaattata ggtgttcatc aatcgaaaaa gcaacgtatc ttatttaaag tgcgttgctt    6540
ttttctcatt tataaggtta aataattctc atatatcaag caaagtgaca ggcgccctta    6600
aatattctga caaatgctct ttccctaaac tccccccata aaaaacccg ccgaagcggg    6660 tttttacgtt atttgcggat taacgattac tcgttatcag aaccgcccag ggggcccgag    6720
cttaaccttt ttatttgggg gagagggaag tcatgaaaaa actaaccttt gaaattcgat    6780
ctccagcaca tcagcaaaac gctattcacg cagtacagca aatccttcca gacccaacca    6840
aaccaatcgt agtaaccatt caggaacgca accgcagctt agaccaaaac aggaagctat    6900
gggcctgctt aggtgacgtc tctcgtcagg ttgaatggca tggtcgctgg ctggatgcag    6960
aaagctggaa gtgtgtgttt accgcagcat taaagcagca ggatgttgtt cctaaccttg    7020
ccgggaatgg ctttgtggta ataggccagt caaccagcag gatgcgtgta ggcgaatttg    7080
cggagctatt agagcttata caggcattcg gtacagagcg tggcgttaag tggtcagacg    7140
aagcgagact ggctctggag tggaaagcga gatggggaga cagggctgca tgataaatgt    7200
cgttagtttc tccggtggca ggacgtcagc atatttgctc tggctaatgg agcaaaagcg    7260
acgggcaggt aaagacgtgc attacgtttt catggataca ggttgtgaac atccaatgac    7320
atatcggttt gtcagggaag ttgtgaagtt ctgggtatat ccgctcaccg tattgcaggt    7380
tgatatcaac ccggagcttg acagccaaa tggttatacg gtatgggaac caaaggatat    7440
tcagacgcga atgcctgttc tgaagccatt tatcgtatg gtaaagaaat atggcactcc    7500
atacgtcggc ggcgcgttct gcactgacag attaaaactc gttcccttca ccaaatactg    7560
tgatgaccat ttcgggcgag ggaattacac cacgtggatt ggcatcagag ctgatgaacc    7620
gaagcggcta aagccaaagc ctggaatcag atatcttgct gaactgtcag actttgagaa    7680
ggaagatatc ctcgcatggt ggaagcaaca accattcgat ttgcaaatac cggaacatct    7740
cggtaactgc atattctgca ttaaaaaatc aacgcaaaaa atcggacttg cctgcaaaga    7800
tgaggaggga ttgcagcgtg ttttaatga ggtcatcacg ggatcccatg tgcgtgacgg    7860
acatcgggaa acgccaaagg agattatgta ccgaggaaga atgtcgctgg acggtatcgc    7920
gaaaatgtat tcagaaaatg attatcaagc cctgtatcag acatggtac gagctaaaag    7980 attcgatacc ggctcttgtt ctgagtcatg cgaaatattt ggagggcagc ttgatttcga    8040
```

```
cttcgggagg gaagctgcat gatgcgatgt tatcggtgcg gtgaatgcaa agaagataac      8100
cgcttccgac caaatcaacc ttactggaat cgatggtgtc tccggtgtga agaacacca      8160 acagggtgt  taccactacc gcaggaaaag gaggacgtgt ggcgagacag cgacgaagta      8220
tcaccgacat aatctgcgaa aactgcaaat accttccaac gaaacgcacc agaaataaac      8280
ccaagccaat cccaaaagaa tctgacgtaa aaaccttcaa ctacacggct cacctgtggg      8340
atatccggtg gctaagacgt cgtgcgagga aaacaaggtg attgaccaaa atcgaagtta      8400
cgaacaagaa agcgtcgagc gagctttaac gtgcgctaac tgcggtcaga agctgcatgt      8460
gctggaagtt cacgtgtgtg agcactgctg cgcagaactg atgagcgatc cgaatagctc      8520
gatgcacgag gaagaagatg atggctaaac cagcgcgaag acgatgtaaa aacgatgaat      8580
gccgggaatg gtttcaccct gcattcgcta atcagtggtg gtgctctcca gagtgtggaa      8640
ccaagatagc actcgaacga cgaagtaaag aacgcgaaaa agcggaaaaa gcagcagaga      8700
agaaacgacg acgagaggag cagaaacaga aagataaact taagattcga aaactcgcct      8760
taaagccccg cagttactgg attaaacaag cccaacaagc cgtaaacgcc ttcatcagag      8820
aaagagaccg cgacttacca tgtatctcgt gcggaacgct cacgtctgct cagtgggatg      8880
ccggacatta ccggacaact gctgcggcac ctcaactccg atttaatgaa cgcaatattc      8940
acaagcaatg cgtggtgtgc aaccagcaca aaagcgaaaa tctcgttccg tatcgcgtcg      9000
aactgattag ccgcatcggg caggaagcag tagacgaaat cgaatcaaac cataaccgcc      9060
atcgctggac tatcgaagag tgcaaggcga tcaaggcaga gtaccaacag aaactcaaag      9120
acctgcgaaa tagcagaagt gaggccgcat gacgttctca gtaaaaacca ttccagacat      9180
gctcgttgaa gcatacggaa atcagacaga agtagcacgc agactgaaat gtagtcgcgg      9240
tacggtcaga aaatacgttg atgataaaga cgggaaaatg cacgccatcg tcaacgacgt      9300
tctcatggtt catcgcggat ggagtgaaag agatgcgcta ttacgaaaaa attgatggca      9360
gcaaataccg aaatatttgg gtagttggcg atctgcacgg atgctacacg aacctgatga      9420
acaaactgga tacgattgga ttcgacaaca aaaaagacct gcttatctcg gtgggcgatt      9480
tggttgatcg tggtgcagag aacgttgaat gcctggaatt aatcacattc ccctggttca      9540
gagctgtacg tggaaaccat gagcaaatga tgattgatgg cttatcagag cgtggaaacg      9600
ttaatcactg gctgcttaat ggcggtggct ggttctttaa tctcgattac gacaaagaaa      9660
ttctggctaa agctcttgcc cataaagcag atgaacttcc gttaatcatc gaactggtga      9720
gcaaagataa aaaatatgtt atctgccacg ccgattatcc ctttgacgaa tacgagtttg      9780
gaaagccagt tgatcatcag caggtaatct ggaaccgcga acgaatcagc aactcacaaa      9840
acgggatcgt gaaagaaatc aaaggcgcgg acacgttcat ctttggtcat acgccagcag      9900
tgaaaccact caagtttgcc aaccaaatgt atatcgatac cggcgcagtg ttctgcggaa      9960
acctaacatt gattcaggta cagggagaag gcgcatgaga ctcgaaagcg tagctaaatt     10020
tcattcgcca aaaagcccga tgatgagcga ctcaccacgg gccacggctt ctgactctct     10080
ttccggtact gatgtgatgg ctgctatggg gatggcgcaa tcacaagccg gattcggtat     10140
ggctgcattc tgcggtaagc acgaactcag ccagaacgca aaacaaaagg ctatcaacta     10200
tctgatgcaa tttgcacaca aggtatcggg gaaataccgt ggtgtggcaa agcttgaagg     10260
aaatactaag gcaaaggtac tgcaagtgct cgcaacattc gcttatgcgg attattgccg     10320
tagtgccgcg acgccggggg caagatgcag agattgccat ggtacaggcc gtgcggttga     10380
```

```
tattgccaaa acagagctgt gggggagagt tgtcgagaaa gagtgcggaa gatgcaaagg    10440
cgtcggctat tcaaggatgc cagcaagcgc agcatatcgc gctgtgacga tgctaatccc    10500
aaaccttacc caacccacct ggtcacgcac tgttaagccg ctgtatgacg ctctggtggt    10560
gcaatgccac aaagaagagt caatcgcaga caacattttg aatgcggtca cacgttagca    10620
gcatgattgc cacggatggc aacatattaa cggcatgata ttgacttatt gaataaaatt    10680
gggtaaattt gactcaacga tgggttaatt cgctcgttgt ggtagtgaga tgaaaagagg    10740
cggcgcttac taccgattcc gcctagttgg tcacttcgac gtatcgtctg gaactccaac    10800
catcgcaggc agagaggtct gcaaaatgca atcccgaaac agttcgcagg taatagttag    10860
agcctgcata acggtttcgg gatttttat atctgcacaa caggtaagag cattgagtcg     10920
ataatcgtga agagtcggcg agcctggtta gccagtgctc tttccgttgt gctgaattaa    10980
gcgaataccg gaagcagaac cggatcacca aatgcgtaca ggcgtcatcg ccgcccagca    11040
acagcacaac ccaaactgag ccgtagccac tgtctgtcct gaattcatta gtaatagtta    11100
cgctgcggcc ttttacacat gaccttcgtg aaagcgggtg gcaggaggtc gcgctaacaa    11160
cctcctgccg ttttgcccgt gcatatcggt cacgaacaaa tctgattact aaacacagta    11220
gcctggattt gttctatcag taatcgacct tattcctaat taaatagagc aaatcccctt    11280
attgggggta agacatgaag atgccagaaa aacatgacct gttggccgcc attctcgcgg    11340
caaaggaaca aggcatcggg gcaatccttg cgtttgcaat ggcgtacctt cgcggcagat    11400
ataatggcgg tgcgtttaca aaaacagtaa tcgacgcaac gatgtgcgcc attatcgcct    11460
ggttcattcg tgaccttctc gacttcgccg gactaagtag caatctcgct tatataacga    11520
gcgtgtttat cggctacatc ggtactgact cgattggttc gcttatcaaa cgcttcgctg    11580
ctaaaaaagc cggagtagaa gatggtagaa atcaataatc aacgtaaggc gttcctcgat    11640
atgctggcgt ggtcggaggg aactgataac ggacgtcaga aaaccagaaa tcatggttat    11700
gacgtcattg taggcggaga gctatttact gattactccg atcaccctcg caaacttgtc    11760
acgctaaacc caaaactcaa atcaacaggc gcttaagact ggccgtcgtt ttacaacaca    11820
gaaagagttt gtagaaacgc aaaaaggcca tccgtcaggg gccttctgct tagtttgatg    11880
cctggcagtt ccctactctc gccttccgct tcctcgctca ctgactcgct gcgctcggtc    11940
gttcggctgc ggcgagcggt atcagctcac tcaaaggcgg taatacggtt atccacagaa    12000 tcagggggata acgcaggaaa gaacatgtga gcaaaaggcc agcaaaggc caggaaccgt     12060 aaaaaggccg cgttgctggc gttttttccat aggctccgcc cccctgacga gcatcacaaa    12120
aatcgacgct caagtcagag gtggcgaaac ccgacaggac tataaagata ccaggcgttt    12180 cccccctggaa gctccctcgt gcgctctcct gttccgaccc tgccgcttac cggatacctg    12240
tccgcctttc tcccttcggg aagcgtggcg ctttctcata gctcacgctg taggtatctc    12300
agttcggtgt aggtcgttcg ctccaagctg ggctgtgtgc acgaaccccc cgttcagccc    12360
gaccgctgcg ccttatccgg taactatcgt cttgagtcca acccggtaag acacgactta    12420
tcgccactgg cagcagccac tggtaacagg attagcagag cgaggtatgt aggcggtgct    12480
acagagttct tgaagtggtg ggctaactac ggctacacta agaacagt atttggtatc     12540 tgcgctctgc tgaagccagt taccttcgga aaaagagttg gtagctcttg atccggcaaa    12600
caaaccaccg ctggtagcgg tggtttttt gtttgcaagc agcagattac gcgcagaaaa    12660
aaaggatctc aagaagatcc tttgatcttt tctacgggg ctgacgctca gtggaacgac     12720
gcgcgcgtaa ctcacgttaa gggattttgg tcatgagctt gcgccgtccc gtcaagtcag    12780
```
cgtaatgctc tgcttt                                                          12796

<210> SEQ ID NO 12
<211> LENGTH: 12551
<212> TYPE: DNA
<213> ORGANISM: Artificial Sequence
<220> FEATURE:
<223> OTHER INFORMATION: pAAV.MECP2.copt.hPEX1
<220> FEATURE:
<221> NAME/KEY: misc_feature
<222> LOCATION: (1253)..(5951)
<223> OTHER INFORMATION: AAV expression cassette
<220> FEATURE:
<221> NAME/KEY: misc_feature
<222> LOCATION: (1253)..(1382)
<223> OTHER INFORMATION: 5' ITR
<220> FEATURE:
<221> NAME/KEY: promoter
<222> LOCATION: (1437)..(1665)
<223> OTHER INFORMATION: MECP2 promoter
<220> FEATURE:
<221> NAME/KEY: misc_feature
<222> LOCATION: (1674)..(1682)
<223> OTHER INFORMATION: Kozak
<220> FEATURE:
<221> NAME/KEY: misc_feature
<222> LOCATION: (1683)..(5534)
<223> OTHER INFORMATION: Codon optimized hPEX1
<220> FEATURE:
<221> NAME/KEY: polyA_signal
<222> LOCATION: (5565)..(5772)
<223> OTHER INFORMATION: bGH Poly(A)
<220> FEATURE:
<221> NAME/KEY: misc_feature
<222> LOCATION: (5822)..(5951)
<223> OTHER INFORMATION: 3' ITR

<400> SEQUENCE: 12
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct    180
attaatttcc cctcgtcaaa aataaggtta tcaagtgaga atcaccatg agtgacgact     240 gaatccggtg agaatggcaa aagtttatgc atttcttcc agacttgttc aacaggccag    300
ccattacgct cgtcatcaaa atcactcgca tcaaccaaac cgttattcat tcgtgattgc    360
gcctgagcga ggcgaaatac gcgatcgctg ttaaaaggac aattacaaac aggaatcgag    420
tgcaaccggc gcaggaacac tgccagcgca tcaacaatat tttcacctga atcaggatat    480
tcttctaata cctggaacgc tgtttttccg gggatcgcag tggtgagtaa ccatgcatca    540
tcaggagtac ggataaaatg cttgatggtc ggaagtggca taaattccgt cagccagttt    600
agtctgacca tctcatctgt aacatcattg gcaacgctac ctttgccatg tttcagaaac    660
aactctggcg catcgggctt cccatacaag cgatagattg tcgcacctga ttgcccgaca    720
ttatcgcgag cccatttata cccatataaa tcagcatcca tgttggaatt taatcgcggc    780
ctcgacgttt cccgttgaat atggctcata ttcttccttt ttcaatatta ttgaagcatt    840
tatcagggtt attgtctcat gagcggatac atatttgaat gtatttagaa aaataaacaa    900
ataggggtca gtgttacaac caattaacca attctgaaca ttatcgcgag cccatttata    960
cctgaatatg gctcataaca ccccttgttt gcctggcggc agtagcgcgg tggtcccacc   1020
tgaccccatg ccgaactcag aagtgaaacg ccgtagcgcc gatggtagtg tggggactcc   1080
ccatgcgaga gtagggaact gccaggcatc aaataaaacg aaaggctcag tcgaaagact   1140

-continued

```
gggcctttcg cccgggctaa ttaggggtg tcgcccttat tcgactctat agtgaagttc    1200
ctattctcta gaaagtatag gaacttctga agtggggtcg acttaattaa ggctgcgcgc    1260
tcgctcgctc actgaggccg cccgggcaaa gcccgggcgt cgggcgacct ttggtcgccc    1320
ggcctcagtg agcgagcgag cgcgcagaga gggagtggcc aactccatca ctaggggttc    1380
cttgtagtta atgattaacc cgccatgcta cttatctacg tagcaagcta gcgcttagct    1440
gaatggggtc cgcctctttt ccctgcctaa acagacagga actcctgcca attgagggcg    1500
tcaccgctaa ggctccgccc cagcctgggc tccacaacca atgaagggta atctcgacaa    1560
agagcaaggg gtggggcgcg ggcgcgcagg tgcagcagca cacaggctgg tcgggagggc    1620
ggggcgcgac gtctgccgtg cggggtcccg gcatcggttg cgcgcgcggc cgcgccgcca    1680
ccatgtgggg aagcgacaga ctggccgag ctggagggg aggagcagcc gtcaccgtgg    1740
cgttcactaa cgcgcgggac tgcttctcc atctgccgcg gaggctggtc gcccagctgc    1800
acctcctgca gaaccaggcc atcgaggtgg tgtggtccca ccaaccggcc ttttgagct    1860
gggtcgaggg aaggcacttt tcggaccagg agaaaatgt ggcggagatc aaccgccagg    1920
tcggccagaa gctgggactg tccaacggcg acaggtgtt cctcaagccg tgcagccacg    1980
tggtgtcctg ccaacaggtg gaagtggagc cgctctccgc cgacgactgg gagatcctcg    2040
aattgcatgc cgtgagcctc gaacagcatc tgttggacca gattcgcatt gtgttcccga    2100
aggccatatt ccccgtgtgg gtcgatcagc agacctatat cttcatccag attgtggccc    2160
tcatcccggc cgcctcatac ggacggctgg aaactgacac caagctgctg attcaaccta    2220
agaccccgag ggcaaagaa aacaccttct ccaaggccga cgctgagtac aagaagctcc    2280
actcctacgg acgggaccag aaggggatga tgaaggagct gcaaaccaag cagctccaga    2340
gcaacaccgt ggggatcacc gagtccaatg aaaacgagtc ggaaatccca gtcgattcat    2400
cttccgtggc cagcctgtgg actatgatcg gttccatttt ctcgttccaa tctgagaaga    2460
agcaggaaac tagctggggg ctgactgaga tcaacgcctt caagaacatg cagtccaaag    2520
tggtgcctct ggataacatc tttcgcgtgt gcaagtccca accgccctca atctacaacg    2580
cgtccgctac ctccgtgttt cataagcact gtgccatcca cgtgttccca tgggatcagg    2640
aatacttcga tgtcgaacct tccttcaccg tgacttacgg gaagcttgtc aagctcctca    2700
gccccaagca gcagcaatcg aaaactaagc agaacgtgct ttccccggag aaggagaagc    2760
aaatgtcaga accactcgac cagaagaaaa tcagatcgga tcataacgaa gaggacgaga    2820
aggcctgcgt ccttcaggtg gtctggaacg gcctggagga gctgaacaac gcgattaagt    2880
acaccaagaa cgtcgaggtc cttcacctgg gaaaggtgtg gattccggat gatctgagga    2940
aacgcctcaa catcgaaatg cacgctgtgg tgcggattac cccggtcgag gtcaccccaa    3000
agatccctcg ctccttgaag ctgcagccgc gagaaaactt gcccaaggac atttctgaag    3060
aggatatcaa gactgtgttc tactcctggc tgcaacagag cactaccacc atgctccctc    3120
tggtcatttc ggaggaagaa ttcatcaaac tggaaaccaa ggacggactg aaagaattct    3180
ccctgtccat cgtgcactcc tgggaaaagg agaaggacaa gaatatcttc ctgctgtccc    3240
ccaatctgct gcaaaagacc acgatccagg tgctgctcga ccccatggtg aaggaggaaa    3300
actcagaaga gatcgacttc atcctgccgt tccttaagct gagttcactg ggaggcgtga    3360
actcccttgg cgtgtcctcg ctggagcaca tcactcactc actgctgggc cggcctctga    3420
gcagacagct tatgagcttg gtcgccggac tcagaaacgg tgcccctcctg ctcaccggcg    3480
gcaagggatc gggaaagtcc accctcgcta aggccatttg caaagaggca ttcgataagc    3540
```

```
tggacgccca tgtggagcgg gtggactgta aggccctccg cggaaagcga ttggaaaata   3600
ttcaaaagac tctcgaagtc gccttttccg aagccgtctg gatgcagccc tcggtcgtcc   3660
tgctcgacga tctggacctc atcgctgggc tgccggccgt gccggagcat gaacactccc   3720
ctgacgcggt ccagtcgcaa cggctcgccc acgccctgaa cgatatgatt aaggaattca   3780
tctcaatggg atcactggtg gccctgatcg cgacttccca gagccagcag tccctgcacc   3840
ctctgctggt gtcggcccag ggcgtgcaca ttttcagtg tgtgcaacac atccagccgc    3900
ccaaccagga gcagcggtgc gaaatcctgt gcaacgtgat taagaacaag ctggactgcg   3960
atatcaacaa gtttaccgac cttgatctcc aacatgtggc taaggagact gggggcttcg   4020
tggctcggga cttcacagtg ttggtggacc gggcaattca ctccagactg tcccgccaga   4080
gcatttccac ccgcgaaaaa ctggtcctga ccacccctcga cttccagaag gccctcagag   4140
gcttccttcc tgcgagcctc agatccgtca accttcacaa gccgcgggac cttggctggg   4200
acaagatcgg tgggctccac gaggtgcggc agatcctcat ggacaccatt cagctgcctg   4260
caaagtaccc cgagctgttc gccaacttgc cgattcgcca gcgcacggga atcctgctct   4320 acggccccc gggcaccgga aagacccctgc tggccggtgt gatcgcccgg gaatcgagga   4380
tgaacttcat ctccgtgaag ggacccgaac tcctgtccaa gtacatcggt gcctccgaac   4440
aggccgtgcg cgatatattc attagggccc aggccgcgaa gccctgcatt ctgttcttcg   4500
acgagtttga atcgatcgcg ccccggaggg gccacgacaa cacgggagtg accgaccggg   4560
tggtgaacca gctgctcacc caactggatg gcgtggaagg ccttcaggga gtgtacgtgc   4620
tggcggctac ctccagaccg gacctgatcg atccggccct gctgcgcccc gggagactgg   4680
acaagtgcgt gtattgccct cccccctgacc aggtgtcaag gttggaaatc ctcaacgtgc   4740
tctcggactc cctgccactg gcagatgatg tggacctcca gcatgtggcc tccgtgactg   4800
acagcttcac aggagccgat ctgaaggccc tgctttacaa cgcccagttg gaggcgctgc   4860
acggtatgct gctgtcctcc ggtctgcagg atggctcctc ctcttccgat agcgacctgt   4920
cgctgagcag catggtgttc ctgaaccatt ccagcggctc cgatgacagc gcgggcgacg   4980
gagaatgtgg actggatcaa tccctggtgt ccctggagat gagcgagatt ctgccagacg   5040
agtccaagtt caacatgtac aggctgtact tcggcagcag ctacgagtcc gagctgggaa   5100
atggtacctc gtccgacctg tcaagccagt gcctgtccgc gccttcctcc atgacccagg   5160
acctccctgg agtgccaggg aaggatcagc tgttcagcca gcctccgtg ctgcgcactg    5220 cgagccagga agggtgccag gaattgaccc aagagcagcg ggaccaactg cgcgcggaca   5280
tttcgatcat caaaggcaga taccgctccc aatccgggga ggacgaaagc atgaaccagc   5340
ccgggcctat caagactaga ctggcaatct cccaaagcca cctgatgacc gcactgggac   5400
acacccggcc ctcgatctcg gaggacgact ggaagaactt cgctgagctg tacgaatcct   5460
tccagaatcc gaagcggaga aagaaccaga gcggaactat gttccggccc ggacagaagg   5520
tgaccctggc ctgaagtact gcggatcctg cagatctgcc tcgactgtgc cttctagttg   5580
ccagccatct gttgtttgcc cctccccgt gccttccttg acctggaag gtgccactcc     5640 cactgtcctt tcctaataaa atgaggaaat tgcatcgcat tgtctgagta ggtgtcattc   5700
tattctgggg ggtggggtgg ggcaggacag caaggggag gattgggaag acaatagcag    5760
gcatgctggg gactcgagtt ctacgtgat aagtagcatg gcgggttaat cattaactac     5820
aaggaacccc tagtgatgga gttggccact ccctctctgc gcgctcgctc gctcactgag   5880
```

-continued

```
gccgggcgac caaaggtcgc ccgacgcccg ggctttgccc gggcggcctc agtgagcgag    5940
cgagcgcgca gccttaatta acctaaggaa aatgaagtga agttcctata ctttctagag    6000
aataggaact tctatagtga gtcgaataag ggcgacacaa aatttattct aaatgcataa    6060
taaatactga taacatctta tagtttgtat tatattttgt attatcgttg acatgtataa    6120
ttttgatatc aaaaactgat tttccctttta ttattttcga gatttatttt cttaattctc    6180
tttaacaaac tagaaatatt gtatatacaa aaatcataa ataatagatg aatagtttaa     6240
ttataggtgt tcatcaatcg aaaaagcaac gtatcttatt taaagtgcgt tgcttttttc    6300
tcatttataa ggttaaataa ttctcatata tcaagcaaag tgacaggcgc ccttaaatat    6360
tctgacaaat gctctttccc taaactcccc ccataaaaaa acccgccgaa gcgggttttt    6420
acgttatttg cggattaacg attactcgtt atcagaaccg cccaggggggc ccgagcttaa    6480 ccttttttatt tgggggagag ggaagtcatg aaaaaactaa cctttgaaat tcgatctcca    6540
gcacatcagc aaaacgctat tcacgcagta cagcaaatcc ttccagaccc aaccaaacca    6600
atcgtagtaa ccattcagga acgcaaccgc agcttagacc aaaacaggaa gctatgggcc    6660
tgcttaggtg acgtctctcg tcaggttgaa tggcatggtc gctggctgga tgcagaaagc    6720
tggaagtgtg tgtttaccgc agcattaaag cagcaggatg ttgttcctaa ccttgccggg    6780
aatggctttg tggtaatagg ccagtcaacc agcaggatgc gtgtaggcga atttgcggag    6840
ctattagagc ttatacaggc attcggtaca gagcgtggcg ttaagtggtc agacgaagcg    6900
agactggctc tggagtggaa agcgagatgg ggagacaggg ctgcatgata aatgtcgtta    6960
gtttctccgg tggcaggacg tcagcatatt tgctctggct aatggagcaa aagcgacggg    7020
caggtaaaga cgtgcattac gttttcatgg atacaggttg tgaacatcca atgacatatc    7080
ggtttgtcag ggaagttgtg aagttctggg atataccgct caccgtattg caggttgata    7140
tcaacccgga gcttggacag ccaaatggtt atacggtatg ggaaccaaag gatattcaga    7200
cgcgaatgcc tgttctgaag ccatttatcg atatggtaaa gaaatatggc actccatacg    7260
tcggcggcgc gttctgcact gacagattaa aactcgttcc cttcaccaaa tactgtgatg    7320
accatttcgg gcgagggaat tacaccacgt ggattggcat cagagctgat gaaccgaagc    7380
ggctaaagcc aaagcctgga atcagatatc ttgctgaact gtcagacttt gagaaggaag    7440
atatcctcgc atggtggaag caacaaccat tcgatttgca ataccggaa catctcggta     7500 actgcatatt ctgcattaaa aaatcaacgc aaaaaatcgg acttgcctgc aaagatgagg    7560
agggattgca gcgtgttttt aatgaggtca tcacgggatc ccatgtgcgt gacggacatc    7620
gggaaacgcc aaaggagatt atgtaccgag aagaatgtc gctggacggt atcgcgaaaa     7680
tgtattcaga aaatgattat caagccctgt atcaggacat ggtacgagct aaaagattcg    7740
ataccggctc ttgttctgag tcatgcgaaa tatttggagg gcagcttgat ttcgacttcg    7800
ggagggaagc tgcatgatgc gatgttatcg gtgcggtgaa tgcaaagaag ataaccgctt    7860
ccgaccaaat caaccttact ggaatcgatg gtgtctccgg tgtgaaagaa caccaacagg    7920
ggtgttacca ctaccgcagg aaaaggagga cgtgtggcga cagcgacg aagtatcacc     7980 gacataatct gcgaaaactg caaataccct tccaacgaaac gcaccagaaa taaacccaag    8040
ccaatcccaa aagaatctga cgtaaaaacc ttcaactaca cggctcacct gtgggatatc    8100
cggtggctaa gacgtcgtgc gaggaaaaca aggtgattga ccaaaatcga agttacgaac    8160
aagaaagcgt cgagcgagct ttaacgtgcg ctaactgcgg tcagaagctg catgtgctgg    8220
aagttcacgt gtgtgagcac tgctgcgcag aactgatgag cgatccgaat agctcgatgc    8280
```

```
acgaggaaga agatgatggc taaaccagcg cgaagacgat gtaaaaacga tgaatgccgg    8340
gaatggtttc accctgcatt cgctaatcag tggtggtgct ctccagagtg tggaaccaag    8400
atagcactcg aacgacgaag taaagaacgc gaaaaagcgg aaaaagcagc agagaagaaa    8460
cgacgacgag aggagcagaa acagaaagat aaacttaaga ttcgaaaact cgccttaaag    8520
ccccgcagtt actggattaa acaagcccaa caagccgtaa acgccttcat cagagaaaga    8580
gaccgcgact taccatgtat ctcgtgcgga acgctcacgt ctgctcagtg ggatgccgga    8640
cattaccgga caactgctgc ggcacctcaa ctccgattta tgaacgcaa tattcacaag     8700 caatgcgtgg tgtgcaacca gcacaaaagc ggaaatctcg ttccgtatcg cgtcgaactg    8760
attagccgca tcgggcagga agcagtagac gaaatcgaat caaaccataa ccgccatcgc    8820
tggactatcg aagagtgcaa ggcgatcaag gcagagtacc aacagaaact caaagacctg    8880
cgaaatagca gaagtgaggc cgcatgacgt tctcagtaaa aaccattcca gacatgctcg    8940
ttgaagcata cggaaatcag acagaagtag cacgcagact gaaatgtagt cgcggtacgg    9000
tcagaaaata cgttgatgat aaagacggga aaatgcacgc catcgtcaac gacgttctca    9060
tggttcatcg cggatggagt gaaagagatg cgctattacg aaaaaattga tggcagcaaa    9120
taccgaaata tttgggtagt tggcgatctg cacggatgct acacgaacct gatgaacaaa    9180
ctggatacga ttggattcga caacaaaaaa gacctgctta tctcggtggg cgatttggtt    9240
gatcgtggtg cagagaacgt tgaatgcctg gaattaatca cattcccctg gttcagagct    9300
gtacgtggaa accatgagca aatgatgatt gatggcttat cagagcgtgg aaacgttaat    9360
cactggctgc ttaatggcgg tggctggttc tttaatctcg attacgacaa agaaattctg    9420
gctaaagctc ttgcccataa agcagatgaa cttccgttaa tcatcgaact ggtgagcaaa    9480
gataaaaaat atgttatctg ccacgccgat tatccctttg acgaatacga gtttggaaag    9540
ccagttgatc atcagcaggt aatctggaac cgcgaacgaa tcagcaactc acaaaacggg    9600
atcgtgaaag aaatcaaagg cgcggacacg ttcatctttg gtcatacgcc agcagtgaaa    9660
ccactcaagt ttgccaacca aatgtatatc gataccggcg cagtgttctg cggaaaccta    9720
acattgattc aggtacaggg agaaggcgca tgagactcga aagcgtagct aaatttcatt    9780
cgccaaaaag cccgatgatg agcgactcac cacgggccac ggcttctgac tctctttccg    9840
gtactgatgt gatggctgct atggggatgg cgcaatcaca agccggattc ggtatggctg    9900
cattctgcgg taagcacgaa ctcagccaga acgacaaaca aaaggctatc aactatctga    9960
tgcaatttgc acacaaggta tcggggaaat accgtggtgt ggcaaagctt gaaggaaata   10020
ctaaggcaaa ggtactgcaa gtgctcgcaa cattcgctta tgcggattat tgccgtagtg   10080
ccgcgacgcc gggggcaaga tgcagagatt gccatggtac aggccgtgcg gttgatattg   10140
ccaaaacaga gctgtggggg agagttgtcg agaaagagtg cggaagatgc aaaggcgtcg   10200
gctattcaag gatgccagca agcgcagcat atcgcgctgt gacgatgcta atcccaaacc   10260
ttacccaacc cacctggtca cgcactgtta agccgctgta tgacgctctg gtggtgcaat   10320
gccacaaaga agagtcaatc gcagacaaca ttttgaatgc ggtcacacgt tagcagcatg   10380
attgccacgg atgcaacat attaacggca tgatattgac ttattgaata aaattgggta    10440
aatttgactc aacgatgggt taattcgctc gttgtggtag tgagatgaaa agaggcggcg   10500
cttactaccg attccgccta gttggtcact tcgacgtatc gtctggaact ccaaccatcg   10560
caggcagaga ggtctgcaaa atgcaatccc gaaacagttc gcaggtaata gttagagcct   10620
```

```
gcataacggt tcgggatttt tttatatctg cacaacaggt aagagcattg agtcgataat    10680
cgtgaagagt cggcgagcct ggttagccag tgctctttcc gttgtgctga attaagcgaa    10740
taccggaagc agaaccggat caccaaatgc gtacaggcgt catcgccgcc cagcaacagc    10800
acaacccaaa ctgagccgta gccactgtct gtcctgaatt cattagtaat agttacgctg    10860
cggcctttta cacatgacct tcgtgaaagc gggtggcagg aggtcgcgct aacaacctcc    10920
tgccgttttg cccgtgcata tcggtcacga acaaatctga ttactaaaca cagtagcctg    10980
gatttgttct atcagtaatc gaccttattc ctaattaaat agagcaaatc cccttattgg    11040
gggtaagaca tgaagatgcc agaaaaacat gacctgttgg ccgccattct cgcggcaaag    11100
gaacaaggca tcggggcaat ccttgcgttt gcaatggcgt accttcgcgg cagatataat    11160
ggcggtgcgt ttacaaaaac agtaatcgac gcaacgatgt cgccattat cgcctggttc     11220
attcgtgacc ttctcgactt cgccggacta agtagcaatc tcgcttatat aacgagcgtg    11280
tttatcggct acatcggtac tgactcgatt ggttcgctta tcaaacgctt cgctgctaaa    11340
aaagccggag tagaagatgg tagaaatcaa taatcaacgt aaggcgttcc tcgatatgct    11400
ggcgtggtcg gagggaactg ataacggacg tcagaaaacc agaaatcatg gttatgacgt    11460
cattgtaggc ggagagctat ttactgatta ctccgatcac cctcgcaaac ttgtcacgct    11520
aaacccaaaa ctcaaatcaa caggcgctta agactggccg tcgttttaca acacagaaag    11580
agtttgtaga aacgcaaaaa ggccatccgt caggggcctt ctgcttagtt tgatgcctgg    11640
cagttcccta ctctcgcctt ccgcttcctc gctcactgac tcgctgcgct cggtcgttcg    11700
gctgcggcga gcggtatcag ctcactcaaa ggcggtaata cggttatcca cagaatcagg    11760
ggataacgca ggaaagaaca tgtgagcaaa aggccagcaa aaggccagga accgtaaaaa    11820
ggccgcgttg ctggcgtttt tccataggct ccgcccccct gacgagcatc acaaaaatcg    11880
acgctcaagt cagaggtggc gaaacccgac aggactataa agataccagg cgtttccccc    11940
tggaagctcc ctcgtgcgct ctcctgttcc gaccctgccg cttaccggat acctgtccgc    12000
ctttctccct tcgggaagcg tggcgctttc tcatagctca cgctgtaggt atctcagttc    12060
ggtgtaggtc gttcgctcca agctgggctg tgtgcacgaa ccccccgttc agcccgaccg    12120
ctgcgcctta tccggtaact atcgtcttga gtccaacccg gtaagacacg acttatcgcc    12180
actggcagca gccactggta acaggattag cagagcgagg tatgtaggcg gtgctacaga    12240
gttcttgaag tggtgggcta actacggcta cactagaaga acagtatttg gtatctgcgc    12300
tctgctgaag ccagttacct tcggaaaaag agttggtagc tcttgatccg gcaaacaaac    12360
caccgctggt agcggtggtt tttttgtttg caagcagcag attacgcgca gaaaaaaagg    12420
atctcaagaa gatcctttga tcttttctac ggggtctgac gctcagtgga acgacgcgcg    12480
cgtaactcac gttaagggat tttggtcatg agcttgcgcc gtcccgtcaa gtcagcgtaa    12540
tgctctgctt t                                                        12551
```

```
<210> SEQ ID NO 13
<211> LENGTH: 12835
<212> TYPE: DNA
<213> ORGANISM: Artificial Sequence
<220> FEATURE:
<223> OTHER INFORMATION: pAAV.CMV.hPEX1
<220> FEATURE:
<221> NAME/KEY: misc_feature
<222> LOCATION: (1253)..(6235)
<223> OTHER INFORMATION: AAV expression cassette
<220> FEATURE:
<221> NAME/KEY: misc_feature
```

<222> LOCATION: (1253)..(1382)
<223> OTHER INFORMATION: 5' ITR
<220> FEATURE:
<221> NAME/KEY: enhancer
<222> LOCATION: (1433)..(1736)
<223> OTHER INFORMATION: CMV enhancer
<220> FEATURE:
<221> NAME/KEY: promoter
<222> LOCATION: (1737)..(1940)
<223> OTHER INFORMATION: CMV promoter
<220> FEATURE:
<221> NAME/KEY: misc_feature
<222> LOCATION: (1958)..(1966)
<223> OTHER INFORMATION: Kozak
<220> FEATURE:
<221> NAME/KEY: misc_feature
<222> LOCATION: (1967)..(5818)
<223> OTHER INFORMATION: Cdodon optimized hPEX1
<220> FEATURE:
<221> NAME/KEY: polyA_signal
<222> LOCATION: (5849)..(6056)
<223> OTHER INFORMATION: bGH Poly(A)
<220> FEATURE:
<221> NAME/KEY: misc_feature
<222> LOCATION: (6106)..(6235)
<223> OTHER INFORMATION: 3' ITR

<400> SEQUENCE: 13

```
tagaaaaact catcgagcat caaatgaaac tgcaatttat tcatatcagg attatcaata      60
ccatattttt gaaaaagccg tttctgtaat gaaggagaaa actcaccgag gcagttccat     120
aggatggcaa gatcctggta tcggtctgcg attccgactc gtccaacatc aatacaacct     180
attaatttcc cctcgtcaaa aataaggtta tcaagtgaga atcaccatg agtgacgact      240 gaatccggtg agaatggcaa aagtttatgc atttctttcc agacttgttc aacaggccag     300
ccattacgct cgtcatcaaa atcactcgca tcaaccaaac cgttattcat tcgtgattgc     360
gcctgagcga ggcgaaatac gcgatcgctg ttaaaaggac aattacaaac aggaatcgag     420
tgcaaccggc gcaggaacac tgccagcgca tcaacaatat tttcacctga atcaggatat     480
tcttctaata cctggaacgc tgttttttcg gggatcgcag tggtgagtaa ccatgcatca     540
tcaggagtac ggataaaatg cttgatggtc ggaagtggca taaattccgt cagccagttt     600
agtctgacca tctcatctgt aacatcattg gcaacgctac ctttgccatg tttcagaaac     660
aactctggcg catcgggctt cccatacaag cgatagattg tcgcacctga ttgcccgaca     720
ttatcgcgag cccatttata cccatataaa tcagcatcca tgttggaatt taatcgcggc     780
ctcgacgttt cccgttgaat atggctcata ttcttccttt ttcaatatta ttgaagcatt     840
tatcagggtt attgtctcat gagcggatac atatttgaat gtatttagaa aaataaacaa     900
ataggggtca gtgttacaac caattaacca attctgaaca ttatcgcgag cccatttata     960
cctgaatatg gctcataaca ccccttgttt gcctggcggc agtagcgcgg tggtcccacc    1020 tgacccccatg ccgaactcag aagtgaaacg ccgtagcgcc gatggtagtg tggggactcc    1080
ccatgcgaga gtagggaact gccaggcatc aaataaaacg aaaggctcag tcgaaagact    1140
gggcctttcg cccgggctaa ttagggggtg tcgcccttat tcgactctat agtgaagttc    1200
ctattctcta gaaagtatag gaacttctga agtggggtcg acttaattaa ggctgcgcgc    1260
tcgctcgctc actgaggccg cccgggcaaa gcccgggcgt cgggcgacct ttggtcgccc    1320
ggcctcagtg agcgagcgag cgcgcagaga gggagtggcc aactccatca ctaggggttc    1380
cttgtagtta atgattaacc cgccatgcta cttatctacg tagcaagcta gccgttacat    1440
aacttacggt aaatggcccg cctggctgac cgcccaacga ccccgccca ttgacgtcaa     1500
```

```
taatgacgta tgttcccata gtaacgccaa tagggacttt ccattgacgt caatgggtgg    1560
agtatttacg gtaaactgcc cacttggcag tacatcaagt gtatcatatg ccaagtacgc    1620
cccctattga cgtcaatgac ggtaaatggc ccgcctggca ttatgcccag tacatgacct    1680
tatgggactt tcctacttgg cagtacatct acgtattagt catcgctatt accatggtga    1740
tgcggttttg gcagtacatc aatgggcgtg gatagcggtt tgactcacgg ggatttccaa    1800
gtctccaccc cattgacgtc aatgggagtt tgttttggca ccaaaatcaa cgggactttc    1860
caaaatgtcg taacaactcc gccccattga cgcaaatggg cggtaggcgt gtacggtggg    1920
aggtctatat aagcagagct gtacactag cggccgcgcc gccaccatgt ggggaagcga    1980
cagactggcc ggagctggag ggggaggagc agccgtcacc gtggcgttca ctaacgcgcg    2040
ggactgcttt ctccatctgc cgcggaggct ggtcgcccag ctgcacctcc tgcagaacca    2100
ggccatcgag gtggtgtggt cccaccaacc ggccttttg agctgggtcg agggaaggca    2160
cttttcggac cagggagaaa atgtggcgga gatcaaccgc caggtcggcc agaagctggg    2220
actgtccaac ggcggacagg tgttcctcaa gccgtgcagc cacgtggtgt cctgccaaca    2280
ggtggaagtg gagccgctct ccgccgacga ctgggagatc ctcgaattgc atgccgtgag    2340
cctcgaacag catctgttgg accagattcg cattgtgttc ccgaaggcca tattcccgt    2400 gtgggtcgat cagcagacct atatcttcat ccagattgtg ccctcatcc cggccgcctc    2460 atacggacgg ctgaaactg acaccaagct gctgattcaa cctaagaccc ggagggccaa    2520
agaaaacacc ttctccaagg ccgacgctga gtacaagaag ctccactcct acggacggga    2580
ccagaagggg atgatgaagg agctgcaaac caagcagctc cagagcaaca ccgtggggat    2640
caccgagtcc aatgaaaacg agtcggaaat cccagtcgat tcatcttccg tggccagcct    2700
gtggactatg atcggttcca ttttctcgtt ccaatctgag aagaagcagg aaactagctg    2760
ggggctgact gagatcaacg ccttcaagaa catgcagtcc aaagtggtgc ctctggataa    2820
catctttcgc gtgtgcaagt cccaaccgcc ctcaatctac aacgcgtccg ctacctccgt    2880
gtttcataag cactgtgcca tccacgtgtt cccatgggat caggaatact tcgatgtcga    2940
accttccttc accgtgactt acgggaagct tgtcaagctc ctcagccca agcagcagca    3000 atcgaaaact aagcagaacg tgctttcccc ggagaaggag aagcaaatgt cagaaccact    3060
cgaccagaag aaaatcagat cggatcataa cgaagaggac gagaaggcct gcgtccttca    3120
ggtggtctgg aacggcctgg aggagctgaa caacgcgatt aagtacacca gaacgtcga    3180 ggtccttcac ctgggaaagg tgtggattcc ggatgatctg aggaaacgcc tcaacatcga    3240
aatgcacgct gtggtgcgga ttaccccggt cgaggtcacc ccaaagatcc ctcgctcctt    3300
gaagctgcag ccgcgagaaa acttgcccaa ggacattct gaagaggata tcaagactgt    3360
gttctactcc tggctgcaac agagcactac caccatgctc cctctggtca tttcggagga    3420
agaattcatc aaactggaaa ccaaggacgg actgaaagaa ttctccctgt ccatcgtgca    3480
ctcctgggaa aaggagaagg acaagaatat cttcctgctg tcccccaatc tgctgcaaaa    3540
gaccacgatc caggtgctgc tcgaccccat ggtgaaggag gaaaactcag aagagatcga    3600
cttcatcctg ccgttcctta agctgagttc actgggaggc gtgaactccc ttggcgtgtc    3660
ctcgctggag cacatcactc actcactgct gggccggcct ctgagcagac agcttatgag    3720
cttggtcgcc ggactcagaa acggtgccc cctgctcacc gcggcaagg gatcgggaaa    3780 gtccacccta gctaaggcca tttgcaaaga ggcattcgat aagctggacg cccatgtgga    3840
gcgggtggac tgtaaggccc tccgcggaaa gcgattggaa aatattcaaa agactctcga    3900
```

```
agtcgccttt tccgaagccg tctggatgca gccctcggtc gtcctgctcg acgatctgga    3960
cctcatcgct gggctgccgg ccgtgccgga gcatgaacac tccccctgacg cggtccagtc   4020
gcaacggctc gcccacgccc tgaacgatat gattaaggaa ttcatctcaa tgggatcact    4080
ggtggccctg atcgcgactt cccagagcca gcagtccctg caccctctgc tggtgtcggc    4140
ccagggcgtg cacatttttc agtgtgtgca acacatccag ccgcccaacc aggagcagcg    4200
gtgcgaaatc ctgtgcaacg tgattaagaa caagctggac tgcgatatca acaagtttac    4260
cgaccttgat ctccaacatg tggctaagga gactgggggc ttcgtggctc gggacttcac    4320
agtgttggtg gaccgggcaa ttcactccag actgtcccgc cagagcattt ccacccgcga    4380
aaaactggtc ctgaccaccc tcgacttcca gaaggccctc agaggcttcc ttcctgcgag    4440
cctcagatcc gtcaaccttc acaagccgcg ggaccttggc tggacaagaa tcggtgggct    4500
ccacgaggtg cggcagatcc tcatggacac cattcagctg cctgcaaagt accccgagct    4560
gttcgccaac ttgccgattc gccagcgcac gggaatcctg ctctacgcc ccccgggcac     4620
cggaaagacc ctgctggccg tgtgatcgc ccgggaatcg aggatgaact tcatctccgt     4680
gaagggaccc gaactcctgt ccaagtacat cggtgcctcc gaacaggccg tgcgcgatat    4740
attcattagg gcccaggccg cgaagccctg cattctgttc ttcgacgagt ttgaatcgat    4800
cgcgccccgg aggggccacg acaacacggg agtgaccgac cgggtggtga accagctgct    4860
cacccaactg gatggcgtgg aaggccttca gggagtgtac gtgctggcgg ctacctccag    4920
accgacctg atcgatccgg ccctgctgcg ccccgggaga ctggacaagt gcgtgtattg     4980
ccctcccct gaccaggtgt caaggttgga atcctcaac gtgctctcgg actccctgcc      5040
actggcagat gatgtggacc tccagcatgt ggcctccgtg actgacagct tcacaggagc    5100
cgatctgaag gccctgcttt acaacgccca gttggaggcg ctgcacggta tgctgctgtc    5160
ctccggtctg caggatggct cctcctcttc cgatagcgac ctgtcgctga gcagcatggt    5220
gttcctgaac cattccagcg gctccgatga cagcgcgggc gacggagaat gtggactgga    5280
tcaatccctg gtgtccctgg agatgagcga gattctgcca gacgagtcca agttcaacat    5340
gtacaggctg tacttcggca gcagctacga gtccgagctg ggaaatggta cctcgtccga    5400
cctgtcaagc cagtgcctgt ccgcgccttc ctccatgacc caggacctcc ctggagtgcc    5460
agggaaggat cagctgttca gccagcctcc cgtgctgcgc actgcgagcc aggaagggtg    5520
ccaggaattg acccaagagc agcgggacca actgcgcgcg gacatttcga tcatcaaagg    5580
cagataccgc tcccaatccg gggaggacga aagcatgaac cagcccgggc ctatcaagac    5640
tagactggca atctcccaaa gccacctgat gaccgcactg ggacacaccc ggccctcgat    5700
ctcggaggac gactggaaga acttcgctga gctgtacgaa tccttccaga atccgaagcg    5760
gagaaagaac cagagcggaa ctatgttccg gcccggacag aaggtgaccc tggcctgaag    5820
tactgcggat cctgcagatc tgcctcgact gtgccttcta gttgccagcc atctgttgtt    5880
tgcccctccc ccgtgccttc cttgaccctg gaaggtgcca ctcccactgt ccttcctaa    5940
taaaatgagg aaattgcatc gcattgtctg agtaggtgtc attctattct gggggtggg    6000
gtggggcagg acagcaaggg ggaggattgg gaagacaata gcaggcatgc tggggactcg    6060
agttctacgt agataagtag catggcgggt taatcattaa ctacaaggaa cccctagtga    6120
tggagttggc cactccctct ctgcgcgctc gctcgctcac tgaggccggg cgaccaaagg    6180
tcgcccgacg cccgggcttt gcccgggcgg cctcagtgag cgagcgagcg cgcagcctta    6240
```

```
attaacctaa ggaaaatgaa gtgaagttcc tatactttct agagaatagg aacttctata    6300
gtgagtcgaa taagggcgac acaaaattta ttctaaatgc ataataaata ctgataacat    6360
cttatagttt gtattatatt ttgtattatc gttgacatgt ataattttga tatcaaaaac    6420
tgattttccc tttattattt tcgagattta ttttcttaat tctctttaac aaactagaaa    6480
tattgtatat acaaaaaatc ataaataata gatgaatagt ttaattatag gtgttcatca    6540
atcgaaaaag caacgtatct tatttaaagt gcgttgcttt tttctcattt ataaggttaa    6600
ataattctca tatatcaagc aaagtgacag gcgcccttaa atattctgac aaatgctctt    6660
tccctaaact ccccccataa aaaaacccgc cgaagcgggt ttttacgtta tttgcggatt    6720
aacgattact cgttatcaga accgcccagg gggcccgagc ttaacctttt tatttggggg    6780
agagggaagt catgaaaaaa ctaacctttg aaattcgatc tccagcacat cagcaaaacg    6840
ctattcacgc agtacagcaa atccttccag acccaaccaa accaatcgta gtaaccattc    6900
aggaacgcaa ccgcagctta gaccaaaaca ggaagctatg ggcctgctta ggtgacgtct    6960
ctcgtcaggt tgaatggcat ggtcgctggc tggatgcaga aagctggaag tgtgtgttta    7020
ccgcagcatt aaagcagcag gatgttgttc ctaaccttgc cgggaatggc tttgtggtaa    7080
taggccagtc aaccagcagg atgcgtgtag gcgaatttgc ggagctatta gagcttatac    7140
aggcattcgg tacagagcgt ggcgttaagt ggtcagacga agcgagactg gctctggagt    7200
ggaaagcgag atgggagac agggctgcat gataaatgtc gttagtttct ccggtggcag    7260
gacgtcagca tatttgctct ggctaatgga gcaaaagcga cgggcaggta aagacgtgca    7320
ttacgttttc atggatacag gttgtgaaca tccaatgaca tatcggtttg tcagggaagt    7380
tgtgaagttc tgggatatac cgctcaccgt attgcaggtt gatatcaacc cggagcttgg    7440
acagccaaat ggttatacgg tatgggaacc aaaggatatt cagacgcgaa tgcctgttct    7500
gaagccattt atcgatatgg taaagaaata tggcactcca tacgtcggcg gcgcgttctg    7560
cactgacaga ttaaaactcg ttcccttcac caaatactgt gatgaccatt cgggcgagg    7620
gaattacacc acgtggattg gcatcagagc tgatgaaccg aagcggctaa agccaaagcc    7680
tggaatcaga tatcttgctg aactgtcaga cttttgagaag gaagatatcc tcgcatggtg    7740
gaagcaacaa ccattcgatt tgcaaatacc ggaacatctc ggtaactgca tattctgcat    7800
taaaaaatca acgcaaaaaa tcggacttgc ctgcaaagat gaggagggat tgcagcgtgt    7860
ttttaatgag gtcatcacgg gatcccatgt gcgtgacgga catcgggaaa cgccaaagga    7920
gattatgtac cgaggaagaa tgtcgctgga cggtatcgcg aaaatgtatt cagaaaatga    7980
ttatcaagcc ctgtatcagg acatggtacg agctaaaaga ttcgataccg gctcttgttc    8040
tgagtcatgc gaaatatttg gagggcagct tgatttcgac ttcggagggg aagctgcatg    8100
atgcgatgtt atcggtgcgg tgaatgcaaa gaagataacc gcttccgacc aaatcaacct    8160
tactggaatc gatggtgtct ccggtgtgaa agaacaccaa cagggtgtt accactaccg    8220
caggaaaagg aggacgtgtg gcgagacagc gacgaagtat caccgacata atctgcgaaa    8280
actgcaaata ccttccaacg aaacgcacca gaaataaacc caagccaatc ccaaaagaat    8340
ctgacgtaaa aaccttcaac tacacggctc acctgtggga tatccggtgg ctaagacgtc    8400
gtgcgaggaa acaaggtga ttgaccaaaa tcgaagttac gaacaagaaa gcgtcgagcg    8460
agctttaacg tgcgctaact gcggtcagaa gctgcatgtg ctggaagttc acgtgtgtga    8520
gcactgctgc gcagaactga tgagcgatcc gaatagctcg atgcacgagg aagaagatga    8580
tggctaaacc agcgcgaaga cgatgtaaaa acgatgaatg ccgggaatgg tttcaccctg    8640
```

```
cattcgctaa tcagtggtgg tgctctccag agtgtggaac caagatagca ctcgaacgac    8700
gaagtaaaga acgcgaaaaa gcggaaaaag cagcagagaa gaaacgacga cgagaggagc    8760
agaaacagaa agataaactt aagattcgaa aactcgcctt aaagccccgc agttactgga    8820
ttaaacaagc ccaacaagcc gtaaacgcct tcatcagaga aagagaccgc gacttaccat    8880
gtatctcgtg cggaacgctc acgtctgctc agtgggatgc cggacattac cggacaactg    8940
ctgcggcacc tcaactccga tttaatgaac gcaatattca caagcaatgc gtggtgtgca    9000
accagcacaa aagcggaaat ctcgttccgt atcgcgtcga actgattagc cgcatcgggc    9060
aggaagcagt agacgaaatc gaatcaaacc ataaccgcca tcgctggact atcgaagagt    9120
gcaaggcgat caaggcagag taccaacaga aactcaaaga cctgcgaaat agcagaagtg    9180
aggccgcatg acgttctcag taaaaaccat tccagacatg ctcgttgaag catacggaaa    9240
tcagacagaa gtagcacgca gactgaaatg tagtcgcggt acggtcagaa aatacgttga    9300
tgataaagac gggaaaatgc acgccatcgt caacgacgtt ctcatggttc atcgcggatg    9360
gagtgaaaga gatgcgctat tacgaaaaaa ttgatggcag caaataccga aatatttggg    9420
tagttggcga tctgcacgga tgctacacga acctgatgaa caaactggat acgattggat    9480
tcgacaacaa aaaagacctg cttatctcgg tgggcgattt ggttgatcgt ggtgcagaga    9540
acgttgaatg cctggaatta atcacattcc cctggttcag agctgtacgt ggaaaccatg    9600
agcaaatgat gattgatggc ttatcagagc gtggaaacgt taatcactgg ctgcttaatg    9660
gcggtggctg gttctttaat ctcgattacg acaaagaaat tctggctaaa gctcttgccc    9720
ataaagcaga tgaacttccg ttaatcatcg aactggtgag caaagataaa aaatatgtta    9780
tctgccacgc cgattatccc tttgacgaat acgagtttgg aaagccagtt gatcatcagc    9840
aggtaatctg gaaccgcgaa cgaatcagca actcacaaaa cgggatcgtg aaagaaatca    9900
aaggcgcgga cacgttcatc tttggtcata cgccagcagt gaaaccactc aagtttgcca    9960
accaaatgta tatcgatacc ggcgcagtgt tctgcggaaa cctaacattg attcaggtac    10020
agggagaagg cgcatgagac tcgaaagcgt agctaaattt cattcgccaa aaagcccgat    10080
gatgagcgac tcaccacggg ccacggcttc tgactctctt tccggtactg atgtgatggc    10140
tgctatgggg atggcgcaat cacaagccgg attcggtatg gctgcattct gcggtaagca    10200
cgaactcagc cagaacgaca aacaaaaggc tatcaactat ctgatgcaat ttgcacacaa    10260
ggtatcgggg aaataccgtg gtgtggcaaa gcttgaagga aatactaagg caaaggtact    10320
gcaagtgctc gcaacattcg cttatgcgga ttattgccgt agtgccgcga cgccggggc    10380 aagatgcaga gattgccatg gtacaggccg tgcggttgat attgccaaaa cagagctgtg    10440
ggggagagtt gtcgagaaag agtgcggaag atgcaaaggc gtcggctatt caaggatgcc    10500
agcaagcgca gcatatcgcg ctgtgacgat gctaatccca aaccttaccc aacccacctg    10560
gtcacgcact gttaagccgc tgtatgacgc tctggtggtg caatgccaca agaagagtc    10620 aatcgcagac aacattttga atgcggtcac acgttagcag catgattgcc acggatggca    10680
acatattaac ggcatgatat tgacttattg aataaaattg ggtaaatttg actcaacgat    10740
gggttaattc gctcgttgtg gtagtgagat gaaagagggc ggcgcttact accgattccg    10800
cctagttggt cacttcgacg tatcgtctgg aactccaacc atcgcaggca gagaggtctg    10860
caaaatgcaa tccgaaaaca gttcgcaggt aatagttaga gcctgcataa cggtttcggg    10920
attttttata tctgcacaac aggtaagagc attgagtcga taatcgtgaa gagtcggcga    10980
```

```
gcctggttag ccagtgctct ttccgttgtg ctgaattaag cgaataccgg aagcagaacc    11040
ggatcaccaa atgcgtacag gcgtcatcgc cgcccagcaa cagcacaacc caaactgagc    11100
cgtagccact gtctgtcctg aattcattag taatagttac gctgcggcct tttacacatg    11160
accttcgtga agcgggtgg caggaggtcg cgctaacaac ctcctgccgt tttgcccgtg     11220
catatcggtc acgaacaaat ctgattacta acacagtag cctggattg ttctatcagt     11280 aatcgacctt attcctaatt aaatagagca atccccctta ttgggggtaa gacatgaaga   11340
tgccagaaaa acatgacctg ttggccgcca ttctcgcggc aaaggaacaa ggcatcgggg   11400
caatccttgc gtttgcaatg gcgtaccttc gcggcagata taatggcggt gcgtttacaa   11460
aaacagtaat cgacgcaacg atgtgcgcca ttatcgcctg gttcattcgt gaccttctcg   11520
acttcgccgg actaagtagc aatctcgctt atataacgag cgtgtttatc ggctacatcg   11580
gtactgactc gattggttcg cttatcaaac gcttcgctgc taaaaaagcc ggagtagaag   11640
atggtagaaa tcaataatca acgtaaggcg ttcctcgata tgctggcgtg gtcggaggga   11700
actgataacg gacgtcagaa accagaaat catggttatg acgtcattgt aggcggagag    11760
ctatttactg attactccga tcaccctcgc aaacttgtca cgctaaaccc aaaactcaaa   11820
tcaacaggcg cttaagactg gccgtcgttt tacaacacag aaagagtttg tagaaacgca   11880
aaaaggccat ccgtcagggg ccttctgctt agtttgatgc ctggcagttc cctactctcg   11940
ccttccgctt cctcgctcac tgactcgctg cgctcggtcg ttcggctgcg cgagcggta    12000 tcagctcact caaaggcggt aatacggtta tccacagaat caggggataa cgcaggaaag   12060
aacatgtgag caaaaggcca gcaaaaggcc aggaaccgta aaaaggccgc gttgctggcg   12120 ttttccata ggctccgccc ccctgacgag catcacaaaa atcgacgctc aagtcagagg    12180
tggcgaaacc cgacaggact ataaagatac caggcgtttc cccctggaag ctccctcgtg   12240
cgctctcctg ttccgaccct gccgcttacc ggatacctgt ccgcctttct cccttcggga   12300
agcgtggcgc tttctcatag ctcacgctgt aggtatctca gttcggtgta ggtcgttcgc   12360
tccaagctgg gctgtgtgca cgaaccccc gttcagcccg accgctgcgc cttatccggt    12420
aactatcgtc ttgagtccaa cccggtaaga cacgacttat cgccactggc agcagccact   12480
ggtaacagga ttagcagagc gaggtatgta ggcggtgcta cagagttctt gaagtggtgg   12540
gctaactacg gctacactag aagaacagta tttggtatct gcgctctgct gaagccagtt   12600
accttcggaa aaagagttgg tagctcttga tccggcaaac aaaccaccgc tggtagcggt   12660 ggttttttg tttgcaagca gcagattacg cgcagaaaaa aaggatctca agaagatcct    12720
ttgatctttt ctacggggtc tgacgctcag tggaacgacg cgcgcgtaac tcacgttaag   12780 ggatttggt catgagcttg cgccgtcccg tcaagtcagc gtaatgctct gcttt         12835
```

GENE THERAPY FOR TREATING PEROXISOMAL DISORDERS

CROSS-REFERENCE TO RELATED APPLICATIONS

This is a National Stage Entry under 35 U.S.C. 371 of International Patent Application No. PCT/CA2018/050642, filed May 31, 2018, which claims priority to U.S. Provisional Patent Application No. 62/513,156, filed May 31, 2017. These applications are incorporated by reference herein.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-17-8142P2_ST25.txt".

BACKGROUND OF THE INVENTION

Peroxisomes are small enzyme-containing cytoplasmic vesicular organelles found in the majority of eukaryotic cells that carry out a number of essential metabolic functions. For example, peroxisomal enzymes participate in oxidative reactions which protect the cell against hydrogen peroxide and reactive oxygen species. They assist in decomposition of fatty acids (including very long chain fatty acids, branched chain fatty acids, polyamines, D-amino acids) and also in biosynthesis of phospholipids (including plasmalogens and docosahexaenoic acid). Peroxisomes are also essential for bile acid synthesis. Thus, disorders of peroxisomes affect the central nervous system as well as many other organ systems. Peroxisome biogenesis disorders result in a large number of autosomal recessive diseases, often termed Zellweger Spectrum Disorder, and individuals born with these diseases can suffer from cognitive dysfunction, skeletal and craniofacial dysmorphic changes (including tooth enamel), lung and liver malfunction, and retinal and cochlear degeneration. Mutations in 13 different Peroxin (PEX) genes can result in these disorders, the most common ones being PEX1, PEX6, PEX10, PEX12 and PEX26. Peroxisomal biogenesis disorders occur in 1/50,000 births in the USA and there are >200 registered patients. PEX1 mutations account for 70% of the cases. See, e.g. Majewski, Jacek, et al. "A new ocular phenotype associated with an unexpected but known systemic disorder and mutation: novel use of genomic diagnostics and exome sequencing." Journal of medical genetics 48.9 (2011): 593-596. Currently treatment is mainly supportive and palliative. A diet low in phytanic acid may be provided and individuals may be supplemented with docosahexaenoic acid, cholic acid, vitamin K and fat-soluble vitamins. Patients are given anti-epileptic drugs, hearing aids and cochlear implants. However, there is no cure and there are no long-term effective treatments.

The closest area is gene therapy targeting adrenoleukodystrophy (http://myelin.org/2016/04/bluebirds-genetherapy-shows-promise-for-ald-treatment/); however this approach uses a lentivirus and involves ex vivo hematopoietic stem cell infection.

There remains a need in the art for compositions and methods for treating peroxisome biogenesis disorders.

SUMMARY OF THE INVENTION

The present invention relates to a method of treating a deficiency in PEX1, by providing PEX1 sequence to cells. The PEX1 sequence may be provided by gene therapy methods. The method may involve, for example, providing a cDNA encoding PEX1 or an RNA encoding PEX1.

More particularly, the present invention relates to a method of treating a peroxisomal biogenesis disease by providing human PEX1 to human cells. The present invention provides a gene encoding human PEX1, which when expressed in cells from the eye allows for improvement of retinal function, including cone and rod photoreceptor function.

In one aspect, a codon optimized, engineered nucleic acid sequence of SEQ ID NO: 1 encoding human PEX1 is provided. In another aspect, an expression cassette encoding human PEX1 is provided. More particularly, the expression cassette may comprise the codon optimized nucleic acid sequence SEQ ID NO: 1.

In a further aspect, the present invention provides a recombinant virus that may comprise a ligand having specificity for a retinal cell receptor and a genome allowing expression of human PEX1 in the eye (e.g., retinal cells).

In another aspect, a recombinant adeno-associated virus (rAAV) is provided. The rAAV may include an AAV capsid, and a vector genome packaged therein, said vector genome may comprise (a) an AAV 5' inverted terminal repeat (ITR) sequence; (b) a promoter; (c) a coding sequence encoding a human PEX1; and (d) an AAV 3' ITR. In one embodiment, the coding sequence of (c) is a codon optimized human PEX1, which may be, for example, at least 70% identical to the native human PEX1 coding sequence of SEQ ID NO: 2. In another embodiment, the coding sequence of (c) is or comprises SEQ ID NO: 1.

In another aspect, a composition comprising the recombinant virus or the rAAV and pharmaceutical acceptable carrier or excipient is provided. In one embodiment, the composition may be suitable for delivery to the eye. In another embodiment, the composition may be suitable for delivery to the liver. In another embodiment, the composition may be suitable for delivery to the CNS.

In another aspect, an aqueous suspension suitable for administration to a PDB patient is provided. In one embodiment, said suspension may include an aqueous suspending liquid and the recombinant virus or rAAV described herein. In an exemplary embodiment the viral particles may be provided at a dosage of about $1 \times 10^{10}$ GC viral particles to about $1 \times 10^{12}$ GC of viral particles per eye.

In yet another aspect, a method of treating a subject having PBD with the recombinant virus or with the rAAV described herein is provided.

In another aspect, the use of a recombinant virus or rAAV as described herein is provided for treating a peroxisomal biogenesis disorder selected from Zellweger syndrome, neonatal adrenoleukodystrophy, and infantile Refsum disease.

Other aspects and advantages of these methods and compositions are described further in the following detailed description.

Figure 1A:
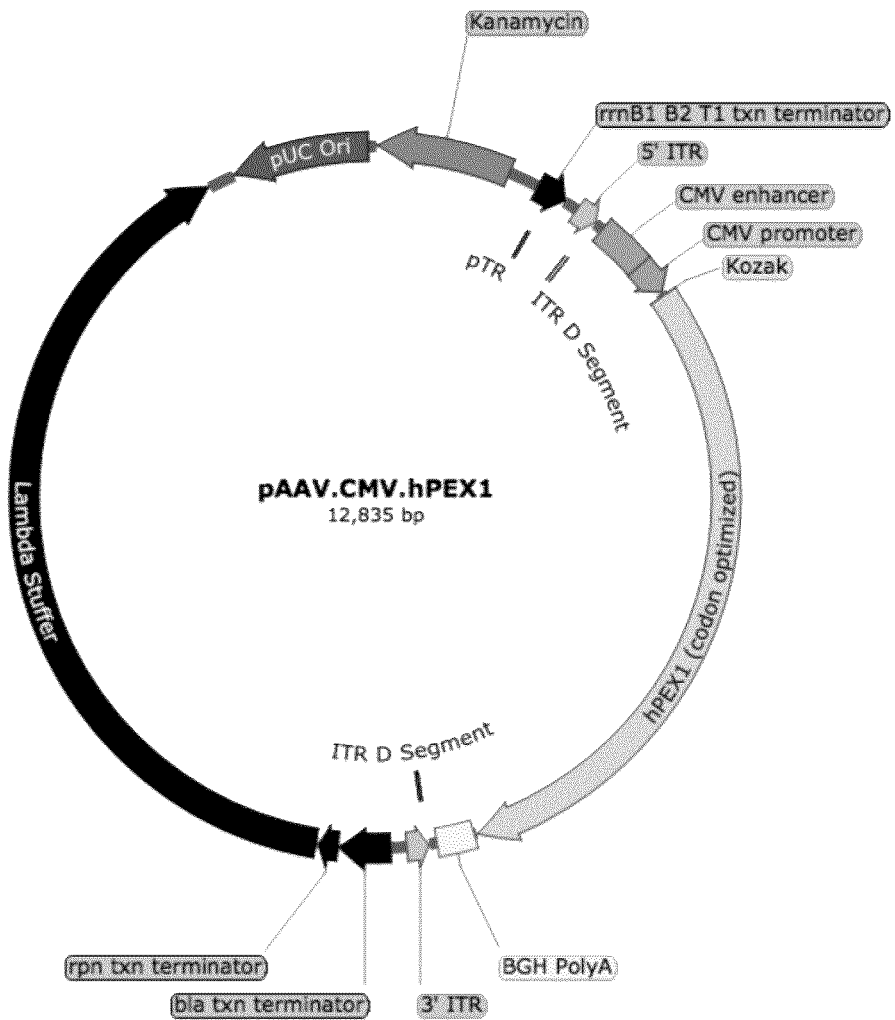
FIG. 1A provides a schematic representation of pAAV-CMV-hPEX1 plasmid. pAAV-CMV-hPEX1 is an AAV proviral expression plasmid encoding the human PEX1 codon-optimized cDNA. Expression of the transgene is driven by the canonical cytomegalovirus (CMV) enhancer and promoter. The PEX1 sequence terminates into a bovine growth hormone (bGH) polyadenylation signal. The entire AAV expression cassette is flanked by the canonical AAV2 inverted terminal repeats (ITRs) to enable sufficient packaging of the cassette into recombinant AAV particles.
Figure 1B:
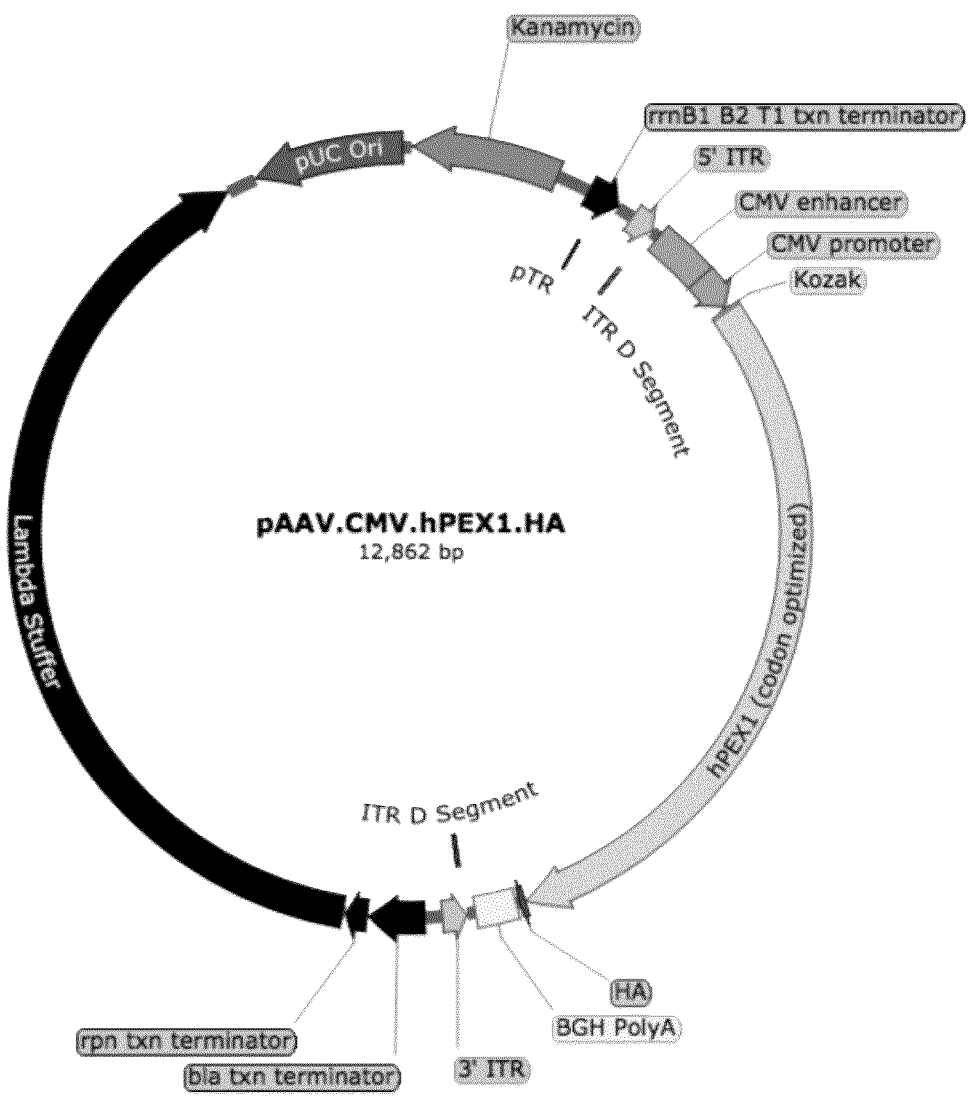

FIG. 1B provides a schematic representation of pAAV-CMV-hPEX1-HA plasmid. pAAV-CMV-hPEX1-HA contains identical sequence components to those described for pAAV-CMV-hPEX1 with the only variation being the inclusion of an HA epitope tag at the C-terminal end of the PEX1 coding sequence.

Figure 2A:
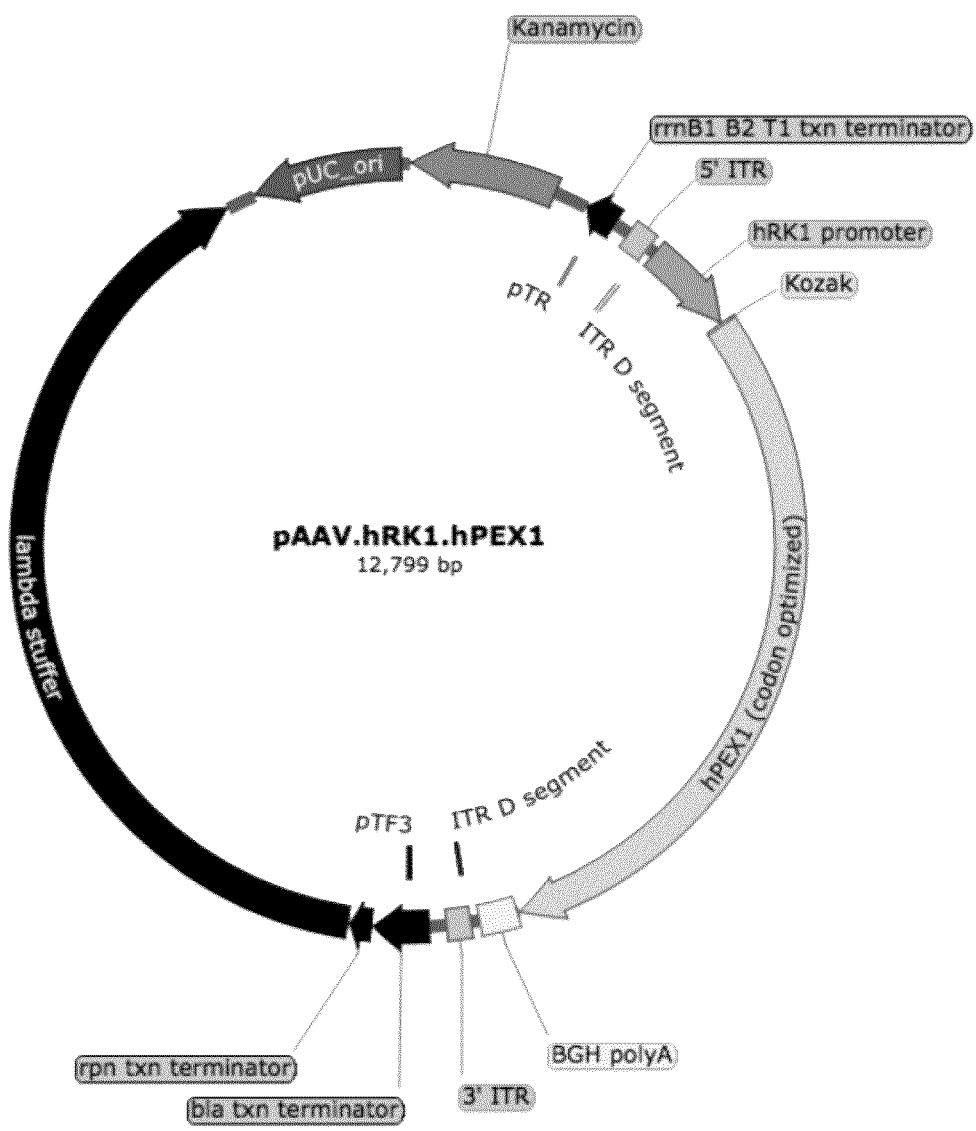

FIG. 2A provides a schematic representation of pAAV-hRK1-hPEX1 plasmid. pAAV-hRK1-hPEX1 is an AAV proviral expression plasmid encoding the human PEX1 sequence that is codon-optimized for enhanced gene expression. The transgene is driven by the human rhodopsin kinase-1 promoter (hRK1) to provide photoreceptor-specific expression in vivo and potentially within iPSC-derived in vitro models. The PEX1 sequence terminates into a bovine growth hormone (bGH) polyadenylation signal. The entire AAV expression cassette is flanked by the canonical AAV2 inverted terminal repeats (ITRs) to enable sufficient packaging into recombinant AAV particles.

Figure 2B:
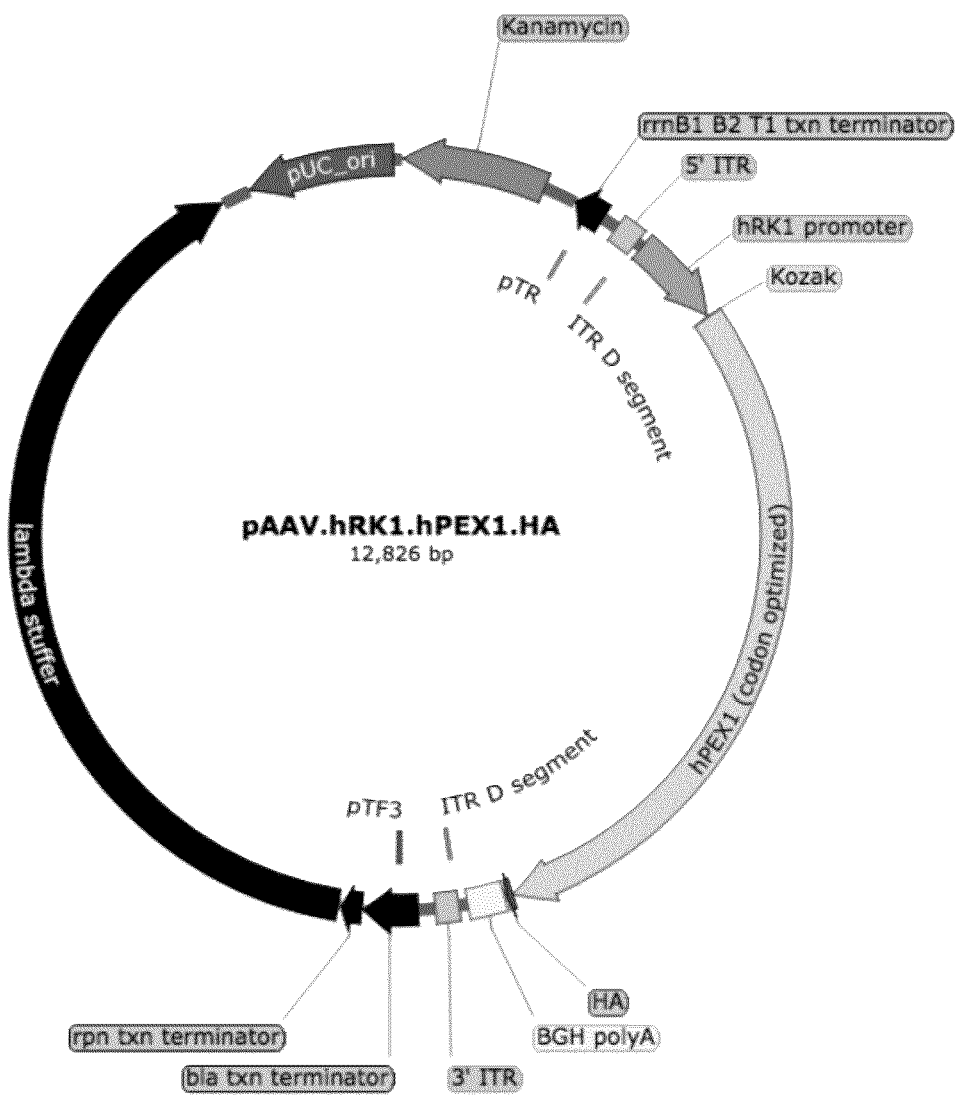

FIG. 2B provides a schematic representation of pAAV-hRK1-hPEX1-HA plasmid. pAAV-hRK1-hPEX1-HA has sequence components that are identical to those described for pAAV-hRK1-hPEX1 with the only variation being the inclusion of an HA epitope tag at the C-terminal end of the PEX1 coding sequence.

Figure 3A:
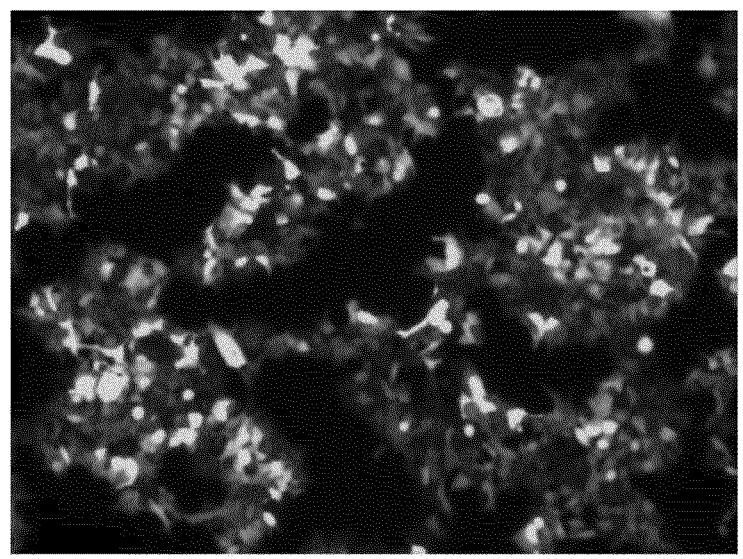

FIG. 3A provides a representative result via fluorescent imaging showing expression of AAV8-CMV-eGFP in 84-31 cells (48 hours post-transduction).

Figure 3B:
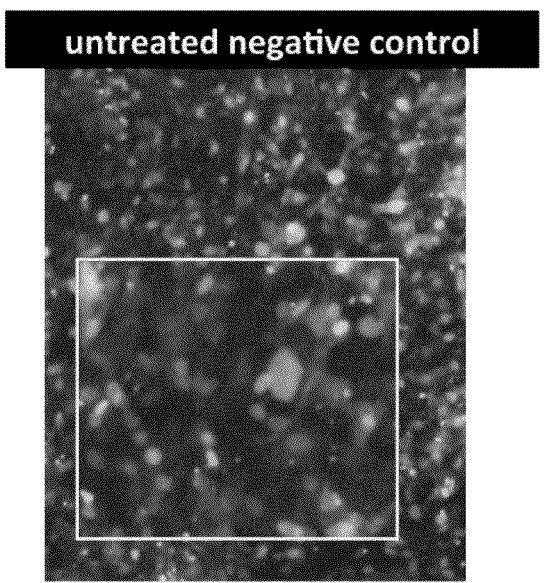
Figure 3C:
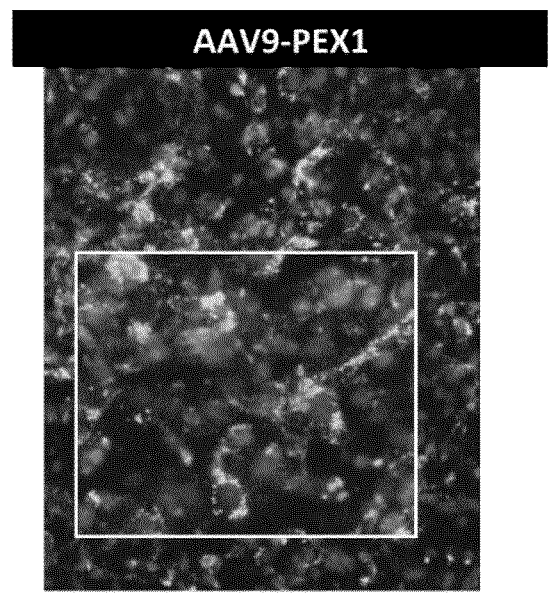

FIGS. 3B-3C provide a representative result via fluorescent imaging showing fibroblasts from a homozygote knock-in (Pex1$^{G844D}$) mouse. The fibroblasts are expressing a GFP-tagged peroxisome targeting signal reporter (GFP-PTS1). The reporter is primarily cytosolic at baseline (FIG. 3B), indicating dysfunctional peroxisome import. When the mouse fibroblasts are transduced with AAV9.hPEX1 there is re-localization of the reporter to punctate structures that co-localize with peroxisomes (i.e. rescued import of reporter) (FIG. 3C). This signifies rescue of peroxisome import by human PEX1 protein.

Figure 3D:
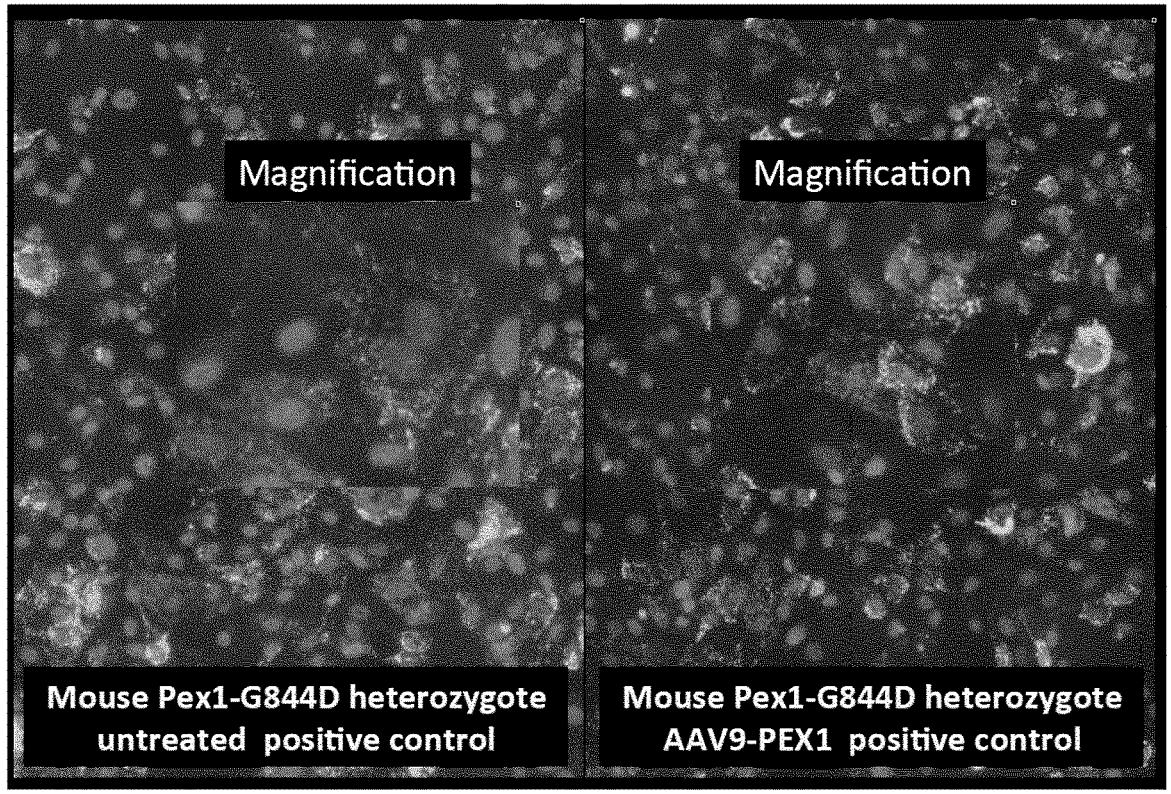
Figure 3E:
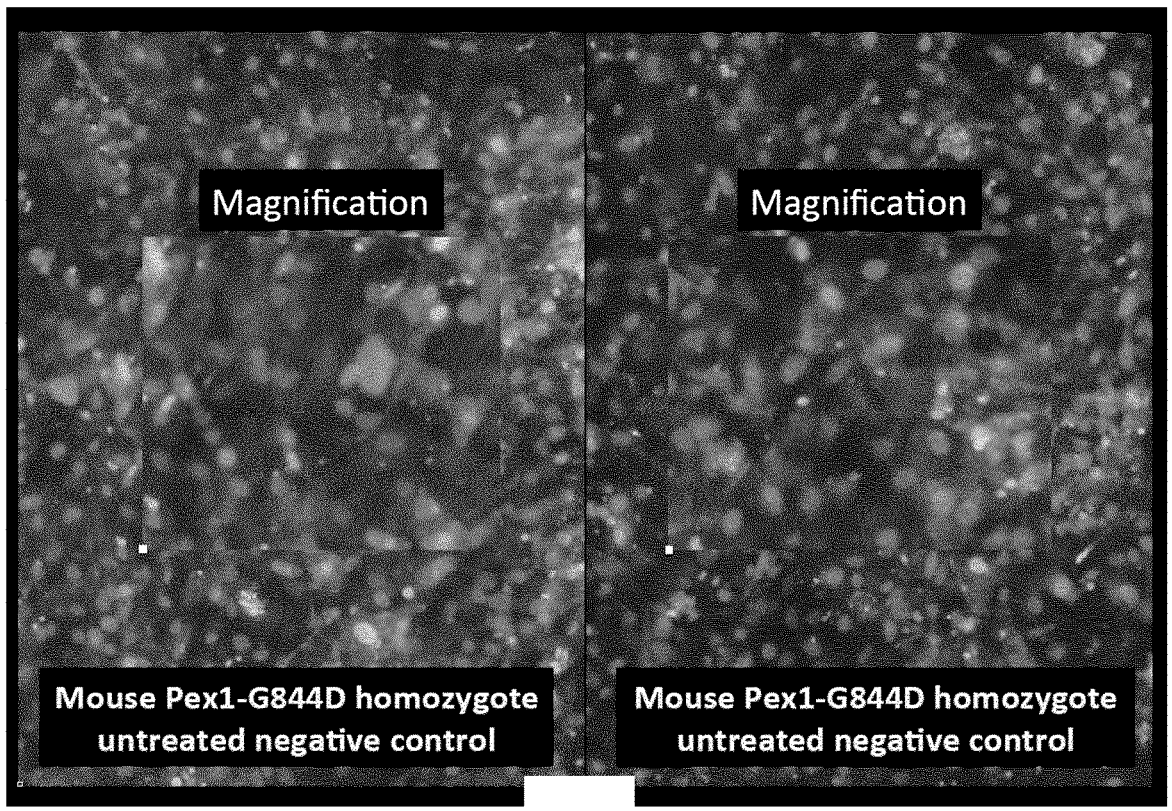
Figure 3F:
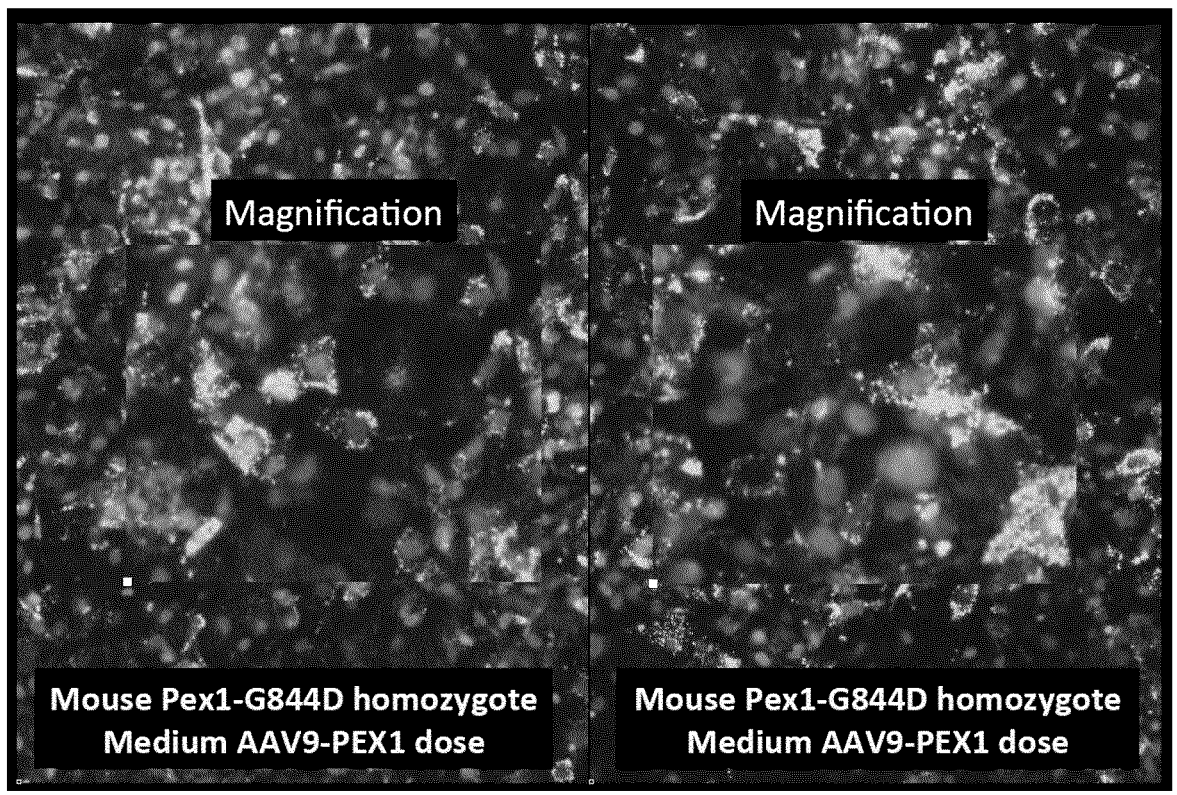
Figure 3G:
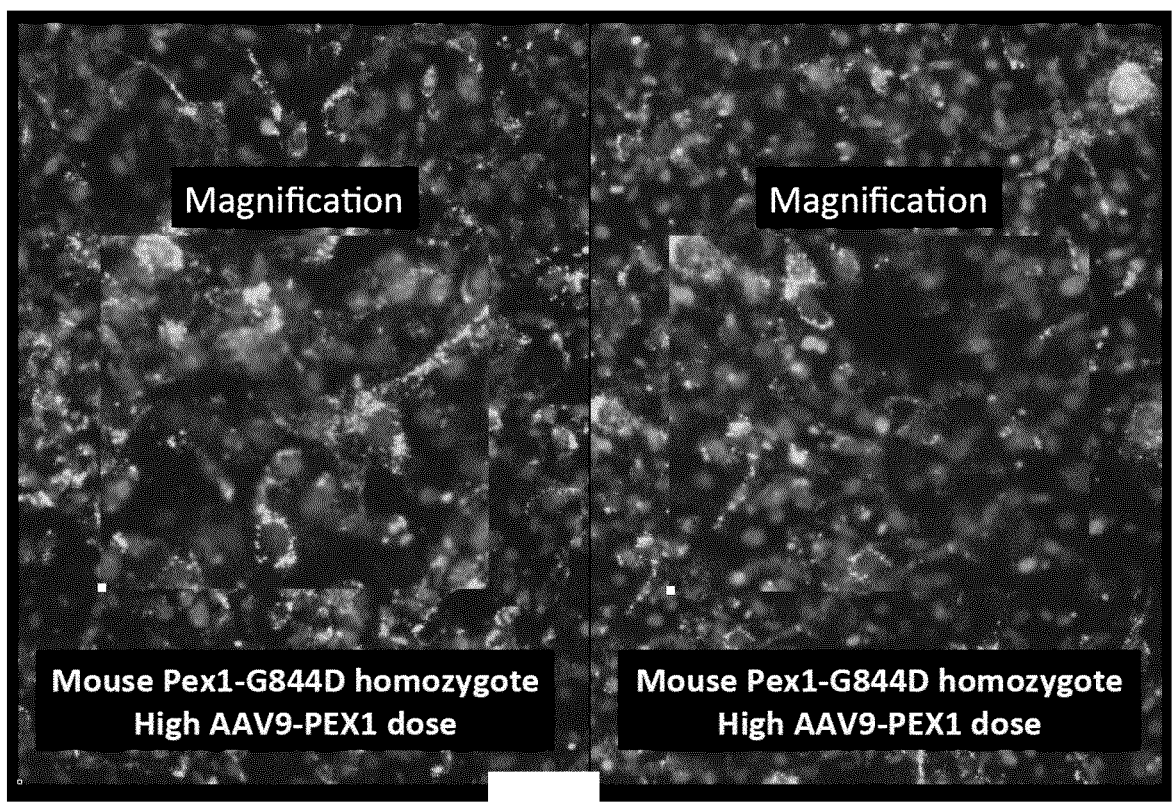

FIGS. 3D-3G provide representative results of fluorescent imaging showing Pex1$^{wt/G844D}$ heterozygote mouse fibroblasts expressing a GFP-tagged peroxisome targeting signal reporter (GFP-PTS1). There is no difference in import regardless of transduction with AAV.PEX1 (i.e. wild-type phenotype) (FIG. 3D). In Pex1$^{G844D/G844D}$ mouse fibroblasts the reporter is primarily cytosolic (FIG. 3E). Transduction with medium dose (5×10$^5$ viral particles/cell) AAV9.PEX1 (FIG. 3F) or high dose (10×10$^5$ viral particles/cell) AAV9.PEX1 (FIG. 3G) results in re-localization of the reporter to punctate structures that co-localize with peroxisomes (i.e. rescued import of reporter). This signifies rescue of peroxisome import by human PEX1 protein.

Figure 4A:
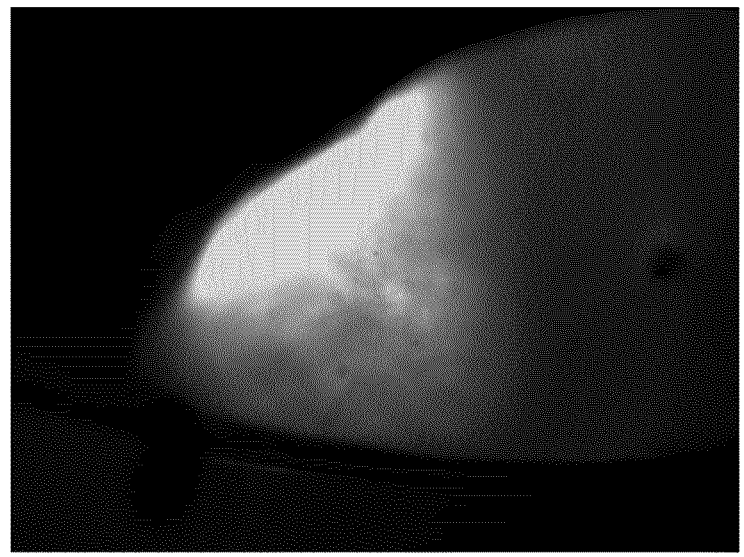

FIG. 4A provides a representative result via fluorescent imaging showing AAV8-CMV-eGFP expression in an explant of an adult dissected mouse retina that had received subretinal injection one week earlier. The injected portion of the retina has high levels of eGFP protein.

Figure 4B:
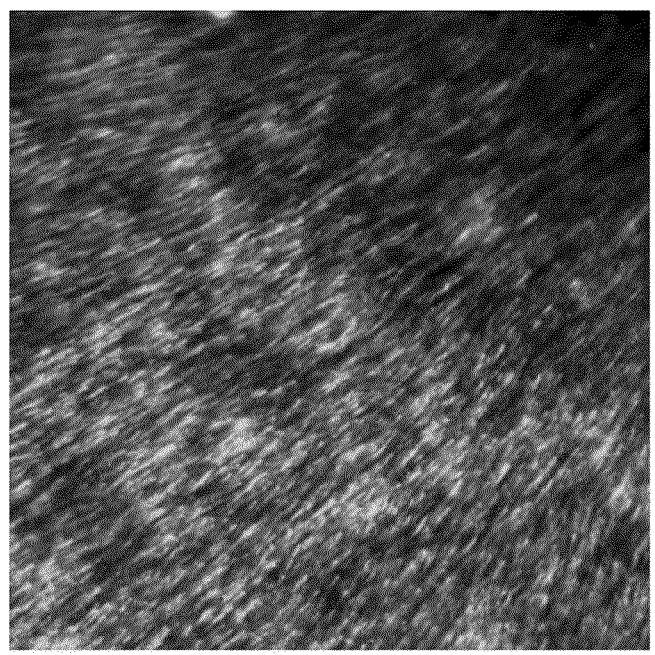

FIG. 4B provides a representative result via fluorescent imaging showing AAV8-CMV-eGFP expression in an explanted mouse retina 1 week after subretinal injection. eGFP protein is apparent in inner and outer segments of the outer aspect of the retina.

Figure 5:
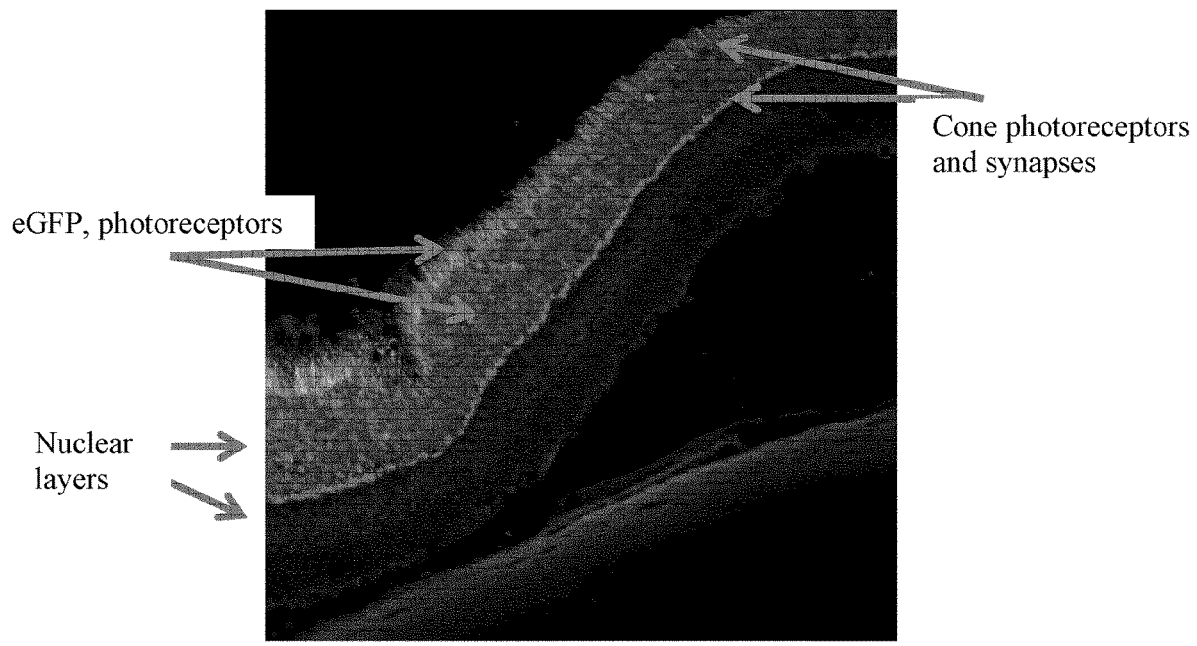

FIG. 5 provides a representative fluorescent image of a cryosection of a retina from an adult mouse that had received an intravitreal injection two weeks earlier with AAV7m8-hRK1-eGFP. eGFP is present only in the photoreceptors after injection of this AAV that penetrates the mouse neural retina after intravitreal injection. Nuclei are stained blue with DAPI; Peanut lectin (PNA) stains cone photoreceptors and synapses red (and also the lens capsule).

Figure 6A:
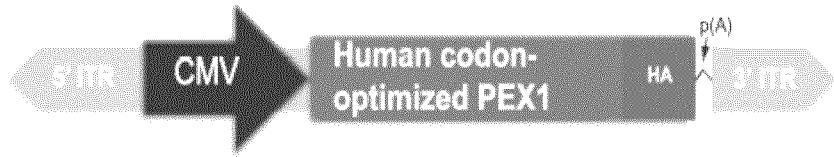
Figure 6B:
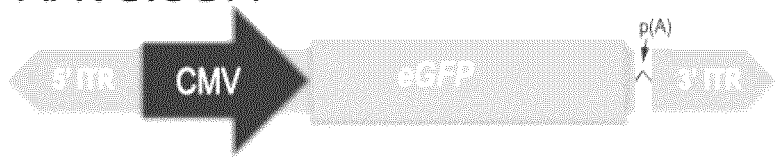

FIGS. 6A-6B provide schematics of the components of the transgene cassettes in AAV.hPEX1-HA (FIG. 6A) and AAV.eGFP (FIG. 6B).

Figure 7:
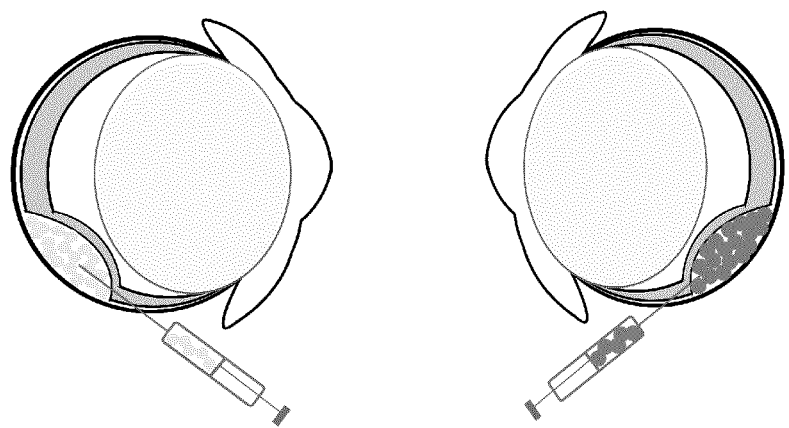

FIG. 7 provides a diagram of experimental paradigm. AAV.eGFP is illustrated by dots in the left panel; AAV.hPEX1-HA is illustrated by dots in the right panel.

Figure 8:
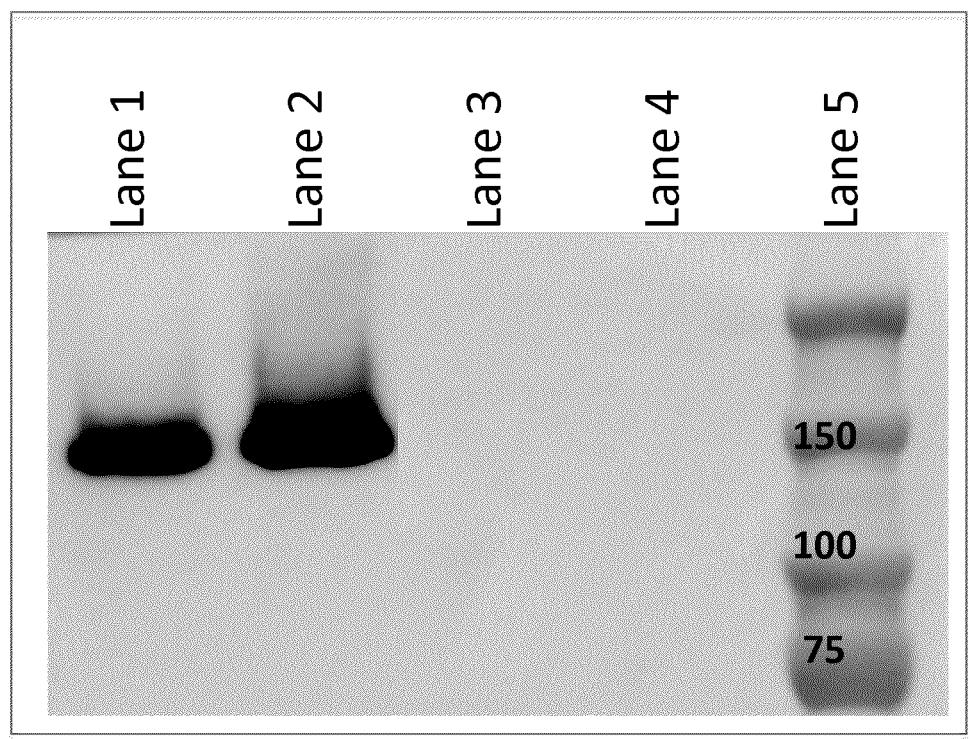

FIG. 8 provides western blot demonstrating production of an HA-tagged protein with the predicted size of PEX1 after infection of 84-31 cells with AAV8.hPEX1.HA. Lane 1 was loaded with samples treated with AAV8.hPEX1.HA with an MOI at 1×10$^5$; Lane 2 was loaded with samples treated with AAV8.hPEX1.HA with an MOI at 2×10$^5$; Lane 3 was loaded with samples treated with AAV8.eGFP with an MOI at 1×10$^5$; Lane 4 is a negative control (NA); and Lane 5 was loaded with ladder.

Figure 9:
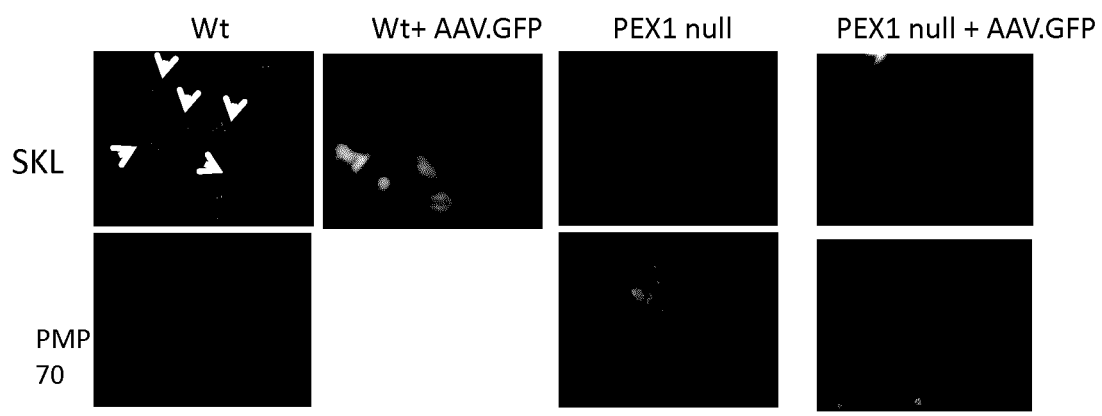

FIG. 9 provides fluorescent images showing no peroxisome import was observed in PEX1-null HepG2 cells compared to that in wild type cells. WT indicates wildtype while AAV.GFP indicates AAV8.CMV.eGFP. Cells were also stained for PMP70, a peroxisome membrane marker (red, bottom panel). This marker is present in all cells, but peroxisomes are less numerous and larger in PEX1 null cells.

Figure 10:
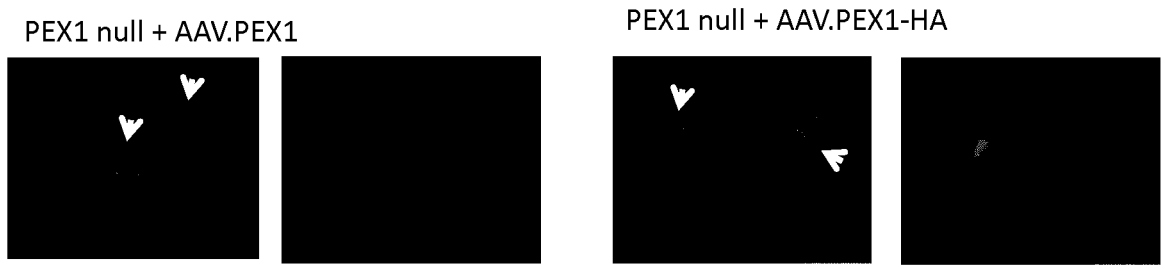

FIG. 10 provides fluorescent images showing AAV8-hPEX1-HA recovered peroxisome import in PEX1-null HepG2 cells. WT, wildtype; AAV.GFP, AAV8.CMV.eGFP. Cells are also stained for PMP70.

Figure 11:
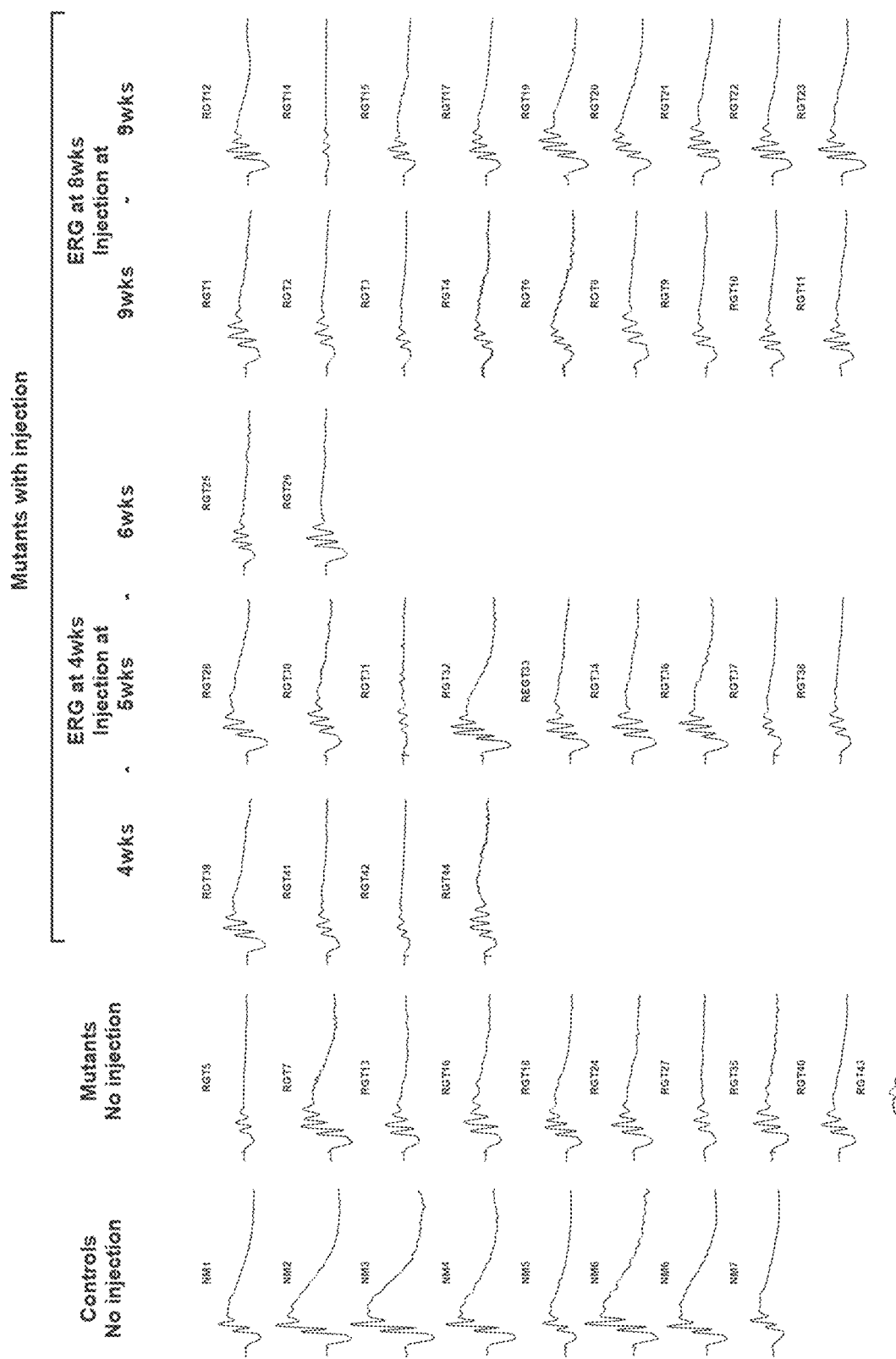

FIG. 11 provides results of baseline scotopic ERGs in wildtype and Pex1-G844D mutant mice. Control mice with no injection (Controls, No Injection) and Pex1-G844D mice with no injection (Mutants, No Injection) were provided as controls. Pex1-G844D mice were injected as described in Example 3.

Figure 12A:
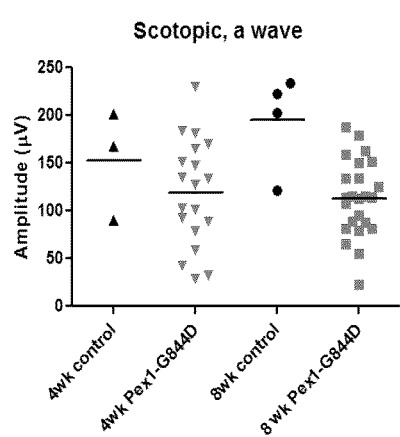
Figure 12B:
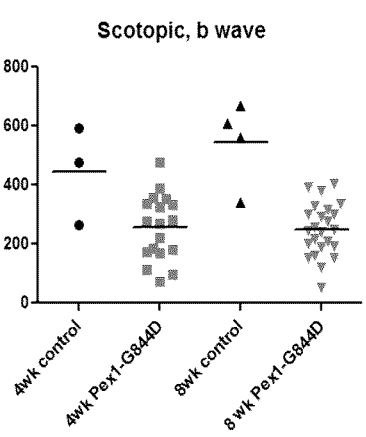
Figure 12C:
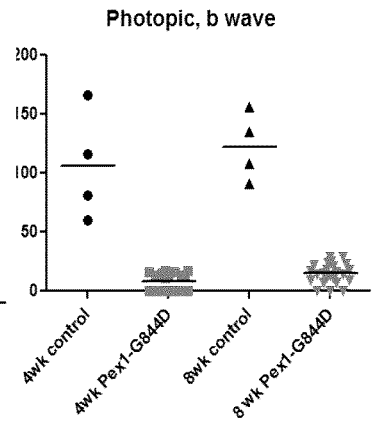

FIGS. 12A-12C provides average scotopic (a wave, FIG. 12A; b wave, FIG. 12B) and photopic ERG (FIG. 12C) amplitudes in untreated wildtype and Pex1-G844D mutant mice at age of 4 and 8 weeks.

Figure 13:
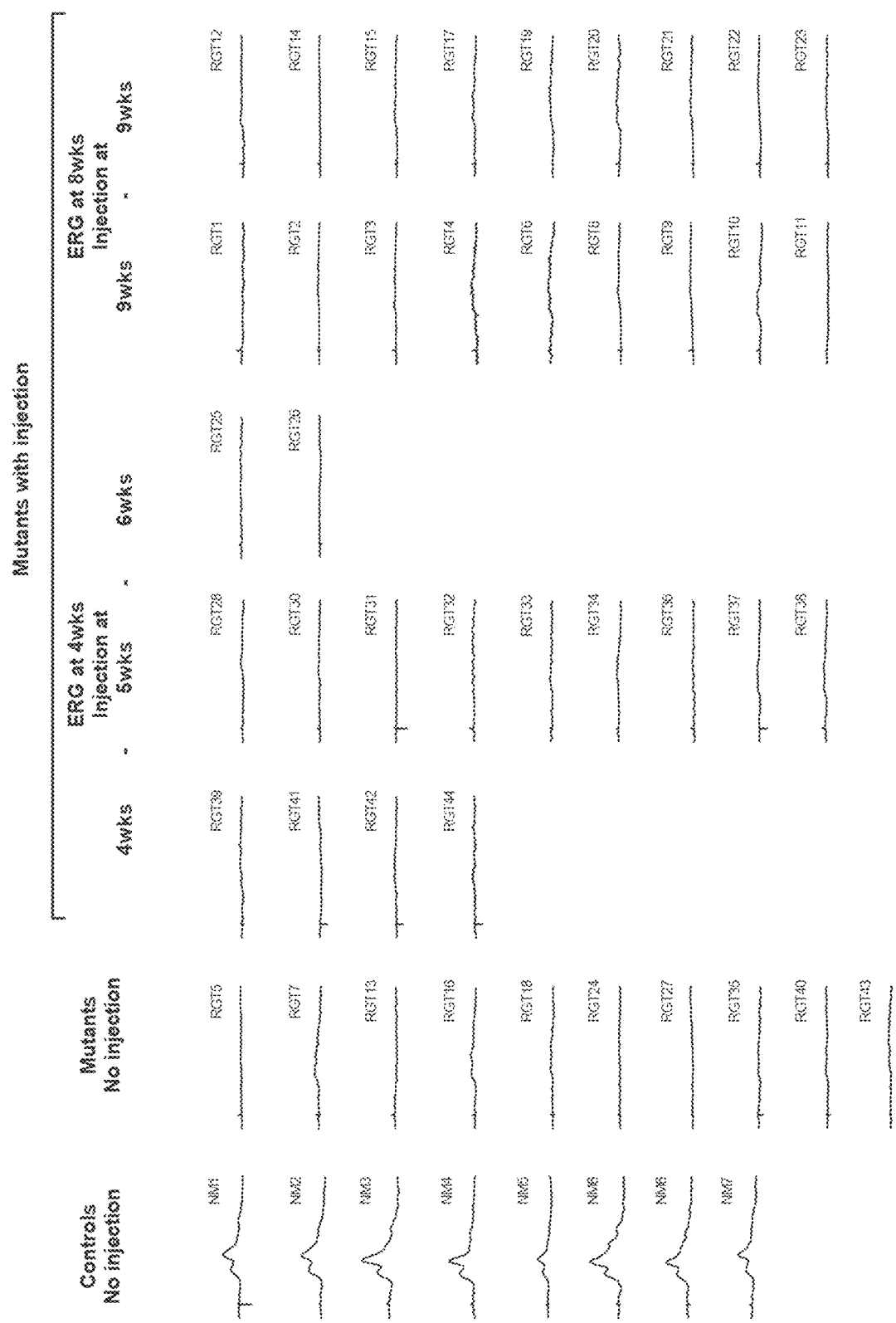

FIG. 13 provides results of baseline photopic ERGs in individual wildtype and Pex1-G844D mutant mice. Note that photopic ERGs are close to flat at baseline (at 4 weeks at 8 weeks) in Pex1-G844D mice. Control mice with no injection (Controls, No Injection) and Pex1-844D mice with no injection (Mutants, No Injection) were provided as controls. Pex1-G844D mice were injected as described in Example 3.

FIGS. 14A-14C provides comparison between right and left eyes of scotopic (a wave, FIG. 14A; b wave, FIG. 14B) and photopic (FIG. 14C) ERG amplitudes.

FIG. 15 provides results of optokinetic response (OKR) testing in 10-13-week-old untreated wildtype vs Pex1-G844D mice. *, $p<0.1$; , $p<0.01$; *, $p<0.001$.

Figure 16:
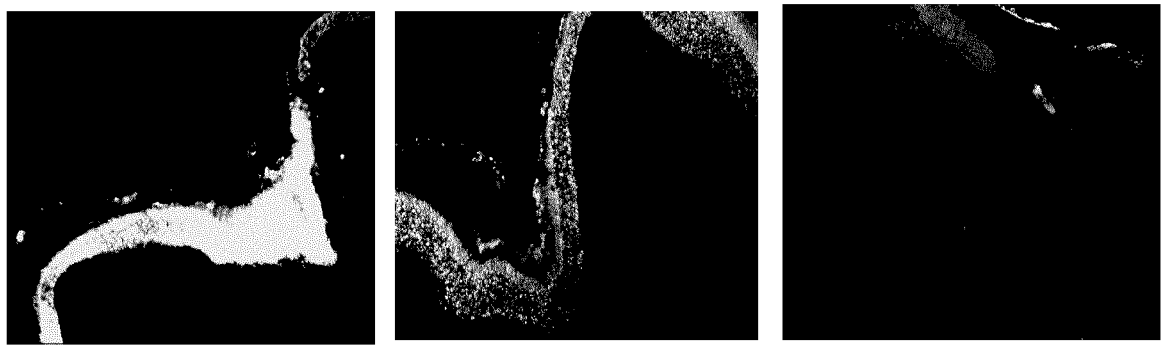

FIG. 16 provides fluorescent images of AAV.GFP-injected retinas. Injections were performed at age 9 weeks.

Figure 17:
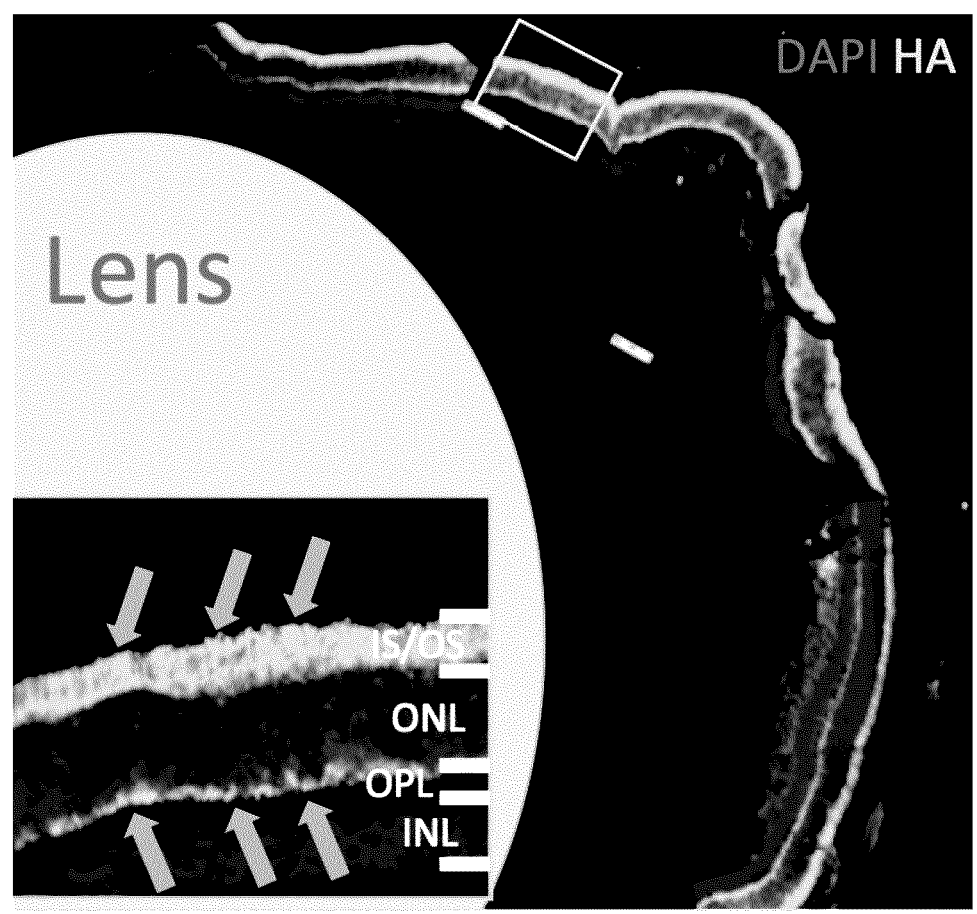

FIG. 17 provides fluorescent images of retinas from AAV8.CMV.hPEX1-HA injected left eyes after cryosectioning and staining for presence of the HA tag (green). The transgene is present in eight of eight AAV.PEX1-HA-injected retinas and in the majority of photoreceptors (in the outer nuclear layer (ONL) and in high concentration in inner/outer segments (IS/OS) and outer synaptic layer (OPL)).

FIGS. 18A-18C provide comparison of scotopic (a wave, FIG. 18A; b wave, FIG. 18B) and photopic (FIG. 18C) ERG amplitudes in the eye treated with AAV.Pex1-HA (left eye) compared to the AAV.GFP-injected control eye (right eye) 8 weeks after injection. The left eye showed significantly high amplitude photopic b-wave response. *, p<0.1; , p<0.01; *, p<0.001.

FIGS. 19A-19C provide plots of photopic (FIG. 19C) and scotopic (a wave, FIG. 19A; b wave, FIG. 19B) ERG amplitudes twenty weeks after injection of AAV.PEX1-HA- in the left retinas of 5-week-old Pex1-G844D mice compared to control-injected eyes and eyes of non-injected littermates. *, p<0.1; , p<0.01; *, p<0.001. The average value obtained for the wild type (Wild-type avg) and the G844D non injected (G844 non-inj avg) controls is illustrated with dotted lines.

FIGS. 20A-20C provide plots of photopic (FIG. 20C) and scotopic (a wave, FIG. 20A; b wave, FIG. 20B) ERG amplitudes sixteen weeks after injection of AAV.PEX1-HA- in the left retinas of 9-week-old Pex1-G844D mice compared to control-injected eyes and eyes of non-injected littermates. There was a significant improvement in scotopic b-waves of treated vs control eyes. *, p<0.1; , p<0.01; *, p<0.001. The average value obtained for the wild type (Wild-type avg) and the G844D non injected (G844 non-inj avg) controls is illustrated with dotted lines.

Figure 21:
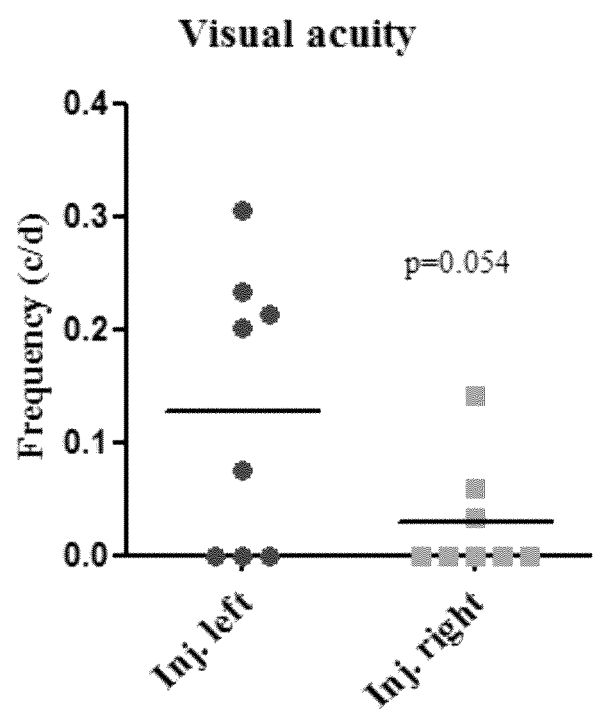

FIG. 21 provides results of optokinetic testing comparing responses of experimental vs control eyes. The results showed a trend in improved visual acuity in the AAV.PEX1- HA-treated (left) eyes compared to AAV.eGFP-treated controls (P=0.0054). The average for the AAV.PEX1-HA-injected retinas was 0.206, whereas that of the AAV.eGFP-injected retinas was 0.047.

Figure 22A:
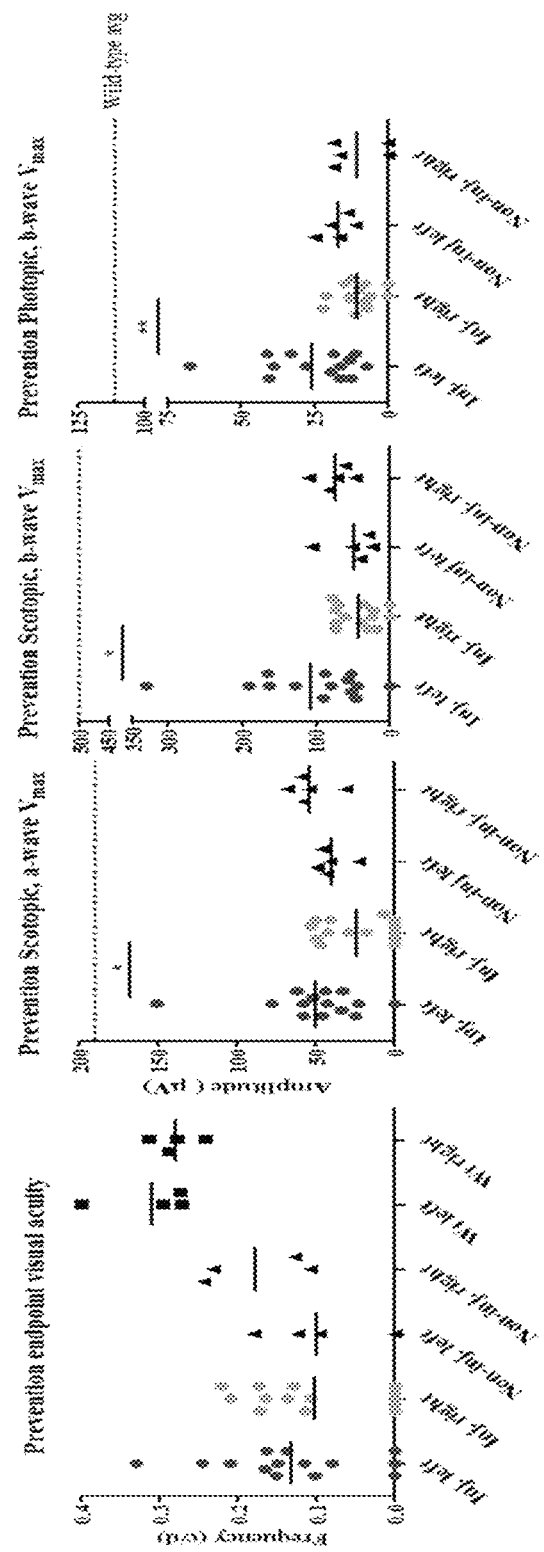

FIG. 22A provides results of visual acuity, scotopic and photopic a wave and b wave obtained at end-point (31 weeks old and 6 months post gene delivery) for the prevention cohort. *, p<0.1; , p<0.01; *, p<0.001

Figure 22B:
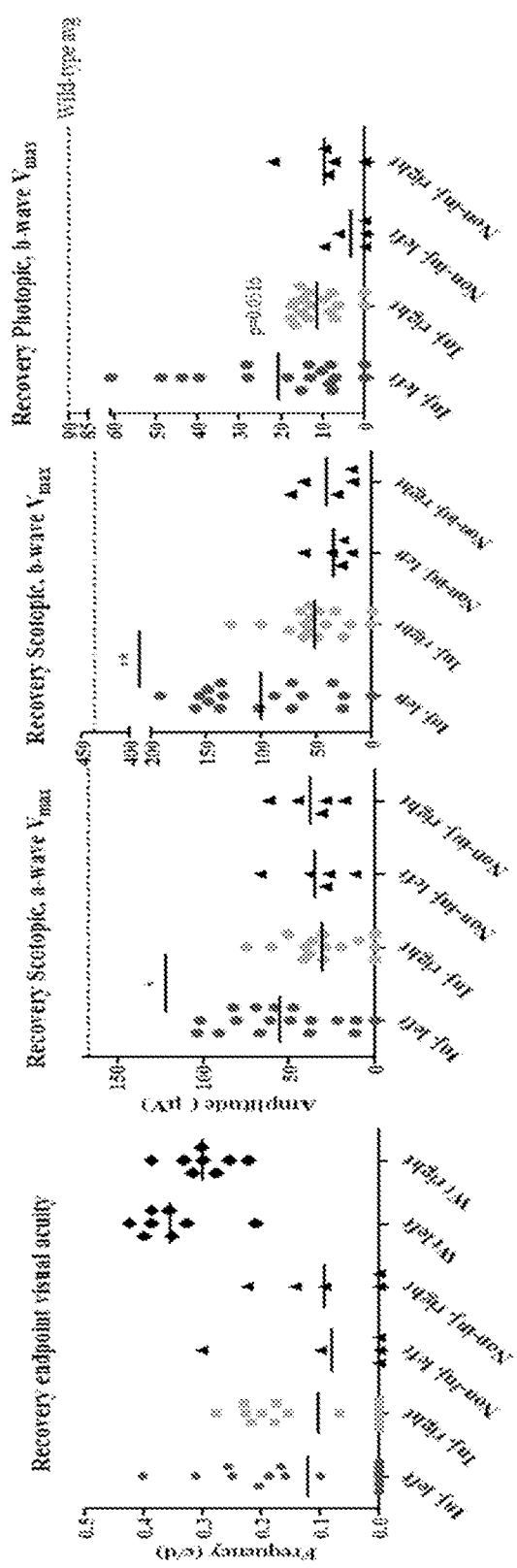

FIG. 22B provides results of visual acuity, scotopic and photopic a wave and b wave obtained at end-point (31 weeks old and 5 months post gene delivery) for the recovery cohort. *, p<0.1; , p<0.01; *, p<0.001

Figure 23:
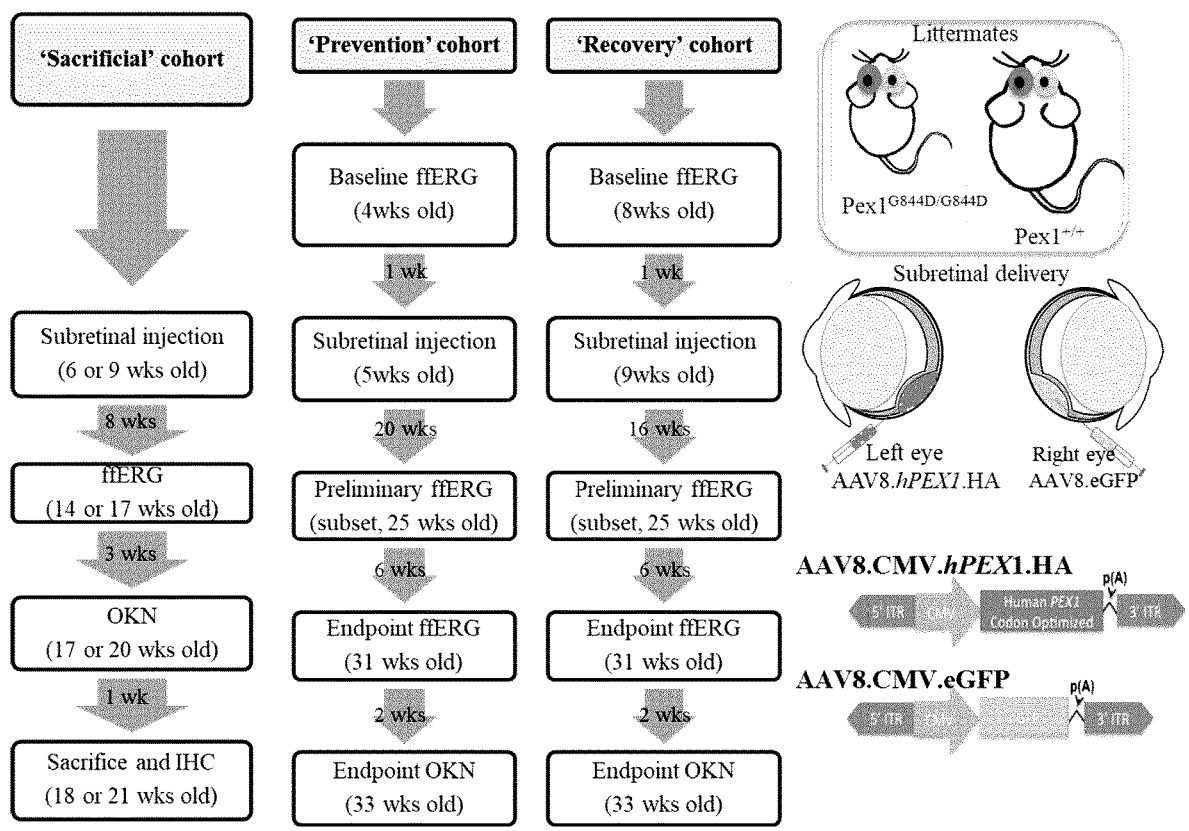

FIG. 23 is a schematic representation of the experimental design for in vivo delivery of the PEX1 gene.

FIGS. 24A-24N provide an alignment of the following sequences: Codon optimized hPEX1, SEQ ID NO: 1; CDS_of_transcript_variant_1, coding DNA sequence (CDS) of human PEX1, transcript variant 1 with NCBI Reference Sequence: NM_000466.2, nt 97 to nt 3948 of SEQ ID NO: 2; CDS_of_transcript_variant_2, CDS of human PEX1, transcript variant 2 with NCBI Reference Sequence: NM_001282677.1, nt 97 to nt 3777 of SEQ ID NO: 3; CDS_of_transcript_variant_3, CDS of human PEX1, transcript variant 3 with NCBI Reference Sequence: NM_001282678.1, nt 756 to nt 3983 of SEQ ID NO: 4; and CDS_of_transcript_variant_X2, CDS of human PEX1, transcript variant X2 with NCBI Reference Sequence: XM_017012319.1, nt 766 to nt 2868 of SEQ ID NO: 5.

Figure 25A:
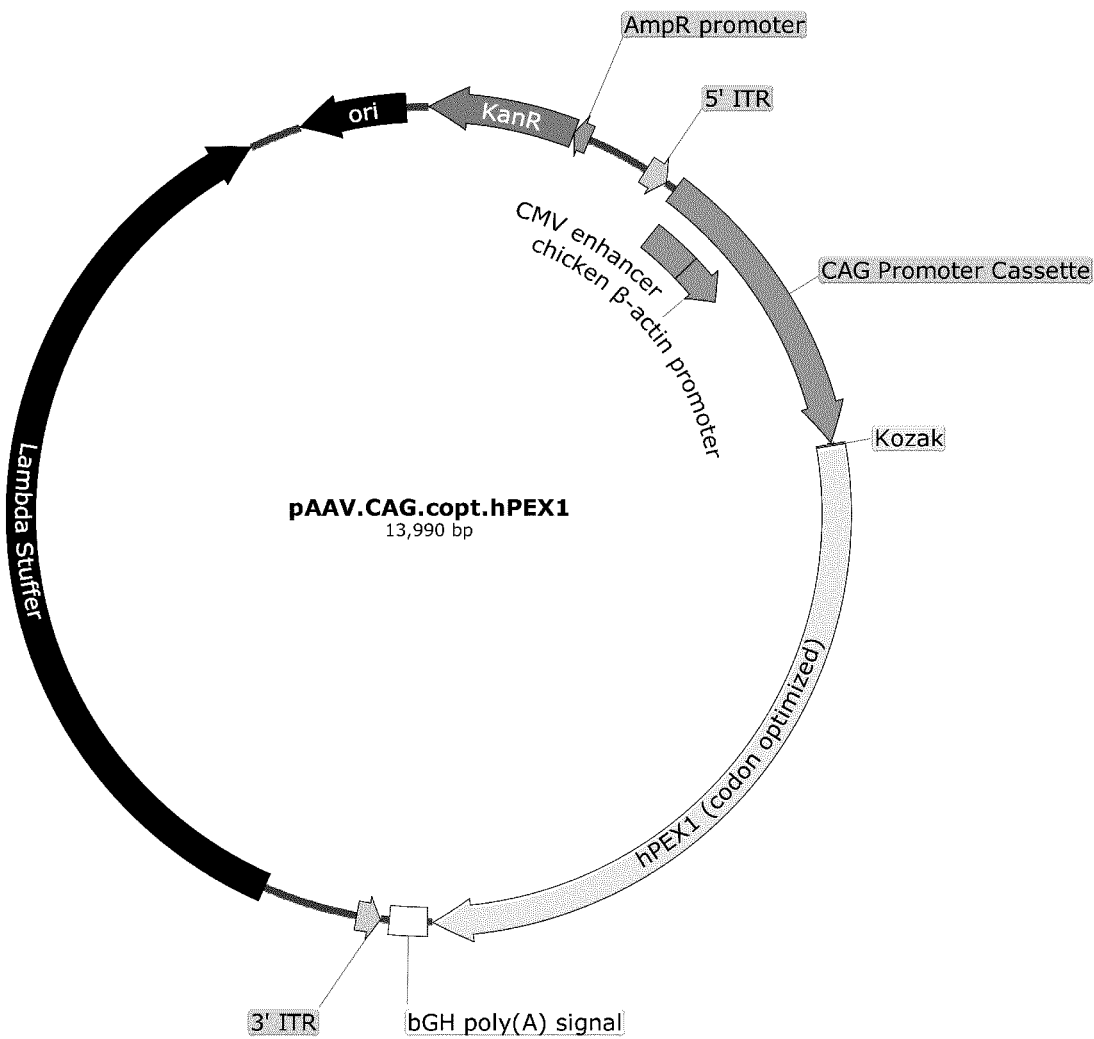

FIG. 25A is a schematic representation of the pAAV.CAG.copt.hPEX1 plasmid comprising an expression cassette under the control of a CMV enhancer and chicken beta actin promoter.

Figure 25B:
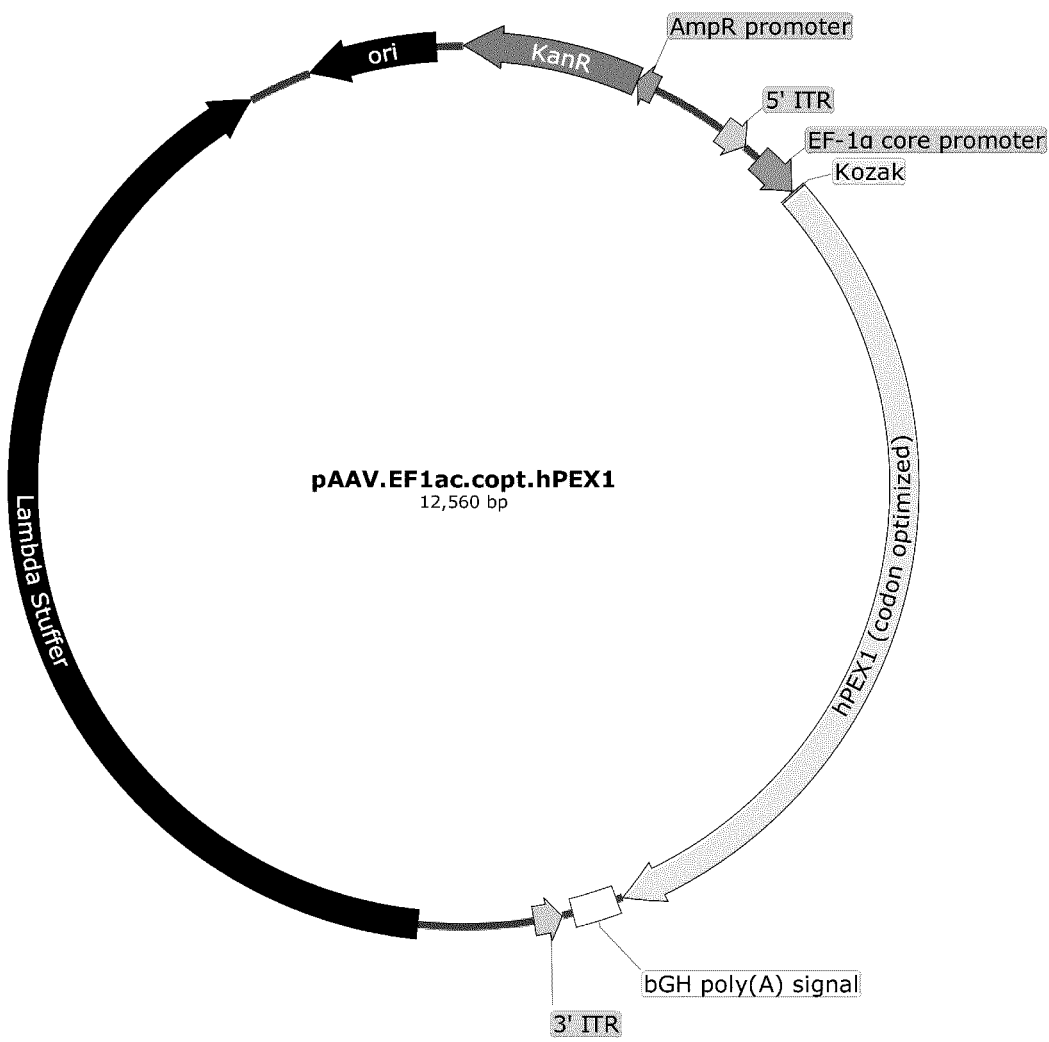

FIG. 25B is a schematic representation of the pAAV.EF1ac.copt.hPEX1 plasmid comprising an expression cassette under the control of the EF1a core promoter.

Figure 25C:
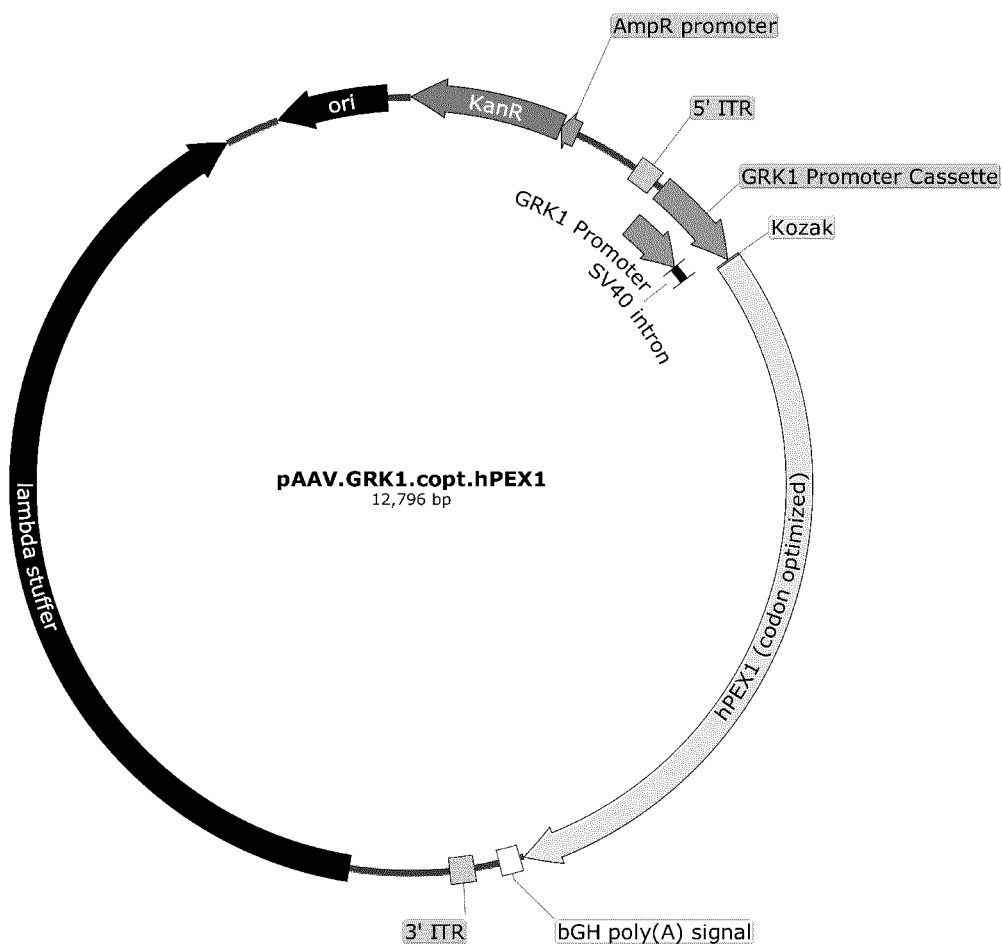

FIG. 25C is a schematic representation of the pAAV.GRK1.copt.hPEX1 plasmid comprising an expression cassette under the control of the GRK1 promoter.

Figure 25D:
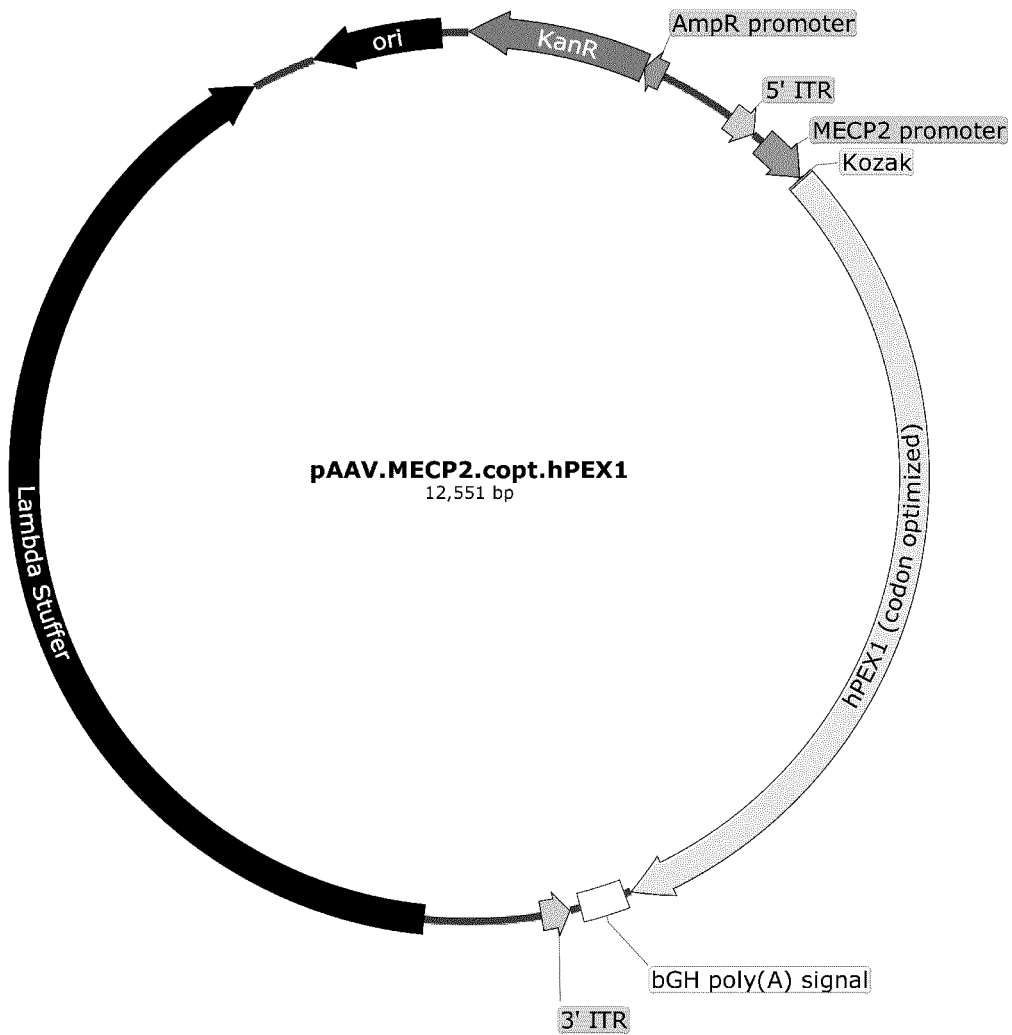

FIG. 25D is a schematic representation of the pAAV.MECP2.copt.hPEX1 plasmid comprising an expression cassette under the control of the MECP2 promoter.

DETAILED DESCRIPTION OF THE INVENTION

Described herein are methods of treating a deficiency in PEX1, by providing PEX1 sequence to cells using a gene therapy method.

Also described herein are reagents and methods that are used to restore function and health to various organ systems that are impaired due to malfunctioning peroxisomes. At least two of the promoters exemplified herein are shown to drive high levels of and long-lived transgene expression in target cells. Delivery of PEX1 can be used to improve retinal, liver and CNS function and thus improve both quality of life and potentially longevity.

Viral vectors capable of delivering peroxisomal (PEX) genes namely PEX1 to the retinal cells in the eye are provided. Failure of the body to produce peroxisomes that function properly result in peroxisome biogenesis disorders (PBDs). It is estimated that 1 in 50,000 births are affected by PBDs in North America. PBDs or Zellweger spectrum disorder (ZSD) encompass three autosomal recessive conditions: Zellweger syndrome is the most severe form; neonatal adrenoleukodystrophy (NALD) is the intermediate form; and infantile Refsum disease (IRD) is the mildest form. Zellweger Syndrome patients rarely survive the first year of life due to cerebral dysgenesis. In contrast, the majority of ZSD patients have intermediate and milder phenotypes and are born without major malformations, but have a progressive disease due to ongoing peroxisome dysfunction. This progression includes the development of leukodystrophy, adrenal insufficiency, and retinal pigmentary changes leading to blindness. ZSDs are primarily caused by mutations in any of 14 different PEX genes, which code for peroxins, proteins involved in peroxisome assembly. While mutations in PEX1 account for nearly 70% of all ZSD cases, another 26% of cases are caused by mutations in PEX6, PEX10, PEX12, or PEX26, with the majority of these cases involving PEX6 mutations. As used herein, Zellweger syndrome disorder (ZSD) and peroxisome biogenesis disorder (PBD) are used interchangeably to refer to a disorder in which the PEX1 protein or coding sequence is affected, including, without limitation, Zellweger syndrome; neonatal adrenoleukodystrophy (NALD); and infantile Refsum disease (IRD).

The inventors have exemplified herein a retinal gene therapy approach that addresses visual deterioration in patients with milder forms of disease. Optical coherence tomography (OCT) has demonstrated that the cone photoreceptor cells are most significantly affected by loss of peroxisome functions in such patients. These visual phenotypes are recapitulated in a mouse model of the milder form of the disease that expresses the murine equivalent of most common PEX1 mutation found in patients (PEX1-p.G843D). Electroretinogram (ERG) analyses indicated severe impairment of the cone visual pathway in these homozygous Pex1-mutant mice by 4 weeks of age with the rod visual system being relatively preserved at 4-6 weeks of age then progressively declining.

Described herein are rAAV vectors and recombinant AAV (rAAV) particles used to deliver a nucleic acid encoding PEX1 (e.g., a codon optimized PEX1) for enhanced gene expression to the retina. In one embodiment, the transgene expression is driven by the CMV promoter. The viral vector may include, for example, AAV8.CMV.hPEX1.HA. In another embodiment the transgene expression is driven by the chicken beta actin promoter. In yet another embodiment the transgene expression is driven by the human rhodopsin kinase-1 promoter (hRK1) to provide photoreceptor-specific expression in vivo. In an additional embodiment the transgene expression is driven by the EF1a core promoter. In yet an additional embodiment, the transgene expression is driven by the GRK1 promoter. In a further embodiment, the transgene expression is driven by the MECP2 promoter.

In one embodiment, the PEX1 sequence terminates into a bovine growth hormone (bGH) polyadenylation signal. In one embodiment, the entire AAV expression cassette is flanked by the canonical AAV2 inverted terminal repeats (ITRs) to enable sufficient packaging into recombinant AAV particles. It is shown herein that codon optimized PEX1 cDNA delivery to the retina rescues the retinal/visual deficit in this animal model. Baseline retinal function was evaluated with electroretinograms (ERGs). Subretinal injections of AAV8.CMV.hPEX1.HA were carried out unilaterally in 5 week old, 9 week old and adult Pex1G844D and wild-type littermate mice. Contralateral eyes were injected with AAV8.CMV.eGFP. Concurrent untreated mutant and wild-type control animals were included). The eyes were evaluated by ophthalmoscopy and ERGs. It is shown herein that ERGs show improvement of cone and rod photoreceptor function.

The PEX1 (Peroxisomal Biogenesis Factor 1) gene encodes a member of the AAA ATPase family, PEX1 protein, a large group of ATPases associated with diverse cellular activities. PEX1 protein is cytoplasmic but is often anchored to a peroxisomal membrane where it forms a heteromeric complex and plays a role in the import of proteins into peroxisomes and peroxisome biogenesis. Mutations in this gene have been associated with complementation group 1 peroxisomal disorders such as neonatal adrenoleukodystrophy, infantile Refsum disease, and Zellweger syndrome. Alternatively spliced transcript variants have been found for this gene. [provided by RefSeq, September 2013].

As used herein, the term "PEX1" refers to either the PEX1 protein or the nucleic acid sequence encoding the PEX1 protein. In one embodiment, the native human (h) PEX1 (hPEX1) is that of hPEX1 transcript variant 1:NM 000466.2 shown in SEQ ID NO: 2. In one embodiment, the native hPEX1 is that of hPEX1 transcript variant 2: NM_001282677.1 shown in SEQ ID NO: 3. In one embodiment, the native hPEX1 is that of hPEX1 transcript variant 3: NM 001282678.1 shown in SEQ ID NO: 4. In one embodiment, the native hPEX1 is that of hPEX1 transcript variant X2:XM_017012319.1 shown in SEQ ID NO: 5. In another embodiment, the hPEX1 coding sequence is a codon optimized sequence. In one embodiment, the codon optimized sequence is that shown in SEQ ID NO: 1. In one embodiment, the coding sequence encodes the PEX1 amino acid sequence shown in SEQ ID NO: 7. In another embodiment the nucleic acid may encode a functional variant of SEQ ID NO.:7. For example, a variant having at least 90%, at least 95% or at least 99% identity with SEQ ID NO: 7.

Peroxisomes are present in almost all eukaryotic cells although the number, morphology, and protein content can vary. The play key roles in lipid metabolism including very long and branched chain fatty acid catabolism, docosahexaenoic acid and plasmalogen biosynthesis, and other metabolic pathways including Bile acid synthesis, D-amino acid oxidation, polyamine oxidation and oxygen metabolism. See, Fagarasanu et al Ann. Rev. Cell Dev. Biol. 23: 321-344 (2007).

As used herein, "disease", "disorder" and "condition" are used interchangeably, to indicate an abnormal state in a subject. In one embodiment, the disease is.

"Patient" or "subject" as used herein means a male or female mammalian animal, including a human, a veterinary or farm animal, a domestic animal or pet, and animals normally used for clinical research. In one embodiment, the subject of these methods and compositions is a human. In one embodiment, the subject of these methods and compositions is a male or female human. In one embodiment, the patient or subject has a PBD.

It should be understood that while various embodiments in the specification are presented using "comprising" language, under various circumstances, a related embodiment is also described using "consisting of" or "consisting essentially of" language. "Comprising" is a term meaning inclusive of other components or method steps. When "comprising" is used, it is to be understood that related embodiments include descriptions using the "consisting of" terminology, which excludes other components or method steps, and "consisting essentially of" terminology, which excludes any components or method steps that substantially change the nature of the embodiment or invention.

With regard to the description of these inventions, it is intended that each of the compositions herein described, is useful, in another embodiment, in the methods of the invention. In addition, it is also intended that each of the compositions herein described as useful in the methods, is, in another embodiment, itself an embodiment of the invention.

It is to be noted that the term "a" or "an", refers to one or more, for example, "a Target", is understood to represent one or more Target(s). As such, the terms "a" (or "an"), "one or more," and "at least one" is used interchangeably herein.

As used herein, the term "about" or "~" means a variability of plus or minus 10% from the reference given, unless otherwise specified.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 15 amino acids, about 150 amino acids, or a peptide fragment thereof or the corresponding nucleic acid sequence coding sequencers. A suitable amino acid fragment may be at least about 4 amino acids in length, and may be up to about 200 or up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., (THOMPSON, et al. (1999). "A comprehensive comparison of multiple sequence alignment programs." *Nucleic acids research* 27(13): 2682-2690).

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

Multiple sequence alignment programs are also available for nucleic acid sequences. Examples of such programs include, "Clustal Omega", "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™ a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

As used herein the term "codon-optimized" refers to a sequence for which a codon has been changed for another codon encoding the same amino acid but that is preferred or that performs better in a given tissue (e.g., may increase expression, minimize secondary structures in RNA etc.). "Codon-optimized" sequences may be obtained, using publicly available softwares or via service providers including GenScript (OptimumGene™, U.S. Pat. No. 8,326,547).

In one aspect, a codon optimized, engineered nucleic acid sequence encoding human PEX1 is provided. Preferably, the codon optimized PEX1 coding sequence has less than about 80% identity, preferably about 75% identity or less to the full-length native PEX1 coding sequence (SEQ ID NO: 2). In one embodiment, the codon optimized PEX1 coding sequence has about 73% identity with the native PEX1 coding sequence of SEQ ID NO: 2. In one embodiment, the codon optimized PEX1 coding sequence is characterized by improved translation rate as compared to native PEX1 following AAV-mediated delivery (e.g., rAAV). In one embodiment, the codon optimized PEX1 coding sequence shares less than about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or less identity to the full length native PEX1 coding sequence of SEQ ID NO: 2, SEQ ID NO: 3, SEQ ID NO: 4 or SEQ ID NO: 5. In one embodiment, the codon optimized nucleic acid sequence is a variant of SEQ ID NO: 1. In another embodiment, the codon optimized nucleic acid sequence a sequence sharing about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or greater identity with SEQ ID NO: 1. In one embodiment, the codon optimized nucleic acid sequence is SEQ ID NO: 1. In another embodiment, the nucleic acid sequence is codon optimized for expression in humans. In other embodiments, a different PEX1 coding sequence is selected.

Codon-optimized coding regions can be designed by various different methods. This optimization may be performed using methods which are available on-line (e.g., GeneArt), published methods, or a company which provides codon optimizing services, e.g., DNA2.0 (Menlo Park, Calif.). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

By "engineered" is meant that the nucleic acid sequences encoding the PEX1 protein described herein are assembled and placed into any suitable genetic element, e.g., naked DNA, phage, transposon, cosmid, episome, etc., which transfers the PEX1 sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, the term "host cell" may refer to the packaging cell line in which a recombinant AAV is produced from a production plasmid. In the alternative, the term "host cell" may refer to any target cell in which expression of the coding sequence is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. In certain embodiments herein, the term "host cell" refers to the cells employed to generate and package the viral vector or recombinant virus. In other embodiments herein, the term "host cell" refers to cultures of ocular cells of various mammalian species for in vitro assessment of the compositions described herein. Still in other embodiments, the term "host cell" is intended to reference the ocular cells of the subject being treated in vivo for PBD. Still in other embodiments, the term "host cell" is intended to reference the liver cells of the subject being treated in vivo for PBD. Still in other embodiments, the term "host cell" is intended to reference the central nervous system cells or tissues of the subject being treated in vivo for PBD.

As used herein, the term "ocular cells" refers to any cell in, or associated with the function of, the eye. The term may refer to any one of photoreceptor cells, including rod photoreceptors, cone photoreceptors and photosensitive ganglion cells, retinal pigment epithelium (RPE) cells, Mueller cells, choroidal cells, bipolar cells, horizontal cells, and amacrine cells. In one embodiment, the ocular cells are the photoreceptor cells. In another embodiment, the ocular cells are cone photoreceptors. In another embodiment, the ocular cells are rod photoreceptors.

As used herein, the term "central nervous system cell or tissue" refers to any cell in or associated with the central nervous system. The term may refer to any cell of the brain or spinal cord, including neurons.

In one embodiment, the nucleic acid sequence encoding PEX1 may further comprise a nucleic acid encoding a tag polypeptide covalently linked thereto. The tag polypeptide may be selected from known "epitope tags" including, without limitation, a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin (HA) tag polypeptide, a flag tag polypeptide, and a maltose binding protein tag polypeptide. See FIGS. 1B and 2B for examples of PEX1 plasmids incorporating HA tags.

In another aspect, an expression cassette comprising a nucleic acid sequence that encodes PEX1 is provided. In one embodiment, the sequence is a codon optimized sequence. In another embodiment, the codon optimized nucleic acid sequence is SEQ ID NO: 1 encoding human PEX1.

As used herein, an "expression cassette" refers to a nucleic acid molecule which comprises the coding sequences for PEX1 protein, promoter, and may include other regulatory sequences therefor. The expression cassette may contain elements allowing packaging into the capsid of a viral vector (e.g., a viral particle). Typically, such an expression cassette for generating a viral vector contains the PEX1 sequences described herein flanked by packaging signals of the viral genome and other expression control sequences such as those described herein. For example, for an AAV viral vector, the packaging signals are the 5' inverted terminal repeat (ITR) and the 3' ITR. When packaged into the AAV capsid, the ITRs in conjunction with the expression cassette may be referred to herein as the "recombinant AAV (rAAV) genome" or "vector genome". In one embodiment, an expression cassette comprises a codon optimized nucleic acid sequence that encodes PEX1 protein. In one embodiment, the cassette provides the codon optimized PEX1 operatively associated with expression control sequences that direct expression of the codon optimized nucleic acid sequence that encodes PEX1 in a host cell. In one embodiment, the vector genome is that shown in SEQ ID NO: 6. In another embodiment, the vector genome is that shown in SEQ ID NO: 8.

In another embodiment, an expression cassette for use in an AAV vector is provided. In that embodiment, the AAV expression cassette includes at least one AAV inverted terminal repeat (ITR) sequence. In another embodiment, the expression cassette comprises 5' ITR sequences and 3' ITR sequences. In one embodiment, the 5' and 3' ITRs flank the codon optimized nucleic acid sequence that encodes PEX1, optionally with additional sequences which direct expression of the codon optimized nucleic acid sequence that encodes PEX1 in a host cell. Thus, as described herein, a AAV expression cassette encompasses an expression cassette as described above flanked on its 5' end by a 5'AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting viral vector may be termed pseudotyped. Typically, the AAV vector genome comprises an AAV 5' ITR, the PEX1 coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. Each rAAV genome can be then introduced into a production plasmid.

In an embodiment of the invention, the AAV expression cassette may comprise nucleotides 1253 to 7390 of the pAAV.CAG.copt.hPEX1 plasmid (SEQ ID NO: 9). In a further embodiment, the AAV expression cassette may comprise nucleotides 1253 to 5960 of the pAAV.EF1ac.copt.hPEX1 plasmid (SEQ ID NO: 10). In an additional embodiment, the AAV expression cassette may comprise nucleotides 1253 to 6196 of the pAAV.GRK1.copt.hPEX1 plasmid (SEQ ID NO: 11). In yet an additional embodiment, the AAV expression cassette may comprise nucleotides 1253 to 5951 of the pAAV.MECP2.copt.hPEX1 plasmid (SEQ ID NO: 12). In a further embodiment the AAV expression cassette may comprise nucleotides 1253 to 6235 of the pAAV.CMV.hPEX1 plasmid (SEQ ID NO:13). Expression cassettes encompassed by the present invention also comprise those that are at least 80%, at least 85%, at least 90%, at least 95% or at least 99% identical to the expression cassettes described herein, provided that they encode a functional PEX1 protein.

As used herein, the term "regulatory sequences", "transcriptional control sequence" or "expression control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "operably linked" or "operatively associated" refers to both expression control sequences that are contiguous with the nucleic acid sequence encoding the PEX1 and/or expression control sequences that act in trans or at a distance to control the transcription and expression thereof.

In one aspect, a vector comprising any of the expression cassettes described herein is provided. As described herein, such vectors can be plasmids of variety of origins and are useful in certain embodiments for the generation of recombinant replication defective viruses as described further herein.

A "vector" as used herein is a nucleic acid molecule into which an exogenous or heterologous or engineered nucleic acid transgene may be inserted which can then be introduced into an appropriate host cell. Vectors preferably have one or more origin of replication, and one or more site into which the recombinant DNA can be inserted. Vectors often have means by which cells with vectors can be selected from those without, e.g., they encode drug resistance genes. Common vectors include plasmids, viral genomes, and (primarily in yeast and bacteria) "artificial chromosomes." Certain plasmids are described herein.

In one embodiment, the vector is a non-viral plasmid that comprises an expression cassette described thereof, e.g., "naked DNA", "naked plasmid DNA", RNA, and mRNA; coupled with various compositions and nano particles, including, e.g., micelles, liposomes, cationic lipid-nucleic acid compositions, poly-glycan compositions and other polymers, lipid and/or cholesterol-based-nucleic acid conjugates, and other constructs such as are described herein. See, e.g., X. Su et al, Mol. Pharmaceutics, 2011, 8 (3), pp 774-787; web publication: Mar. 21, 2011; WO2013/182683, WO 2010/053572 and WO 2012/170930, all of which are incorporated herein by reference. Such non-viral PEX1 vector may be administered by the routes described herein. The viral vectors, or non-viral vectors, can be formulated with a physiologically acceptable carrier for use in gene transfer and gene therapy applications.

In another embodiment, the vector may comprise an expression cassette described therein.

As used herein the term "viral vector" refers to viral particles containing a viral genome comprising a coding sequence for PEX1 and more particularly for human PEX1.

"Viral vectors" encompass replication defective viruses containing the exogenous or heterologous PEX1 nucleic acid transgene. In one embodiment, an expression cassette as described herein may be engineered onto a plasmid which is used for drug delivery or for production of a viral vector. Suitable viral vectors are preferably replication defective and selected from amongst those which target ocular cells, or other desired tissue, such as liver or CNS. Viral vectors may include any virus suitable for gene therapy, including but not limited to adenovirus; herpes virus; lentivirus; retrovirus; parvovirus, etc. However, for ease of understanding, the adeno-associated virus is referenced herein as an exemplary virus vector.

A "replication-defective virus" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In another embodiment, a recombinant adeno-associated virus (rAAV) vector is provided. The rAAV compromises an AAV capsid, and a vector genome packaged therein. The vector genome comprises, in one embodiment: (a) an AAV 5' inverted terminal repeat (ITR) sequence; (b) a promoter; (c) a coding sequence encoding a human PEX1; and (d) an AAV 3' ITR. In another embodiment, the vector genome is the expression cassette described herein. In one embodiment, the PEX1 sequence encodes a full length PEX1 protein. In one embodiment, the PEX1 sequence is the protein sequence of SEQ ID NO: 7 or a functional variant thereof. The term "functional variant" with respect to the protein sequence of SEQ ID NO: 7 means a protein that have some amino acid difference with respect to SEQ ID NO: 7 while still allowing a normal peroxisome function.

In another embodiment, the coding sequence is SEQ ID NO: 1 or a variant thereof. In one embodiment, the vector genome is the sequence shown in SEQ ID NO: 6. In one embodiment, the vector genome is the sequence shown in SEQ ID NO: 8.

Adeno-associated virus (AAV), a member of the Parvovirus family, is a small nonenveloped, icosahedral virus with single-stranded linear DNA genomes of 4.7 kilobases (kb) to 6 kb. Among known AAV serotypes are AAV1, AAV2, AAV3, AAV4, AAV5, AAV6, AAV7, AAV8, AAV9 and others. The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, Va.). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc. In one embodiment, the AAV capsid is an AAV8 capsid. In another embodiment, the AAV capsid is an AAV9 capsid. In yet another embodiment, the AAV capsid is an AAV2 capsid.

Fragments of AAV may be readily utilized in a variety of vector systems and host cells. Among desirable AAV fragments are the cap proteins, including the vp1, vp2, vp3 and hypervariable regions, the rep proteins, including rep 78, rep 68, rep 52, and rep 40, and the sequences encoding these proteins. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. In one embodiment, a vector contains the AAV8 cap and/or rep sequences of the invention. See e.g., US patent application publication No. US2009/0227030, incorporated by reference herein.

The term "AAV" or "AAV serotype" as used herein refers to the dozens of naturally occurring and available adeno-associated viruses, as well as artificial AAVs. Among the AAVs isolated or engineered from human or non-human primates (NHP) and well characterized, human AAV2 is the first AAV that was developed as a gene transfer vector; it has been widely used for efficient gene transfer experiments in different target tissues and animal models. Unless otherwise specified, the AAV capsid, ITRs, and other selected AAV components described herein, may be readily selected from among any AAV, including, without limitation, AAV1, AAV2, AAV3, AAV4, AAV5, AAV6, AAV7, AAV8, AAV9, AAV8bp, AAV7M8 and AAVAnc80, variants of any of the known or mentioned AAVs or AAVs yet to be discovered or variants or mixtures thereof. See, e.g., WO 2005/033321, which is incorporated herein by reference. In another embodiment, the AAV capsid is an AAV8bp capsid, which preferentially targets bipolar cells. See, WO 2014/024282, which is incorporated herein by reference. In another embodiment, the AAV capsid is an AAV7m8 capsid, which has shown preferential delivery to the outer retina. See, Dalkara et al, In Vivo-Directed Evolution of a New Adeno-Associated Virus for Therapeutic Outer Retinal Gene Delivery from the Vitreous, Sci Transl Med 5, 189ra76 (2013), which is incorporated herein by reference. In another embodiment, the rAAV capsid is selected from an AAV8 capsid or variant thereof, an AAV6 capsid or variant thereof, an AAV9 capsid or variant thereof, an AAV7 capsid or variant thereof, an AAV5 capsid or variant thereof, an AAV2 capsid or variant thereof, an AAV1 capsid or variant thereof, an AAV3 capsid or variant thereof, and an AAV4 capsid or variant thereof.

In one embodiment, a recombinant adeno-associated virus (rAAV) vector is provided which comprises an AAV8 capsid and an expression cassette described herein, wherein said expression cassette comprises nucleic acid sequences encoding PEX1, inverted terminal repeat sequences and expression control sequences that direct expression of PEX1 in a host cell.

In one embodiment, a recombinant adeno-associated virus (rAAV) vector is provided which comprises an AAV9 capsid and an expression cassette described herein, wherein said expression cassette comprises nucleic acid sequences encoding PEX1, inverted terminal repeat sequences and expression control sequences that direct expression of PEX1 in a host cell.

In still a further embodiment, a recombinant adeno-associated virus (AAV) vector is provided for delivery of the PEX1 constructs and optimized sequences described herein. An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAVs may be selected as sources for capsids of AAV viral vectors as identified above. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10) and (Dalkara D, Byrne L C, Klimczak R R, Visel M, Yin L, Merigan W H, et al. In vivo-directed evolution of a new adeno-associated virus for therapeutic outer retinal gene delivery from the vitreous. Sci Transl Med (2013) 5(189):189ra76. doi: 10.1126/scitranslmed.3005708.) (AAV7m8). Each of these documents is incorporated herein by reference. These documents also describe other AAV capsids which may be selected for generating AAV and are incorporated by reference. In some embodiments, an AAV cap for use in the viral vector can be generated by mutagenesis (i.e., by insertions, deletions, or substitutions) of one of the aforementioned AAV capsids or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

As used herein, relating to AAV, the term variant means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV capsid. When determining the percent identity of an AAV capsid, the comparison may be made over any of the variable proteins (e.g., vp1, vp2, or vp3). In one embodiment, the AAV capsid shares at least 95% identity with the AAV8 over the vp1, vp2 or vp3. In another embodiment, the capsid is an AAV8 capsid with Y447F, Y733F and T494V mutations (also called "AAV8(C&G+T494V)" and "rep2-cap8(Y447F+733F+T494V)"), as described by Kay et al, Targeting Photoreceptors via Intravitreal Delivery Using Novel, Capsid-Mutated AAV Vectors, PLoS One. 2013; 8(4): e62097. Published online 2013 Apr. 26, which is incorporated herein by reference.

In one embodiment, it is desirable to utilize an AAV capsid, which shows tropism for the desired target cell, e.g., photoreceptors (e.g., rods and/or cones), RPE or other ocular cells. In one embodiment, the AAV capsid is a tyrosine capsid-mutant in which certain surface exposed tyrosine residues are substituted with phenylalanine (F). Such AAV variants are described, e.g., in Mowat et al, Tyrosine capsid-mutant AAV vectors for gene delivery to the canine retina from a subretinal or intravitreal approach, Gene Therapy 21, 96-105 (January 2014), which is incorporated herein by reference. In another embodiment, the AAV supplying the capsid is AAV9.

In another embodiment, it is desirable to utilize an AAV capsid which shows tropism for liver. In one embodiment, the AAV supplying the capsid is AAV8. In another embodiment, the AAV supplying the capsid is AAVrh.10. In yet another embodiment, the AAV supplying the capsid is a Clade E AAV. Such AAV include rh.2; rh.10; rh. 25; bb.1, bb.2, pi.1, pi.2, pi.3, rh.38, rh.40, rh.43, rh.49, rh.50, rh.51, rh.52, rh.53, rh.57, rh.58, rh.61, rh.64, hu.6, hu.17, hu.37, hu.39, hu.40, hu.41, hu.42, hu.66, and hu.67. This clade further includes modified rh. 2; modified rh. 58; and modified rh.64. See, WO 2005/033321, which is incorporated herein by reference. However, any of a number of rAAV vectors with liver tropism can be used.

In another embodiment, it is desirable to utilize an AAV capsid which shows tropism for CNS. In one embodiment, the AAV capsid is selected from AAV1, AAV2, AAV7, AAV8, AAV9, AAVrh.10, AAV5, AAVhu.11, AAV8DJ, AAVhu.32, AAVhu.37, AAVpi.2, AAVrh.8, AAVhu.48R3 and variants thereof. See, Royo, et al, Brain Res, 2008 January, 1190:15-22; Petrosyan et al, Gene Therapy, 2014 December, 21(12):991-1000; Holehonnur et al, BMC Neuroscience, 2014, 15:28; and Cearley et al, Mol Ther. 2008 October; 16(10): 1710-1718, each of which is incorporated herein by reference. Other AAV capsids useful herein include AAVrh.39, AAVrh.20, AAVrh.25, AAV10, AAVbb.1, and AAV bb.2 and variants thereof.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/5 and AAV2/8 are exemplary pseudotyped vectors.

In another embodiment, a self-complementary AAV is used. "Self-complementary AAV" refers to a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596, 535; 7,125,717; and 7,456,683, each of which is incorporated herein by reference in its entirety.

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence which with which the protein or nucleic acid in question is not found in the same relationship to each other in nature.

In still another embodiment, the expression cassette, including any of those described herein is employed to generate a recombinant AAV genome.

In one embodiment, the expression cassette described herein is engineered into a suitable genetic element (vector) useful for generating viral vectors and/or for delivery to a host cell, e.g., naked DNA, phage, transposon, cosmid, episome, etc., which transfers the PEX1 sequences carried thereon. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, N.Y.

For packaging an expression cassette or rAAV genome or production plasmid into virions, the ITRs are the only AAV components required in cis in the same construct as the expression cassette. In one embodiment, the coding sequences for the replication (rep) and/or capsid (cap) are removed from the AAV genome and supplied in trans or by a packaging cell line in order to generate the AAV vector.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

In yet another system, the expression cassette flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

"Plasmids" generally are designated herein by a lower case p preceded and/or followed by capital letters and/or numbers, in accordance with standard naming conventions that are familiar to those of skill in the art. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

In one embodiment, the production plasmid is that described herein, or as described in WO2012/158757, which is incorporated herein by reference. Various plasmids are known in the art for use in producing rAAV vectors, and are useful herein. The production plasmids are cultured in the host cells which express the AAV cap and/or rep proteins. In the host cells, each rAAV genome is rescued and packaged into the capsid protein or envelope protein to form an infectious viral particle.

In one aspect, a production plasmid comprising an expression cassette described above is provided. In one embodiment, the production plasmid is one of those shown in FIGS. 1A-2B and FIGS. 25A to 25D. Such a plasmid is one that contains a 5' AAV ITR sequence; a selected promoter; a polyA sequence; and a 3' ITR; additionally, it also contains a stuffer sequence, such as lambda. In one embodiment, a non-coding lambda stuffer region is included in the vector backbone. In a further embodiment, the stuffer sequence keeps the rAAV vector genome with a size between about 3 kilobases (kb) to about 6 kb, about 4.7 kb to about 6 kb, about 3 kb to about 5.5 kb, or about 4.7 kb to 5.5 kb. In another embodiment, the production plasmid is modified to optimized vector plasmid production efficiency. Such modifications include addition of other neutral sequences, or deletion of portion(s) of or the entire lambda stuffer sequence to modulate the level of supercoil of the vector plasmid. Such modifications are contemplated herein. In other embodiments, terminator and other sequences are included in the plasmid. Exemplary embodiments of plasmids comprising the expression cassette of the present invention are provided in SEQ ID NO: 9, SEQ ID NO: 10, SEQ ID NO: 11, SEQ ID NO: 12 and SEQ ID NO:13. Plasmids encompassed by the present invention also comprise those comprising an expression cassette that is at least 80%, at least 85%, at least 90%, at least 95% or at least 99% identical to the expression cassette described herein, provided that they encode a functional PEX1 protein. More particularly, the plasmids includes those having at least 80%, at least 85%, at least 90%, at least 95% or at least 99% sequence identity with SEQ ID NO: 9, SEQ ID NO: 10, SEQ ID NO: 11, SEQ ID NO: 12 or SEQ ID NO:13.

In certain embodiments, the rAAV expression cassette, the vector (such as rAAV vector), the virus (such as rAAV), and/or the production plasmid comprises AAV inverted terminal repeat sequences, a codon optimized nucleic acid sequence that encodes PEX1, and expression control sequences that direct expression of the encoded proteins in a host cell. In other embodiments, the rAAV expression cassette, the virus, the vector (such as rAAV vector), and/or the production plasmid further comprise one or more of an intron, a Kozak sequence, a polyA, post-transcriptional regulatory elements and others. In one embodiment, the post-transcriptional regulatory element is Woodchuck Hepatitis Virus (WHP) Posttranscriptional Regulatory Element (WPRE).

The expression cassettes, vectors and plasmids include other components that can be optimized for a specific species using techniques known in the art including, e.g, codon optimization, as described herein. The components of the cassettes, vectors, plasmids and viruses or other compositions described herein include a promoter sequence as part of the expression control sequences. In another embodiment, the promoter is cell-specific. The term "cell-specific" means that the particular promoter selected for the recombinant vector can direct expression of the optimized PEX1 coding sequence in a particular cell type. In one embodiment, the promoter is specific for expression of the transgene in photoreceptor cells. In another embodiment, the promoter is specific for expression in the rods and cones. In another embodiment, the promoter is specific for expression in the rods. In another embodiment, the promoter is specific for expression in the cones. In one embodiment, the photoreceptor-specific promoter is a human rhodopsin kinase promoter. The rhodopsin kinase promoter has been shown to be active in both rods and cones. See, e.g., Sun et al, Gene Therapy with a Promoter Targeting Both Rods and Cones Rescues Retinal Degeneration Caused by AIPL1 Mutations, Gene Ther. 2010 January; 17(1): 117-131, which is incorporated herein by reference in its entirety. In one embodiment, the promoter is a human rhodopsin kinase promoter, such as that shown in SEQ ID NO: 8, nt 175 to 684 (FIG. 2A).

In one embodiment, the promoter is modified to include restriction on the ends for cloning. See, e.g, Nathans and Hogness, Isolation and nucleotide sequence of the gene encoding human rhodopsin, PNAS, 81:4851-5 (August 1984), which is incorporated herein by reference in its entirety. In another embodiment, the promoter is a portion or fragment of the human rhodopsin promoter, or the full length promoter. In another embodiment, the promoter is a variant of the human rhodopsin promoter.

Other exemplary promoters include the human G-protein-coupled receptor protein kinase 1 (GRK1) promoter (Genbank Accession number AY327580). In another embodiment, the promoter is a 292 nt fragment (positions 1793-2087) of the GRK1 promoter (See, Beltran et al, Gene Therapy 2010 17:1162-74, which is hereby incorporated by reference in its entirety). In another preferred embodiment, the promoter is the human interphotoreceptor retinoid-binding protein proximal (IRBP) promoter. In one embodiment, the promoter is a 235 nt fragment of the hIRBP promoter. In one embodiment, the promoter is the RPGR proximal promoter (Shu et al, IOVS, May 2102, which is incorporated by reference in its entirety). Other promoters useful in the invention include, without limitation, the rod opsin promoter, the red-green opsin promoter, the blue opsin promoter, the cGMP-β-phosphodiesterase promoter (Qgueta et al, IOVS, Invest Ophthalmol Vis Sci. 2000 December; 41(13):4059-63), the mouse opsin promoter (Beltran et al 2010 cited above), the rhodopsin promoter (Mussolino et al, Gene Ther, July 2011, 18(7):637-45); the alpha-subunit of cone transducin (Morrissey et al, BMC Dev, Biol, January 2011, 11:3); beta phosphodiesterase (PDE) promoter; the retinitis pigmentosa (RP1) promoter (Nicord et al, J. Gene Med, December 2007, 9(12):1015-23); the NXNL2/NXNL1 promoter (Lambard et al, PLoS One, October 2010, 5(10): e13025), the RPE65 promoter; the retinal degeneration slow/peripherin 2 (Rds/perph2) promoter (Cai et al, Exp Eye Res. 2010 August; 91(2):186-94); and the VMD2 promoter (Kachi et al, Human Gene Therapy, 2009 (20:31-9)). Each of these documents is incorporated by reference herein in its entirety. In another embodiment, the promoter is selected from human EF1α promoter, rhodopsin promoter, interphotoreceptor binding protein (IRBP), cone opsin promoters (red-green, blue), cone opsin upstream sequences containing the red-green cone locus control region, cone transducing, and transcription factor promoters (neural retina leucine zipper (Nrl) and photoreceptor-specific nuclear receptor Nr2e3, bZIP).

In another embodiment, the promoter is a ubiquitous or constitutive promoter. An example of a suitable promoter is a cytomegalovirus (CMV) promoter with CMV enhancer elements, such as the sequence shown in SEQ ID NO: 6, nt 485 to 688 (FIG. 1A).

In another embodiment, the promoter is the CB7 promoter. Other suitable promoters include the human β-actin promoter, the human elongation factor-1α promoter, the cytomegalovirus (CMV) promoter, the CBA promoter with CMV enhancer, the simian virus 40 promoter, and the herpes simplex virus thymidine kinase promoter. See, e.g., Damdindorj et al, (August 2014) A Comparative Analysis of Constitutive Promoters Located in Adeno-Associated Viral Vectors. PLoS ONE 9(8): e106472. Still other suitable promoters include viral promoters, constitutive promoters, regulatable promoters [see, e.g., WO 2011/126808 and WO 2013/04943]. Alternatively a promoter responsive to physiologic cues may be utilized in the expression cassette, rAAV genomes, vectors, plasmids and viruses described herein. In one embodiment, the promoter is of a small size, under 1000 bp, due to the size limitations of the AAV vector. In another embodiment, the promoter is under 400 bp. Other promoters may be selected by one of skill in the art.

In a further embodiment, the promoter is selected from SV40 promoter, the dihydrofolate reductase promoter, and the phosphoglycerol kinase (PGK) promoter, rhodopsin kinase promoter, the rod opsin promoter, the red-green opsin promoter, the blue opsin promoter, the inter photoreceptor binding protein (IRBP) promoter and the cGMP-β-phosphodiesterase promoter, a phage lambda (PL) promoter, a herpes simplex viral (HSV) promoter, a tetracycline-controlled trans-activator-responsive promoter (tet) system, a long terminal repeat (LTR) promoter, such as a RSV LTR, MoMLV LTR, BIV LTR or an HIV LTR, a U3 region promoter of Moloney murine sarcoma virus, a Granzyme A promoter, a regulatory sequence(s) of the metallothionein gene, a CD34 promoter, a CD8 promoter, a thymidine kinase (TK) promoter, a B19 parvovirus promoter, a PGK promoter, a glucocorticoid promoter, a heat shock protein (HSP) promoter, such as HSP65 and HSP70 promoters, an immunoglobulin promoter, an MMTV promoter, a Rous sarcoma virus (RSV) promoter, a lac promoter, a CaMV 35S promoter, a nopaline synthetase promoter, an MND promoter, or an MNC promoter. The promoter sequences thereof are known to one of skill in the art or available publically, such as in the literature or in databases, e.g., GenBank, PubMed, or the like.

In another embodiment, the promoter is an inducible promoter. The inducible promoter may be selected from known promoters including the rapamycin/rapalog promoter, the ecdysone promoter, the estrogen-responsive promoter, and the tetracycline-responsive promoter, or heterodimeric repressor switch. See, Sochor et al, An Autogenously Regulated Expression System for Gene Therapeutic Ocular Applications. Scientific Reports, 2015 Nov. 24; 5:17105 and Daber R, Lewis M., A novel molecular switch. J Mol Biol. 2009 Aug. 28; 391(4):661-70, Epub 2009 Jun. 21 which are both incorporated herein by reference in their entirety.

In other embodiments, the expression cassette, vector, plasmid and viral genome described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein.

Examples of suitable polyA sequences include, e.g., a synthetic polyA or from bovine growth hormone (bGH), human growth hormone (hGH), SV40, rabbit β-globin (RGB), or modified RGB (mRGB). In one embodiment, the poly A has a nucleic acid sequence from nt 4573 to nt 4684 of SEQ ID NO:8.

Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), an APB enhancer, ABPS enhancer, an alpha mic/bik enhancer, TTR enhancer, en34, ApoE amongst others.

In one embodiment, a Kozak sequence is included upstream of the PEX1 coding sequence to enhance translation from the correct initiation codon. In one embodiment, the PEX1 coding sequence is placed under the control of a cytomegalovirus (CMV) promoter. In another embodiment, the PEX1 coding sequence is placed under the control of a rhodopsin kinase promoter.

In one embodiment, the expression cassette, the vector, the plasmid and the viral genome contain a 5' ITR, CMV promoter, CMV enhancer, human codon optimized PEX1 sequence, bGH poly A and 3' ITR. In a further embodiment, the expression cassette includes nt 1 to 4871 of SEQ ID NO: 6. In yet a further embodiment, the 5' ITR has a nucleic acid sequence from nt 1 to nt 130 of SEQ ID NO: 6 and the 3'ITR has a nucleic acid sequence from nt 4854 to nt 4871 of SEQ ID NO: 6.

In one embodiment, the expression cassette, the vector, the plasmid and the viral genome contain a 5' ITR, rhodopsin kinase promoter, human codon optimized PEX1 sequence, bGH poly A and 3' ITR. In a further embodiment, the expression cassette includes nt 1 to 4947 of SEQ ID NO: 8.

In another aspect, a method for treating PBD caused by a defect in the PEX1 gene and/or restoring visual function in a subject having PBD comprises delivering to a subject in need thereof a vector (such as rAAV) which encodes PEX1, as described herein. In one embodiment, a method of treating a subject having PBD with a rAAV described herein is provided.

By "administering" as used in the methods means delivering the composition to the target selected cell which is characterized by PBD. In one embodiment, the method involves delivering the composition by subretinal injection to the RPE, photoreceptor cells or other ocular cells. In another embodiment, intravitreal injection to the subject is employed. In another embodiment, subretinal injection to the subject is employed. In still another method, intravascular injections, such as injection via the palpebral vein may be employed. In another method, delivery to the liver is employed, such as via portal vein. In another method, delivery to the CNS is employed, such as via intraventricular, intrathecal or interstitial delivery. Still other methods of administration may be selected by one of skill in the art given this disclosure.

By "administering" or "route of administration" is delivery of composition described herein, with or without a pharmaceutical carrier or excipient, of the subject. Routes of administration may be combined, if desired. In some embodiments, the administration is repeated periodically. The pharmaceutical compositions described herein are designed for delivery to subjects in need thereof by any suitable route or a combination of different routes. In some embodiments, direct delivery to the eye (optionally via ocular delivery, subretinal injection, intra-retinal injection, intravitreal, topical) is utilized. In other embodiments delivery via systemic routes is employed, e.g., intravascular, intraarterial, intraocular, intravenous, intramuscular, subcutaneous, intradermal, and other parental routes of administration. In one embodiment, delivery to the liver is employed. In another embodiment, delivery to the CNS is employed.

The nucleic acid molecules, the expression cassette and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins.

Also provided herein are pharmaceutical compositions. The pharmaceutical compositions described herein are designed for delivery to subjects in need thereof by any suitable route or a combination of different routes. These delivery means are designed to avoid direct systemic delivery of the suspension containing the AAV composition(s) described herein. Suitably, this may have the benefit of reducing dose as compared to systemic administration, reducing toxicity and/or reducing undesirable immune responses to the AAV and/or transgene product.

In yet other aspects, these nucleic acid sequences, vectors, expression cassettes and rAAV viral vectors are useful in a pharmaceutical composition, which also comprises a pharmaceutically acceptable carrier, excipient, buffer, diluent, surfactant, preservative and/or adjuvant, etc. Such pharmaceutical compositions are used to express the optimized PEX1 in the host cells through delivery by such recombinantly engineered AAVs or artificial AAVs.

To prepare these pharmaceutical compositions containing the nucleic acid sequences, vectors, expression cassettes and rAAV viral vectors, the sequences or vectors or viral vector is preferably assessed for contamination by conventional methods and then formulated into a pharmaceutical composition suitable for administration to the eye. Such formulation involves the use of a pharmaceutically and/or physiologically acceptable vehicle or carrier, particularly one suitable for administration to the eye, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, surfactant, or excipient etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravitreal or subretinal delivery, a pH of 6.8 to about 7.2 may be desired. However, other pHs within the broadest ranges and these subranges may be selected for other route of delivery.

A suitable surfactant, or combination of surfactants, may be selected from among nonionic surfactants that are nontoxic. In one embodiment, a difunctional block copolymer surfactant terminating in primary hydroxyl groups is selected, e.g., such as Pluronic® F68 [BASF], also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate.7H2O), potassium chloride, calcium chloride (e.g., calcium chloride.2H2O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution [Lukare Medical]. In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intravitreal delivery. In one example, the composition is formulated for subretinal delivery.

In one exemplary specific embodiment, the composition of the carrier or excipient contains 180 mM NaCl, 10 mM NaPi, pH7.3 with 0.0001%-0.01% Pluronic F68 (PF68). The exact composition of the saline component of the buffer ranges from 160 mM to 180 mM NaCl. Optionally, a different pH buffer (potentially HEPES, sodium bicarbonate, TRIS) is used in place of the buffer specifically described. Still alternatively, a buffer containing 0.9% NaCl is useful.

In the case of AAV viral vectors, quantification of the genome copies ("GC"), vector genomes ("VG"), or virus particles may be used as the measure of the dose contained in the formulation or suspension. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal). In another method, the effective dose of a recombinant adeno-associated virus carrying a nucleic acid sequence encoding the optimized PEX1 coding sequence is measured as described in S. K. McLaughlin et al, 1988 J. Virol., 62:1963, which is incorporated by reference in its entirety.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the codon optimized nucleic acid sequences encoding PEX1 as described herein that is in the range of about $1.0 \times 10^9$ GC to about $1.0 \times 10^{15}$ GC per dose including all integers or fractional amounts within the range. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range. All dosages may be measured by any known method, including as measured by qPCR or digital droplet PCR (ddPCR) as described in, e.g., M. Lock et al, Hum Gene Ther Methods. 2014 April; 25(2):115-25. doi: 10.1089/hgtb.2013.131, which is incorporated herein by reference.

In one embodiment, an aqueous suspension suitable for administration to an PBD patient is provided. In one embodiment, for ocular delivery, the suspension comprises an aqueous suspending liquid and about $1 \times 10^{10}$ GC or viral particles to about $1\times10^{12}$ GC or viral particles per eye of a recombinant adeno-associated virus (rAAV) described herein useful as a therapeutic for PBD. In another embodiment, the suspension comprises an aqueous suspending liquid and about $1\times10^{10}$ GC or viral particles to about $1\times10^{14}$ GC or viral particles per dose of a recombinant adeno-associated virus (rAAV) described herein useful as a therapeutic for PBD.

It may also be desirable to administer multiple "booster" dosages of the pharmaceutical compositions of this invention. For example, depending upon the duration of the transgene within the ocular target cell, one may deliver booster dosages at 6 month intervals, or yearly following the first administration. The fact that AAV-neutralizing antibodies were not generated by administration of the rAAV vector should allow additional booster administrations.

Such booster dosages and the need therefor can be monitored by the attending physicians, using, for example, the retinal and visual function tests and the visual behavior tests described in the examples below. Other similar tests may be used to determine the status of the treated subject over time. Selection of the appropriate tests may be made by the attending physician. Still alternatively, the method of this invention may also involve injection of a larger volume of virus-containing solution in a single or multiple infection to allow levels of visual function close to those found in wildtype retinas.

In another embodiment, the amount of the vectors, the virus and the replication-defective virus described herein carrying the codon optimized nucleic acid sequences encoding PEX1 are in the range of about $1.0\times10^{7}$ VG per eye or dose to about $1.0\times10^{15}$ VG per eye or dose including all integers or fractional amounts within the range. In one embodiment, the amount thereof is at least $1\times10^{7}$, $2\times10^{7}$, $3\times10^{7}$, $4\times10^{7}$, $5\times10^{7}$, $6\times10^{7}$, $7\times10^{7}$, $8\times10^{7}$, or $9\times10^{7}$ VG per eye or dose including all integers or fractional amounts within the range. In one embodiment, the amount thereof is at least $1\times10^{8}$, $2\times10^{8}$, $3\times10^{8}$, $4\times10^{8}$, $5\times10^{8}$, $6\times10^{8}$, $7\times10^{8}$, $8\times10^{8}$, or $9\times10^{8}$ VG per eye or dose including all integers or fractional amounts within the range. In one embodiment, the amount thereof is at least $1\times10^{9}$, $2\times10^{9}$, $3\times10^{9}$, $4\times10^{9}$, $5\times10^{9}$, $6\times10^{9}$, $7\times10^{9}$, $8\times10^{9}$, or $9\times10^{9}$ VG per eye or dose including all integers or fractional amounts within the range. In one embodiment, the amount thereof is at least $1\times10^{10}$, $2\times10^{10}$, $3\times10^{10}$, $4\times10^{10}$, $5\times10^{10}$, $6\times10^{10}$, $7\times10^{10}$, $8\times10^{10}$, or $9\times10^{10}$ VG per eye or dose including all integers or fractional amounts within the range. In one embodiment, the amount thereof is at least $1\times10^{11}$, $2\times10^{11}$, $3\times10^{11}$, $4\times10^{11}$, $5\times10^{11}$, $6\times10^{11}$, $7\times10^{11}$, $8\times11$, or $9\times10^{11}$ VG per eye or dose including all integers or fractional amounts within the range. In one embodiment, the amount thereof is at least $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ VG per eye or dose including all integers or fractional amounts within the range. In one embodiment, the amount thereof is at least $1\times10^{13}$, $2\times10^{13}$, $3\times10^{13}$, $4\times10^{13}$, $5\times10^{13}$, $6\times10^{13}$, $7\times10^{13}$, $8\times10^{13}$, or $9\times10^{13}$ VG per eye or dose including all integers or fractional amounts within the range. In one embodiment, the amount thereof is at least $1\times10^{14}$, $2\times10^{14}$, $3\times10^{14}$, $4\times10^{14}$, $5\times10^{14}$, $6\times10^{14}$, $7\times10^{14}$, $8\times10^{14}$, or $9\times10^{14}$ VG per eye or dose including all integers or fractional amounts within the range. In one embodiment, the amount thereof is at least $1\times10^{15}$, $2\times10^{15}$, $3\times10^{15}$, $4\times10^{15}$, $5\times10^{15}$, $6\times10^{15}$, $7\times10^{15}$, $8\times10^{15}$, or $9\times10^{15}$ GC per eye or dose including all integers or fractional amounts within the range. In one embodiment, the methods comprise doses ranging from $1\times10^{9}$ to about $1\times10^{13}$ VG per eye or dose including all integers or fractional amounts within the range. In another embodiment, the method comprises delivery of the vector in an aqueous suspension. In another embodiment, the method comprises administering the rAAV described herein in a dosage of from $1\times10^{9}$ to $1\times10^{13}$ GC in a volume about or at least 150 microliters, thereby restoring visual function in said subject. All dosages may be measured by any known method, including as measured by oqPCR or digital droplet PCR (ddPCR) as described in, e.g., M. Lock et al, Hum Gene Ther Methods. 2014 April; 25(2):115-25. doi: 10.1089/hgtb.2013.131, which is incorporated herein by reference.

These above doses may be administered in a variety of volumes of carrier, excipient or buffer formulation, ranging from about 25 to about 1000 microliters, for ocular delivery, including all numbers within the range, depending on the size of the area to be treated, the viral titer used, the route of administration, and the desired effect of the method. In one embodiment, the volume of carrier, excipient or buffer is at least about 25 μL. In one embodiment, the volume is about 50 μL. In another embodiment, the volume is about 75 μL. In another embodiment, the volume is about 100 μL. In another embodiment, the volume is about 125 μL. In another embodiment, the volume is about 150 μL. In another embodiment, the volume is about 175 μL. In yet another embodiment, the volume is about 200 μL. In another embodiment, the volume is about 225 μL. In yet another embodiment, the volume is about 250 μL. In yet another embodiment, the volume is about 275 μL. In yet another embodiment, the volume is about 300 μL. In yet another embodiment, the volume is about 325 μL. In another embodiment, the volume is about 350 μL. In another embodiment, the volume is about 375 μL. In another embodiment, the volume is about 400 μL. In another embodiment, the volume is about 450 μL. In another embodiment, the volume is about 500 μL. In another embodiment, the volume is about 550 μL. In another embodiment, the volume is about 600 μL. In another embodiment, the volume is about 650 μL. In another embodiment, the volume is about 700 μL. In another embodiment, the volume is about 800 μL. In another embodiment, the volume is between about 150 and 800 μL. In another embodiment, the volume is between about 700 and 1000 μL. In another embodiment, the volume is between about 250 and 500 μL.

In one embodiment, the viral constructs may be delivered in doses of from at least $1\times10^{9}$ to about least $1\times10^{11}$ GCs in volumes of about 1 μL to about 3 μL for small animal subjects, such as mice. For larger veterinary subjects having eyes about the same size as human eyes, the larger human dosages and volumes stated above are useful. See, e.g., Diehl et al, J. Applied Toxicology, 21:15-23 (2001) for a discussion of good practices for administration of substances to various veterinary animals. This document is incorporated herein by reference.

For other delivery routes, the above doses may be administered in a variety of volumes of carrier, excipient or buffer formulation, ranging from about 100 microliters to about 50 mL, including all numbers within the range, depending on the size of the patient, the viral titer used, the route of administration, and the desired effect of the method. In one embodiment, the volume of carrier, excipient or buffer is at least about 500 μL. In one embodiment, the volume is about 750 μL. In another embodiment, the volume is about 1 mL. In another embodiment, the volume is about 2 mL. In another embodiment, the volume is about 3 mL. In another embodiment, the volume is about 4 mL. In another embodiment, the volume is about 5 mL. In another embodiment, the volume is about 6 mL. In another embodiment, the volume is about 7 mL. In another embodiment, the volume is about 8 mL. In another embodiment, the volume is about 9 mL. In another embodiment, the volume is about 10 mL. In another embodiment, the volume is about 11 mL. In another embodiment, the volume is about 12 mL. In another embodiment, the volume is about 13 mL. In another embodiment, the volume is about 14 mL. In another embodiment, the volume is about 15 mL. In another embodiment, the volume is about 16 mL. In another embodiment, the volume is about 17 mL. In another embodiment, the volume is about 18 mL. In another embodiment, the volume is about 19 mL. In another embodiment, the volume is about 20 mL. In another embodiment, the volume is about 21 mL. In another embodiment, the volume is about 22 mL. In another embodiment, the volume is about 23 mL. In another embodiment, the volume is about 24 mL. In another embodiment, the volume is about 25 mL or more. In one embodiment, the maximum injected volume is about 10% of total cerebrospinal fluid volume.

It is desirable that the lowest effective concentration of virus or other delivery vehicle be utilized in order to reduce the risk of undesirable effects, such as toxicity, retinal dysplasia and detachment. Still other dosages in these ranges may be selected by the attending physician, taking into account the physical state of the subject, preferably human, being treated, the age of the subject, the PBD and the degree to which the disorder, if progressive, has developed.

Yet another aspect described herein is a method for treating, retarding or halting progression of PBD in a mammalian subject. In one embodiment, an rAAV carrying the PEX1 native, modified or codon optimized sequence, preferably suspended in a physiologically compatible carrier, diluent, excipient and/or adjuvant, may be administered to a desired subject including a human subject. This method comprises administering to a subject in need thereof any of the nucleic acid sequences, expression cassettes, rAAV genomes, plasmids, vectors or rAAV vectors or compositions containing them. In one embodiment, the composition is delivered subretinally. In another embodiment, the composition is delivered intravitreally. In still another embodiment, the composition is delivered using a combination of administrative routes suitable for treatment of PBD, and may also involve administration via the palpebral vein or other intravenous or conventional administration routes.

For use in these methods, the volume and viral titer of each dosage is determined individually, as further described herein, and may be the same or different from other treatments performed in the same, or contralateral, eye. The dosages, administrations and regimens may be determined by the attending physician given the teachings of this specification. In one embodiment, the composition is administered in a single dosage selected from those above listed in an affected eye. In another embodiment, the composition is administered as a single dosage selected from those above listed in a both affected eyes, either simultaneously or sequentially. Sequential administration may imply a time gap of administration from one eye to another from intervals of minutes, hours, days, weeks or months. In another embodiment, the method involves administering the compositions to an eye two or more dosages (e.g., split dosages). In another embodiment, multiple injections are made in different portions of the same eye. In another embodiment, a second administration of an rAAV including the selected expression cassette (e.g., PEX1 containing cassette) is performed at a later time point. Such time point may be weeks, months or years following the first administration. Such second administration is, in one embodiment, performed with an rAAV having a different capsid than the rAAV from the first administration. In another embodiment, the rAAV from the first and second administration have the same capsid.

In still other embodiments, the compositions described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

In certain embodiments of the invention, it is desirable to perform non-invasive retinal imaging and functional studies to identify areas of the rod and cone photoreceptors to be targeted for therapy as well as to test the efficacy of treatment. In these embodiments, clinical diagnostic tests are employed to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (cSLO) and optical coherence tomography (OCT), topographical mapping of cone density via adaptive optics (AO), functional eye exam, Multi-electrode array (MEA), Pupillary Light Responses, etc, depending upon the species of the subject being treated, their physical status and health and the dosage. In view of the imaging and functional studies, in some embodiments of the invention one or more injections are performed in the same eye in order to target different areas of the affected eye. The volume and viral titer of each injection is determined individually, as further described herein, and may be the same or different from other injections performed in the same, or contralateral, eye. In another embodiment, a single, larger volume injection is made in order to treat the entire eye. In one embodiment, the volume and concentration of the rAAV composition is selected so that only the region of damaged ocular cells is impacted. In another embodiment, the volume and/or concentration of the rAAV composition is a greater amount, in order reach larger portions of the eye, including non-damaged photoreceptors.

In another embodiment, the method includes performing additional studies, e.g., functional and imaging studies to determine the efficacy of the treatment. For examination in animals, such tests include retinal and visual function assessment via electroretinograms (ERGs) looking at rod and cone photoreceptor function, optokinetic nystagmus, pupillometry, water maze testing, light-dark preference, optical coherence tomography (to measure thickness of various layers of the retina), histology (retinal thickness, rows of nuclei in the outer nuclear layer, immunofluorescence to document transgene expression, cone photoreceptor counting, staining of retinal sections with peanut agglutinin—which identifies cone photoreceptor sheaths).

Specifically for human subjects, following administration of a dosage of a compositions described in this specification, the subject is tested for efficacy of treatment using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), and reading speed test. Other useful post-treatment efficacy test to which the subject is exposed following treatment with a pharmaceutical composition described herein are functional magnetic resonance imaging (fMRI), full-field light sensitivity testing, retinal structure studies including optical coherence tomography, fundus photography, fundus autofluorescence, adaptive optics laser scanning ophthalmoscopy, mobility testing, test of reading speed and accuracy, microperimetry and/or ophthalmoscopy. These and other efficacy tests are described in U.S. Pat. No. 8,147,823; in co-pending International patent application publication WO 2014/011210 or WO 2014/124282, incorporated by reference.

In one embodiment of the methods described herein, a one-time intra-ocular delivery of a composition as described herein, e.g., an AAV delivery of an optimized PEX1 cassette, is useful in treating PBD in a subject. In another embodiment of the methods described herein, a one-time intra-ocular delivery of a composition as described herein, e.g., an AAV delivery of an optimized PEX1 cassette, is useful in treating PBD in a subject at risk.

Thus, in one embodiment, the composition is administered before disease onset. In another embodiment, the composition is administered prior to the initiation of vision impairment or loss. In another embodiment, the composition is administered after initiation of vision impairment or loss. In yet another embodiment, the composition is administered when less than 90% of the rod and/or cones or photoreceptors are functioning or remaining, as compared to a non-diseased eye. In one embodiment, neonatal treatment is defined as being administered a PEX1 coding sequence, expression cassette or vector as described herein within 8 hours, the first 12 hours, the first 24 hours, or the first 48 hours of delivery. In another embodiment, particularly for a primate (human or non-human), neonatal delivery is within the period of about 12 hours to about 1 week, 2 weeks, 3 weeks, or about 1 month, or after about 24 hours to about 48 hours. In another embodiment, the composition is delivered after onset of symptoms. In one embodiment, treatment of the patient (e.g., a first injection) is initiated prior to the first year of life. In another embodiment, treatment is initiated after the first 1 year, or after the first 2 to 3 years of age, after 5 years of age, after 11 years of age, or at an older age. In one embodiment, treatment is initiated from ages about 4 years of age to about 12 years of age. In one embodiment, treatment is initiated on or after about 4 years of age. In one embodiment, treatment is initiated on or after about 5 years of age. In one embodiment, treatment is initiated on or after about 6 years of age. In one embodiment, treatment is initiated on or after about 7 years of age. In one embodiment, treatment is initiated on or after about 8 years of age. In one embodiment, treatment is initiated on or after about 9 years of age. In one embodiment, treatment is initiated on or after about 10 years of age. In one embodiment, treatment is initiated on or after about 11 years of age. In one embodiment, treatment is initiated on or after about 12 years of age. However, treatment can be initiated on or after about 15, about 20, about 25, about 30, about 35, or about 40 years of age. In one embodiment, treatment in utero is defined as administering the composition as described herein in the fetus. See, e.g., David et al, Recombinant adeno-associated virus-mediated in utero gene transfer gives therapeutic transgene expression in the sheep, Hum Gene Ther. 2011 April; 22(4):419-26. doi: 10.1089/hum.2010.007. Epub 2011 Feb. 2, which is incorporated herein by reference.

In another embodiment, the composition is readministered at a later date. Optionally, more than one readministration is permitted. Such readministration may be with the same type of vector, a different viral vector, or via non-viral delivery as described herein. In one embodiment, the vector is readministered to the patient to a different portion of the initially injected retina. In one embodiment, the vector is readministered to the patient to the same portion of the initially injected retina.

In yet another embodiment, any of the above described methods is performed in combination with another, or secondary, therapy. The secondary therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated.

In one embodiment, a method of generating a recombinant rAAV comprises obtaining a plasmid containing an AAV expression cassette as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver the codon optimized PEX1 in the expression cassettes and genomes described above and in the examples below.

In certain embodiments of this invention, a subject has a peroxisome biogenesis disorder (PBD), for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

As used herein, the term "treatment" or "treating" is defined encompassing administering to a subject one or more compounds or compositions described herein for the purposes of amelioration of one or more symptoms of PBD. "Treatment" can thus include one or more of reducing onset or progression of PBD, preventing disease, reducing the severity of the disease symptoms, or retarding their progression, including the progression of blindness, removing the disease symptoms, delaying onset of disease or monitoring progression of disease or efficacy of therapy in a given subject.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

The term "regulation" or variations thereof as used herein refers to the ability of a composition to inhibit one or more components of a biological pathway.

Unless defined otherwise in this specification, technical and scientific terms used herein have the same meaning as commonly understood by one of ordinary skill in the art and by reference to published texts, which provide one skilled in the art with a general guide to many of the terms used in the present application.

In one embodiment, treatment using the rAAV compositions described herein is combined with New born Screening (NBS), such as measuring Levels of a peroxisome metabolite by tandem mass spectroscopy and screening for X-linked adrenoleukodystrophy.

EXAMPLES

The invention is now described with reference to the following examples. These examples are provided for the purpose of illustration only and the invention should in no way be construed as being limited to these examples but rather should be construed to encompass any and all variations that become evident as a result of the teaching provided herein.

Example 1

Generation of AAV.hPEX1 Vectors

Viral vectors capable of delivering PEX1 to diseased tissue, including retinal cells in the eye, were generated. This vector could be used to treat disease classified as Zellweger syndrome, infantile Refsum disease and neonatal adrenoleukodystrophy. Results indicate that delivery of a recombinant adeno-associated virus (AAV) containing the human PEX1 cDNA (AAV.hPEX1) to tissue of mice lacking Pex1 corrects the disorder and that delivery of AAV.hPEX1 to affected cells in vivo could potentially ameliorate or even cure the disorder.

One of the challenges of delivering PEX1 using AAV is that the cDNA is large (3852 bp). Because of the limited cargo capacity of rAAV vectors (4.8 kb), small regulatory sequences were incorporated into the proviral plasmid. These included a cytomegalovirus (CMV) promoter, a chicken beta actin (CBA) promoter and a rhodopsin kinase promoter, thereby generating pAAV-CMV-hPEX1 (FIG. 1A, SEQ ID NO: 6) and pAAV-hRK1-hPEX1 (FIG. 2A, SEQ ID NO: 8). The human rhodopsin kinase-1 promoter (hRK1) was utilized to provide photoreceptor-specific expression in vivo. Additional versions carried a non-biologically active tag (HA). See, FIG. 1B and FIG. 2B. The coding sequences of transgenes terminated into a bovine growth hormone (bGH) polyadenylation signal. The entire AAV expression cassette was flanked by the canonical AAV2 inverted terminal repeats (ITRs) to enable sufficient packaging into recombinant AAV particles. Thus, AAV vectors to deliver codon optimized PEX1 for enhanced gene expression to the retina were developed.

Furthermore, additional vectors carrying coding sequence of green fluorescent protein (GFP, or eGFP) as a tag for hPEX1 or as the only transgene without hPEX1 were generated with components described above, resulting in vectors such as AAV.CMV.eGFP or AAV.CMV.eGFP, AAV.hRK1.eGFP and AAV9.CBA.PEX1-eGFP. The expressions thereof in both cell culture and the mouse retina were evaluated.

Additionally, various capsid proteins of AAV were utilized to pack said vector sequence and thus indicated in the names of the vectors if applicable. Such capsids include AAV8, AAV9 and AAV7m8.

Data showed that the CMV enhancer and promoter drove efficient transgene expression in vitro in 84-31 cells (FIG. 3A), in Pex1$^{G844D/G844D}$ mouse fibroblasts (FIGS. 3B-3G) and in vivo in the mouse retina (FIGS. 4A-4B). The CMV enhancer/promoter was used in FIGS. 3A, 4A, 4B and the CBA promoter was used in FIGS. 3C-3D. The rhodopsin kinase (RK) promoter drove expression specifically in photoreceptors as shown by injections in the wildtype mouse (FIG. 5).

Example 2

Summary of rAAV Mediated PEX1 Gene Augmentation

Optical coherence tomography (OCT) demonstrated that the cone photoreceptor cells were most significantly affected by loss of peroxisome functions in patients described herein. These visual phenotypes were recapitulated in a knock-in mouse model (indicated as Pex1$^{G844D}$, Pex1G844D, Pex1-G844D, or Pex1-mutant mice) of the milder form of the disease that expresses the murine equivalent of most common PEX1 mutation found in patients (PEX1-p.G843D). Baseline retinal function was evaluated with electroretinograms (ERGs). D. Zack et al demonstrated a severe impairment of the cone visual pathway in these homozygous Pex1-mutant mice by 4 months of age with the rod visual system being relatively preserved. See, Hiebler, Shandi, et al. "The Pex1-G844D mouse: a model for mild human Zellweger spectrum disorder." Molecular genetics and metabolism 111.4 (2014): 522-532.

Studies in the homozygous Pex1$^{G844D}$ mouse were performed to determine whether delivery of the human PEX1 cDNA to the retina rescues the retinal/visual deficit in this animal model. Baseline retinal function was evaluated with electroretinograms (ERGs). Subretinal injections of AAV8.CMV.hPEX1.HAwere carried out unilaterally in both neonatal and adult Pex1$^{G844D}$ mice. Contralateral eyes were injected with AAV carrying eGFP as control. Concurrent untreated cohort were used as control (see FIG. 23). After the injections, antibiotic ointment was placed on eyes of the mice. The eyes were evaluated by ophthalmoscopy and ERGS. In addition, optokinetic nystagmus was used to measure visual acuity in experimental and control eyes. Finally, eyes were evaluated histologically for safety and efficacy. ERGs showed improvement of rod and cone photoreceptor function. Rescues of the retinal/visual deficit were observed. Expression of vector-delivered protein with no histological damage or cellular infiltrated were observed. Additional in vitro studies evaluate efficacy in induced pluripotent stem cell (iPSC) models of PEX1 disease. For example, PEX1−/− iPSCs are differentiated along a hepatocyte or neuronal cell lineage and the effect of PEX1 gene delivery are assessed biochemically and from a cell biology perspective. Given promising proof-of-concept data, preclinical toxicology studies are carried out followed by a human gene therapy clinical trial.

Example 3 rAAV Mediated PEX1 Gene Augmentation Improves Visual Function in a Mouse Model for Zellweger Spectrum Disorder (ZSD)

Zellweger Spectrum Disorder (ZSD) is a peroxisome biogenesis disorder. Diagnosis is usually made in infancy after patients present with weak muscle tone and delayed physical development, (Steinberg S J, et al. Peroxisome Biogenesis Disorders, Zellweger Syndrome Spectrum. In:

Pagon R A, et al., editors. GeneReviews(R). Seattle (WA) (1993)) and vision and hearing defects become apparent later in childhood. Mutations in peroxin or peroxisomal biogenesis factor (PEX) genes and consequent PEX protein deficiency prevent normal peroxisome formation. This leads to defects in lipid metabolism and waste degradation. Treatments are supportive, but no cure is available.

Given recent successes in preclinical models and in human clinical trials evaluating gene augmentation therapy, there is hope that a gene augmentation approach can be applied to treat ZSD. One of the tissues that is most promising with respect to gene therapy is the retina. In fact, gene therapy trials for an inherited congenital blindness may lead to the first approved gene therapy from the US FDA. See Bennett J. Taking Stock of Retinal Gene Therapy: Looking Back and Moving Forward. *Molecular Therapy* (2017). Here proof-of-concept of gene augmentation therapy was tested targeting the retinal dystrophy caused by PEX1 mutations.

The mouse Pex1-G844D model was used. Previously, Pex1-G844D mice showed progressive cone and rod photoreceptor dysfunction and degeneration, measurable through reduction over time in electrophysiologic (electroretinography (ERG)) responses. See, Hiebler S, Masuda T, Hacia J G, Moser A B, Faust P L, Liu A, et al. The Pex1-G844D mouse: a model for mild human Zellweger spectrum disorder. *Mol Genet Metab* (2014) 111(4):522-32. doi: 10.1016/j.ymgme.2014.01.008. PubMed PMID: 24503136; PubMed Central PMCID: PMCPMC4901203.

An adeno-associated virus (AAV) serotype 8 vector (AAV8.CMV.hPEX1.HA) was generated. AAV8.CMV.hPEX1.HA carries the hemagglutinin (HA)-tagged wildtype human PEX1-encoding cDNA driven by a cytomegalovirus (CMV) promoter/enhancer. AAV8 was used as this transduces photoreceptors efficiently and leads to early onset transgene expression. See, Vandenberghe L, Bell P, Maguire A, Cearley C, Xiao R, Calcedo R, et al. Dosage Thresholds for AAV2 and AAV8 Photoreceptor Gene Therapy in Monkey. *Sci Transl Med* (2011) 3(88): 88ra54. Epub 22 June 2011. In vitro studies verified that this virus delivers the ~150 kDa PEX1 protein. For in vivo studies, AAV8.CMV.hPEX1.HA was delivered unilaterally in cohorts of juvenile (5 week old) and adult (9 week old) Pex1-G844D mice. Contralateral eyes received injection of AAV8.CMV.eGFP as control. AAVs were delivered by subretinal injection, which results in direct apposition of the vector with photoreceptors. A total of 1 µL of 1.03-1.40× $10^{10}$ vector genomes (vg)/uL AAV was delivered into each eye. The injections were well tolerated and there was no apparent inflammation as judged by ophthalmoscopy. Effects were measured serially in vivo by ERG and through use of a behavioral test that reflects visual acuity, the optokinetic response (OKR).

Results in the mice treated as adults showed a gradual improvement in cone and rod ERG responses in treated vs. control eyes persisting through the 5-month post-injection timepoint. There was also improvement in the scotopic ERG responses and also OKR responses of the treated (but not control) eyes by 2-3 months post injection.

Results 2-3 months after injection in the mice treated as juveniles also showed robust ERG responses in experimental compared to control eyes, and this was sustained to 6 months post injection.

Histological analysis confirmed presence of the PEX1-HA protein in photoreceptor cells in the AAV8.CMV.PEX1-HA-injected retinas. There was no evidence of cellular infiltrate or loss of cells.

In summary, acquired data indicates that said gene augmentation therapy ameliorated the cone and rod photoreceptor phenotype in Pex1-G844D mice and that improvements in photoreceptor function were stable over time. The results showed that gene therapy approach could potential improve retinal function in individuals with PEX1-based Zellweger Spectrum Disorder.

A. Methods a. Generation of Recombinant Adeno-Associated Viruses

A new AAV cloning backbone was generated that contains the full length CMV enhancer/promoter (p1107, SEQ ID NO: 6). This was made by removing the CMV/CBA promoter cassette and replacing it with the full length CMV enhancer/promoter to create this new backbone (p1107). The human PEX1 codon-optimized cDNA or PEX1-HA sequences (generated by DNA 2.0) were then inserted into p1107 under control of the CMV enhancer/promoter and containing a bovine growth hormone poly(A) (FIG. 1A). The plasmids were used to generate AAV8.CMV.hPEX1-HA (FIG. 1B) and AAV8.CMV.EGFP, respectively, through triple transfection. More particularly, standard AAV production of individual viruses was performed as previously described (Grieger et al, 2006; Nat Protoc. 2006; 1:1412-1428) by triple transfection of HEK293 cells with branched polyethylenimine (PEI) (Polysciences, no. 23966) with a plasmid containing the transgene between the ITRs of AAV2, the AAV-helper plasmid encoding Rep2 and Cap for serotype variants, and the pHGTI-Adeno1 plasmid harboring helper adenoviral genes. The HEK293 cells express the helper E1A/E1b gene (American Type Culture Collection, catalogue number CRL-157). Vectors were purified using a discontinuous iodixanol gradient (Sigma, Optiprep). Encapsidated DNA was quantified by TaqMan RT-PCR, following denaturation of the AAV particles by proteinase-K, and titers were calculated as genome copies (gc) per ml.

Expression of hPEX1-HA was verified through Western blot analysis using an anti-HA antibody (Cell Signaling 3724S, Danvers, Mass.). Verification of restoration of function in cells in vitro was carried out using immortalized human hepatocytes (HepG2 cells) that had been modified to carry a null PEX1 gene using CRISPR-Cas9.

b. Animal Studies

Pex1-G844D mice were generated through crosses of Pex1-G844D heterozygotes. Animals were genotyped prior to assignment in the study. For wildtype controls, Pex1$^{+/+}$ littermates were used.

Animals received baseline ERGs in the week prior to vector delivery (age 4 or 8 weeks). Cohorts of mice were injected at an average of 5 weeks (range 4-6 weeks; juveniles) and at 9 weeks of age (adults; Table 1).

Subretinal Injections (FIG. 7) were used in order to assure infection of cone and rod photoreceptors. For each animal, 1 µL of AAV8.hPEX1-HA (1.03×$10^{10}$ vg/µL) was delivered into the left eye, and 1 µL of AAV8.eGFP reporter vector (1.40×$10^{10}$ vg/µL) was delivered into the right eye.

Animals received ophthalmoscopic evaluation after treatment to evaluate for inflammation. A subset of animals received post-treatment ERGs 8, 16, and 20 weeks after injection and a subset of animals treated at age 9 weeks, received optokinetic reflex testing 11 weeks after injection. Endpoint ERGs were performed on all animals when each cohort reached 31 weeks of age (5 or 6 months post gene delivery). Endpoint visual acuity was determined on all animals when each cohort reached 33 weeks of age.

B. Results a. In Vitro Studies—Expression mediated by AAV8-hPEX1-HA

Western blot analysis showed that infection of 84-31 cells with AAV8.CMV.hPEX1-HA resulted in production of the expected ~150 kDa protein (FIG. 8).

b. In Vitro Studies—Treatment of PEX1-null HepG2 cells with AAV8-hPEX1-HA resulted in recovery of peroxisome import.

Peroxisomes present in almost all eukaryotic cells while number, morphology, and protein content can vary. Key roles of peroxisomes lie in lipid metabolism, especially very long and branched chain fatty acid catabolism, and docosahexaenoic acid and plasmalogen biosynthesis. Peroxisomes are also involved in other metabolic pathways, such as bile acid synthesis, D-amino acid oxidation, polyamine oxidation and Oxygen metabolism. Models for peroxisome biogenesis and division have been investigated and are known to one of skills in the art. See, e.g. Fagarasanu et al Ann. Rev. Cell Dev. Biol. 23: 321-344 (2007). About 70 different enzymes are shown to be needed for peroxisome function.

PEX1 mutations prevent substrates, such as endogenous enzymes with the peroxisome targeting motif, SKL, from being imported in peroxisomes. Thus, in untreated PEX1-null cells, SKL remains cytosolic. Once the normal copy of PEX1 is delivered through AAV8-hPEX1-HA, SKL-containing molecules appear punctate, reflecting correction of the peroxisomal defect as substrates are imported into the peroxisome (arrows in FIGS. 9-10).

Because HepG2 cells divide frequently and because AAV-delivered transgenes remain episomal, the cells infected with the virus were surrounded by new daughter cells that are negative for the transgene.

c. In Vivo Studies

Homozygous Pex1-G844D mice were bred for baseline testing, injection, and post-treatment testing. Table 1 summarizes the numbers of animals used for each condition.

In all cases, the left eye was designated the experimental (AAV.Pex1-HA-treated) eye. The right eye was treated with AAV.eGFP as control (FIG. 7).

TABLE 1

Cohorts of experimental and control wildtype and Pex1-G844D mice; * Animals were an average of 5-weeks old at the time of injection (with range 4-6 weeks)

| Group | 5-weeks old * at injection | 9-weeks old at injection |
|---|---|---|
| AAV.Pex1-HA-treated Pex1-G844D (injected) | 15 | 18 |
| AAV.Pex1-HA treated Pex1-G844D (injected; for immunohistochemistry) | 3 | 6 |
| Non-injected Pex1-G844D controls | 4 | 6 |
| Wild-type controls | 4 | 4 |
| Wild-type AAV.Pex1-HA-injected | 2 | 4 |

All Pex1-G844D animals were smaller and weighed less than wildtype or heterozygous littermates.

Baseline measurements on retinal and visual function were carried out prior to subretinal injections. Pex1-G844D mice had scotopic ERG responses which were recordable but which were reduced in amplitude compared to wildtype mice (FIG. 11). Averages from untreated control mice showed that at age 4 weeks (i.e. prior to injection of the 5-week-old cohort), wildtype mice had scotopic a-wave amplitudes of ~150 µV whereas Pex1-G844D mice had amplitudes of ~120 µV. At 4 weeks of age, wildtype mice had scotopic b-wave amplitudes of ~425 uv whereas Pex1-G844D mice had amplitudes ~250 µV.

All Pex1-G844D mice also had recordable scotopic ERGs at age 8 weeks (before injection; FIGS. 11, and 12A-12C) although amplitudes of scotopic a and b waves were reduced compared to those in wildtype animals (FIGS. 12A and 12B). Averages from untreated control mice showed that at age 8 weeks (i.e., just before injection of the 9-week-old cohort), wildtype mice had scotopic b-wave amplitudes of ~195 µV whereas Pex1-G844D mice had amplitudes of ~105 µV. At 4 weeks of age, wildtype mice had scotopic b-wave amplitudes of ~500 uv whereas Pex1-G844D mice had amplitudes ~225 µV (FIGS. 12A and 12B).

The photopic ERG was more severely affected in Pex1-G844D mice than the scotopic ERG. As shown in FIG. 13, Pex1-G844D mice had nearly flat photopic ERGs at baseline. Photopic b wave averaged in 4-week-old wildtype control mice average 105 µV. In contrast, those of 4-week-old Pex1-G844D mice averaged 5 µV. The same trend was found in older mice: in 8-week-old wildtype controls, the photopic b wave averaged 120 µV; in Pex1-G844D mice, it averaged 10 µV (FIG. 12C and FIG. 13).

There were no significant differences in either scotopic or photopic responses from untreated right and left eyes of Pex1-G844D mice (FIGS. 14A-14C).

At baseline, optokinetic response (OKR) testing showed that Pex1-G844D mice had a reduced visual acuity compared to wildtype littermates at 11-13 weeks of age (FIG. 15)

d. In Vivo Studies—Effects of Injection of AAV8.PEX1-HA and AAV8.GFP

After injection, 6/6 retinas injected with AAV.GFP as control showed numerous GFP-positive cells in the neural retina and retinal pigment epithelium (FIG. 16). Similarly, 8/8 of the AAV.PEX1-HA-injected retinas showed presence of HA through immunohistochemistry (FIG. 17).

Group analysis showed there was a significant improvement in photopic (and, to a lesser extent, scotopic) ERG amplitudes in Pex1-G844D mice that was evident 8 weeks after injection (FIGS. 18A-18C)).

Significant improvement in photopic b-wave response was observed in the eye treated with AAV.Pex1-HA (left eye) compared to the AAV.GFP-injected control eye (right eye) 8 weeks post injection, at 16 weeks of age (FIGS. 18A-18C).

Significant improvement in both photopic and scotopic ERG amplitudes were apparent in AAV.PEX1-HA-injected eyes of twenty weeks after injection of 5-week-old Pex1-G844D mice compared to control-injected eyes and non-injected littermates (FIGS. 19A-19C).

In mice that were injected later in life (9 weeks of age), there was evidence of improvement in scotopic b waves (FIGS. 20A-20C) sixteen weeks after injection, when mice were 25 weeks of age.

Optokinetic nystagmus testing was used to assess visual acuity of the control and AAV.Pex1-HA-injected mice 11 weeks after injection. Results show a trend in improved visual acuity in the treated (left) eyes compared to AAV.eGFP-injected controls (P=0.054) (FIG. 21).Endpoint ERGs were performed when each cohort reached 31 weeks of age, 5 or 6 months post gene delivery for the 'recovery' or 'prevention' cohorts, respectively. In both cohorts, the average scotopic a-wave, scotopic b-wave, and photopic b-wave amplitude of the therapeutic vector-treated (left) eyes, was two-fold that of the control injected (right) eyes (FIGS. 22A, 22B).

In Pex1-G844D mice, the retinal response of the control injected (right) eyes did not differ from that of either eye in non-injected mutant concurrent controls (FIGS. 22A, 22B). Furthermore, in PEX1-injected eyes the endpoint photopic ERG response improved one- to ten-fold over baseline in 22/33 mice over baseline. The decline in scotopic response was ameliorated compared to GFP-injected eyes in both 'prevention' and 'recovery' groups, with 4 animals even improving over time. Average visual acuity trended higher in the PEX1-injected (left) versus GFP-injected (right) eyes, but this was not statistically significant (FIGS. 22A, 22B). For both electroretinogram (ERG) and visual acuity measures, there was no difference between wild-type animals with or without subretinal injection. These values are thus grouped together for representation in FIGS. 22A, 22B.

A schematic summarizing the in vivo experimental design is presented in FIG. 23. The effect of AAV8-mediated gene delivery was tested by full-field electroretinogram (ffERG) and visual acuity (optokinetic reflex, OKN) at two different ages, representing the 'prevention' and 'recovery' cohorts, exposed to vector for 6 or 5 months, respectively. A 'sacrificial' cohort was used to obtain preliminary functional measures and validate vector expression in the retina. Pex1-G844D and wild-type littermate mice received AAV8.CMV.hPEX1.HA in the left eye and AAV8.CMV.eGFP in the right eye by subretinal injection. Non-injected Pex1-G844D and wild-type mice were also included in each cohort. The flow chart shows the ages of mice at intervention and assessment, and time between each event.

C. Discussion

Zellweger Spectrum Disorder (ZSD) is a hereditary progressive degenerative disorder that affects multiple organ systems. Retina was selected for study due to the many advantages of this organ with respect to proof-of-concept of gene augmentation therapy, including the fact that one eye can be used to test intervention and the contralateral can serve as internal control. Further, loss of vision in ZSD patients is debilitating for both the patients and their families, so that a means of preventing this loss or of restoring function would be meaningful. If effective in the retina, the same vector could potentially be used to restore function in extra-ocular tissue.

A recombinant AAV carrying a codon-optimized wildtype cDNA encoding human PEX1 was generated. The PEX1 cDNA was tagged with a marker (HA) so that location of this protein can be tracked. The AAV8 vector targets retinal photoreceptors (and other diverse cell types) efficiently and results in stable expression. Additional vectors were generated which lacked the HA tag and in which the PEX1 cDNA was driven by photoreceptor-specific promoters (hRK1).

The results acquired shows that the transgene cassette allows production of PEX1 protein of the expected size and with the predicted ability to restore peroxisomal function/localization. Subretinal delivery of AAV8.CMV.hPEX1.HA into both the 6 week (juvenile) and the 9-week-old Pex1-G844D (adult) retina is safe as assessed by the lack of toxicity to photoreceptors and the lack of inflammation. Subretinal delivery of AAV8.CMV.hPEX1.HA into the 9-week-old (adult) Pex1-G844D results in improved cone and rod photoreceptor-mediated retinal responses (ERGs) through at least 5 months after gene delivery, compared to control eyes. Subretinal delivery of AAV8.CMV.hPEX1.HA into the 9-week-old (adult) Pex1-G844D results in improved visual acuity (OKR) through at least 11 weeks after gene delivery, compared to control eyes. Subretinal delivery of AAV8.CMV.hPEX1.HA into the 5-week-old Pex1-G844D (juvenile) retina results in improved retinal responses (ERGs) 6 months after gene delivery and improved visual acuity (OKR) through at least 11 weeks after gene delivery, compared to control eyes.

Studies allowing clinical translation further optimizes the transgene cassette. For retinal studies, optimizations include using additional AAV serotypes, incorporating photoreceptor-specific promoters, and eliminating the HA tag, adding additional non-invasive tests to evaluate and quantify improvements in photoreceptor function mediated by this approach. Such tests include pupillometry, optical coherence tomography (OCT), visual behavior (modified water maze testing assessing light sensitivity, contrast sensitivity and colour perception), and additional immunocytochemical analyses.

The data shows that subretinal delivery of AAV8.CMV.hPEX1 results in improved rod and cone photoreceptor function (manifest by improved visual acuity and ERG).

A similar approach as described here is used to evaluate the possibility of rescuing peroxisomal function in extra-ocular tissue (including liver, cochlea, brain, etc). For those studies, appropriate regulatory elements are selected as well as appropriate surgical delivery and implementation of outcome measures specific to the various organ systems. Since the Pex1-G844D mouse manifests disease in its liver (similar to the human patients), the liver in under investigation as a tissue to target in in vivo proof-of-concept studies.

Preclinical toxicity studies in large animal models are also under investigation.

AAV serotype 9 vector (AAV9.CMV.hPEX1.HA) is generated and evaluated as described above.

SEQUENCE TABLES

SEQ ID NO: 1
```
atgtggggaagcgacagactggccggagctggaggggggaggagcagccgtcaccgtggcgttcactaacgcgcggga
ctgctttctccatctgccgcggaggctggtcgcccagctgcacctcctgcagaaccaggccatcgaggtggtgtggt
cccaccaaccggccttttttgagctgggtcgagggaaggcactttttcggaccagggagaaaatgtggcggagatcaac
cgccaggtcggccagaagctgggactgtccaacggcggacaggtgttcctcaagccgtgcagccacgtggtgtcctg
ccaacaggtggaagtggagccgctctccgccgacgactgggagatcctcgaattgcatgccgtgagcctcgaacagc
atctgttggaccagattcgcattgtgttcccgaaggccatattcccgtgtgggtcgatcagcagacctatatcttc
atccagattgtggccctcatccccggccgcctcatacggacggctggaaactgacaccaagctgctgattcaacctaa
gacccggagggccaaagaaaacaccttctccaaggccgacgctgagtacaagaagctccactcctacggacgggacc
agaaggggatgatgaaggagctgcaaaccaagcagctccagagcaacaccgtggggatcaccgagtccaatgaaaac
gagtcggaaatcccagtcgattcatcttccgtggccagcctgtggactatgatcggttccatttttctcgttccaatc
tgagaagaagcaggaaactagctggggggctgactgagatcaacgccttcaagaacatgcagtccaaagtggtgcctc
tggataacatctttcgcgtgtgcaagtcccaaccgccctcaatctacaacgcgtccgctacctccgtgtttcataag
cactgtgccatccacgtgttcccatgggatcaggaatacttcgatgtcgaaccttccttcaccgtgacttacgggaa
gcttgtcaagctcctcagcccccaagcagcagcaatcgaaaactaagcagaacgtgctttcccccggagaaggagaagc
aaatgtcagaaccactcgaccagaagaaaatcagatcggatcataacgaagaggacgagaaggcctgcgtccttcag
gtggtctggaacggcctggaggagctgaacaacgcgattaagtacaccaagaacgtcgaggtccttcacctgggaaa
```

SEQUENCE TABLES

```
ggtgtggattccggatgatctgaggaaacgcctcaacatcgaaatgcacgctgtggtgcggattaccccggtcgagg
tcaccccaaagatccctcgctccttgaagctgcagccgcgagaaaacttgcccaaggacatttctgaagaggatatc
aagactgtgttctactcctggctgcaacagagcactaccaccatgctccctctggtcatttcggaggaagaattcat
caaactggaaaccaaggacggactgaaagaattctccctgtccatcgtgcactcctgggaaaaggagaaggacaaga
atatcttcctgctgtccccaatctgctgcaaaagaccacgatccaggtgctgctcgaccccatggtgaaggaggaa
aactcagaagagatcgacttcatcctgccgttccttaagctgagttcactgggaggcgtgaactcccttggcgtgtc
ctcgctggagcacatcactcactgctgggccggcctctgagcagacagcttatgagcttggtcgccggactca
gaaacggtgccctcctgctcaccggcggcaagggatcgggaaagtccaccctcgctaaggccatttgcaaagaggca
ttcgataagctggacgccatgtggagcgggtggactgtaaggccctccgcggaaagcgattggaaaatattcaaaa
gactctcgaagtcgccttttccgaagccgtctggatgcagccctcggtcgtcctgctcgacgatctggacctcatcg
ctgggctgccggccgtgccggagcatgaacactccctgacgcggtccagtcgcaacggctcgcccacgccctgaac
gatatgattaaggaattcatctcaatgggatcactggtggccctgatcgcgacttcccagagccagcagtccctgca
ccctctgctggtgtcggcccagggcgtgcacattttcagtgtgtgcaacacatccagccgcccaaccaggagcagc
ggtgcgaaatcctgtgcaacgtgattaagaacaagctggactgcgatatcaacaagtttaccgaccttgatctccaa
catgtggctaaggagactgggggcttcgtggctcgggacttcacagtgttggtggaccgggcaattcactccagact
gtcccgccagagcatttccacccgcgaaaaactggtcctgaccacccctcgacttccagaaggccctcagaggcttcc
ttcctgcgagcctcagatccgtcaaccttcacaagcgcgggaccttggctgggacaagatcggtgggctccacgag
gtgcggcagatcctcatggacaccattcagctgcctgcaaagtaccccgagctgttcgccaacttgccgattcgcca
gcgcacgggaatcctgctctacggccccccgggcaccggaaagaccctgctggccggtgtgatcgcccgggaatcga
ggatgaacttcatctccgtgaaggacccgaactcctgtccaagtacatccggtgcctccggactccctgccactggc
agatgatgtggacctccagcatgtggcctccgtgactgacagcttcacaggagccgatctgaaggccctgctttaca
acgcccagttggaggcgctgcacggtatgctgctgtcctccggtctgcaggatggctcctcctcttccgatagcgac
ctgtcgctgagcagcatggtgttcctgaaccattccagcggctccgatgacagcgcgggcgacggagaatgtggact
ggatcaatccctggtgtccctggagatgagcgagattctgccagacgagtccaagttcaacatgtacaggctgtact
tcggcagcagctacgagtccgagctgggaaatggtacctcgtccgacctgtcaagccagtgcctgtccgcgccttcc
tccatgacccaggaccctccctggagtgccagggaaggatcagctgttcagcagcctcccgtgctgcgcactgcgag
ccaggaagggtgccaggaattgacccaagagcagcgggaccaactgcgcgcggacatttcgatcatcaaaggcagat
accgctcccaatccggggaggacgaaagcatgaaccagcccgggcctatcaagactagactggcaatctcccaaagc
cacctgatgaccgcactgggacacaccccggccctcgatctcggaggacgactggaagaacttcgctgagctgtacga
atccttccagaatccgaagcggagaaagaaccagagcggaactatgttccggcccggacagaaggtgaccctggcct
ga SEQ ID NO: 2
cgatcgatctcctccggctccgacgtcctcggcctgccgggtcccgggtcctttgcggcgctagggtgggcgaaccc
agagcgacgctccgggacgatgtggggcagcgatcgcctggcgggtgctgggggaggcggggcggcagtgactgtgg
ccttcaccaacgctcgcgactgcttcctccacctgccgcggcgtctcgtgcccagctgcatctgctgcagaatcaa
gctataagaagtggtctggagtcaccagcctgcattcttgagctgggtggaaggcaggcatttagtgatcaaggtga
aaatgtggctgaaattaacagacaagttggtcaaaaacttggactctcaaatgggggacaggtatttctcaagccat
gttcccatgtggtatcttgtcaacaagttgaggtggaaccccctcagcagatgattgggagatactggagctgcat
gctgtttcccttgaacaacatcttctagatcaaattcgaatagttttccaaaagccatttttcctgtttgggttga
tcaacaaacgtacatatttatccaaattgttgcactaatacccagctgcctcttatggaaggctggaaactgacacca
aactccttattcagccaaagacacgccgagccaaagagaatacattttcaaaagctgatgctgaatataaaaaactt
catagttatggaagagaccagaaggaatgatgaagaacttcaaaccaagcaacttcagtcaaatactgtgggaat
cactgaatctaatgaaaacgagtcagagattccagttgactcatcatcagtagcaagtttatggactatgataggaa
gcatttttccttttcaatctgagaagaaacaagagacatcttgggtttaactgaatcaatgcattcaaaaatatg
cagtcaaaggttgttcctctagacaatattttcagagtatgcaaatctcaacctcctagtatatataacgcgtcagc
aacctctgtttttcataaacactgtgccattcatgtatttccatgggaccaggaatattttgatgtgagcccagct
ttactgtgacatatggaaagctagttaagctactttctccaaagcaacagcaaagtaaaacaaaacaaatgtgtta
tcacctgaaaaagagaagcagatgtcagagccactagatcaaaaaaaaaattaggtcagatcataatgaagaagatga
gaaggcctgtgtgctacaagtagtctggaatggacttgaagaattgaacaatgccatcaaatataccaaaaatgtag
aagttctccatcttgggaaagtctggattccagatgacctgaggaagagactaaatatagaaatgcatgccgtagtc
aggataactccagtggaagttacccctaaaattccaagatctctaaagttacaacctagagagaatttacctaaaga
cataagtgaagaagacataaaaactgtatttttattcatggctacagcagtctactaccaccatgcttcctttggta
tatcagaggaagaatttattaagctggaaactaaagatggactggaggaatttctctgagtatagttcattcttgg
gaaaaagaaaaagataaaaatattttttctgttgagtcccaatttgctgcagaagactacaatacaagtccttctaga
tcctatggtaaaagaagaaaacagtgaggaaattgactttattcttcctttttttaaagctgagctctttggaggag
tgaattccttaggcgtatcctccttgggagcacatcactcacagcctcctgggacgcccttgtctcggcagctgatg
tctcttgttgcaggacttaggaatggagctcttttactcacaggggaagggaagtggaaaatcaacttttagccaa
agcaatctgtaaagaagcatttgacaaactggatgccatggtggagagagttgactgtaaagctttacgaggaaaaa
ggcttgaaaacatacaaaaaccctagaggtggctttctcagaggcagtgtggatgcagccatctgttgtcctgctg
gatgaccttgacctcattgctggactgcctgctgtcccgaacatgagcacagtcctgatgcggtgcagagccagcg
gcttgctcatgctttgaatgatatgataaaagagtttatctccatgggaagtttggttgcactgattgccacaagtc
agtctcagcaatctctacatccttacttgttctgtcaaggagttcacatatttcagtgcgtccaacacattcag
cctcctaatcaggaacaaagatgtgaaattctgtgtaatgtaataaaaaataaattggactgtgatataaacaagtt
caccgatcttgacctcagcatgtagctaaagaaactggcgggtttgtggctagagattttacagtacttgtggatc
gagccatacattctcgactctctcgtcagagtatatccaccagagaaaaattagttttaacaacattggacttccaa
aaggctctccgcggatttcttcctgcgtctttgcgaagtgtcaacctgcataaacctagagacctgggttgggacaa
gattggtgggttacatgaagttaggcagtactcatggatactatccagttacctgccaagtatccagaattatttg
caaacttgcccatacgacaaagaacaggaatactgttgtatggtccgcctggaacaggaaaaaccttactagctggg
gtaattgcacgagagagtagaatgaatttttataagtgtcaaggggccagagttactcagcaaatacattggagcaag
tgaacaagctgttcgggatattttttattagagcacaggctgcaaagccctgcattcttttctttgatgaattgaat
ccattgctcctcggcggggtcatgataatacaggagttacagaccgagtagttaaccagttgctgactcagttgat
ggagtagaaggcttacagggtgtttatgtattggctgctactagtcgccctgacttgattgaccctgccctgcttag
```

SEQUENCE TABLES gcctggtcgactagataaatgtgtatactgtcctcctcctgatcaggtgtcacgtcttgaaattttaaatgtcctca
gtgactctctacctctggcagatgatgttgaccttcagcatgtagcatcagtaactgactcctttactggagctgat
ctgaaagctttactttacaatgcccaattggaggccttacatggaagtgctgctctcgagtggactccaggatggaag
ttccagctctgatagtgacctaagtctgtcttcaatggtcttttcttaaccatagcagtggctctgacgattcagctg
gagatggagaatgtggcttagatcagtcccttgtttctttagagatgtccgagatccttccagatgaatcaaaattc
aatatgtaccggctctactttggaagctcttatgaatcagaacttggaaatggaacctcttctgatttgagctcaca
atgtctctctgcaccaagctccatgactcaggatttgcctggagttcctgggaaagaccagttgttttcacagcctc
cagtgttaaggacagcttcacaagagggttgccaagaacttacacaagaacaaagagatcaactgagggcagatatc
agtattatcaaaggcagataccggagccaaagtggagaggacgaatccatgaaccaaccaggaccaatcaaaaccag
actggctattagtcagtcacatttaatgactgcacttggtcacacaagaccatccattagtgaagatgactggaaga
atttgctgagctatatgaaagctttcaaaatccaaagaggagaaaaaatcaaagtggaacaatgtttcgacctgga
cagaaagtaactttagcataaaatatacttcttttttgatttggttctgttaagtttttgatggcttttccatatgt
tgtaacaggaaaaaaatggtgtctatgaatttcttcttaatttaacaaatttggttaatttataaaatcacagattg
gtaaatgctataattatgtaatgatcaggattgagattaatactgtagtataaattgggacattataacagattcca
tattttatttcctaaaatctaaattcagtctttaatgaaataatattagccaaatggtggaactaattttattctttt
tgaggaaaagataataaagaatgtaattaaatttaaatttcttggaattcccagttgtatattcatcacctttgtag
catttgacaaattttatgcttagcagcttcttcactgttttgaaataaaatatcctattacctactgataaaaaaaa
a SEQ ID NO: 3
cgatcgatctcctccggctccgacgtcctcggcctgccgggtcccgggtcctttgcggcgctagggtgggcgaaccc
agagcgacgctccgggacgatgtggggcagcgatcgcctggcgggtgctggggaggcggggcggcagtgactgtgg
ccttcaccaacgctcgcgactgcttcctccacctgccgcggcgtctcgtggcccagctgcatctgctgcagaatcaa
gctataagaagtggtctggagtcaccagcctgcattcttgagctgggtggaaggcaggcattttagtgatcaaggtga
aaatgtggctgaaattaacagacaagttggtcaaaaacttggactctcaaatggggacaggtatttctcaagccat
gttcccatgtggtatctgtcaacaagttgaggtggaaccccctctcagcagatgattgggagatactggagctgcat
gctgtttcccttgaacaacatcttctagatcaaattcgaatagttttttccaaaagccattttcctgtttgggttga
tcaacaaacgtacatatttatccaaattgttgcactaataccagctgcctcttatggaaggctggaaactgacacca
aactccttattcagccaaagacacgccgagccaaagagaatacatttcaaaagctgatgctgaatataaaaaactt
catagttatggaagagaccagaaaggaatgatgaaagaacttcaaaccaagcaacttcagtcaaatactgtgggaat
cactgaatctaatgaaaacgagtcagagattccagttgactcatcatcagtagcaagtttatggactatgataggaa
gcattttttcctttcaatctgagaagaaacaagagacatcttggggtttaactgaaatcaatgcattcaaaaatatg
cagtcaaaggttgttcctctagacaatattttcagagtatgcaaatctcaacctccctagtatatataacgcgtcagc
aacctctgttttcataaacactgtgccattcatgtatttccatgggaccaggaatattttgatgtagagcccagct
ttactgtgacatatggaaagctagttaagctactttctccaaagcaacagcaaagtaaaacaaaacaaaatgtgtta
tcacctgaaaaagagaagcagatgtcagagccactagatcaaaaaaaaattaggtcagatcataatgaagaagatga
gaaggcctgtgtgctacaagtagtctggaatggacttgaagaattgaacaatgccatcaaatataccaaaaatgtag
aagttctccatcttgggaaagtctggattccagatgacctgaggaagagactaaatatagaaatgcatgccgtagtc
aggataactccagtggaagttaccccctaaaattccaagatctctaaagttacaacctagagagaattttacctaaaga
cataagtgaagaagacataaaaactgtatttttattcatggctacagcagtctactaccaccatgcttcctttggtaa
tatcagaggaagaatttattaagctgtgaaactaaagatggactgaaggaattttctctgagtatagttcattcttgg
gaaaaagaaaaagataaaaatattttttctgttgagtcccaatttgctgcagaagactacaatacaagtccttctaga
tcctatggtaaaagaagaaaacagtgaggaaattgactttattcttcctttttaaagctgagctctttgggaggag
tgaattccttaggcgtatcctccttgggcacatcactcacagcctcctgggacgccctttgtctcggcagctgatg
tctcttgttgcaggacttaggaatggagctcttttactcacaggaggaaagggaagtggaaaatcaactttagccaa
agcaatctgtaaagaagcatttgacaaactggatgcccatgtggagagagttgactgtaaagctttacgagctttga
atgatatgataaaagagtttatctccatgggaagtttggttgcactgattgccacaagtcagtctcagcaatctcta
catcctttacttgtttctgctcaaggagttcacatatttcagtgcgtccaacacattcagcctcctaatcaggaaca
aagatgtgaaattctgtgtaatgtaataaaaaataaattggactgtgatataaacaagttcaccgatcttgacctgc
agcatgtagctaaagaaactggcgggtttgtggctagagattttacagtacttgtggatcgagccatacattctcga
ctctctcgtcagagtatatccaccagagaaaaattagttttaacaacattggacttccaaaaggctctccgcggatt
tcttcctgcgtctttgcgaagtgtcaacctgcataaacctagagacctgggttgggacaagattggtgggttacatg
aagttaggcagatactcatggatactatccagttacctgccaagtatccagaattatttgcaaacttgcccatacga
caaagaacaggaatactgttgtatggtccgcctggaacaggaaaaaacttactagctggaggtaattgcacgagagag
tagaatgaattttataagtgtcaaggggccagagttactcagcaaatacattggagcaagtgaacaagctgttcggg
atatttttattagagcacaggctgcaaagccctgcattcttttctttgatgaatttgaatccattgctcctcggcgg
ggtcatgataatacaggagttacagaccgagtagttaaccagttgctgactcagttggatggagtagaaggcttaca
gggtgtttatgtattggctgctactagtcgccctgacttgattgaccctgccctgcttaggcctggtcgactagata
aatgtgtatactgtcctcctcctgatcaggtgtcacgtcttgaaattttaaatgtcctcagtgactctctacctctg
gcagatgatgttgaccttcagcatgtagcatcagtaactgactcctttactggagctgatctgaaagctttacttta
caatgcccaattggaggccttacatggaatgctgctctcgagtggactccaggatggaagttccagctctgatagtg
acctaagtctgtcttcaatggtcttttcttaaccatagcagtggctctgacgattcagctggagatggagaatgtggc
ttagatcagtcccttgtttctttagagatgtccgagatccttccagatgaatcaaaattcaatatgtaccggctcta
ctttggaagctcttatgaatcagaacttggaaatggaacctcttctgatttgagctccacaatgtctctctgccacaa
gctccatgactcaggatttgcctggagttcctgggaaagaccagttgttttcacagcctccagtgttaaggacagct
tcacaagagggttgccaagaacttacacaagaacaaagagatcaactgagggcagatatcagtattatcaaaggcag
ataccggagccaaagtggagaggacgaatccatgaaccaaccaggaccaatcaaaaccagactggctattagtcagt
cacatttaatgactgcacttggtcacacaagaccatccattagtgaagatgactggaagaattttgctgagctatat
gaaagctttcaaaatccaaagaggagaaaaaatcaaagtggaacaatgtttcgacctggacagaaagtaactttagc
ataaaatatacttcttttttgatttggttctgttaagtttttgatggcttttccatatgttgtaacaggaaaaaaat
ggtgtctatgaatttcttcttaatttaacaaatttggttaatttataaaatcacagattggtaaatgctataattat
gtaatgatcaggattgagattaatactgtagtataaattgggacattataacagattccatattttatttcctaaaa
tctaaattcagtctttaatgaaataatattagccaaatggtggaactaattttattcttttgaggaaaagataataa
agaatgtaattaaatttaaatttcttggaattcccagttgtatattcatcacctttgtagcatttgacaaattttat
gcttagcagcttcttcactgttttgaaataaaatatcctattacctactgataaaaaaaaaa

SEQUENCE TABLES

SEQ ID NO: 4
cgatcgatctcctccggctccgacgtcctcggcctgccgggtcccgggtcctttgcggcgctagggtgggcgaaccc
agagcgacgctccgggacgatgtggggcagcgatcgcctggcgggtgctgggggaggcgggcggcagtgactgtgg
ccttcaccaacgctcgcgactgcttcctccacctgccgcggcgtctcgtggcccagctgcatctgctgcagaatcaa
gctatagaagtggtctggagtcaccagcctgcattcttgagctgggtggaaggcaggcattttagtgatcaaggtga
aaatgtggctgaaattaacagacaagttggtcaaaaacttggactctcaaatgggggacaggtattttctcaagccat
gttcccatgtggtatcttgtcaacaagttgaggtggaaccccctctcagcagatgattgggagatactggtaaagaaa
accaaataagaactatctcatttaaggagctgcatgctgtttcccttgaacaacatcttctagatcaaattcgaata
gttttccaaaagccattttttcctgtttgggttgatcaacaaacgtacatatttatccaaattgttgcactaatacc
agctgcctcttatggaaggctggaaactgacaccaaactccttattcagccaaagacacgccgagccaaagagaata
cattttcaaaagctgatgctgaatataaaaaacttcatagttatggagagagccagaaaggaatgatgaaagaactt
caaaccaagcaacttcagtcaaatactgtgggaatcactgaatctaatgaaaacgagtcagagattccagttgactc
atcatcagtagcaagtttatggactatgataggaagcattttttcctttcaatctgagaagaaacaagagacatctt
ggggtttaactgaaatcaatgcattcaaaaatatgcagtcaaaggttgttcctctagacaatattttcagagtatgc
aaatctcaacctcctagtatatataacgcgtcagcaacctctgtttttcataaacactgtgccattcatgtatttcc
atgggaccaggaatattttgatgtagagcccagctttactgtgacatatggaaagctagttaagctactttctccaa
agcaacagcaaagtaaaacaaaacaaaatgtgttatcacctgaaaaagagaagcagatgtcagagccactagatcaa
aaaaaaattaggtcagatcataatgaagaagatgagaaggcctgtgtgctacaagtagtctggaatggacttgaaga
attgaacaatgccatcaaatataccaaaaatgtagaagtttctccatcttgggaaagtctggattccagatgacctga
ggaagagactaaatatagaaatgcatgccgtagtcaggataactccagtggaagttaccccctaaaattccaagatct
ctaaagttacaacctagagagaatttacctaaagacataagtgaagaagacataaaaactgtattttattcatggct
acagcagtctactaccaccatgcttcctttggtaatatcagaggaagaatttattaagctggaaactaaagatggac
tgaaggaattttctctgagtatagttcattcttgggaaaaagaaaaagataaaaatattttttctgttgagtcccaat
ttgctgcagaagactacaatacaagtccttctagatcctatgtaaaagaagaaaacagtgaggaaattgacttat
tcttcctttttttaaagctgagctctttgggaggagtgaattccttaggcgtatcctccttggagcacatcactcaca
gcctcctgggacgccctttgtctcggcagctgatgtctcttgttgcaggacttaggaatggagctcttttactcaca
ggaggaaagggaagtggaaaatcaactttagccaaagcaatctgtaaagaagcatttgacaaactggatgcccatgt
ggagagagttgactgtaaagctttacgaggaaaaaggcttgaaaacatacaaaaaacctagaggtggctttctcag
aggcagtgtggatgcagccatctgttgtcctgctggatgaccttgacctcattgctggactgcctgctgtcccggaa
catgagcacagtcctgatgcggtgcagagccagcggcttgctcatgctttgaatgatatgataaaagagtttatctc
catgggaagttttggttgcactgattgccacaagtcagtctcagcaatctctacatcctttacttgtttctgctcaag
gagttcacatatttcagtgcgtccaacacattcagcctcctaatcaggaacaaagatgtgaaattctgtgtaatgta
ataaaaaatattggactgtgatataaacaagttcaccgatcttgacctgcagcatgtagctaaagaaactggcgg
gtttgtggctagagattttacagtacttgtggatcgagccatacattctcgactctctcgtcagagtatatccacca
gagaaaaattagtttaacaacattggacttccaaaaggctctccgcggatttcttcctgcgtctttgcgaagtgtc
aacctgcataaacctagagacctgggtggggacaagattggtggggttacatgaagttaggcagatactcatggatac
tatccagttacctgccaagtatccagaattatttgcaaacttgcccatacgacaaagaacaggaatactgttgtatg
gtccgcctggaacaggaaaaacctactagctggggtaattgcacgagagagtagaatgaatttataagtgtcaag
gggccagagttactcagcaaatacattggagcaagtgaacaagctgttcgggatattttttattagagcacaggctgc
aaagccctgcattcttttctttgatgaatttgaatccattgctcctcggcggggtcatgataatacaggagttacag
accgagtagttaaccagttgctgactcagttggatggagtagaaggctttacagggtgtttatgtattggctgctact
agtcgccctgacttgattgaccctgccctgcttaggcctggtcgactagataaatgtgtatactgtcctcctcctga
tcaggtgtcacgtcttgaaattttaaatgtcctcagtgactctctacctctggcagatgatgttgaccttcagcatg
tagcatcagtaactgactcccttactggagctcgatctgaaagctttactttacaatgcccaattggaggccttacat
ggaatgctgctctcgagtggactccaggatggaagttccagctctgatagtgacctaagtctgtcttcaatggtctt
tcttaaccatagcagtggctctgacgattcagctggagatggagaatgtggcttagatcagtcccttgtttctttag
agatgtccgagatccttccagatgaatcaaaattcaatatgtaccggctctactttggaagctcttatgaatcagaa
cttggaaatggaacctcttctgatttgagctcacaatgtctctctgcaccaagctccatgactcaggattttgcctgg
agttcctgggaaagaccagttgttttcacagcctccagtgttaaggacagcttcacaagaggggttgccaagaactta
cacaagaacaaagagatcaactgagggcagatatcagtattatcaaaggcagataccggagccaaagtggagaggac
gaatccatgaaccaaccaggaccaatcaaaaccagactggctattagtcagtcacatttaatgactgcacttggtca
cacaagaccatccattagtgaagatgactggaagaattttgctgagcctatatgaaagctttcaaaatccaaagagga
gaaaaaatcaaagtggaacaatgtttcgacctggacagaaagtaactttagcataaaatatacttctttttgatttg
gttctgttaagttttttgatggcttttccatatgttgtaacaggaaaaaaatggtgtctatgaatttcttcttaatt
taacaaatttggttaatttataaaatcacagattggtaaatgctataattatgtaatgatcaggattgagattaata
ctgtagtataaattgggacattataacagattccatattttatttcctaaaatctaaattcagtctttaatgaaata
atattagccaaatggtggaactaatttatttcttttgaggaaaagataataaagaatgtaattaaatttaaatttct
tggaattcccagttgtatattcatcacctttgtagcatttgacaaattttatgcttagcagcttcttcactgtttttg
aaataaaatatcctattacctactgataaaaaaaaaaa SEQ ID NO: 5
cagcaacctctgtttttcataaacactgtgccattcatgtatttccatgggaccaggaatattttgatgtagagccc
agctttactgtgacatatggaaagctagttaagctactttctccaaagcaacagcaaagtaaaacaaaacaaaatgt
gttatcacctgaaaaagagaagcagatgtcagagccactagatcaaaaaaaaattaggtcagatcataatgaagaag
atgagaaggcctgtgtgctacaagtagtctggaatggacttgaagaattgaacaatgccatcaaatataccaaaaat
gtagaagttctccatcttgggaaagtctggattccagatgacctgaggaagagactaaatatagaaatgcatgccgt
agtcaggataactccagtggaagttaccccctaaaattccaagatctctaaagttacaacctagagagaatttaccta
aagacataagtgaagaagacataaaaactgtattttattcatggctacagcagtctactaccaccatgcttcctttg
gtaatatcagaggaagaatttattaagctggaaactaaagatggactgaaggaattttctctgagtatagttcattc
ttgggaaaagaaaaagataaaaatattttttctgttgagtcccaatttgctgcagaagactacaatacaaaggagtg
aattccttaggcgtatcctccttggagcacatcactcacagcctcctgggacgccctttgtctcggcagctgatgtc
tcttgttgcaggacttaggaatggagctcttttactcacaggaggaaagggaagtggaaaatcaactttagccaaag
caatctgtaaagaagcatttgacaaactggatgcccatgtggagagagttgactgtaaagctttacgaggaaaaagg
cttgaaaacatacaaaaaacctagaggtggctttctcagaggcagtgtggatgcagccatctgttgtcctgctgga
tgaccttgacctcattgctggactgcctgctgtcccggaacatgagcacagtcctgatgcggtgcagagccagcggc
ttgctcatgctttgaatgatatgataaaagagtttatctccatgggaagtttggttgcactgattgccacaagtcag

SEQUENCE TABLES

```
tctcagcaatctctacatcctttacttgtttctgctcaaggagttcacatatttcagtgcgtccaacacattcagcc
tcctaatcaggaacaaagatgtgaaattctgtgtaatgtaataaaaaataaattggactgtgatataaacaagttca
ccgatcttgacctgcagcatgtagctaaagaaactggcgggtttgtggctagagattttacagtacttgtggatcga
gccatacattctcgactctctcgtcagagtatatccaccagagaaaaattagttttaacaacattggacttccaaaa
ggctctccgcggatttcttcctgcgtctttgcgaagtgtcaacctgcataaacctagagacctgggttgggacaaga
ttggtgggttacatgaagttaggcagatactcatggatactatccagttacctgccaagtatccagaattatttgca
aacttgcccatacgacaaagaacaggaatactgttgtatggtccgcctggaacaggaaaaaccttactagctggggt
aattgcacgagagagtagaatgaattttataagtgtcaagggccagagttactcagcaaatacattggagcaagtg
aacaagctgttcgggatattttttattagagcacaggctgcaaagccctgcattcttttcttttgatgaatttgaatcc
attgctcctcggcgggtcatgataatacaggagttacagaccgagtagttaaccagttgctgactcagttggatgg
agtagaaggcttacagggtgtttatgtattggctgctactagtcgccctgacttgattgaccctgccctgcttaggc
ctggtcgactagataaatgtgtatactgtcctcctcctgatcaggtgtcacgtcttgaaattttaaatgtcctcagt
gactctctacctctggcagatgatgttgacctcagcatgtagcatcagtaactgactccttttactggagctgatct
gaaagctttactttacaatgcccaattggaggccttacatggaatgctgctctcgagtggactccaggatggaagtt
ccagctctgatagtgacctaagtctgtcttcaatggtctttcttaaccatagcagtggctctgacgattcagctgga
gatggagaatgtggcttagatcagtccctgttcttagagatgtccgagatccttccagatgaatcaaaattcaa
tatgtaccggctctactttggaagctcttatgaatcagaacttggaaatggaacctcttctgatttgagctcacaat
gtctctctgcaccaagctccatgactcaggatttgcctggagttcctgggaaagaccagttgttttcacagcctcca
gtgttaaggacagcttcacaagaggggtgccaagaacttacacaagaacaaagagatcaactgagggcagatatcag
tattatcaaaggcagataccggagccaaagtggagaggacgaatccatgaaccatcaggaccaatcaaaaccagac
tggctattagtcagtcacatttaatgactgcacttggtcacacaagaccatccattagtgaagatgactggaagaat
tttgctgagctatatgaaagctttcaaaatccaaagaggagaaaaaatcaaagtggaacaatgtttcgacctggaca
gaaagtaactttagcataaaatatacttcttttttgatttggttctgttaagttttttgatggcttttccatatgttg
taacaggaaaaaatggtgtctatgaattctttcttaatttaacaaatttggttaatttataaaatcacagattggt
aaatgctataattatgtaatgatcaggattgagattaatactgtagtataaattgggacattataacagattccata
ttttatttcctaaaatctaaattcagtctttaatgaaataatattagccaaatggtggaactaatttatttcttttg
aggaaaagataataaagaatgtaattaaatttaaa
```

SEQ ID NO: 6

```
ctgcgcgctcgctcgctcactgaggccgcccgggcaaagcccgggcgtcgggcgacctttggtcgcccggcctcagt
gagcgagcgagcgcgcagagagggagtggccaactccatcactaggggttccttgtagttaatgattaacccgccat
gctacttatctacgtagcaagctagccgttacataacttacggtaaatggccgcctggctgaccgcccaacgaccc
ccgcccattgacgtcaataatgacgtatgttcccatagtaacgccaataggggactttccattgacgtcaatgggtgg
agtatttacggtaaactgcccacttggcagtacatcaagtgtatcatatgccaagtacgccccctattgacgtcaat
gacggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcacggg
gatttccaagtctccacccccattgacgtcaatggagtttgtttttggcaccaaaatcaacgggactttccaaaatgt
cgtaacaactccgccccattgacgcaaatgggcggtaggcgtgtacggtgggaggtctatataagcagagcttgtac
actagcggccgcgccgccaccatgtggggaagcgacagactggccggagctggaggggaggagcagccgtcaccgt
ggcgttcactaacgcgcgggactgcttctccatctgccgcggaggctggtcgcccagctgcacctcctgcagaacc
aggccatcgaggtggtgtggtcccaccaaccggccttttttgagctgggtcgagggaaggcactttttcggaccaggga
gaaaatgtggcggagatcaaccgccaggtcggccagaagctgggactgtccaacgccggacaggtgttcctcaagcc
gtgcagccacgtggtgtcctgccaacaggtggaagtggaccgctctccgccgacgactgggagatcctcgaattgc
atgccgtgagcctcgaacagcatctgttggaccagattcgcattgtgttcccgaaggccatattcccgtgtgggtc
gatcagcagacctatatcttcatccagattgtggcctcatccccggccgcctcatacggacggctggaaactgacac
caagctgctgattcaacctaagacccggagggccaaagaaaacaccttctccaaggccgacgctgagtacaagaagc
tccactcctacggacgggaccagaaggggatgatgaaggagctgcaaaccaagcagctccagagcaacaccgtgggg
atcaccgagtccaatgaaaacgagtcggaaatcccagtcgattcatcttccgtggccagcctgtggactatgatcgg
ttccattttctcgttccaatctgagaagaagcaggaaaactagctgggggctgactgagatcaacgccttcaagaaca
tgcagtccaaagtggtgcctctggataacatctttcgcgtgtgcaagtcccaacgccctcaatctacaacgcgtcc
gctacctccgtgtttcataagcactgtgccatccacgtgttcccatgggatcaggaatacttcgatgtcgaaccttc
cttcaccgtgacttacgggaagcttgtcaagctcctcagccccaagcagcagcaatcgaaaactaagcagaacgtgc
tttccccggagaaggagaagcaaatgtcagaaccactcgaccagaagaaaatcaagtggcggatcataacgaagaggac
gagaaggcctgcgtccttcaggtggtctggaacggcctggaggagctgaacaacgcgattaagtacaccaagaacgt
cgaggtccttcacctgggaaaggtgtggattccggatgatctgaggaaacgcctcaacatcgaaatgcacgctgtgg
tgcggattacccggtcgaggtcacccaaagatccctcgctccttgaagctgcagccgcgagaaaacttgcccaag
gacatttctgaagaggatatcaagactgtgttctactcctggctgcaacagagcactaccaccatgtctccctctggt
catttcggaggaagaattcatcaaactggaaaccaaggacggactgaaagaattctccctgtccatcgtgcactcct
gggaaaaggagaaggacaagaatatcttcctgctgtccccaatctgctgcaaaagaccacgatccaggtgctgctc
gaccccatggtgaaggaggaaaactcagaagagatcgacttcatcctgccgttccttaagctgagttcactgggagg
cgtgaactccttggcgtgtcctcgctggagcacatcactcactcactgctgggccggcctctgagcagacagctta
tgagcttggtcgccggactcagaaacggtgccctcctgctcaccgggcaagggatcgggaaagtccacccctgct
aaggccatttgcaaagaggcattcgataagctggacgcccatgtggagcgggtggactgtaaggccctccgcgcaaa
gcgattggaaaatattcaaaagactctcgaagtcgccttttccgaagccgtctggatgcagccctcggtcgtcctgc
tcgacgatctgacctcatcgctgggctgccggccgtgccggagcatgaacactcccctgacgcggtccagtcgcaa
cggctcgcccacgccctgaacgatatgattaaggaattcatctcaatgggatcactggtggcctgatcgcgacttc
ccagagccagcagtccctgcaccctctgctggtgtcggccagggcgtgcactttttcagtgtgtgcaacacatcc
agccgcccaaccaggagcagcggtgcgaaatcctgtgcaacgtgattaagaacaagctggactgcgatatcaacaag
tttaccgaccttgatctccaacatgtggctaaggagactggggggcttcgtggctcgggacttcacagtgttggtgga
ccgggcaattcactccagactgtcccgccagagcatttccacccgcgaaaaactggtcctgaccaccctcgacttcc
agaaggccctcagaggcttccttcctgcgagcctcagatccgtcaaccttcacaagccgcgggaccttggctgggac
aagatcggtgggctccacgaggtgcggcagatcctcatggacaccattcagctgcctgcaaagtaccccgagctgtt
cgccaacttgccgattcgccagcgcacggaatcctgctctacggccccccgggcaccgaaagaccctgctggccg
gtgtgatcgcccgggaatcgaggatgaacttcatctccgtgaaggaccgaactcctgtccaagtacatcggtgcc
tccgaacaggccgtgcgcgatatattcatagggcccaggccgcgaagccctgcattctgttcttcgacgagtttga
atcgatcgcgccccggaggggccacgacaacacgggagtgaccgaccgggtggtgaaccagctgctcacccaactgg
atggcgtggaaggccttcagggagtgtacgtgctggcggctacctccagaccggacctgatcgatccggccctgctg
```

-continued

SEQUENCE TABLES cgccccgggagactggacaagtgcgtgtattgccctcccctgaccaggtgtcaaggttggaaatcctcaacgtgct
ctcggactccctgccactggcagatgatgtggacctccagcatgtggcctccgtgactgacagcttcacaggagccg
atctgaaggccctgcttttacaacgcccagttggaggcgctgcacggtatgctgctgtcctccggtctgcaggatggc
tcctcctcttccgatagcgacctgtcgctgagcagcatggtgttcctgaaccattccagcggctccgatgacgacgc
gggcgacggagaatgtggactggatcaatccctggtgtccctggagatgagcgagattctgccagacgagtccaagt
tcaacatgtacaggctgtacttcggcagcagctacgagtccgagctgggaaatggtacctcgtccgacctgtcaagc
cagtgcctgtccgcgccttcctccatgacccaggacctccctggagtgccagggaaggatcagctgttcagccagcc
tcccgtgctgcgcactgcgagccaggaagggtgccaggaattgacccaagagcagcgggaccaactgcgcgcggaca
tttcgatcatcaaaggcagataccgctcccaatccggggaggacgaaagcatgaaccagcccgggcctatcaagact
agactggcaatctcccaaagccacctgatgaccgcactgggacacacccggccctcgatctcggaggacgactggaa
gaacttcgctgagctgtacgaatccttccagaatccgaagcggagaaagaaccagagcggaactatgttccggcccg
gacagaaggtgaccctggcctgaagtactgcggatcctgcagatctgcctcgactgtgccttctagttgccagccat
ctgttgtttgccctcccccgtgccttccttgacctggaaggtgccactcccactgtccttctctaataaaatgag
gaaattgcatcgcattgtctgagtaggtgtcattctattctgggggtggggtggggcaggacagcaaggggagga
ttgggaagacaatagcaggcatgctggggactcgagttctacgtagataagtagcatggcgggttaatcattaacta
caaggaacccctagtgatggagttggccactccctctctgcgcgctcgctcgctcactgaggccgggcgaccaaagg
tcgcccgacgcccgggctttgcccgggcggcctcagtgagcgagcgagcgcgcag SEQ ID NO: 7
MWGSDRLAGAGGGGAAVTVAFTNARDCFLHLPRRLVAQLHLLQNQAIEVVWSHQPAELSWVEGRHFSDQGENVAEIN
RQVGQKLGLSNGGQVFLKPCSHVVSCQQVEVEPLSADDWEILELHAVSLEQHLLDQIRIVFPKAIFPVWVDQQTYIF
IQIVALIPAASYGRLETDTKLLIQPKTRRAKENTESKADAEYKKLHSYGRDQKGMMKELQTKQLQSNTVGITESNEN
ESEIPVDSSSVASLWTMIGSIFSFQSEKKQETSWGLTEINAFKNMQSKVVPLDNIFRVCKSQPPSIYNASATSVFHK
HCAIHVFPWDQEYEDVEPSFTVTYGKLVKLLSPKQQQSKTKQNVLSPEKEKQMSEPLDQKIRSDHNEEDEKACVLQ
VVWNGLEELNNAIKYTKNVEVLHLGKVWIPDDLRKRLNIEMHAVVRITPVEVTPKIPRSLKLQPRENLPKDISEEDI
KTVEYSWLQQSITTMLPLVISEEEFIKLETKDGLKEFSLSIVHSWEKEKDKNIFLLSPNLLQKTTIQVLLDPMVKEE
NSEEIDFILPFLKLSSLGGVNSLGVSSLEHITHSLLGRPLSRQLMSLVAGLRNGALLLIGGKGSGKSTLAKAICKEA
FDKLDAHVERVDCKALRGKRLENIQKTLEVAPSEAVWMQPSVVLLDDLDLIAGLPAVPEHEHSPDAVQSQRLAHALN
DMIKEFISMGSLVALIATSQSQQSLHPLLVSAQGVHIFQCVQHIQPPNQEQRCEILCNVIKNKLDCDINKFTDLDLQ
HVAKETGGEVARDETVLVDRAIHSRLSRQSISTREKLVLITLDFQKALRGELPASLRSVNLHKPRDLGWDKIGGLHE
VRQILMDTIQLPAKYPELFANLPIRQRTGILLYGPPGIGKILLAGVIARESRMNFISVKGPELLSKYIGASEQAVRD
IFIRAQAAKPCILFFDEFESIAPRRGHDNIGVTDRVVNQLLTQLDGVEGLQGVYVLAATSRPDLIDPALLRPGRLDK
CVYCPPPDQVSRLEILNVLSDSLPLADDVDLQHVASVIDSFTGADLKALLYNAQLEALHGMLLSSGLQDGSSSSDSD
LSLSSMVELNHSSGSDDSAGDGECGLDQSLVSLEMSEILPDESKFNMYRLYEGSSYESELGNGTSSDLSSQCLSAPS
SMTQDLPGVPGKDQLFSQPPVLRTASQEGCQELTQEQRDQLRADISIIKGRYRSQSGEDESMNQPGPIKTRLAISQS
HLMTALGHTRPSISEDDWKNFAELYESFQNPKRRKNQSGTMERPGQKVTLA SEQ ID NO: 8
ctgcgcgctcgctcgctcactgaggccgcccgggcaaagcccgggcgtcgggcgacctttggtcgcccggcctcagt
gagcgagcgagcgcgcagagagggagtggccaactccatcactagggggttccttgtagttaatgattaacccgccat
gctacttatctacgtagcaagctagcaagatccaagctcagatctcgatcgagttgggccccagaagcctggtggtt
gtttgtcctctcaggggaaaagtgaggcggcccttggaggaagggccgggcagaatgatctaatcggattccaa
gcagctcaggggattgtcttttttctagcaccttcttgccactcctaagcgtcctccgtgaccccggctgggatttag
cctggtgctgtgtcagcccggtctcccagggggcttcccagtggtccccaggaaccctcgacagggcccggtctctc
tcgtccagcaagggcagggacgggccacaggccgatcggagaacttgaaaaaccagaaagttaactgg
taagtttagtcttttttgtcttttatttcaggtcccggatccggtggtggtgcaaatcaaagaactgctcctcagtgg
atgttgcctttacttctaggcctgacggaagtgttacttctgctctaaaagctgcggaattgtacccgcggccgcc
gccaccatgtggggaagcgacagactggccggagctggagggggaggagcagccgtcaccgtggcgttcactaacgc
gcgggactgctttctccatctgccgcggaggctggtcgcccagctgcacctcctgcagaaccaggccatcgaggtgg
tgtggtcccaccaaccggcctttttgagctgggtcgagggaaggcacttttcggaccagggagaaaatgtggcggag
atcaaccgccaggtcggccagaagctgggactgtccaacggcggacaggtgttcctcaagccgtgcagccacgtggt
gtcctgccaacaggtggaagtggagccgctctccgccgacgactgggagatcctcgaattgcatgccgtgagcctcg
aacagcatctgttggaccagattcgcattgtgttcccgaaggccatattccccgtgtgggtcgatcagcagacctat
atcttcatccagattgtggccctcatcccggccgcctcatacggacggctggaaactgacaccaagctgctgattca
acctaagacccggagggccaaagaaaacacctctccaaggccgacgctgagtacaagaagctccactcctacggac
gggaccagaaggggatgatgaaggagctgcaaaccaagcagctccagagcaacaccgtggggatcaccgagtccaat
gaaaacgagtcggaaatcccagtcgattcatcttccgtggccagcctgtggactatgatcggttccattttctcgtt
ccaatctgagaagaagcaggaaactagctggggggctgactgagatcaacgccttcaagaacatgcagtccaaagtgg
tgcctctggataacatctttcgcgtgtgcaagtcccaacgccctcaatctacaacgcgtccgctacctccgtgttt
cataagcactgtgccatccacgtgttcccatgggatcaggaatacttcgatgtcgaacctttccttcaccgtgactta
cgggaagcttgtcaagctcctcagccccaagcagcagcaatcgaaaactaagcagaacgtgctttccccggagaagg
agaagcaaatgtcagaaccactcgaccagaagaaaatcagatcggatcgtaaggccaagggacgagaaggcctgcgtc
cttcaggtggtctggaacggcctggaggagctgaacaacgcgattaagtacaccaagaactcgaggtccttcacct
gggaaaggtgtggattccggatgatctgaggaaacgcctcaacatcgaaatgcacgctgtggtgcggattacccgg
tcgaggtcaccccaaagatccctcgctccttgaagctgcagccgcgagaaaacttgcccaaggacatttctgaagag
gatatcaagactgtgttctactcctggctgcaacagcaccaccatgctccctctggtcatttcggaggaaga
attcatcaaactggaaaccaaggacggactgaaagaattctccctgtccatcgtgcactcctggaaaaggaagaagg
acaagaatatcttcctgctgtccccaatctgctgcaaaagacacagcatccaggtgctgctcgacccatggtgaag
gaggaaaactcagaagagatcgacttcatcctgccgttccttaagctgagttcactggggaggcgtgaactccttgg
cgtgtcctcgctggagcacatcactcactcactgctgggccggcctctgagcagacagcttatgagcttggtcgccg
gactcagaaacggtgccctcctgctcaccggcggcaagggatcgggaaagtccaccctcgctaaggccatttgcaaa
gaggcattcgataagctggacgcccatgtggacgcggggtgagctgtaaggcccttccgggaaagcgattggaaaatat
tcaaagactctcgaagtcgccttttccgaagccgtctggatgcagccctcggtcgtcctgctcgacgatctggacc
tcatcgctgggctgccggccgtgccggagcatgaacactcccctgacgcggtccagtcgcaacggctcgcccacgcc
ctgaacgatatgattaaggaattcatctcaatgggatcactggtggccctgatcgcgacttcccagagccagcagtc
cctgcaccctctgctggtgtcggcccagggcgtgcacattttcagtgtgtgcaacacatccagccgcccaaccagg
agcagcggtgcgaaatcctgtgcaacgtgattaagaacaagctggactgcgatatcaacaagtttaccgaccttgat

SEQUENCE TABLES ctccaacatgtggctaaggagactgggggcttcgtggctcgggacttcacagtgttggtggaccgggcaattcactc
cagactgtcccgccagagcatttccaccgcgaaaaactggtcctgaccaccctcgacttccagaaggccctcagag
gcttccttcctgcgagcctcagatccgtcaaccttcacaagccgcgggacctggctgggacaagatcggtgggctc
cacgaggtgcggcagatcctcatggacaccattcagctgcctgcaaagtaccccgagctgttcgccaacttgccgat
cgccagcgcacgggaatcctgctctacggcccccgggcaccggaaagaccctgctggccggtgtgatcgcccggg
aatcgaggatgaacttcatctccgtgaagggaccgaactcctgtccaagtacatcggtgcctccgaacaggccgtg
cgcgatatattcattagggcccaggccgcgaagccctgcattctgttcttcgacgagtttgaatcgatcgcgcccg
gaggggccacgacaacacgggagtgaccgaccgggtggtgaaccagctgctcacccaactggatggcgtggaaggcc
ttcagggagtgtacgtgctggcggctacctccagaccggacctgatcgatccggccctgctgcgccccgggagactg
gacaagtgcgtgtattgccctcccctgaccaggtgtcaaggttggaaatcctcaacgtgctctcggactccctgcc
actggcagatgatgtggacctccagcatgtggcctccgtgactgacagcttcacaggagccgatctgaaggccctgc
tttacaacgcccagttggaggcgctgcacggtatgctgctgtcctccggtctgcaggatggctcctcctcttccgat
agcgacctgtcgctgagcagcatggtgttcctgaaccattccagcggctccgatgacagcgcgggcgacggagaatg
tggactggatcaatccctggtgtccctggagatgagcgagattctgccagacgagtccaagttcaacatgtacaggc
tgtacttcggcagcagctacgagtccgagctgggaaatggtacctcgtccgacctgtcaagccagtgcctgtccgcg
ccttcctccatgaccaggaccctcctggagtgccagggaaggatcagctgttcagccagcctcccgtgctgcgcac
tgcgagccaggaagggtgccaggaattgacccaagagcagcgggaccaactgcgcgcggacatttcgatcatcaaag
gcagataccgctcccaatccggggaggacgaaagcatgaaccagcccgggcctatcaagactagactggcaatctcc
caaagccacctgatgaccgcactgggacacacccggccctcgatctcggaggacgactggaagaacttcgctgagct
gtacgaatccttccagaatccgaagcggaagaaccagagcgagaactatgttccggcccggacagaaggtgaccc
tggcctgatgtacaagtaataagcctcgactgtgccttctagttgccagccatctgttgtttgccctccccgtgc
cttccttgaccctggaaggtgccactcccactgtcctttcctaataaaatgaggaaattgcatcgcattgtctgagt
aggtgtcattctattctgggggtggggtggggcaggacagcaaggggggaggattgggaagacaatagcaggtcgag
ttctacgtagataagtagcatggcgggttaatcattaactacaaggaaccctagtgatggagttggccactccctc
tctgcgcgctcgctcgctcactgaggccgggcgaccaaaggtcgcccgacgcccgggctttgcccgggcggcctcag
tgagcgagcgagcgcgcag SEQ ID NO: 9
tagaaaaactcatcgagcatcaaatgaaactgcaatttattcatatcaggattatcaataccatattttgaaaaag
ccgtttctgtaatgaaggagaaaactcaccgaggcagttccataggatggcaagatcctggtatcggtctgcgattc
cgactcgtccaacatcaatacaacctattaatttccctcgtcaaaaataaggttatcaagtgagaaatcaccatga
gtgacgactgaatccggtgagaatggcaaaagtttatgcatttctttccagacttgttcaacaggccagccattacg
ctcgtcatcaaaatcactcgcatcaaccaaaccgttattcattcgtgattgcgcctgagcgaggcgaaatacgcgat
cgctgttaaaggacaattacaaacaggaatcgagtgcaaccggcgcaggaacactgccagcgcatcaacaatatt
tcacctgaatcaggatattcttctaatacctggaacgctgttttccggggatcgcagtggtgagtaaccatgcatc
atcaggagtacggataaaatgcttgatggtcggaagtggcataaattccgtcagccagtttagtctgaccatctcat
ctgtaacatcattggcaacgctacctttgccatgtttcagaaacaactcggggcatcgggcttcccatacaagcga
tagattgtcgcacctgattgcccgacattatcgcgagcccatttatacccatataaatcagcatccatgttggaatt
taatcgcggcctcgactgtttcccgttgaatatggctcatattcttcttttttcaatattattgaagcatttatcagg
gttattgtctcatgagcggatacatatttgaatgtatttagaaaataaacaaatagggtcagtgttacaaccaat
taaccaattctgaacattatcgcgagcccatttatacctgaatatgctcataacaccccttgtttgcctggcca
gtagcgcggtggtcccacctgaccccatgccgaactcagaagtgaaacgccgtagcgccgatggtagtgtgggact
ccccatgcgagagtagggaactgccaggcatcaaatgaaacgaaaggctcagtcgaaagactgggcctttcgcccgg
gctaattaggggggtgtcgcccttattcgactctatagtgaagttcctattctctagaaagtataggaacttctgaag
tgggtgcacttaattaaggctgcgcgctcgctcgctcactgaggccgcccgggcaaagcccgggcgtcggggcgacc
tttggtcgcccggcctcagtgagcgagcgagcgcgcagagagggagtggccaactccatcactaggggttccttgta
gttaatgattaacccgccatgctacttatcacgtagcaagctagctagttattaatagtaatcaattacgggtca
ttagttcatagcccatatatggagttccgcgttacataacttacggtaaatggcccgcctggctgaccgcccaacga
cccccgcccattgacgtcaataatgacgtatgttcccatagtaacgccaatagggactttccattgacgtcaatggg
tggagtatttacggtaaactgcccacttggcagtacatcaagtgtatcatatgccaagtacgccccctattgacgtc
aatgacggtaaatggcccgcctggcattatgcccagtacatgaccttatgggactttcctacttggcagtacatcta
cgtattagtcatcgctattaacatggtcgaggtgagccccacgttctgcttcactctccccatctccccccctccc
cacccccaattttgtatttatttattttttaattatttttgtgcagcgatggggcggggggggggggggggcgcgcg
ccaggcggggcggggcgggggagggggcgggcgggcgaggcggagaggtgcggcggcagccaatcagagcggcgc
gctccgaaagtttccttttatggcgaggcggcggcggcggcggccctataaaagcgaagcgcgcggcgggcgggga
gtcgctgcgacgctgccttcgccccgtgccccgctccgccgccgcctcgcgccgcccgccccggctctgactgaccg
cgttactcccacaggtgagcgggcgggacggcccttctcctccgggctgtaattagcgcttggtttaatgacggctt
gtttcttttctgtggctgcgtgaaagccttgaggggctccgggagggccctttgtgcgggggggagcggctcggggag
tgcgtgcgtgtgtgtgtgcgtgggggagcgccgcgtgcggctccgcgctgcccggcggctgtgagcgctgcgggcgcg
gcgcggggctttgtgcgctccgcagtgtgcgcgaggggagcgcggccggggcggtgcccgcggtgcgggggggc
tgcgaggggaacaaaggctgcgtgcggggtgtgtgcgtgggggggtgagcagggggtgtgggcgcgtcggtcgggct
gcaaccccctgcacccccctccccgagttgctgagcacggcccggcttcgggtgcggggtccgtacggggcgtg
gcgcggggctcgccgtgccgggcgggggtggcggcaggtggggggtgccgggcgggggggggccgcctcgggccggg
gagggctcggggagggggcgcggcggcccccggagcgccggcggctgtcgaggcgcggcgagccgcagccattgcct
tttatggtaatcgtgcgagagggcgcagggacttcctttgtcccaaatctgtgcggagccgaaatctgggaggcgcc
gccgcacccctctagcgggcgcggggcgaagcggtgcgcgccggcaggaaggaaatgggcggggagggccttcgt
gcgtcgccgcgccgtccccttctccctctccagcctcgggctgtccgcgggggacggctgccttcggggggg
acggggcagggcggggttcggcttctggcgtgtgaccggcggctctagacaattgtactaaccttcttctcttttcct
ctcctgacaggttggtgtacactagcggccgcgccgccaccatgtggggaagcgacagactggccggagctggaggg
ggaggagcagccgtcaccgtggcgttcactaacgcgcgggactgcttctccatctgccgcggaggctggtcgccca
gctgcacctcctgcagaaccaggccatcgaggtggtgtggtcccaccaaccggcttttttgagctgggtcgagggaa
tgcacttttcggaccagggagaaaatgtggcggagatcaaccgccagcggttcggctgacaagaagtgtcaacgg
ggacaggtgttcctcaagccgtgcagcacgtggtgtcctgccaacaggtggaagtggagcgctctccgccgacga
ctgggagatcctcgaattgcatgccgtgagcctgaacagcatctgttgaccagattcgcattgtgttcccgaagg
ccatattccccgtgtgggtcgatcagcagacctatatcttcatccagattgtggccctcatcccggccgcctcatac
ggacggctggaaactgacaccaagctgctgattcaacctaagacccggaggggccaaagaaaacacctctccaaggc
cgacgctgagtacaagaagctccactcctacggacgggaccagaaggggatgatgaaggagctgcaaaccaagcagc -continued

SEQUENCE TABLES

```
tccagagcaacaccgtggggatcaccgagtccaatgaaaacgagtcggaaatcccagtcgattcatcttccgtggcc
agcctgtggactatgatcggttccattttctcgttccaatctgagaagaagcaggaaactagctgggggctgactga
gatcaacgccttcaagaacatgcagtccaaagtggtgcctctggataacatcttcctgctgcgtgtgcaagtcccaaccgc
cctcaatctacaacgcgtccgctacctccgtgtttcataagcactgtgccatccacgtgttcccatgggatcaggaa
tacttcgatgtcgaaccttccttcaccgtgacttacgggaagcttgtcaagctcctcagcccccaagcagcagcaatc
gaaaactaagcagaacgtgctttccccggagaaggagaagcaaatgtcagaaccactcgaccagaagaaaatcagat
cggatcataacgaagaggacgagaaggcctgcgtccttcaggtggtctggaacggcctggaggagctgaacaacgcg
attaagtacaccaagaacgtcgaggtccttcacctgggaaaggtgtggattccggatgatctgaggaaacgcctcaa
catcgaaatgcacgctgtggtgcggattaccccggtcgaggtcaccccaaagatccctcgctccttgaagctgcagc
cgcgagaaaacttgcccaaggacatttctgaagaggatatcaagactgtgttctactcctggctgcaacagagcact
accaccatgctccctctggtcatttcggaggaagaattcatcaaactggaaaccaaggacggactgaaagaattctc
cctgtccatcgtgcactcctgggaaaaggagaaggacaagaatatcttcctgctgtccccccaatctgctgcaaaaga
ccacgatccaggtgctgctcgaccccatggtgaaggaggaaaactcagaagagatcgacttcatcctgccgttcctt
aagctgagttcactgggaggcgtgaactcccttggcgtgtcctcgctggagcacactcactcactgctgggccg
gcctctgagcagacagcttatgagcttggtcgccggactcagaaacggtgccctcctgctcaccggcggcaagggat
cgggaaagtccaccctcgctaaggccatttgcaaagaggcattcgataagctggacgcccatgtggagcgggtgac
tgtaaggccctccgcgcgaaagcgattggaaaatattcaaaagactctcgaagtcgcctttccgaagccgtctggat
gcagccctcggtcgtcctgctcgacgatctggacctcatcgctgggctgccggccgtgccggagcatgaacactccc
ctgacgcggtccagtcgcaacggctcgcccacgccctgaacgatatgattaaggaattcatctcaatgggatcactg
gtggccctgatcgcgacttcccagagccagcagtccctgcaccctctgctggtgtcggcccagggcgtgcacattt
tcagtgtgtgcaacacatccagccgcccaaccaggagcagcggtgcgaaatcctgtgcaacgtgattaagaacaagc
tggactgcgatatcaacaagtttaccgaccttgatctccaacatgtggctaaggagactgggggcttcgtggctcgg
gacttcacagtgttggtggaccgggcaattcactccagactgtcccgccagagcatttccacccgcgaaaaactggt
cctgaccaccctcgacttccagaaggccctcagaggcttccttcctgcgagcctcagatccgtcaaccttcaaagc
cgcgggaccttggctgggacaagatcggtgggctccacgaggtgcggcagatcctcatggacaccattcagctgcct
gcaaagtaccccgagctgttcgccaacttgccgattcgccagcgcacgggaatcctgctctacggccccccgggcac
cggaaagaccctgctggccggtgtgatcgcccgggaatcgaggatgaacttcatctccgtgaagggacccgaactcc
tgtccaagtacatcggtgcctccgaacaggccgtgcgcgatatattcattagggcccaggccgcgaagccctgcatt
ctgttcttcgacgagtttgaatcgatcgcgccccggagggccacgacaacacgggagtgaccgaccgggtggtgaa
ccagctgctcacccaactggatggcgtggaaggccttcagggagtgtacgtgctggcggctacctccagaccggacc
tgatcgatccggccctgctgcgccccgggagactggacaagtgcgtgtattgccctcccctgaccaggtgtcaagg
ttggaaatcctcaacgtgctctcggactccctgccactggcagatgatgtggacctccagcatgtggcctccgtgac
tgacagcttcacaggagccgatctgaaggccctgctttacaacgcccagttggaggcgctgcacggtatgctgctgt
cctccggtctgcaggatggctcctcctcttccgatagcgacctgtcgctgagcagcatggtgttcctgaaccattcc
agcggctccgatgacagcgcgggcgacggagaatgtggactggatcaatccctggtgtccctggagatgagcgagat
tctgccagacgagtccaagttcaacatgtacaggcgtacttcggcagcagctacgagtccgagctgggaaatggta
cctcgtccgacctgtcaagccagtgcctgtccgcgccttcctccatgacccaggaccctccctggagtgccagggaag
gatcagctgttcagccagcctcccgtgctgcgcactgcgagccaggaagggtgccaggaattgacccaagagcagcg
ggaccaactgcgcgcggacatttcgatcatcaaaggcagataccgctcccaatccggggaggacgaaagcatgaacc
agcccggcctatcaagactagactggcaatctcccaaagccacctgatgaccgcactgggacacacccggccctcg
atctcggaggacgactggaagaacttcgctgagctgtacgaatccttccagaatccgaagcggagaaagaaccagag
cggaactatgttccggcccggacagaaggtgaccctggcctgaagtactgcggatcctgcagatctgcctcgactgt
gccttctagttgccagccatctgttgtttgcccctccccgtgccttccttgaccctggaaggtgccactccactg
tcctttcctaataaaatgaggaaattgcatcgcattgtctgagtaggtgtcattctattctgggggggtggtgggg
caggacagcaaggggggaggattgggaagacaatagcaggcatgctggggactcgagttctacgtagataagtagcat
ggcgggttaatcattaactacaaggaaccccctagtgatggagttggccactccctctctgcgcgctcgctcgctcac
tgaggccgggcgaccaaaggtcgcccgacgcccgggctttgcccgggcggcctcagtgagcgagcgagcgcgcagcc
ttaattaacctaaggaaaatgaagtgaagttcctatactttctagagaataggaacttctatagtgagtcgaataag
ggcgacaaaattattctaaatgcataataaatactgataacatcttatagtttgtattatattttgtattatcg
ttgacatgtataattttgatatcaaaaactgattttcccttattatttttcgagattttattttcttaattctcttta
acaaactagaaatattgtatatacaaaaaatcataaataatagatgaatagtttaattataggtgttcatcaatcga
aaaagcaacgtatcttatttaaagtgcgttgcttttttctcatttataaggttaaataattctcatatatcaagcaa
agtgacaggcgcccttaaatattctgacaaatgctctttccctaaactcccccccataaaaaaaccccgccgaagcggg
tttttacgttatttgcggattaacgattactcgttatcagaaccgcccaggggggcccgagcttaacctttttatttg
ggggagagggaagtcatgaaaaaactaacctttgaaattcgatctccagcacatcagcaaaacgctattcacgcagt
acagcaaatccttccagacccaaccaaaccaatcgtagtaaccattcaggaacgcaaccgcagcttagaccaaaaca
ggaagctatgggcctgcttaggtgacgtctctcgtcaggttgaatggcatggtcgctggctggatgcagaaagctgg
aagtgtgtttaccgcagcattaaagcagcaggatgttgttcctaaccttgccgggaatggcttttgtggtaatagg
ccagtcaaccagcaggatgcgtgtaggcgaatttgcggagctattagagcttatacaggcattcggtacagagcgtg
gcgttaagtggtcagacgaagcgagactggctctggagtggaaagcgagatgggagacagggctgcatgataaatg
tcgttagtttctccggtggcaggacgtcagcatatttgctctggctaatggagcaaaagcgacgggcaggtaaagac
gtgcattacgttttcatggatacaggttgtgaacatccaatgacaatccggttcaggggaagttgtgaagttctg
ggatataccgctcaccgtattgcaggttgatatcaacccggagcttggacagcaaatggttatacggtatgggaac
caaaggatattcagacgcgaatgcctgttctgaagcatttatcgatatggtaaagaaatatggcactccatacgtc
ggcggcgcgttctgcactgacagtaaaactcgttcccttcaccaaatactgtgatgaccatttcgggcgagggaa
ttacaccacgtggattggcatcagagctgatgaaccgaagcggctaaagccaaagcctgaatcagatatcttgctg
aactgtcagactttgagaaggaagatatcctcgcatggtggaagcaacaacattcgatttgcaaataccggaacat
ctcggtaactgcatattctgcattaaaaaatcaacgcaaaaaatcggacttgcctgcaaagatgaggagggattgca
gcgtgttttaatgaggtcatcacgggatcccatgtgcgtgacggacatcgggaaacgccaaaggagattatgtacc
gaggaagaatgtcgctggacgtatcgcgaaatgtattcagaaaatgattatcaagccctgtcaggacatggta
cgagctcaaaagattcgataccggctcttgttctgagtcatgcgaaatatttggagggcagcttgatttcgacttcgg
gagggaagctgcatgatgcgatgttatcggtgcggtgaatgcaaagaagataaccgcttccgaccaaatcaaccttta
ctggaatcgatggtgtctccggtgtgaaagaacaccaacagggggtgttaccactaccgcaggaaaaggaggacgtgt
ggcgagacagcgacgaagtatcaccgacataatctgcgaaaactgcaaataccttccaacgaaacgcaccagaaata
aacccaagccaatcccaaaagaatctgacgtaaaaaccttcaactacacggctcacctgtgggatatccggtggcta
agacgtcgtgcgaggaaaacaaggtgattgaccaaaatcgaagttacgaacaagaaagcgtcgagcgagctttaacg
tgcgctaactgcggtcagaagctgcatgtgctggaagttcacgtgtgtgagcactgctgcgcagaactgatgagcga
```

SEQUENCE TABLES

```
tccgaatagctcgatgcacgaggaagaagatgatggctaaaccagcgcgaagacgatgtaaaaacgatgaatgccgg
gaatggtttcaccctgcattcgctaatcagtggtggtgctctccagagtgtggaaccaagatagcactcgaacgacg
aagtaaagaacgcgaaaaagcggaaaaagcagcagagaagaaaacgacgacgagaggagcagaaacagaaagataaac
ttaagattcgaaaactcgccttaaagccccgcagttactggattaaacaagcccaacaagccgtaaacgccttcatc
agagaaagagaccgcgacttaccatgtatctcgtgcggaacgctcacgtctgctcagtgggatgccggacattaccg
gacaactgctgcggcacctcaactccgatttaatgaacgcaatattcacaagcaatgcgtggtgtgcaaccagcaca
aaagcggaaatctcgttccgtatcgcgtcgaactgattagccgcatcgggcaggaagcagtagacgaaatcgaatca
aaccataaccgccatcgctggactatcgaagagtgcaaggcgatcaaggcaggtaccaacagaaactcaaagacct
gcgaaatagcagaagtgaggccgcatgacgttctcagtaaaaaccattccagacatgctcgttgaagcatacggaaa
tcagacagaagtagcacgcagactgaaatgtagtcgcggtacggtcagaaaatacgttgatgataaagacgggaaaa
tgcacgccatcgtcaacgacgttctcatggttcatcgcggatggagtgaaagagatgcgctattacgaaaaaattga
tggcagcaaataccgaaatatttgggtagttggcgatctgcacggatgctacacgaacctgatgaacaaactggata
cgattggattcgacaacaaaaaagacctgcttatctcggtgggcgatttggttgatcgtggtgcagagaacgttgaa
tgcctggaattaatcacattcccctggttcagagctgtacgtggaaaccatgagcaaatgatgattgatggcttatc
agagcgtggaaacgttaatcactggctgcttaatggcggtggctggttcttttaatctcgattacgacaaagaaattc
tggctaaagctcttgcccataaagcagatgaacttccgttaatcatcgaacttggtgagcaaagataaaaaatatgtt
atctgccacgccgattatccctttgacgaatacgagtttggaaagccagttgatcatcagcaggtaatctggaaccg
cgaacgaatcagcaactcacaaaacgggatcgtgaaagaaatcaaaggcgcggacacgttcatcttttggtcatacgc
cagcagtgaaaccactcaagtttgccaaccaaatgtatatcgataccggcgcagttgttctgcggaaacctaacattg
attcaggtacagggagaaggcgcatgagactcgaaagcgtagctaaatttcattcgccaaaaagcccgatgatgagc
gactcaccacgggccacggcttctgactctctttccggtactgatgtgatggctgctatggggatggcgcaatcaca
agccggattcggtatggctgcattctgcggtaagcacgaactcagccagaacgacaaacaaaaggctatcaactatc
tgatgcaatttgcacacaaggtatcggggaaataccgtggtgtggcaaagcttgaaggaaatactaaggcaaaggta
ctgcaagtgctcgcaacattcgcttatgcggtattgccgtagtgccgcgacgccgggggcaagatgcagagattg
ccatggtacaggccgtgcggttgatattgccaaaacagagctgtggggggagagttgtcgagaaagagtgcggaagat
gcaaaggcgtcggctattcaaggatgccagcaagcgcagcatatcgcgctgtgacgatgctaatcccaaaccttacc
caacccacctggtcacgcactgttaagccgctgtatgacgctctggtggtgcaatgccacaaagaagagtcaatcgc
agacaacattttgaatgcggtcacacgttagcacgcatgattgccaacgatgcaacatattaacggcatgatattga
cttattgaataaaattgggtaaatttgactcaacgatgggttaattcgctcgttgtggtagtgagatgaaaagaggc
ggcgcttactaccgattccgcctagttggtcacttcgacgtatcgtctggaactccaaccatcgcaggcagagaggt
ctgcaaaatgcaatcccgaaacagttcgcaggtaatagttagagcctgcataacggtttcgggatttttttatatctg
cacaacaggtaagagcattgagtcgataatcgtgaagagtcggcgagcctggttagccagtgctctttccgttgtgc
tgaattaagcgaataccggaagcagaaccggatcaccaaatgcgtacaggcgtcatcgccgcccagcaacagcacaa
cccaaactgagccgtagccactgtctgtcctgaattcattagtaatagttacgctgcggccttttacacatgacctt
cgtgaaagcgggtggcaggaggtcgcgctaacaacctcctgccgttttgcccgtgcatatcggtcacgaacaaatct
gattactaaacacagtagcctggatttgttctatcagtaatcgaccttattcctaattaaatagagcaaatcccctt
attgggggtaagacatgaagatgccagaaaaacatgacctgttggcgccattctcgcggcaaaggaacaaggcatc
ggggcaatccttgcgtttgcaatggcgtaccttcgcggcagatataatggcggtgcgtttacaaaaacagtaatcga
cgcaacgatgtgcgccattatcgcctggttcattcgtgaccttctcgacttcgccggactaagtagcaatctcgctt
atataacgagcgtgtttatcggctacatcggtactgactcgattggttcgcttatcaaacgcttcgctgctaaaaaa
gccggagtagaagatggtagaaatcaataatcaacgtaaggcgttcctcgatatgctggcgtggtcggagggaactg
ataacggacgtcagaaaaccagaaatcatggttatgacgtcattgtaggcggagagctatttactgattactccgat
cacccctcgcaaacttgtcacgctaaacccaaaactcaaatcaacaggcgcttaagactggccgtcgttttacaacac
agaaagagtttgtagaaacgcaaaaggccatccgtcaggggccttctgcttagtttgatgcctggcagttccctac
tctcgccttccgcttcctcgctcactgactcgctgcgctcggtcgttcggctgcggcagcggtatcagctcactca
aaggcggtaatacggttatccacagaatcaggggataacgcaggaaagaacatgtgagcaaaaggccagcaaaaggc
caggaaccgtaaaaaggccgcgttgctggcgtttttccataggctccgcccccctgacgagcatcacaaaaatcgac
gctcaagtcagaggtggcgaaacccgacaggactataaagataccaggcgtttccccctggaagctccctcgtgcgc
tctcctgttccgaccctgccgcttaccggatacctgtccgcctttctcccttcgggaagcgtggcgctttctcatag
ctcacgctgtaggtatctcagttcggtgtaggtcgttcgctccaagctgggctgtgtgcacgaaccccccgttcagc
ccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtgggctaactacgg
ctacactagaagaacagtatttggtatctgcgctctgctgaagccagttacctttcggaaaaagagttggtagctctt
gatccggcaaacaaaccaccgctggtagcggtggttttttttgtttgcaagcagcagattacgcgcagaaaaaagga
tctcaagaagatcctttgatcttttctacggggtctgacgctcagtggaacgacgcgcgtaactcacgttaaggg
attttggtcatgagcttgcgccgtcccgtcaagtcagcgtaatgctctgcttt SEQ ID NO: 10
tagaaaaactcatcgagcatcaaatgaaactgcaatttattcatatcaggattatcaataccatattttttgaaaaag
ccgtttctgtaatgaaggagaaaactcaccgaggcagttccataggatggcaagatcctggtatcggtctgcgattc
cgactcgtccaacatcaatacaacctattaatttcccctcgtcaaaaataaggttatcaagtgagaaatcaccatga
gtgacgactgaatccggtgagaatggcaaaagtttatgcatttctttccagacttgttcaacaggccagccattacg
ctcgtcatcaaaatcactcgcatcaaccaaaccgttattcattcgtgattgcgcctgagcgaggcgaaatacgcgat
cgctgttaaaaggacaattacaaacaggaatcgagtgcaaccggcgcaggaacactgccagcgcatcaacaatattt
tcacctgaatcaggatattcttctaatacctggaacgctgtttttccggggatcgcagtggtgagtaaccatgcatc
atcaggagtacggataaaatgcttgatggtcggaagtggcataaattccgtcagccagtttagtctgaccatctcat
ctgtaacatcattggcaacgctacctttgccatgtttcagaaacaactctggcgcatcgggcttcccatacaagcga
tagattgtcgcacctgattgcccgacattatcgcgagcccatttatacccatataaatcagcatccatgttggaatt
taatcgcggcctcgacgtttcccgttgaatatggctcatattcttcctttttcaatattattgaagcatttatcagg
gttattgtctcatgagcggatacatatttgaatgtatttagaaaaataaacaaataggggtcagtgttacaaccaat
taaccaattctgaacattatcgcgagcccatttatacctgaatatggctcataacacccttgtttgcctggcggca
gtagcgcggtggtcccacctgaccccatgccgaactcagaagtgaaacgccgtagcgccgatggtagtgtggggact
cccatgcgagagtagggaactgccaggcatcaaataaaacgaaaggctcagtcgaaagactgggcctttcgccgg
gctaattaggggggtgtcgcccttattcgactctatagtgaagttcctattctctagaaagtataggaacttctgaag
tggggtcgacttaattaaggctgcgcgctcgctcgctcactgaggccgcccgggcaaagcccgggcgtcgggcgacc
tttggtcgcccggcctcagtgagcgagcgagcgcgcagagagggagtggccaactccatcactagggggttccttgta
gttaatgattaacccgccatgctacttatctacgtagcaagctagcgagtgggaattggctccggtgcccgtcagtg
```

SEQUENCE TABLES

```
ggcagagcgcacatcgcccacagtccccgagaagttgggggagggtcggcaattgatccggtgcctagagaaggt
ggcgcggggtaaactgggaaagtgatgtcgtgtactggctccgccttttcccgagggtgggggagaaccgtatata
agtgcagtagtcgccgtgaacgttctttttcgcaacgggtttgccgccagaacacaggcggccgcgccgccaccatg
tggggaagcgacagactggccggagctggagggggaggagcagccgtcaccgtggcgttcactaacgcgcgggactg
ctttctccatctgccgcggaggctggtcgcccagctgcacctcctgcagaaccaggccatcgaggtggtgtggtccc
accaaccggccttttgagctgggtcgagggaaggcacttttcggaccagggagaaaatgtggcggagatcaaccgc
caggtcggccagaagctgggactgtccaacggcggacaggtgttcctcaagccgtgcagccacgtggtgtcctgcca
acaggtggaagtggagccgctctccgccgacgactgggagatcctcgaattgcatgccgtgagcctcgaacagcatc
tgttggaccagattcgcattgtgttcccgaaggccatattccccgtgtgggtcgatcagcagacctatatcttcatc
cagattgtggccctcatcccggccgcctcatacgacggctggaaactgacaccaagctgctgattcaacctaagac
ccggagggccaaagaaaacaccttctccaaggcgacgctgagtacaagaagctccactcctacggacgggaccaga
agggatgatgaaggagctgcaaaccaagcagctccagacaaccaccgtgggatcaccgagtccaatgaaaacgag
tcggaaatcccagtcgattcatcttccgtggccagcctgtggactatgatcggttccattttctcgttccaatctga
gaagaagcaggaaactagctgggggctgactgagatcaacgccttcaagaacatgcagtccaaagtggtgcctctgg
ataacatctttcgcgtgtgcaagtcccaaccgccctcaatctacaacgcgtccgctacctccgtgtttcataagcac
tgtgccatccacgtgttcccatgggatcaggaatacttcgatgtcgaaccttccttcaccgtgacttacgggaagct
tgtcaagctcctcagccccaagcagcagcaatcgaaaactaagcagaacgtgctttccccggagaaggagaagcaaa
tgtcagaaccactcgaccagaagaaaatcagatcggatcataacgaagaggacgagaaggcctgcgtccttcaggtg
gtctggaacggcctggaggagctgaacaacgcgattaagtacaccaagaacgtcgaggtccttcacctgggaaaggt
gtggattccggatgatctgaggaaacgcctcaacatcgaaatgcacgctgtggtgcggattacccggtcgaggtca
ccccaaagatccctcgctccttgaagctgcagccgcgagaaaactgcccaaggacattctgaagaggatatcaag
actgtgttctactcctggctgcaacagagcactaccaccatgctccctctggtcatttcggaggaagaattcatcaa
actggaaaccaaggacggactgaaagaattctccctgtccatcgtgcactcctgggaaaaggagaaggacaagaata
tcttcctgctgtcccccaatctgctgcaaaagaccacgatccaggtgctgctcgaccccatggtgaaggaggaaaac
tcagaagagatcgacttcatcctgccgttccttaagctgagttcactgggaggcgtgaactcccttggcgtgtcctc
gctggagcacatcactcactcactgctgggccggcctctgagcagacagcttatgagcttggtcgccggactcagaa
acggtgccctcctgctcaccggcggcaagggatcgggaaagtccaccctcgctaaggccatttgcaaagaggcattc
gataagctggacgcccatgtggacgcgggtgactgtaaggccctccgcggaaagcgattggaaaatattcaaaagac
tctcgaagtcgccttttccgaagccgtctggatgcagccctcggtcgtcctgctcgacgatctggacctcatcgctg
ggctgccggccgtgccggagcatgaacactccctgacgcggtccagtcgcaacggctcgcccacgccctgaacgat
atgattaaggaattcatctcaatgggatcactggtggccctgatcgcgacttcccagagccagcagtccctgcaccc
tctgctggtgtcggcccagggcgtgcacatttttcagtgtgtgcaacacatccagccgccccaaccaggagcagcggt
gcgaaatcctgtgcaacgtgattaagaacaagctggactgcgatatcaacaagttaccgaccttgatctccaacat
gtggctaaggagactgggggcttcgtggctcgggacttcacagtgttggtggaccgggcaattcactccagactgtc
ccgccagagcatttccaccgcgcgaaaaactggtcctgaccaccctcgactttccagaaggccctcagaggcttccttc
ctgcgagcctcagatccgtcaaccttcacaagccgcgggacctggctgggacaagatcggtgggctccacgaggtg
cggcagatcctcatggacaccattcagctgcctgcaaagtaccccgagctgttcgccaacttgccgattcgccagcg
cacgggaatcctgctctacggccccccgggcaccggaaagaccctgctggccggtgtgatcgccgggaatcgagga
tgaacttcatctccgtgaagggacccgaactcctgtccaagtacatcggtgcctccgaacaggccgtgcgcgatata
ttcattagggcccaggccgcgaagccctgcattctgttcttcgacgagtttgaatcgatcgcgcccggagggcca
cgacaacacgggagtgaccgaccgggtggtgaaccagctgctcaaccaagtcgtggaaggccttcagggag
tgtacgtgctggcggctacctccagaccggacctgatcgatccggccctgctgcgccccgggagactggacaagtgc
gtgtattgccctccccctgaccaggtgtcaaggttggaaatcctcaacgtgctctcggactccctgccactggcaga
tgatgtggacctccagcatgtggcctccgtgactgacagcttcacaggagccgatctgaaggccctgctttacaacg
cccagttggaggcgctgcacggtatgctgctgtcctccggtctgcaggatggctctcctcctcttccgatagcgacctg
tcgctgagcagcatggtgttcctgaaccattccagcggctccgatgacagccgcgggcgacggagaatgtggactgga
tcaatccctggtgtccctggagatgagcgagattctgccagacgagtccaagttcaacatgtacaggctgtacttcg
gcagcagctacgagtccgagctgggaaatggtacctcgtccgacctgtcaagccagtgcctgtccgcgccttcctcc
atgacccaggacctccctggagtgccagggaaggatcagctgttcaggccacgaaaggtgaccctggcctgccgca
ggaagggtgccaggaattgacccaagagcagcgggaccaactgcgcgcggacatttcgatcatcaaaggcagatacc
gctcccaatccggggaggacgaaaagcatgaaccagcccgggcctatcaagactagactggcaatctcccaaagccac
ctgatgaccgcactgggacacaccggccctcgatctcggaggacgactggaagaacttcgctgagctgtacgaatc
cttccagaatccgaagcggaaagaaaccagagccggaactatgttccggccggacagaaggtgaccctggcctggcaa
gtactgcggatcctgcagatctgcctcgactgtgccttctagttgccagccatctgttgtttgccctccccccgtgc
cttccttgaccctggaaggtgccactcccactgtcctttcctaataaaatgaggaaattgcatcgcattgtctgagt
aggtgtcattctattctgggggtggtggggcaggacagcaaggggggaggattgggaagacaatagcaggcatgc
tggggactcgagttctacgtagataagtagcatggcgggttaatcattaactacaaggaaccccctagtgatggagtt
ggccactccctctctgcgcgctcgctcgctcactgaggccgggcgaccaaaggtcgcccgacgcccgggctttgccc
gggcggcctcagtgagcgagcgagcgcgcagccttaattaacctaaggaaatgaagtgaagttcctatactttcta
gagaataggaacttctatagtgagtcgaataagggcgacacaaaatttattctaaatgcataataaatactgataac
atcttatagtttgtattatattttgtattatcgttgacatgtataattttgatatcaaaaactgatttttccctttat
tatttttcgagattttattttcttaattctctttaacaaaactagaaaattgtatatacaaaaaatcataaataataga
tgaatagtttaattataggtgttcatcaatcgaaaaagcaacgtatctatttaaagtgcgttgcttttttctcatt
tataaggttaaataattctcatatatcaagcaaagtgacaggcgcccttaaatattctgacaaatgctcttcccta
aactcccccataaaaaacccgccgaagcgggttttttacgttatttgcggattaacgattactcgttatcagaacc
gcccaggggcccgagcttaaccttttatttgggggagagggaagtcatgaaaaaactaacctttgaaattcgatc
tccagcacatcagcaaaacgctattcacgcagtacagcaaatccttccagaccccaaccaaaccaatcgtagtaacca
ttcaggaacgcaaccgcagcttagaccaaaacaggaagctatggccctgcttaggtgacgtctctcgtcaggttgaa
tggcatggtcgctggctggatcagaaagctggaagtgtgtgtttaccgcagcattaaagcagcaggatgttgttcc
taaccttgccgggaatggctttgtggtaataggccagtcaaccagcaggatgcgtgtaggcgaatttgcggagctat
tagagcttatacaggcattcggtacagagcgtggcgttaagtggtcagacgaagcgagactggctctggagtggaaa
gcgagatggggagacagggctgcatgataaatgtcgttagtttctccggtggcaggacgtcagcatatttgctctgg
ctaatggagcaaaagcgacgggcaggtaaagacgtgcattacgttttcatggatacaggttgtgaacatccaatgac
atatcggtttgtcagggaagttgtgaagttctgggatataccgctcaccgtattgcaggtgatatcaacccggagc
ttggacagccaaatggttatacggtatgggaaccaaaggatattcagacgcgaatgcctgttctgaagccatttatc
gatatggtaaagaaatatggcactccatacgtcggcggcgcgttctgcactgacagattaaaactcgttcccttcac
caaatactgtgatgaccatttcgggcgagggaattacaccacgtggattggcatcagagctgatgaaccgaagcggc
```

-continued

SEQUENCE TABLES taaagccaaagcctggaatcagatatcttgctgaactgtcagactttgagaaggaagatatcctcgcatggtggaag
caacaaccattcgatttgcaaataccggaacatctcggtaactgcatattctgcattaaaaaatcaacgcaaaaaat
cggacttgcctgcaaagatgaggagggattgcagcgtgtttttaatgaggtcatcacgggatcccatgtgcgtgacg
gacatcgggaaacgccaaaggagattatgtaccgaggaagaatgtcgctggacggtatcgcgaaaatgtattcagaa
aatgattatcaagccctgtatcaggacatggtacgagctaaaagattcgataccggctcttgttctgagtcatgcga
aatatttggagggcagcttgatttcgacttcgggagggaagctgcatgatgcgatgtttatcggtgcggtgaatgcaa
agaagataaccgcttccgaccaaatcaaccttactggaatcgatggtgtctccggtgtgaaagaacaccaacagggg
tgttaccactaccgcaggaaaaggaggacgtgtggcgagacagcgacgaagtatcaccgacataatctgcgaaaact
gcaaataccttccaacgaaacgcaccagaaataaaccccaagccaatcccaaaagaatctgacgtaaaaaccttcaac
tacacggctcacctgtgggatatccggtggctaagacgtcgtgcgaggaaaacaaggtgattgaccaaaatcgaagt
tacgaacaagaaagcgtcgagcgagctttaacgtgcgctaactgcggtcagaagctgcatgtgctggaagttcacgt
gtgtgagcactgctgcgcagaactgatgagcgatccgaatagctcgatgcacgaggaagaagatgatggctaaacca
gcgcgaagacgatgtaaaaacgatgaatgccgggaatggtttcaccctgcattcgctaatcagtggtggtgctctcc
agagtgtggaaccaagatagcactcgaacgacgaagtaaagaacgcgaaaaagcggaaaaagcagcagagaagaaac
gacgacgagaggagcagaaacagaaagataaacttaagattcgaaaactcgccttaaagccccgcagttactggatt
aaacaagcccaacaagccgtaaacgccttcatcagagaaagagaccgcgacttaccatgtatctcgtgcggaacgct
cacgtctgctcagtgggatgccggacattaccggacaactgctgcggcacctcaactccgatttaatgaacgcaata
ttcacaagcaatgcgtggtgtgcaaccagcacaaaagcggaaatctcgttccgtatcgcgtcgaactgattagccgc
atcgggcaggaagcagtagacgaaatcgaatcaaaccataaccgccatcgctggactatcgaagagtgcaaggcgat
caaggcagagtaccaacagaaactcaaagacctgcgaaatagcgaagtgaggccgcatgacgttctcagtaaaaac
cattccagacatgctcgttgaagcatacggaaatcagacagaagtagcacgcagactgaaatgtagtcgcggtacgg
tcagaaaatacgttgatgataaagacgggaaatgcacgccatcgtcaacgacgttctcatggttcatcgcggatgg
agtgaaagagatgcgctattacgaaaaaattgatggcagcaaataccgaaatatttgggtagttggcgatctgcacg
gatgctacacgaacctgatgaacaaactggatacgattggattcgacaacaaaaaagacctgcttatctccggtgggc
gatttggttgatcgtggtgcagagaacgttgaatgcctggaattaatcacattccccctggttcagagctgtacgtgg
aaaccatgagcaaatgatgattgatggcttatcagagcgtggaaacgttaatcactggctgcttaatggcggtggct
ggttcttaatctcgattacgacaaagaaattctggctaaagctcttgcccataaagcagatgaacttccgttaatc
atcgaactggtgagcaaagataaaaaatatgttatctgccacgccgattatcccttttgacgaatacgagtttggaa
gccagttgatcatcagcaggtaatctggaaccgcgaacgaatcagcaactcacaaaacgggatcgtgaaagaaatca
aaggcgcggacacgttcatctttggtcatacgccagcagtgaaaccactcaagtttgccaaccaaatgtatatcgat
accggcgcagtgttctgcgaaaacctaacattgattcaggtacagggagaaggcgcatgagactcgaaagcgtagct
aaatttcattcgccaaaaagcccgatgatgagcgactcaccacgggccacggcttctgactctctttccggtactga
tgtgatggctgctatggggatggcgcaatcacaagccggattcggtatggctgcattctgcggtaagcacgaactca
gccagaacgacaaacaaaaggctatcaactatctgatgcaatttgcacacaaggtatcggggaaataccgtggtgtg
gcaaagcttgaaggaaatactaaggcaaaggtactgcaagtgctcgcaacattcgcttatgcggattattgccgtag
tgccgcgacgccgggggcaagatgcagagattgccatggtacaggccgtgcggttgatattgccaaaacagagctgt
gggggagagttgtcgagaaagagtgcggaagatgcaaaggcgtcggctattcaaggatgccagcaagcgcagcatat
cgcgctgtgacgatgctaatcccaaaccttacccaacccacctggtcacgcactgttaagccgctgtatgacgctct
ggtggtgcaatgccacaaagaagagtcaatcgcagacaacattttgaatgcggtcacacgttagcagcatgattgcc
acggatggcaacatattaacggcatgatattgacttattgaataaaattgggtaaatttgactcaacgatgggttaa
ttcgctcgttgtggtagtgagatgaaaagaggcggcgcttactaccgattcgcctagttggtcacttcgacgtatc
gtctggaactccaaccatcgcaggcagagaggtctgcaaaatgcaatcccgaaacagttcgcaggtaatagttagag
cctgcataacggtttcgggatttttttatatctgcacaacaggtaagagcattgagtcgataatcgtgaagagtcggc
gagcctggttagccagtgctctttccgttgtgctgaattaagcgaataccggaagcagaaccggatcaccaaatgcg
tacaggcgtcatcgccgcccagcaacagcacaacccaaactgagccgtagccactgtctgtcctgaattcattagta
atagttacgctgcggccttttacacatgaccttcgtgaaagcgggtggcaggaggtcgcgctaacaacctcctgccg
ttttgcccgtgcatatcggtcacgaacaaatctgattactaaacacagtagcctggatttgttctatcagtaatcga
ccttattcctaattaaatagagcaaatccccttattgggggtaagacatgaagatgccagaaaaacatgacctgttg
gccgccattctcgcggcaaaggaacaaggcatcggggcaatccttgcgtttgcaatggcgtaccttcgcggacagata
taatgcggtgcgtttacaaaaacagtaatcgacgcaacgatgtgcgccattatcgcctggttcattcgtgaccttc
tcgacttcgccggactaagtagcaatctcgcttatataacgagcgtgtttatcggctacatcggtactgactcgatt
ggttcgcttatcaaacgcttcgctgctaaaaaagccggagtagaagatggtagaaatcaataatcaacgtaaggcgt
tcctcgatatgctggcgtggtcggagggaactgataacggacgtcagaaaaccagaaatcatggtttatgacgtcatt
gtaggcggagagctatttactgattactccgatcaccctcgcaaacttgtcacgctaaacccaaaactcaaatcaac
aggcgcttaagactggccgtcgttttacaacacagaaagagtttgtagaaacgcaaaaaggccatccgtcagggggcc
ttctgcttagtttgatgcctggcagttccctactctcgccttccgcttcctcgctcactgactcgctgcgctcggtc
gttcggctgcggcgagcggtcagctcactcaaaggcggtaatacggttatccacagaatcagggggataacgcaggg
aaagaacatgtgagcaaaaggccagcaaaaggccaggaaccgtaaaaaggccgcgttgctggcgtttttccataggc
tccgcccccctgacgagcatcacaaaaatcgacgctcaagtcagaggtggcgaaacccgacaggactataaagatac
caggcgtttccccctggaagctccctcgtgcgctctcctgttccgaccctgccgcttaccggatacctgtccgcctt
tctcccttcgggaagcgtggcgctttctcatagctcacgctgtaggtatctcagttcggtgtaggtcgttcgctcca
agctgggctgtgtgcacgaaccccccgttcagcccgaccgctgcgccttatccggtaactatcgtcttgagtccaac
ccggtaagacacgacttatcgccactggcagcagccactggtaacaggattagcagagcgaggtatgtaggcggtgc
tacagagttcttgaagtggtgggctaactacggctacactagaagaacagtatttggtatctgcgctctgctgaagc
cagttaccttcggaaaagagttggtagctcttgatccggcaaacaaaccaccgctggtagcggtggtttttttgtt
tgcaagcagcagattacgcgcagaaaaaaaggatctcaagaagatcctttgatcttttctacggggtctgacgctca
gtggaacgacgcgcgcgtaactcacgttaagggattttggtcatgagcttgcgccgtcccgtcaagtcagcgtaatg
ctctgcttt SEQ ID NO: 11
tagaaaaactcatcgagcatcaaatgaaactgcaatttattcatatcaggattatcaataccatatttttgaaaaag
ccgtttctgtaatgaaggagaaaactcaccgaggcagttccataggatggcaagatcctggtatcggtctgcgattc
cgactcgtccaacatcaatacaacctattaatttcccctcgtcaaaaataaggttatcaagtgagaaatcaccatga
gtgacgactgaatccggtgagaatggcaaaagtttatgcatttctttccagacttgttcaacaggccagccattacg
ctcgtcatcaaaatcactcgcatcaaccaaaccgttattcattcgtgattgcgcctgagcgaggcgaaatacgcgat
cgctgttaaaaggacaattacaaacaggaatcgagtgcaaccggcgcaggaacactgccagcgcatcaacaatattt
tcacctgaatcaggatattcttctaatacctggaacgctgtttttccggggatcgcagtggtgagtaaccatgcatc

SEQUENCE TABLES

```
atcaggagtacggataaaatgcttgatggtcggaagtggcataaattccgtcagccagtttagtctgaccatctcat
ctgtaacatcattggcaacgctacctttgccatgtttcagaaacaactctggcgcatcgggcttcccatacaagcga
tagattgtcgcacctgattgcccgacattatcgcgagcccatttatacccatataaatcagcatccatgttggaatt
taatcgcggcctcgacgtttcccgttgaatatggctcatattcttccttttcaatattattgaagcatttatcagg
gttattgtctcatgagcggatacatatttgaatgtatttagaaaaataaacaaataggggtcagtgttacaaccaat
taaccaattctgaacattatcgcgagcccatttatacctgaatatggctcataacacccttgtttgcctggcggca
gtagcgcggtggtcccacctgaccccatgccgaactcagaagtgaaacgccgtagcgccgatggtagtgtggggact
ccccatgcgagagtagggaactgccaggcatcaaataaaacgaaaggctcagtcgaaagactgggcctttcgcccgg
gctaattagggggtgtcgcccttattcgactctatagtgaagttcctattctctagaaagtataggaacttctgaag
tggggtcgacttaattaaggctgcgcgctcgctcgctcactgaggccgcccgggcaaagcccgggcgtcgggcgacc
tttggtcgcccggcctcagtgagcgagcgagcgcgcagagagggagtggccaactccatcactaggggttccttgta
gttaatgattaacccgccatgctacttatctacgtagcaagctagcaagatccaagctcagatctcgatcgagttgg
gccccagaagcctggtggttgtttgtccttctcaggggaaaagtgaggcggccccttggaggaagggggccgggcaga
atgatctaatcggattccaagcagctcaggggattgtcttttctagcaccttcttgccactcctaagcgtcctccg
tgaccccggctgggatttagcctggtgctgtgtcagcccggtctcccaggggcttcccagtggtccccaggaaccc
tcgacagggcccggtctctctcgtccagcaagggcagggacgggccacaggccacaggccctcgatcgaggaactga
aaaaccagaaagttaactggtaagtttagtcttttttgtcttttatttcaggtcccggatccggtggtggtgcaaatc
aaagaactgctcctcagtggatgttgcctttacttctaggcctgacggaagtgttacttctgctctaaaagctgcg
gaattgtacccgcggccgccaccatgtggggaagcgacagactggccggagctggaggggaggagcagccgtcacc
gtggcgttcactaacgcgcgggactgcttctccatctgccgcggaggctgtgcgcccagctgcaccctcctgcagaa
ccaggccatcgaggtggtgtggtcccaccaaccggccttttttgagctgggctcgaggggaaggcacttttcggaccagg
gagaaaatgtggcggagatcaaccgccaggtcggccagaagctgggactgtccaacggcggacaggtgttcctcaag
ccgtgcagccacgtggtgtcctgccaacaggtggaagtggagccgctctccgccgacgactgggagatcctcgaatt
gcatgcctgagcctcgaacagcagctcgttggaccagattcgcattgtgttcccgaagcgcatattccccgtgtggg
tcgatcagcagacctatatcttcatccagattgtggccctcatcccggccgcctcatacggacggctggaaactgac
accaagctgctgattcaacctaagacccgaggggccaaagaaaacaccttctccaaggccgacgctgagtacaagaa
gctccactcctacggacgggaccagaaggggatgatgaaggagctgcaaaccaagcagctccagagcaacaccgtgg
ggatcaccgagtccaatgaaaacgagtcgaaatcccagtcgattcatcttccgtggccagcctgtggactatgatc
ggttccattttctcgttccaatctgagaagaagcaggaaactagctgggggctgactgagatcaacgccttcaagaa
catgcagtccaaagtggtgcctctggataacatctttcgcgtgtgcaagtcccaaccgccctcaatctacaacgcgt
ccgctacctccgtgtttcataagcactgtgccatccacgtgttcccatgggatcaggaatacttcgatgtcgaacct
tccttcaccgtgacttacgggaagcttgtcaagctcctcagccccaacgcagcagcaatcgaaaactaagcagaacgt
gctttccccggagaaggagaagcaaatgtcagaaccactcgaccagaagaaaatcagatcggatcataacgaagagg
acgagaaggcctgcgtccttcaggtggtctgaacggcctggaggagctgaacaacgcgattaagtacaccaagaac
gtcgaggtccttcacctgggaaaggtgtggattccggatgatctgaggaaacgcctcaacatcgaaatgcacgctgt
ggtgcggattaccccggtcgaggtcaccccaaagatccctcgctccttgaagctgcagccgcgagaaaacttgccca
aggacatttctgaagaggatatcaagactgtgttctactcctggctgcaacaagcactaccaccatgctccctctg
gtcatttcggaggaagaattcatcaaactggaaccaaggcaggactgaaagaattctccctgtccatcgtgcactc
ctgggaaaaggagaaggacaagaatatcttcctgctgtccccaatctgctgcaaaagaccacgatccaggtgctgc
tcgaccccatggtgaaggaggaaaactcagaagagatcgacttcatcctgccgttccttaagctgagttcactggga
ggcgtgaactccctggcgtgtcctcgctggacacatcactcactcgtgctcactctgagcagacagct
tatgagcttggtcgccggactcagaaacggtgccctcctgctcaccggcggcaagggatcgggaaagtccaccctcg
ctaaggccatttgcaaagaggcattcgataagctggacgcccatgtggagcgggtggactgtaaggccctccgcgga
aagcgattggaaaatattcaaaagactctcgaagtcgccttttccgaagccgtctggatgcagccctcggtcgtcct
gctcgacgatctggacctcatcgctgggctgccggccgtgccggagcatgaacactccccctgacgcggtccagtcgc
aacggctcgcccacgccctgaacgatatgattaaggaattcatctcaatgggatcactggtggccctgatcgcgact
tcccagagccagcagtccctgcaccctctgctggtgtcggcccagggcgtgcacattttttcagtgtgtgcaaacat
ccagccgcccaaccaggagcagcggtgcgaaatcctgtgcaacgtgattaagaacaagctggactgcgatatcaaca
agtttaccgaccttgatctccaacatggctaaggagactgggggcttcgtggctcgggacttcacagtgttggtg
gaccgggcaattcactccagactgtcccgccagagcatttccacccgcgaaaaactggtcctgaccaccctcgactt
ccagaaggccctcagaggcttccttcctgcgagcctcagatccgtcaaccttcacaagccgcgggaccttggctggg
acaagatcggtgggctccacgaggtgcggcagatcctcatggacaccattcagctgcctgcaaagtaccccgagctg
ttcgccaacttgccgattcgccagcgcacgggaatcctgctctacggcccccccggcaccggaaagaccctgctggc
cggtgtgatcgcccgggaatcgaggatgaacttcatctccgtgaaggggacccgaactcctgtccaagtacatcggtg
cctccgaacaggccgtgcgcgatatattcattagggcccaggccgcgaagccctgcattctgttcttcgacgagttt
gaatcgatcgcgccccggaggggccacgacaacacgggagtgaccgaccgggtggtgaaccagctgctcacccaact
ggatggcgtggaaggccttcagggagtgtacgtgctggcggctacctccagaccggacctgatcgatccggccctgc
tgcgccccgggagactggacaagtgcgtgtattgccctccccctgaccaggtgctcaaggttggaaatcctcaacgtg
ctctcggactccctgccactggcagatgatgtggacctccagcatggcctccgtgactgacagcttcacaggagc
cgatctgaaggcccctgctttacaacgcccagttggaggcgctgcacggtatgctgctgtcctccggtctgcaggatg
gctcctcctcttccgatagcgacctgtcgctgagcagcatggtgttcctgaaccattccagcggctccgatgacagc
gcgggcgacggagaatgtggactggatcaatccctggtgtccctggagatgacgagattctgccagacgagtccaa
gttcaacatgtacaggctgtacttcggcagcagctacgagtccgagctgggaaatggtacctcgtccgacctgtcaa
gccagtgcctgtccgcgcctttcctccatgacccaggacctcctgggagtgccagggaaggatcagctgttcagccag
cctcccgtgctgcgcactgcgagccaggaagggtgccaggaattgacccaagagcagcgggaccaactgcgcgcgga
catttcgatcatcaaaggcagataccgctcccaatccggggaggacgaaagcatgaaccagccgggcctatcaaga
ctagactggcaatctcccaaagccacctgatgaccgcactgggacacccggccctcgatctcggaggacgactgg
aagaacttcgctgagctgtacgaatccttccagaatccgaagcggagaaagaaccagagcggaactatgttccggcc
cggacagaaggtgaccctgcctgatgtacaagtaataagcctcgactgtgccttctagttgccagccatctgttgt
ttgcccctccccgtgccttccttgacccttggaaggtgccactcccactgtcctttcctaataaaatgaggaaattg
catcgcattgtctgagtaggtgtcattctattctgggggtggggtggggcaggacagcaaggggaggattgggaa
gacaatgacaggtcgagttctacgtagataagtagcatgggggatttaatcattaactacaaggaaccccctagtgatg
gagttggccactccctctctgcgcgctcgctcgctcactgaggccgggcgaccaaaggtcgcccgacgcccgggctt
tgcccggcggcctcagtgagcgagcgagcgcgcagccttaattaacctaaggaaaatgaagtgaagttcctatact
ttctagagaataggaacttctatagtgagtcgaataagggcgacacaaaatttattctaaatgcataataaatactg
ataacatcttatagtttgtattatattttgtattatcgttgacatgtataattttgatatcaaaaactgattttccc
tttattattttcgagatttattttcttaattctctttaacaaactagaaatattgtatatacaaaaaatcataaata
```

-continued

SEQUENCE TABLES

```
atagatgaatagtttaattataggtgttcatcaatcgaaaagcaacgtatcttatttaaagtgcgttgcttttttc
tcatttataaggttaaataattctcatatatcaagcaaagtgacaggcgcccttaaatattctgacaaatgctcttt
ccctaaactcccccccataaaaaaaccgccgaagcgggtttttacgttatttgcggattaacgattactcgttatca
gaaccgcccaggggggcccgagcttaaccttttttatttgggggagagggaagtcatgaaaaaactaacctttgaaatt
cgatctccagcacatcagcaaaacgctattcacgcagtacagcaaatccttccagacccaaccaaaccaatcgtagt
aaccattcaggaacgcaaccgcagcttagaccaaaacaggaagctatgggcctgcttaggtgacgtctctcgtcagg
ttgaatggcatggtcgctggctggatgcagaaagctggaagtgtgtgtttaccgcagcattaaagcagcaggatgtt
gttcctaaccttgccgggaatggctttgtggtaataggccagtcaaccagcaggatgcgtgtaggcgaatttgcgga
gctattagagcttatacaggcattcggtacagagcgtggcgttaagtggtcagacgaagcgagactggctctggagt
ggaaagcgagatggggagacagggctgcatgataaatgtcgttagtttctccggtggcaggacgtcagcatatttgc
tctggctaatggagcaaaagcgacgggcaggtaaagacgtgcattacgttttcatggatacaggttgtgaacatcca
atgacatatcggtttgtcagggaagtttgtgaagttctggatataccgctcaccgtattgcaggttgatatcaaccc
ggagcttggacagccaaatggttatacggtatgggaaccaaaggatattcagacgcgaatgcctgttctgaagccat
ttatcgatatggtaaagaaatatggcactccatacgtcggcggcgcgttctgcactgacagattaaaactcgttccc
ttcaccaaatactgtgatgaccattcgggcgagggaattacaccacgtggattggcatcagagctgatgaaccgaa
gcggctaaagccaaagcctggaatcagatatcttgctgaactgtcagacttttgagaaggaagatatcctcgcatggt
ggaagcaacaaccattcgatttgcaaataccggaacatctcggtaactgcatattctgcattaaaaaatcaacgcaa
aaaatcggacttgcctgcaaagatgaggagggattgcagcgtgttttaatgaggtcatcacgggatcccatgtgcg
tgacggacatcgggaaacgccaaaggagattatgtaccgaggaagaatgtcgctggacggtatcgcgaaaatgtatt
cagaaaatgattatcaagccctgtatcaggacatggtacgagctaaaagattcgataccggctcttgttctgagtca
tgcgaaatatttggagggcagcttgatttcgacttcgggagggaagctgcatgatgcgatgttatcggtgcggtgaa
tgcaaagaagataaccgcttccgaccaaatcaaccttactggaatcgatggtgtctccggtgtgaaagaacaccaac
agggtgttaccactaccgcaggaaaaggaggacgtgtggcgagacagcgacgaagtatcaccgacataatctgcga
aaactgcaaataccttccaacgaaacgcaccagaaataaaaccaagccaatcccaaaagaatctgacgtaaaaacct
tcaactacacggctcacctgtgggatatccgtggctaagacgtcgtgcgaggaaaacaaggtgattgaccaaaatc
gaagttacgaacaagaaagcgtcgagcgagctttaacgtgcgctaactgcggtcagaagctgcatgtgctggaagtt
cacgtgtgtgagcactgctgcgcagaactgatgagcgatccgaatagctcgatgcacgaggaagaagatgatggcta
aaccagcgcgaagacgatgtaaaaacgatgaatgccgggaatggtttcaccctgcattcgctaatcagtggtggtgc
tctccagagtgtggaaccaagatagcactcgaacgacgaagtaaagaacgcgaaaaagcggaaaaagcagcagagaa
gaaacgacgacgagaggagcagaaacagaaagataaacttaagattcgaaaactcgccttaaagccccgcagttact
ggattaaacaagcccaacaagccgtaaacgccttcatcagagaaagagaccgcgacttaccatgtatctcgtgcgga
acgctcacgtctgctcagtgggatgccggacattaccggacaactgctgcggcacctcaactccgatttaatgaacg
caatattcacaagcaatgcgtggtgtgcaaccagcacaaaagcggaaatctcgttccgtatcgcgtcgaactgatta
gccgcatcgggcaggaagcagtagacgaaatcgaatcaaaccataaccgccatcgctggactatcgaagagtgcaag
gcgatcaaggcagagtaccaacagaaactcaaagacctgcgaaatagcagaagtgaggccgcatgacgttctcagta
aaaaccattccagacatgctcgttgaagcatacggaaatcagacagaagtagcacgcagactgaaatgtagtcgcgg
tacggtcagaaaatacgttgatgataaagacgggaaaatgcacgccatcgtcaacgacgttctcatggttcatcgcg
gatggagtgaaagagatgcgctattacgaaaaaattgatggcagcaaataccgaaatatttgggtagttggcgatct
gcacggatgctacacgaacctgatgaacaaactggatacgattggattcgacaacaaaaaagacctgcttatctcgg
tgggcgatttggttgatcgtggtgcagagaacgttgaatgcctggaattaatcacattccctggttcagagctgta
cgtggaaaccatgagcaaatgatgattgatggcttatcagagcgtggaaacgttaatcactggctgcttaatggcgg
tggctggttctttaatctcgattacgacaaagaaattctggctaaagctcttgcccataaagcagatgaacttccgt
taatcatcgaactggtgagcaaagataaaaaatatgttatctgccacgccgattatccctttgacgaatacgagttt
ggaaagccagttgatcatcagcaggtaatctggaaccgcgaacgaatcagcaactcacaaaacgggatcgtgaaaga
aatcaaaggcgcggacacgtttcatctttggtcatacgccagcagtgaaaatcactcaagtttgccaaccaaatgtata
tcgataccggcgcagtgttctgcggaaaacctaacattgattcaggtacagggagaaggcgcatgagactcgaaagcg
tagctaaatttcattcgccaaaaagcccgatgatgagcgactcaccacgggccacggcttctgactctctttccggt
actgatgtgatggctgctatggggatggcgcaatcacaagccggattcggtatggctgcattctgcggtaagcacga
actcagccagaacgacaaacaaaaggctatcaactatctgatgcaatttgcacacaaggtatcggggaaataccgtg
gtgtggcaaagcttgaaggaaatactaaggcaaaggtactgcaagtgctcgcaacattcgcttatgcggattattgc
cgtagtgccgcgacgccggggcaagatgcagagattgccatggtacaggccgtgcggttgatattgccaaaacaga
gctgtggggagagttgtcgagaaagagtgcggaagatgcaaaggcgtcggctattcaaggatgccagcaagcgcag
catatcgcgctgtgacgatgctaatcccaaaccttacccaacccacctggtcacgcactgttaagccgctgtatgac
gctctggtggtgcaatgccacaaagaagagtcaatcgcagacaacattttgaatgcggtcacacgttagcagcatga
ttgccacggatggcaacatattaacggcatgatattgacttattgaataaaattgggtaaatttgactcaacgatgg
gttaattcgctcgttgtggtagtgagatgaaaagaggcggcgcttactaccgattccgcctagttggtcacttcgac
gtatcgtctggaactccaaccatcgcaggcagagaggtctgcaaaatgcaatcccgaaacagttcgcaggtaatagt
tagagcctgcataacggtttcgggattttttatatctgcaacaggtaagagcattgagtcgataatcgtgaagag
tcggcgagcctggttagccagtgctcttccgttgtgctgaattaagcgaataccggaagcagaaccggatcaccaa
atgcgtacaggcgtcatcgccgcccagcaacagcacaacccaaactgagccgtagccactgtctgtcctgaattcat
tagtaatagttacgctgcggcctttacacatgaccttcgtgaaagcgggtggcaggaggtcgcgctaacaacctcc
tgccgttttgcccgtgcatatcggtcacgaacaaatctgattactaaacacagtagcctggatttgttctatcagta
atcgaccttattcctaattaaatagagcaaatcccttattggggtaagacatgaagatgccagaaaaacatgacc
tgttggccgccattctcgcggcaaaggaacaaggcatcggggcaatccttgcgtttgcaatggcgtaccttcgcggc
agatataatggcggtgcgtttacaaaaacagtaatcgacgcaacgatgtgcgccattatcgcctggttcattcgtga
ccttctcgacttcgccggactaagtagcaatctgcttatataacgagcgtgtttatcggctacatcggtactgact
cgattggttcgcttatcaaacgcttcgctgctaaaaaagccggagtagaagatggtagaaatcaataatcaacgtaa
ggcgttcctcgatatgctggcgtggtcggagggaactgataacggacgtcagaaaaccagaaatcatggttatgacg
tcattgtaggcggagagctatttactgattactccgatcaccctcgcaaacttgtcacgctaaacccaaaactcaaa
tcaacaggcgcttaagactggccgtcgttttacaacacagaaagagtttgtagaaacgcaaaaaggccatccgtcag
gggccttctgcttagtttgatgcctggcagttccctactctcgccttccgcttcctcgctcactgactcgctgcgct
cggtcgttcggctgcggcgagcggtatcagctcactcaaaggcggtaatacggttatccacagaatcaggggataac
gcaggaaagaacatgtgagcaaaaggccagcaaaaggccaggaaccgtaaaaaggccgcgttgctggcgtttttcca
taggctccgcccccctgacgagcatcacaaaaatcgacgctcaagtcagaggtggcgaaacccgacaggactataaa
gataccaggcgtttccccctggaagctccctcgtgcgctctcctgttccgaccctgccgcttaccggatacctgtcc
gcctttctcccttcgggaagcgtggcgctttctcatagctcacgctgtaggtatctcagttcggtgtaggtcgttcg
ctccaagctgggctgtgtgcacgaaccccccgttcagcccgaccgctgcgccttatccggtaactatcgtcttgagt
```

| SEQUENCE TABLES |
|---|
| ccaacccggtaagacacgacttatcgccactggcagcagccactggtaacaggattagcagagcgaggtatgtaggc
ggtgctacagagttcttgaagtggtgggctaactacggctacactagaagaacagtatttggtatctgcgctctgct
gaagccagttaccttcggaaaaagagttggtagctcttgatccggcaaacaaaccaccgctggtagcggtggttttt
ttgtttgcaagcagcagattacgcgcagaaaaaaaggatctcaagaagatcctttgatcttttctacggggtctgac
gctcagtggaacgacgcgcgcgtaactcacgttaagggattttggtcatgagcttgcgccgtcccgtcaagtcagcg
taatgctctgcttt |

SEQ ID NO: 12
tagaaaaactcatcgagcatcaaatgaaactgcaatttattcatatcaggattatcaataccatatttttgaaaaag
ccgtttctgtaatgaaggagaaaactcaccgaggcagttccataggatggcaagatcctggtatcggtctgcgattc
cgactcgtccaacatcaatacaacctattaatttcccctcgtcaaaaataaggttatcaagtgagaaatcaccatga
gtgacgactgaatccggtgagaatggcaaaagtttatgcatttcttttccagacttgttcaacaggccagccattacg
ctcgtcatcaaaatcactcgcatcaaccaaaccgttattcattcgtgattgcgcctgagcgaggcgaaatacgcgat
cgctgttaaaaggacaattacaaacaggaatcgagtgcaaccggcgcaggaacactgccagcgcatcaacaatattt
tcacctgaatcaggatattcttctaatacctggaacgctgtttttccggggatcgcagtggtgagtaaccatgcatc
atcaggagtacggataaaatgcttgatggtcggaagtggcataaattccgtcagccagtttagtctgaccatctcat
ctgtaacatcattggcaacgctacctttgccatgtttcagaaacaactctggcgcatcgggcttcccatacaagcga
tagattgtcgcacctgattgcccgacattatcgcgagcccatttataccatataaatcagcatccatgttggaatt
taatcgcggcctcgacgtttcccgttgaatatggctcatattcttcctttttcaatattattgaagcatttatcagg
gttattgtctcatgagcggatacatatttgaatgtatttagaaaaataaacaaataggggtcagtgttacaaccaat
taaccaattctgaacattatcgcgagcccatttatacctgaatatggctcataacacccttgtttgcctggcggca
gtagcgcggtggtcccacctgaccccatgccgaactcagaagtgaaacgccgtagcgccgatggtagtgtgggact
ccccatgcgagagtagggaactgccaggcatcaaatcaaacgaaaggctcagtcgaaagactgggcctttcgcccgg
gctaattaggggtgtcgcccttattcgactctatagtgagtcgtattaagaaagtataggaacttctgaag
tggggtcgacttaattaaggctgcgcgctcgctcgctcactgaggccgcccgggcaaagcccgggcgtcgggcgacc
tttggtcgcccggcctcagtgagcgagcgagcgcgcagagagggagtggccaactccatcactaggggttccttgta
gttaatgattaacccgccatgctacttatctacgtagcaagctagcgcttagctgaatggggtccgcctcttttccc
tgcctaaacagacaggaactcctgccaattgagggcgtcaccgctaaggctccgcccagcctgggctccacaacca
atgaagggtaatctcgacaaagagcaaggggtggggcgcgggccgcgcaggtgcagcagcacacaggctggtcgggag
ggcggggcgcgacgtctgccgtgcggggtcccggcatcggttgcgcgcgcggccgcgccgccaccatgtgggaagc
gacagactggccggagctggaggggaggagcagccgtcaccgtggcgttcactaacgcgcgggactgctttctcca
tctgccgcggaggctggtcgcccagctgcacctcctgcagaaccaaggccatcgaggtggtgtggtcccaccaaccgg
ccttttgagctgggtcgagggaaggcacttttcggaccagggagaaatgtggcggagatcaaccgccaggtcggc
cagaagctgggactgtccaacggcggacaggtgttcctcaagccgtgcagccacgtggtgtcctgccaacaggtgga
agtggagccgctctccgccgacgactgggagatcctcgaattgcatgccgtgagcctcgaacagcatctgttggacc
agattcgcattgtgttcccgaaggccatattcccgtgtgggtcgatcagcagacctatatcttcatccagattgtg
gccctcatcccggccgcctcatacggacggctggaaactgaccaccaaggctgctgattcaacctaagaccggagggc
caaagaaaacaccttctccaaggccgacgctgagtacaagaagctccactcctacggacgggaccagaaggggatga
tgaaggagctgcaaaccaagcagctccagagcaacaccgtggggatcaccgagtccaatgaaaacgagtcggaaatc
ccagtcgattcatcttccgtggccagcctgtggactatgatcggttccattttctcgttccaatctgagaagaagca
ggaaactagctgggggctgactgagatcaacgccttcaagaacatgcagtccaaagtggtgcctctggataacatct
ttcgcgtgtgcaagtcccaaccgccctcaatctacaacgcgtccgctacctccgtgtttcataagcactgtgccatc
cacgtgttcccatgggatcaggaatacttcgatgtcgaaccttccttcaccgtgacttacgggaagcttgtcaagct
cctcagccccaagcagcagcaatcgaaaactaagcagaacgtgctttccccggagaaggagaagcaaatgtcagaac
cactcgaccagaagaaaatcagatcggatcataacgaagaggacgaaaggcctgcgtccttcaggtggtctggaac
ggcctggaggagctgaacaacgcgattaagtacaccaagaacgtcgaggtccttcacctgggaaaggtgtggattcc
ggatgatctgaggaaacgcctcaacatcgaaatgcacgctgtggtgcggattaccccggtcgaggtcaccccaaaga
tccctcgctccttgaagctgcagccgcgagaaaacttgcccaaggacatttctgaagaggatatcaagactgtgttc
tactcctggctgcaacagagcactaccaccatgctccctctggtcatttcggaggagaattcatcaaactggaaac
caaggacggactgaaagaattctccctgtccatcgtgcactcctgggaaaaggagaaggacaagaatatcttcctgc
tgtcccccaatctgctgcaaaagaccacgatccaggtgctgctcgacccccatggtgaaggaggaaaactcagaagag
atcgacttcatcctgccgttccttaagctgagttcactgggaggcgtgaactcccttggcgtgtcctcgctggagca
catcactcactcactgctgggccggcctctgagcagacagcttatgagcttggtcgggactcagaaacggtgccc
tcctgctcaccggcggcaagggatcgggaaagtccaccctcgctaaggccatttgcaaagaggcattcgataagctg
gacgccatgtggagcgggtggactgtaaggccctccgcggaaagcgattggaaaatattcaaaagactctcgaagt
cgccttttccgaagccgtctgtgatgcagccctcggtcgtcctgctcgacgatctggacctcatcgctgggctgccgg
ccgtgccggagcatgaacactccctgacgcggtccagtcgcaacggctcgcccacgccctgaacgatatgattaag
gaattcatctcaatgggatcactggtggccctgatcgcgacttccagagccagcagtcctgcaccctctgctggt
gtcggcccagggcgtgcacattttcagtgtgtgcaacacatccagccgcccaaccaggagcagcggtgcgaaatcc
tgtgcaacgtgattaagaacaagctggactgcgatatcaacaagtttaccgaccttgatctccaacatgtggctaag
gagactgggggcttcgtggctcgggacttcacagtgttggtggaccgggcaattcactccagactgtcccgccagag
catttccacccgcgaaaaactggtcctgaccaccctcgacttccagaaggccctcagaggcttccttcctgcgagcc
tcagatccgtcaaccttcacaagccgcgggacctggctgggacaagatcggtgggctccacgaggtgcggcagatc
ctcatggacaccattcagctgcctgcaaagtaccccgagctgttcgccaacttgccgattcgccagcgcacgggaat
cctgctctacgcccccgggcaccggaaagaccctgctggccggtgtgatcgcccgggaatcgaggatgaacttca
tctccgtgaagggacccgaactcctgtccaagtacatcggtgcctccgaacaggcctgtgcgcgatatattcattagg
gccaggccgcgaagccctgcattctgttcttcgacgagtttgaatcgatcgcgccccgagggggccaacaacac
gggagtgaccgaccgggtggtgaaccagctgctcacccaactggatggcgtggaaggccttcagggagtgtacgtgc
tggcggctacctccagaccggacctgatcgatccggccctgctgcgcccgggagactggacaagtgcgtgtattgc
cctccccctgaccaggtgtcaaggttggaaatcctcaacgtgctctcggactccctgccactggcagatgatgtgga
cctccagcatgtggcctccgtgactgacagcttcacaggagccgatctgaaggccctgctttacaacgcccagttgg
aggcgctgcacggtatgctgctgtcctccggtctgcaggattggctcctcttccgatagcgacctgtcgctgagc
agcatggtgttcctgaaccattccagcggctccgatgacagcgcggggacggagaatggtggactggatcaatcctc
ggtgtccctggagatgagcgagattctgccagacgagtccaagttcaacatgtacaggctgtacttcggcagcagct
acgagtccgagctgggaaatggtacctcgtccgacctgtcaagccagtgcctgtccgcgccttcctccatgacccag
gacctccctggagtgccagggaaggatcagctgttcagccagcctcccgtgctgcgcactgcgagccaggaagggtg
ccaggaattgacccaagagcagcgggaccaactgcgcgcggacatttcgatcatcaaaggcagataccgctcccaat |

SEQUENCE TABLES

```
ccggggaggacgaaagcatgaaccagcccgggcctatcaagactagactggcaatctcccaaagccacctgatgacc
gcactgggacacacccggccctcgatctcggaggacgactggaagaacttcgctgagctgtacgaatccttccagaa
tccgaagcggagaaagaaccagagcggaactatgttccggcccggacagaaggtgaccctggcctgaagtactgcgg
atcctgcagatctgcctcgactgtgccttctagttgccagccatctgttgtttgccctccccccgtgccttccttga
ccctggaaggtgccactcccactgtccttcctaataaaatgaggaaattgcatcgcattgtctgagtaggtgtcat
tctattctgggggggtgggtggggcaggacagcaaggggggaggattgggaagacaatagcaggcatgctgggactc
gagttctacgtagataagtagcatggcgggttaatcattaactacaaggaacccctagtgatggagttggccactcc
ctctctgcgcgctcgctcgctcactgaggccgggcgaccaaaggtcgcccgacgcccgggcttgcccgggcggcct
cagtgagcgagcgagcgcgcagccttaattaacctaaggaaaatgaagtgaagttcctatacttctctagagaatagg
aacttctatagtgagtcgaataagggcgacacaaaatttattctaaatgcataataaatactgataacatcttatag
tttgtattatattttgtattatcgttgacatgtataattttgatatcaaaaactgattttccctttattatttcga
gatttattttcttaattctctttaacaaactagaaatattgtatatacaaaaaatcataaataatagatgaatagtt
taattataggtgttcatcaatcgaaaaagcaacgtatcttatttaaagtgcgttgcttttttctcatttataaggtt
aaataattctcatatatcaagcaaagtgacaggcgcccttaaatattctgacaaatgctctttccctaaactccccc
cataaaaaaacccgccgaagcgggtttttacgttatttgcggattaacgattactcgttatcagaaccgcccagggg
gcccgagcttaacctttttatttgggggagggaagtcatgaaaaaactaaccttttgaaattcgatctccagcaca
tcagcaaaacgctattcacgcagtacagcaaatccttccagacccaaccaaaccaatcgtagtaaccattcaggaac
gcaaccgcagcttagaccaaaacaggaagctatgggcctgcttaggtgacgtctctcgtcaggttgaatggcatggt
cgctggctggatgcagaaagctggaagtgtgtgtttaccgcagcattaaagcagcaggatgttgttcctaaccttgc
cgggaatggctttgtggtaataggccagtcaaccagcaggatgcgtgtaggcgaatttgcggagctattagagctta
tacaggcattcggtacagagcgtggcgttaagtggtcagacgaagcgagactggctctggagtggaaagcgagatgg
ggagacagggctgcatgataaatgtcgttagtttctccggtggcaggacgtcagcatatttgctctggctaatggag
caaaagcgacgggcaggtaaagacgtgcattacgttttcatggatacaggttgtgaacatccaatgacatatcggtt
tgtcagggaagttgtgaagttctgggatataccgctcaccgtattgcaggttgtatcaacccggagcttggacagc
caaatggttatacggtatgggaaccaaaggatattcagacgcgaatgcctgttctgaagccatttatcgatatggta
aagaaatatggcactccatacgtcggcggcgcgttctgcactgacagattaaaactcgttcccttccaccaaatactg
tgatgaccatttcgggcgagggaattacaccacgtggattggcatcagagctgatgaaccgaagcggctaaagccaa
agcctggaatcagatatcttgctgaactgtcagactttgagaaggaaaacaaggtgattgaccaaaatcgaagttacgaacaa
gaaagcgtcgagcgagctttaacgtgcgctaactgcggtcagaagctgcatgtgctggaagttcacgtgtgtgagca
ctgctgcgcagaactgatgagcgatccgaatagctcgatgcacgaggaagaagatgatggctaaaccagcgcgaaga
cgatgtaaaaacgatgaatgccgggaatggtttcaccctgcattcgctaatcagtggtggtgctctccagagtgtgg
aaccaagatagcactcgaacgacgaagtaaagaacgcgaaaaagcggaaaaagcagcagagaagaaacgacgacgag
aggagcagaaacagaaagataaacttaagattcgaaaactcgcctaaagccccgcagttactggattaaacaagcc
caacaagccgtaaacgccttcatcagagaaagagaccgcgacttaccatgtatctcgtgcggaacgctcacgtctgc
tcagtgggatgccggacattaccggacaactgctgcggcacctcaactccgatttaatgaacgcaatattcacaagc
aatgcgtggtgtgcaaccagcacaaaagcggaaatctcgttccgtatcgcgtcgaactgattagccgcatcgggcag
gaagcagtagacgaaatcgaatcaaaccataaccgccatcgctggactatcgaagagtgcaaggcgatcaaggcaga
gtaccaacagaaactcaaagacctgcgaaatagcagaagtgaggccgcatgacgttctcagtaaaaaccattccaga
catgctcgttgaagcatacggaaatcagacagaagtagcacgcagactgaaatgtagtcgcggtacggtcagaaaat
acgttgatgataaagacgggaaaatgcacgccatcgtcaacgacgttctcatggttcatcgcggatggagtgaaaga
gatgcgctattacgaaaaaattgatggcagcaaataccgaaatattttgggtagttggcgatctgcacggatgctaca
cgaacctgatgaacaaactggatacgattggattcgacaacaaaaaagacctgcttatctcggtgggcgatttggtt
gatcgtggtgcagagaacgttgaatgcctggaattaatcacattcccctggttcagagctgtacgtggaaaccatga
gcaaatgatgattgatggcttatcagagcgtggaaacgttaatcactggctgcttaatggcggtggctggttctta
atctcgattacgacaaagaaattctggctaaagctcttgcccataaagcagatgaacttccgttaatcatcgaactg
gtgagcaaagataaaaaatatgttatctgccacgccgattatcctttgacgaatacgagttggaaagccagtga
tcatcagcaggtaatctggaaccgcgaacgaatcagcaactcacaaaacgggatcgtgaaagaaatcaaaggcgcgg
acacgttcatctttggtcatacgccagcagtgaaaccactcaagtttgccaaccaaatgtatatcgataccggcgca
gtgttctgcggaaacctaacattgattcaggtacagggagaaggcgcatgagactcgaaagcgtagctaaatttcat
tcgccaaaagcccgatgatgagcgactcaccacgggccacggcttctgactctctttccggtactgatgtgatggc
tgctatggggatggcgcaatcacaagccgattcggtatggctgcattctgcggtaagcacgaactcagccagaacg
acaaacaaaaggctatcaactatctgatgcaatttgcacacaaggtatcggggaaataccgtggtgtggcaaagctt
gaaggaaatactaaggcaaaggtactgcaagtgctcgcaacattcgcttatgcggattattgccgtagtgccgcgac
gccggggcaagatgcagagattgccatggtacaggccgtgcggttgatattgccaaaacagagctgtggggggagag
ttgtcgagaaagagtgcggaagatgcaaaggcgtcggctattcaaggatgccagcaagcgcagcatatcgcgctgtg
acgatgctaatcccaaaccttacccaacccacctggtcacgcactgttaagccgctgtatgacgctctggtggtgca
atgccacaaagaagagtcaatcgcagacaacattttgaatgcggtcacacgttagcagcatgattgccacggatggc
aacatattaacggcatgatattgacttattgaataaaattgggtaaatttgactcaacgatgggtttaattcgctcgt
tgtggtagtgagatgaaaagaggcggcgcttactaccgattccgcctagttggtcacttcgacgtatcgtctgaac
tccaaccatcgcaggcagagaggtctgcaaaatgcaatcccgaaacagttcgcaggtaatagttagagcctgcataa
cggtttcgggattttttatatctgcacaacaggtaagagcattgagtcgataatcgtgaagagtcggcgagcctggt
tagccagtgctctttccgttgtgctgaattaagcgaataccggaagcagaaccggatcaccaaatgcgtacaggcgt
catcgccgcccagcaacgacaacccaaactgagcctagccactgtctgtcctgaattcattagtaataagttacg
ctgcggccttttacacatgaccttcgtgaaagcgggtggcaggaggtcgcgctaacaacctcctgccgttttgcccg
tgcatatcggtcacgaacaaatctgattactaaacacagtagcctggatttgttctatcagtaatcgaccttattcc
taattaaatagagcaaatcccttattgggggtaagacatgaagatgccagaaaacatgacctgttggccgccatt
ctcgcggcaaaggaacaaggcatcgggcaatccttgcgtttgcaatggcgtaccttcgcggcagatataatggcgg
tgcgtttacaaaaacagtaatcgacgcaacgatgtgcgccattatcgcctggttcattcgtgaccttctcgacttcg
``` ccggactaagtagcaatctcgcttatataacgagcgtgtttatcggctacatcggtactgactcgattggttcgctt
atcaaacgcttcgctgctaaaaaagccggagtagaagatggtagaaatcaataatcaacgtaaggcgttcctcgata
tgctggcgtggtcggagggaactgataacggacgtcagaaaaccagaaatcatggttatgacgtcattgtaggcgga
gagctatttactgattactccgatcaccctcgcaaacttgtcacgctaaacccaaaactcaaatcaacaggcgctta
agactggccgtcgttttacaacacagaaagagtttgtagaaacgcaaaaaggccatccgtcaggggccttctgctta
gtttgatgcctggcagttccctactctcgccttccgcttcctcgctcactgactcgctgcgctcggtcgttcggctg
cggcgagcggtcagctcactcaaaggcggtaatacggttatccacagaatcaggggataacgcaggaaagaacat
gtgagcaaaaggccagcaaaaggccaggaaccgtaaaaaggccgcgttgctggcgtttttccataggctccgcccc
ctgacgagcatcacaaaaatcgacgctcaagtcagaggtggcgaaacccgacaggactataaagataccaggcgttt
ccccctggaagctccctcgtgcgctctcctgttccgaccctgccgcttaccggatacctgtccgcctttctccctt
gggaagcgtggcgctttctcatagctcacgctgtaggtatctcagttcggtgtaggtcgttcgctccaagctgggct
gtgtgcacgaaccccccgttcagcccgaccgctgcgccttatccggtaactatcgtcttgagtccaacccggtaaga
cacgacttatcgccactggcagcagccactggtaacaggattagcagagcgaggtatgtaggcggtgctacagagtt
cttgaagtggtgggctaactacggctacactagaagaacagtatttggtatctgcgctctgctgaagccagttacct
tcggaaaaagagttggtagctcttgatccggcaaacaaaccaccgctggtagcggtggtttttttgtttgcaagcag
cagattacgcgcagaaaaaaaggatctcaagaagatcctttgatcttttctacggggtctgacgctcagtggaacga
cgcgcgcgtaactcacgttaagggattttggtcatgagcttgcgccgtcccgtcaagtcagcgtaatgctctgcttt SEQ ID NO: 13
tagaaaaactcatcgagcatcaaatgaaactgcaatttattcatatcaggattatcaataccatatttttgaaaaag
ccgtttctgtaatgaaggagaaaactcaccgaggcagttccataggatggcaagatcctggtatcggtctgcgattc
cgactcgtccaacatcaatacaacctattaatttcccctcgtcaaaaataaggttatcaagtgagaaatcaccatga
gtgacgactgaatccggtgagaatggcaaaagtttatgcatttctttccagacttgttcaacaggccagccattacg
ctcgtcatcaaaatcactcgcatcaaccaaaccgttattcatcgtgattgcgcctgagcgaggcgaaatacgcgat
cgctgttaaaaggacaattacaaacaggaatcgagtgcaaccggcgcaggaacactgccagcgcatcaacaatattt
tcacctgaatcaggatattcttctaatacctggaacgctgtttttccggggatcgcagtggtgagtaaccatgcatc
atcaggagtacggataaaatgcttgatggtcggaagtggcataaattccgtcagccagtttagtctgaccatctcat
ctgtaacatcattggcaacgctacctttgccatgtttcagaaacaactcttggcgcatcgggcttcccatacaagcga
tagattgtcgcacctgattgcccgacattatcgcgagcccatttataccatatataaatcagcatccatgttggaatt
taatcgcggcctcgactttcccgttgaatatggctcatattcttcctttttcaatattattgaagcatttatcagg
gttattgtctcatgagcggatacatatttgaatgtatttagaaaaataaacaaataggggtcagtgttacaaccaat
taaccaattctgaacattatcgcgagcccatttatacctgaatatggctcataacaccccttgtttgcctggcggca
gtagcgcggtggtcccacctgacccatgccgaactcagaagtgaaacgccgtagcgccgatggtagtgtggggact
ccccatgcgagagtagggaactgccaggcatcaaatcaaaacgaaaggctcagtcgaaagactgggcctttcgcccgg
gctaattaggggggtgtcgcccttattcgactctatagtgaagttcctattctctagaaagtataggaacttctgaag
tggggtcgacttaattaaggctgcgcgctcgctcgctcactgaggccgcccgggcaaagcccgggcgtcgggcgacc
tttggtcgcccggcctcagtgagcgagcgagcgcgcagagaggggagtggccaactccatcactagggggttccttgta
gttaatgattaacccgccatgctacttatctacgtagcaagctagccgttacataactttacggtaaatggcccgcct
ggctgaccgcccaacgacccccgcccattgacgtcaataatgacgtatgttcccatagtaacgccaatagggacttt
ccattgacgtcaatgggtggagtatttacggtaaactgcccacttggcagtacatcaagtgtatcatatgccaagta
cgccccctattgacgtcaatgacggtaaatggcccgcctggcattatgcccagtacatgaccttatggactttcct
acttggcagtacatctacgtattagtcatcgctattaccatggtgatgcggttttggcagtacatcaatgggcgtgg
atagcggtttgactcacggggatttccaagtctccaccccattgacgtcaatgggagtttgttttggcaccaaaatc
aacgggactttccaaaatgtcgtaacaactccgccccattgacgcaaatgggcggtaggcgtgtacggtgggaggtc
tatataagcagagctttgtacactagcggccgcgaccaccatggtggggaagcgacagactggccggagctctggaggg
ggaggagcagccgtcaccgtgcgtctcactaacgcgcgggactgcttctccatctgccgcggaggctggtcgccca
gctgcacctcctgcagaaccaggccatcgaggtggtgtggtcccaccaaccggcttttttgagctgggtcgagggaa
ggcacttttcggaccagggagaaaatgtggcggagatcaaccgccaggtcggccagaagctgggactgtccaacggc
ggacaggtgttcctcaagccgtgcagccacgtggtgtcctgccaacaggtggaagtggagccgctctccgccgacga
ctggagatcctcgaattgcatgccgtgagcctcgaacagcatctgttggaccagattcgcattgtgttcccgaagg
ccatattccccgtgtgggtcgatcagcagacctatatcttcatccagattgtggccctcatcccggccgcctcatac
ggacggctggaaactgacaccaagctgctgattcaacctaagacccggagggccaaagaaaacaccttctccaaggc
cgacgctgagtacaagaagctccactcctacgacgggaccagaagggatgatggaaggagctgcaaaccaagcagc
tccagagcaacaccgtggggatcaccgagtccaatgaaaacgagtcggaaatcccagtcgattcatcttccgtggcc
agcctgtggactatgatcggttccatttttctcgttccaatctgagaagaagcaggaaactagctgggggctgactga
gatcaacgccttcaagaacatgcagtccaaagtggtgcctctggataacatcttttcgcgtgtgcaagtcccaaccgc
cctcaatctacaacgcgtccgctacctccgtgtttcataagcactgtgccatccacgtgttcccatgggatcaggaa
tacttcgatgtcgaaccttccttcaccgtgacttacgggaagcttgtcaagctcctcagccccaagcagcagcaatc
gaaaactaagcagaacgtgctttccccggagaaggagaagcaaatgtcagaaccactcgaccagaagaaaatcgat
cggatcataacgaagaggacgagaaggcctgcgtccttcaggtggtctgaacgcctggaggagctgaacaacgcg
attaagtacaccaagaacgtcgaggtccttcacctgggaaaggtgtggattccggatgatctgaggaaacgcctcaa
catcgaaatgcaagctgtggtgcggattaccccggtcgaggtcaccccaaagatccctcgctccttgaagctgcagc
cgcgagaaaacttgcccaaggacatttctgaagaggatatcaagactgtgttctactcctggctgcaacagagcact
accaccatgctccctctggtcatttcggaggaagaattcatcaaactggaaaaccaaggacggactgaaagaattctc
cctgtccatcgtgcactcctgggaaaaggagaaggacaagaatatcttcctgctgtcccccaatctgctgcaaaaga
ccacgatccaggtgctgctcgaccccatggtgaaggaggaaaactcagaagagatcgacttcatcctgccgttccttt
aagctgagttcactgggaggcgtgaactccctttggcgtgtcctcgctggagcacatcactcactcactgctgggccg
gcctctgagcagacagcttatgagcttggtcgccggactcagaaacggtgccctcctgctcaccggcggcaagggat
cgggaaagtccaccctcgctaaggccatttgcaaagaggcattcgataagctggacgcccatgtggagcgggtggac
tgtaaggccctccgcgaaagcgattggaaaatattcaaaagactctcgaagtcgccttttccgaagccgtctggat
gcagccctcggtcgtcctgctcgacgatctggacctcatcgctgggctgccggccgtgccggagcatgaacactccc
ctgacgcggtccagtcgcaacggctcgcccacgcccctgaacgatatgattaaggaattcatctcaatgggatcactg
gtggccctgatcgcgacttcccagagccagcagtcccgcacccttgctggtgtcggcccagggcgtgcacattttt
tcagtgtgtgcaacacatccagccgcccaaccaggagcagcggtgcgaaatcctgtcaacgtgattaagaacaagc
tggactgcgatatcaacaagtttaccgaccttgatctccaacatgtggctaaggagactgggggcttcgtggctcgg
gacttcacagtgttggtggaccgggcaattcactccagactgtcccgccagagcatttccacccgcgaaaaactggt
cctgaccaccctcgacttccagaaggccctcagaggcttccttcctgcgagcctcagatccgtcaaccttcacaagc

SEQUENCE TABLES

```
cgcgggaccttggctgggacaagatcggtgggctccacgaggtgcggcagatcctcatggacaccattcagctgcct
gcaaagtaccccgagctgttcgccaacttgccgattcgccagcgcacgggaatcctgctctacggcccccgggcac
cggaaagaccctgctggccggtgtgatcgcccgggaatcgaggatgaacttcatctccgtgaagggacccgaactcc
tgtccaagtacatcggtgcctccgaacaggccgtgcgcgatatattcattagggcccaggccgcgaagcctgcatt
ctgttcttcgacgagtttgaatcgatcgcgccccggaggggccacgacaacacgggagtgaccgaccgggtggtgaa
ccagctgctcacccaactggatggcgtggaaggccttcagggagtgtacgtgctggcggctacctccagaccggacc
tgatcgatccggccctgctgcgccccgggagactggacaagtgcgtgtattgccctccccctgaccaggtgtcaagg
ttggaaatcctcaacgtgctctcggactccctgccactggcagatgatgtggacctccagcatgtggcctccgtgac
tgacagcttcacaggagccgatctgaaggccctgctttacaacgcccagttggaggcgctgcacggtatgctgctgt
cctccggtctgcaggatggctcctcctcttccgatagcgacctgtcgctgagcagcatggtgttcctgaaccattcc
agcggctccgatgacagcgcgggcgacggagaatgtggactggatcaatccctggtgtccctggagatgagcgagat
tctgccagacgagtccaagttcaacatgtacaggctgtacttcggcagcagctacgagtccgagctgggaaatggta
cctcgtccgacctgtcaagccagtgcctgtccgcgccttcctccatgacccaggacctccctggagtgccagggaag
gatcagctgttcagccagcctcccgtgctgcgcactgcgagccaggaagggtgccaggaattgacccaagagcagcg
ggaccaactgcgcgcggacatttcgatcatcaaaggcagataccgctcccaatccggggaggacgaaagcatgaacc
agcccgggcctatcaagactagactggcaatctcccaaagccacctgatgaccgcactgggacacaccccggcctcg
atctcggaggacgactggaagaacttcgctgagctgtacgaatccttccagaatccgaagcggagaaagaaccagag
cggaactatgttccggcccggacagaaggtgaccctggcctgaagtactgcggatcctgcagatctgcctcgactgt
gccttctagttgccagccatctgttgtttgccctcccccgtgccttccttgaccctggaaggtgccactcccactg
tcctttcctaataaaatgaggaaattgcatcgcattgtctgatgtaggtgtcattctattctgggggggtggggtgggg
caggacagcaaggggaggattgggaagacaatagcaggcatgctggggactcgagttctacgtagataagtagcat
ggcgggttaatcattaactacaaggaacccctagtgatggagttggccactccctctgcgcgctcgctcgctcac
tgaggccgggcgaccaaaggtcgcccgacgcccgggctttgcccgggcggcctcagtgagcgagcgagcgcgcagcc
ttaattaacctaaggaaaatgaagtgaagttcctatacttttctagagaaggaacttctatagtgagtcgaataag
ggcgacacaaaatttattctaaatgcataataaatactgataacatcttatagtttgtattatattttgtattatcg
ttgacatgtataattttgatatcaaaaactgattttccctttattattttcgagatttattttcttaattctctta
acaaactagaaatattgtatatacaaaaaatcataaataatagatgaatagtttaattataggtgttcatcaatcga
aaaagcaacgtatcttatttaaagtgcgttgcttttttctcattataaggttaaataattctcatatatcaagcaa
agtgacaggcgcccttaaatattctgacaaatgctctttccctaaactcccccataaaaaaacccgccgaagcggg
ttttttacgttatttgcggattaacgattactcgttatcagaaccgcccaggggcccgagcttaacctttttatttg
ggggagagggaagtcatgaaaaactaaccctttgaaattcgatctccagcacatcagcaaaacgctattcacgcagt
acagcaaatccttccagacccaaccaaaccaatcgtagtaaccattcaggaacgcaaccgcagcttagaccaaaaca
ggaagctatgggcctgcttaggtgacgtctctcgtcaggttgaatggcatggtcgctggctggtgatgcagaaagctgg
aagtgtgtgtttaccgcagcattaaagcagcaggatgttgttcctaaccttgccgggaatggctttgtggtaatagg
ccagtcaaccagcaggatgcgtgtaggcgaatttgcggagctattagagcttatacaggcattcggtacagagcgtg
gcgttaagtggtcagacgaagcgagactggctctggagtggaaagcgagatgggagacagggctgcatgataaatg
tcgttagtttctccggtggcaggacgtcagcatatttgctctggctaatggagcaaaagcgacgggcaggtaaagac
gtgcattacgttttcatggatacaggttgtgaacatccaatgacatatcggtttgtcagggaagttgtgaagttctg
ggatataccgctcaccgtattgcaggttgatatcaacccggagcttggacagccaaatggttatacggtatgggaac
caaaggatattcagacgcgaatgcctgttctgaagccatttatcgatatggtaaagaaatatggcactccatacgtc
ggcggcgcgttctgcactgacagattaaaactcgttcccttcaccaaatactgtgatgaccatttcggcgcgaggaa
ttacaccacgtggattggcatcagagctgatgaaccgaagcggctcaaagccaaagcctggaatcagatatcttgctg
aactgtcagactttgagaaggaagatatcctcgcatggtggaagcaacaaccattcgatttgcaaataccggaacat
ctcggtaactgcatattctgcattaaaaaatcaacgcaaaaaatcggacttgcctgcaaagatgaggagggattgca
gcgtgttttaatgaggtcatcacgggatcccatgtgcgtgaccgacatcgggaagcgccaaaggagattatgtacc
gaggaagaatgtcgctggacggtatcgcgaaaatgtattcagaaaatgattatcaagccctgtatcaggacatggta
cgagctaaaagattcgataccggctcttgttctgagtcatgcgaaatatttggagggcagcttgatttcgacttcgg
gagggaagctgcatgatgcgatgttatcggtgcggtgaatgcaaagaagataaccgcttccgaccaaatcaaccttta
ctggaatcgatggtgtctccggtgtgaaagaacaccaacagggtgttaccactaccgcaggaaaaggaggacgtgt
ggcgagacagcgacgaagtatcaccgacataatctgcgaaaactgcaaataccttccaacgaaacgcaccagaaata
aacccaagccaatcccaaaagaatctgacgtaaaaaccttcaactacacggctcacctgtgggatatccggtggcta
agacgtcgtgcgaggaaaacaaggtgattgaccaaaatcgaagttacgaacaagaaagcgtcgagcgagctttaacg
tgcgctaactgcggtcagaagctgcatgtgctggaagttcacgtgtggaagcactgctgcgcagaactgatgagcga
tccgaatagctcgatgcacgaggaagaagatgatggctaaaccagcgcgaagcgatgtaaaaacgatgaatgccgg
gaatggtttcaccctgcattcgctaatcagtggtggtgctctccagagtgtggaaccaagatagcactcgaacgacg
aagtaaagaacgcgaaaaagcggaaaaagcagcagagaagaaacgacgacgagaggagcagaaacagaaagataaac
ttaagattcgaaaactcgccttaaagcccccgcagttactggattaaaacaagcccaacaagccgtaaacgccttcatc
agagaaagagaccgcgacttaccatgtatctcgtgcggaacgctcacgtctgctcagtgggatgccggacattaccg
gacaactgctgcggcacctcaactccgatttaatgaacgcaatattcacaagcaatgcgtggtgtgcaaccagcaca
aaagcggaaatctcgttccgtatcgcgtcgaactgattagccgcatcgggcaggaagcagtagacgaaatcgaatca
aaccataaccgccatcgctggactatcgaagagtgcaaggcgatcaaggcagagtaccaacagaaactcaaagacct
gcgaaatagcagaagtgaggccgcatgacgttctcagtaaaaaccattccagacgcagcaaaatgctcgttgaagcatcaaggcga
tcagacagaagtagcacgcagactgaaatgtagtcgcggtacggtcagaaaatacgttgatgataaagacgggaaaa
tgcacgccatcgtcaacacgttctcatggttcatcgcggatggagtgaaagagatgcgctattacgaaaaaattga
tggcagcaaataccgaaatatttgggtagttggcgatctgcacggatgctacacgaacctgatgaacaaactggata
cgattggattcgacaacaaaaaagacctgcttatctcggtgggcgatttggttgatcgtggtgcagagaacgttgaa
tgcctggaattaatcacattccccggttcagacgtgcgtgaaccatgcaaatgatgattgatgcttatc
agagcgtggaaacgttaatcactggctgcttaatggcggtggctggttctttaatctcgattacgacaaagaaattc
tggctaaagctcttgcccataaagcagatgaacttccgttaatcatcgaactggttgagcaaagataaaaaatatgtt
atctgccacgccgattatcccttgacgaatacgagtttggaaagccagttgatcatcagcaggtaatctggaaccg
cgaacgaatcagcaactcacaaaacgggatcgtgaaagaaatcaaaggcgcggacacgttcatctttggtcatacgc
cagcagtgaaccactcaagtttgccaaccaaatgtatatcgatcgccagtgttctgcggaaacctaacattg
attcaggtacagggagaaggcgcatgagactcgaaagcgtagctaaatttcattcgccaaaaagcccgatgatgagc
gactcaccacgggccacggcttctgactctctttccggtactgatgtgatggctgctatggggatggcgcaatcaca
agccggattcggtatggctgcattctgcggtaagcacgaactcagccagaacgacaaacaaaggctatcaactatc
tgatgcaatttgcacacaaggtatcggggaaataccgtggtgtggcaaagcttgaaggaaatactaaggcaaaggta
ctgcaagtgctcgcaacattcgcttatgcggattattgccgtagtgccgcgacgccggggcaagatgcagagattg
```

SEQUENCE TABLES

```
ccatggtacaggccgtgcggttgatattgccaaaacagagctgtggggagagttgtcgagaaagagtgcggaagat
gcaaaggcgtcggctattcaaggatgccagcaagcgcagcatatcgcgctgtgacgatgctaatcccaaaccttacc
caacccacctggtcacgcactgttaagccgctgtatgacgctcggtggtgcaatgccacaaagaagagtcaatcgc
agacaacattttgaatgcggtcacacgttagcagcatgattgccacggatggcaacatattaacggcatgatattga
cttattgaataaaattgggtaaatttgactcaacgatgggttaattcgctcgttgtggtagtgagatgaaaagaggc
ggcgcttactaccgattccgcctagttggtcacttcgacgtatcgtctggaactccaaccatcgcaggcagagaggt
ctgcaaaatgcaatcccgaaacagttcgcaggtaatagttagagcctgcataacggtttcgggatttttttatatctg
cacaacaggtaagagcattgagtcgataatcgtgaagagtcggcgagcctggttagccagtgctcttccgttgtgc
tgaattaagcgaataccggaagcagaaccggatcaccaaatgcgtacaggcgtcatcgccgcccagcaacagcacaa
cccaaactgagccgtagccactgtctgtcctgaattcattagtaatagttacgctgcggccttttacacatgaccttt
cgtgaaagcgggtggcaggaggtcgcgctaacaacctcctgccgttttgcccgtgcatatcggtcacgaacaaatct
gattactaaacacagtagcctggatttgttctatcagtaatcgaccttattcctaattaaatagagcaaatcccctt
attgggggtaagacatgaagatgccagaaaaacatgacctgttggccgccattctcgcggcaaaggaacaaggcatc
ggggcaatccttgcgtttgcaatggcgtaccttcgcggcagatataatggcggtgcgtttacaaaaacagtaatcga
cgcaacgatgtgcgccattatcgcctggttcattcgtgaccttctcgacttcgccggactaagtagcaatctcgctt
atataacgagcgtgtttatcggctacatcggtactgactcgattggttcgcttatcaaacgcttcgctgctaaaaaa
gccggagtagaagatggtagaaatcaataatcaacgtaaggcgttcctcgatatgctggcgtggtcggagggaactg
ataacggacgtcagaaaaccagaaatcatggttatgacgtcattgtaggcggagagctatttactgattactccgat
caccctcgcaaacttgtcacgctaaacccaaaactcaaatcaacaggcgcttaagactggccgtcgttttacaacac
agaaagagttttgtagaaacgcaaaaaggccatccgtcaggggccttctgcttagtttgatgcctggcagttccctac
tctcgccttccgcttcctcgctcactgactcgctgcgctcggtcgttcggctgcggcagcggtatcagctcactca
aaggcggtaatacggttatccacagaatcaggggataacgcaggaaagaacatgtgagcaaaaggccagcaaaaggc
caggaaccgtaaaaaggccgcgttgctggcgtttttccataggctccgcccccctgacgagcatcacaaaaatcgac
gctcaagtcagaggtggcgaaacccgacaggactataaagataccaggcgtttccccctggaagctccctcgtgcgc
tctcctgttccgaccctgccgcttaccggatacctgtccgcctttctccctcgggaagcgtggcgctttctcatag
ctcacgctgtaggtatctcagttcggtgtaggtcgttcgctccaagctgggctgtgtgcacgaaccccccgttcagc
ccgaccgctgcgccttatccggtaactatcgtcttgagtccaacccggtaagacacgacttatcgccactggcagca
gccactggtaacaggattagcagagcgaggtatgtaggcggtgctacagagttcttgaagtggtgggctaactacgg
ctacactagaagaacagtatttggtatctgcgctctgctgaagccagttaccttcggaaaaagagttggtagctctt
gatccggcaaacaaaccaccgctggtagcggtggtttttttgtttgcaagcagcagattacgcgcagaaaaaagga
tctcaagaagatcctttgatcttttctacggggtctgacgctcagtggaacgacgcgcgtaactcacgttaaggg
atttggtcatgagcttgcgccgtcccgtcaagtcagcgtaatgctctgcttt
```

What is claimed is:

1. A method of treating a deficiency in peroxisome biogenesis factor 1 (PEX1) in a subject in need thereof, comprising directly administering to an eye of the subject a recombinant adeno-associated virus (rAAV) comprising an AAV capsid having packaged therein a vector genome comprising a nucleic acid sequence that encodes human PEX1, thereby improving visual function in the subject.

2. The method according to claim 1, wherein the rAAV is delivered in a dosage of from about $1\times10^9$ to about $1\times10^{13}$ vector genomes per eye (vg/eye) in an aqueous suspension.

3. The method according to claim 1, wherein the rAAV is administered subretinally.

4. The method according to claim 1, wherein the rAAV is administered in a dosage of from $1\times10^9$ to $1\times10^{13}$ vg/eye in a volume comprising about 150 microliters, thereby treating the PEX1 deficiency in said subject.

5. The method according to claim 1, wherein rAAV is administered in a volume of between 150 to 800 microliters.

6. The method according to claim 1, wherein the subject is human.

7. The method according to claim 1, wherein the subject has a Zellweger Spectrum Disorder selected from Zellweger syndrome, neonatal adrenoleukodystrophy, or infantile Refsum disease.

8. The method of claim 1, wherein the human PEX1 comprises the amino acid sequence of SEQ ID NO 7, or a sequence at least 90% identical to the amino acid sequence set forth in SEQ ID NO: 7.

9. The method of claim 1, wherein nucleic acid sequence comprises SEQ ID NO: 1 or a sequence at least 80% identical to SEQ ID NO: 1.

10. The method of claim 9, wherein the nucleic acid sequence comprises SEQ ID NO: 1.

11. The method of claim 1, wherein AAV capsid is selected from the group consisting of an AAV7m8 capsid or variant thereof, an AAV8 capsid or a variant thereof, an AAV6 capsid or variant thereof, an AAV9 capsid or variant thereof, an AAV7 capsid or variant thereof, an AAV5 capsid or variant thereof, an AAV2 capsid or variant thereof, an AAV1 capsid or variant thereof, an AAV3 capsid or variant thereof, and an AAV4 capsid or variant thereof.

12. The method of claim 1, wherein the rAAV comprises an AAV8 capsid.

13. The method of claim 1, wherein the vector genome comprises
(a) an AAV 5' inverted terminal repeat (ITR) sequence;
(b) a promoter;
(c) a coding sequence encoding a human PEX1; and
(d) an AAV 3' ITR.

14. The method of claim 13, wherein the promoter is a cytomegalovirus (CMV) promoter.

15. The method of claim 13, wherein the promoter is a hybrid promoter comprising a CMV enhancer sequence and a chicken beta actin (CBA) promoter sequence.

16. The method of claim 13, wherein the vector genome further comprises a polyA.

17. The method of claim 1, wherein the vector genome comprises SEQ ID NO: 6, SEQ ID NO: 8, nucleotides 1253 to 7390 of SEQ ID NO: 9, nucleotides 1253 to 5960 of SEQ ID NO: 10, nucleotides 1253 to 6196 of SEQ ID NO: 11, nucleotides 1253 to 5951 of SEQ ID NO: 12 or nucleotides 1253 to 6235 of SEQ ID NO:13.

18. The method according to claim 1, wherein said rAAV is administered in a dosage of from $1\times10^9$ to $1\times10^{13}$ vg/eye in a volume comprising at least 150 microliters, thereby treating the PEX1 disorder in said subject.

19. The method of claim 1, wherein the rAAV comprises an AAV2 capsid.

20. The method according to claim 1, wherein the rAAV is administered intravitreally.

21. The method according to claim 1, wherein visual function is assessed using electroretinograms (ERGs) to examine rod and cone photoreceptor function, pupillometry visual acuity, contrast sensitivity color vision testing, visual field testing (Humphrey visual fields/Goldmann visual fields), perimetry mobility test (obstacle course), or reading speed test.

* * * * *